(12) United States Patent
Yamashita et al.

(10) Patent No.: US 9,260,420 B2
(45) Date of Patent: Feb. 16, 2016

(54) PIPERAZINE-SUBSTITUTED BENZOTHIOPHENE DERIVATIVES AS ANTIPSYCHOTIC AGENTS

(75) Inventors: Hiroshi Yamashita, Osaka (JP); Yohji Sakurai, Osaka (JP); Motoyuki Miyamoto, Osaka (JP); Yuichi Nakamura, Osaka (JP); Hideaki Kuroda, Osaka (JP); Takuya Minowa, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/343,579

(22) PCT Filed: Sep. 7, 2012

(86) PCT No.: PCT/JP2012/073556
§ 371 (c)(1),
(2), (4) Date: Mar. 7, 2014

(87) PCT Pub. No.: WO2013/035892
PCT Pub. Date: Mar. 14, 2013

(65) Prior Publication Data
US 2015/0045356 A1    Feb. 12, 2015

Related U.S. Application Data

(60) Provisional application No. 61/532,393, filed on Sep. 8, 2011.

(51) Int. Cl.
*C07D 409/12* (2006.01)
*C07D 409/14* (2006.01)

(52) U.S. Cl.
CPC ............ *C07D 409/14* (2013.01); *C07D 409/12* (2013.01)

(58) Field of Classification Search
None
See application file for complete search history.

(56) References Cited

FOREIGN PATENT DOCUMENTS

| | | | |
|---|---|---|---|
| JP | 2008-115172 A | 5/2008 | |
| WO | WO 2006/112464 | 10/2006 | |
| WO | WO 2009/128537 A1 | 10/2009 | |
| WO | WO 2010/151689 A1 | 12/2010 | |
| WO | WO 2010/151711 A1 | 12/2010 | |
| WO | WO 2011/084846 A1 | 7/2011 | |
| WO | WO 2011/163594 A2 | 12/2011 | |
| WO | WO 2012/088441 A1 | 6/2012 | |
| WO | WO 2012/129156 A1 | 9/2012 | |

OTHER PUBLICATIONS

Toru et al., "Creativity in the Development of the Drug, Aripiprazole: A Novel Partial Dopamine $D_2$ Receptor Agonist for the Treatment of Schizophrenia", Seishin-Igaku, (Psychiatry), vol. 46, pp. 855-864, (2004).*
Svensson, "$\alpha$-Adrenoceptor Modulation Hypothesis of Antipsychotic Atypicality", Progress in Neuro-Psychopharmacology & Biological Psychiatry, vol. 27, pp. 1145-1158, (2003).*
Pullar et al., "LY367265, An Inhibitor of the 5-Hydroxytryptamine Transporter and 5-Hydroxytryptamine$_{2A}$ Receptor Antagonist: A Comparison With the Antidepressant, Nefazodone", European Journal of Pharmacology, vol. 407, pp. 39-46, (2000).*
Yagcioglu, Turkish Journal of Psychiatry, vol. 18(4), p. 1-10 (2007).*
Office Action for CN Application No. 201280043980.2 dated Feb. 16, 2015.

* cited by examiner

*Primary Examiner* — Emily Bernhardt
(74) *Attorney, Agent, or Firm* — Finnegan, Henderson, Farabow, Garrett & Dunner LLP

(57) ABSTRACT

Provided is a superior, novel heterocyclic compound with improved solubility in oil such as sesame oil and benzyl benzoate, which has a broader treatment spectrum, causes less side effects, and is superior in tolerability and safety, and use thereof. A heterocyclic compound represented by the formula (I) wherein each symbol is as defined in the specification, or a salt thereof.

5 Claims, 1 Drawing Sheet

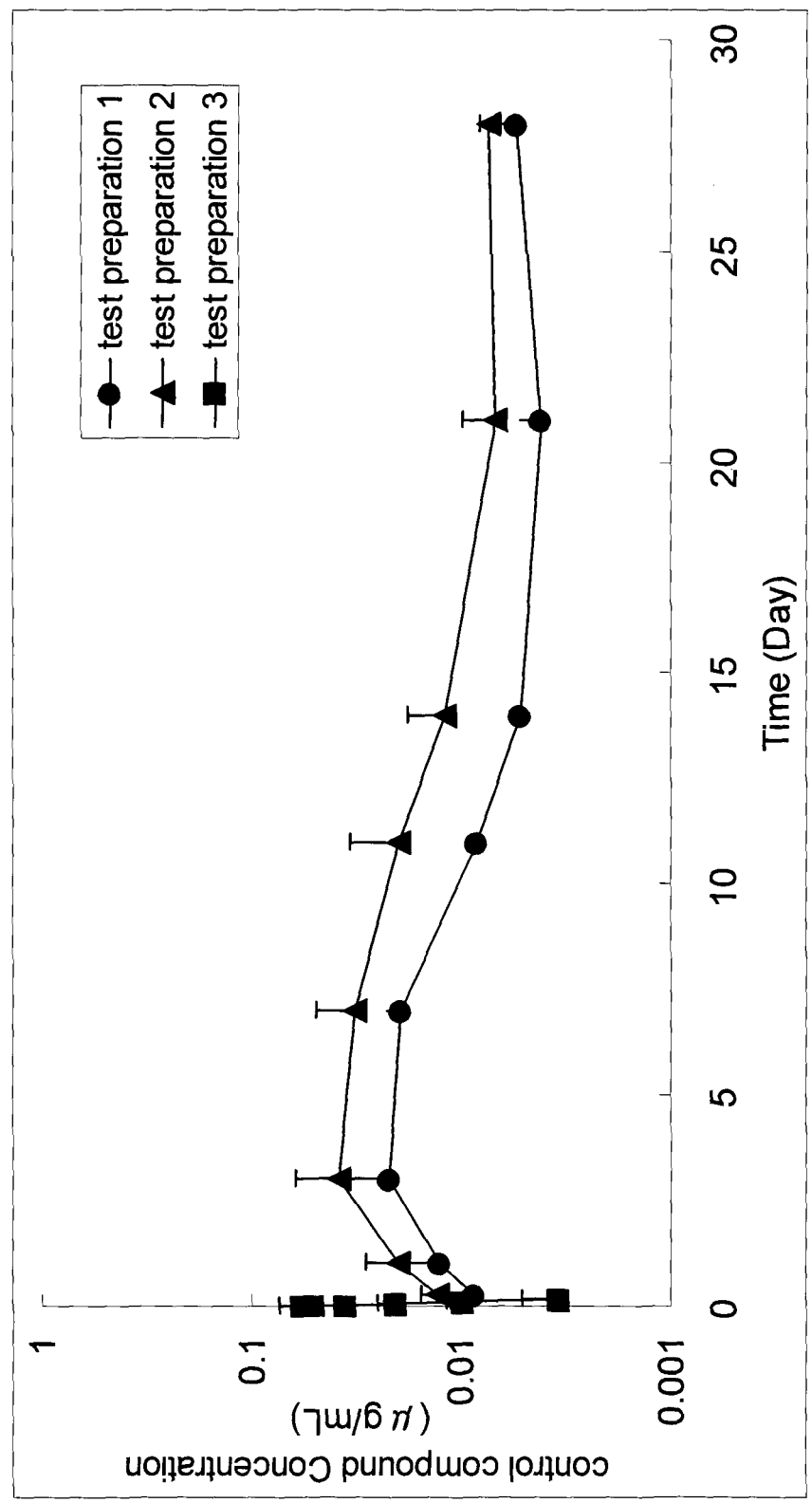

PIPERAZINE-SUBSTITUTED BENZOTHIOPHENE DERIVATIVES AS ANTIPSYCHOTIC AGENTS

CROSS REFERENCE TO RELATED APPLICATIONS

This application is a national phase application based on PCT/JP2012/073556, filed Sept. 7, 2012, which claims the benefit of U.S. Provisional Application No. 61/532,393, filed Sept. 8, 2011, the contents of both of which are incorporated herein by reference.

TECHNICAL FIELD OF THE INVENTION

The present invention relates to a novel heterocyclic compound and use thereof.

BACKGROUND OF THE INVENTION

As a compound having a broad treatment spectrum for central neurological diseases such as schizophrenia and the like, for example, a compound represented by the following formula (1) (hereinafter compound (1)) has been reported (patent document 1).

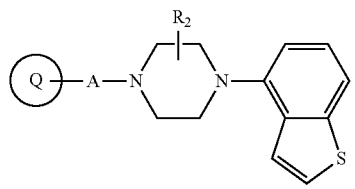

(1)

wherein each symbol is as defined in patent document 1.

The above-mentioned compound (1) is an antipsychotic agent having a broader treatment spectrum as compared to conventional typical antipsychotic agents and atypical antipsychotic agents, causing less side effects, and superior in tolerability and safety. However, this compound is associated with problems in that its application to oil injections is limited and the like, since it is poorly soluble in oil such as sesame oil and benzyl benzoate. Oil injections are useful as compared to aqueous suspensions from the aspects of imparted blood concentration sustainability (control of diffusion in administration site by oily base), shortened liquid preparation time when in use (unnecessitated mixing and shaking), secured sterilization by filtration (oily base filtration), avoidance of physical stimulation at administration site (oily base stability), improved accuracy of filling into injection container (container filled with oily base) and the like.

DOCUMENT LIST

Patent Document patent document 1: WO2006/112464

SUMMARY OF THE INVENTION

Problems to be Solved by the Invention

The problem of the present invention is to provide a superior, novel heterocyclic compound with improved solubility in oil such as sesame oil and benzyl benzoate and use thereof.

Means of Solving the Problems

The present inventors have conducted various studies in an attempt to solve the aforementioned problems and found that the liposolubility of compound (1) can be markedly improved by introducing a substituent into a particular position on ring Q. The present invention has been completed based on such finding.

The present invention preferably provides a heterocyclic compound or a salt thereof shown in the following Items 1-4, a pharmaceutical composition shown in the Item 5, a prophylactic and/or therapeutic agent shown in the Items 6 and 7, use shown in the Item 8, a prophylactic and/or treatment method shown in the Items 9 and 10, and a production method shown in the Item 11.

Item 1. A heterocyclic compound represented by the formula (I)

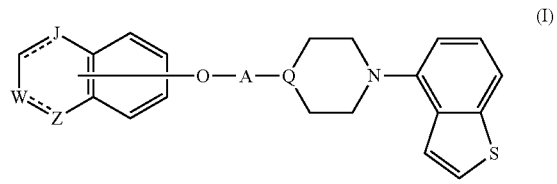

(I)

wherein
A is a lower alkylene group;

in the monocyclic heterocycle containing Q is

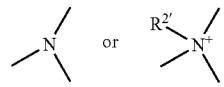

wherein
$R^{2'}$ is the following group

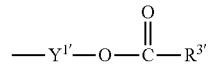

wherein
$Y^{1'}$ is a lower alkylene group,
$R^{3'}$ is
(1) an alkyl group,
(2) a cycloalkyl group optionally substituted by a lower alkyl group,
(3) a phenyl group,
(4) a phenyl lower alkyl group
(5) a lower alkoxy group,
(6) a cycloalkyloxy group,
(7) an amino group optionally having 1 or 2 substituents selected from the group consisting of an alkyl group and a phenyl lower alkyl group, or
(8) a piperidyl group optionally having a piperidyl group;

at the 3-position and the 4-position of the bicyclic heterocycle skeleton containing Z and W is —CH=CH— or

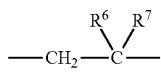

wherein $R^6$ and $R^7$ are the same or different and each is a hydrogen or a lower alkyl group;

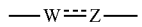

is

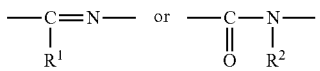

wherein
$R^1$ is
a lower alkoxy lower alkoxy group,
a phosphonooxy lower alkoxy group,
a phenyl lower alkoxy lower alkoxy group,
a phosphonooxy group optionally having 1 or 2 lower alkyl groups,
the following group

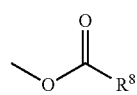

wherein
$R^8$ is
(1) an alkyl group,
(2) a hydroxy-substituted lower alkyl group,
(3) a cycloalkyl group,
(4) a phenyl group,
(5) a phenyl lower alkyl group,
(6) an alkenyl group,
(7) a lower alkoxy group,
(8) a cycloalkyloxy group,
(9) a lower alkoxy lower alkoxy group,
(10) an amino group optionally having 1 or 2 substituents selected from the group consisting of an alkyl group and a hydroxy-substituted lower alkyl group,
(11) a piperidyl group optionally having a piperidyl group,
(12) a piperazinyl group optionally having a lower alkyl group, or
(13) the following group

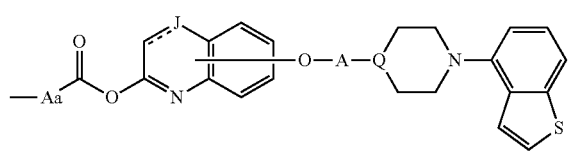

wherein Aa is an alkylene group, and other symbols are as defined above, or
the following group

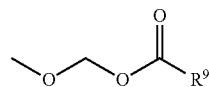

wherein
$R^9$ is
(1) an alkyl group,
(2) a hydroxy-substituted lower alkyl group,
(3) a cycloalkyl group,
(4) a phenyl group,
(5) a phenyl lower alkyl group,
(6) an alkenyl group,
(7) a lower alkoxy group,
(8) a cycloalkyloxy group,
(9) a lower alkoxy lower alkoxy group,
(10) a phenyloxy group,
(11) an amino group optionally having 1 or 2 substituents selected from the group consisting of an alkyl group and a hydroxy-substituted lower alkyl group,
(12) a piperidyl group optionally having a piperidyl group,
(13) a piperazinyl group optionally having a lower alkyl group, or
(14) the following group

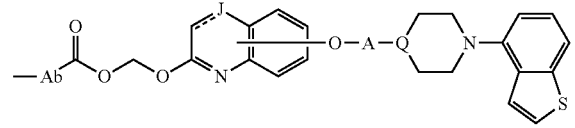

wherein Ab is an alkylene group, and other symbols are as defined above;
$R^2$ is a hydrogen or
the following group

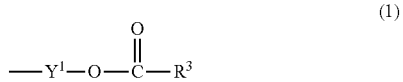
(1)

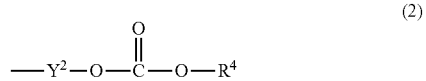
(2)

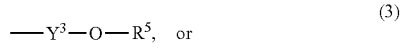
(3)

(4)

wherein
$Y^1$ is a lower alkylene group optionally substituted by
(1) a lower alkoxycarbonyl group or
(2) a lower alkyl group,
$Y^2$ is a lower alkylene group,
$Y^3$ is a single bond or a lower alkylene group optionally substituted by a lower alkyl group,
$R^3$ is
(1) an alkyl group,
(2) a halogen-substituted lower alkyl group,
(3) an alkenyl group,
(4) an amino lower alkyl group,
(5) a cycloalkyl group, (6) a phenyl group,
(7) a phenyl lower alkyl group,
(8) a piperidyl group optionally having 1 or 2 substituents selected from the group consisting of a lower alkyl group and a piperidyl group,
(9) a halogen-substituted piperidyl group,
(10) a morpholinyl group,
(11) a pyrrolidinyl group,
(12) a tetrahydropyranyl group,
(13) a furyl group,
(14) a thienyl group,
(15) a pyridyl group,
(16) a pyrimidinyl group,
(17) a pyridazinyl group,
(18) a benzofuryl group,
(19) a quinolyl group,
(20) a lower alkoxycarbonyl lower alkyl group,
(21) a lower alkoxy lower alkoxy lower alkyl group,
(22) a lower alkoxy lower alkoxy lower alkoxy lower alkyl group,
(23) an amino group optionally having 1 or 2 substituents selected from the group consisting of an alkyl group, a cycloalkyl group, a cycloalkyl lower alkyl group, a lower alkenyl group, a halogen-substituted lower alkyl group, a lower alkoxy group, a lower alkoxy lower alkyl group, a lower alkoxycarbonyl lower alkyl group, a phenyl lower alkyl group, a phenyl lower alkoxy group, a furyl lower alkyl group, a pyridyl lower alkyl group, a hydroxy-substituted lower alkyl group,
(24) an amino lower alkyl group optionally having a lower alkylcarbonyl group,
(25) a piperazinyl group optionally having a lower alkyl group, or
(26) the following group

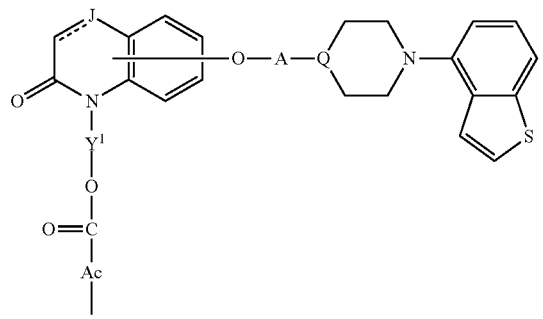

wherein Ac is an alkylene group, and other symbols are as defined above,
$R^4$ is
(1) an alkyl group,
(2) a phenyl group,
(3) a phenyl lower alkyl group,
(4) a halogen-substituted lower alkyl group, or
(5) a cycloalkyl group,
$R^5$ is
(1) a hydrogen,
(2) a lower alkyl group,
(3) a halogen-substituted lower alkyl group,
(4) a phenyl lower alkyl group,
(5) a phenyl lower alkoxy lower alkyl group,
(6) a tri-lower alkylsilyl group,
(7) a tetrahydropyranyl group, or
(8) a phosphono group, $R^{10}$ is
(1) an alkyl group,
(2) an alkenyl group,
(3) a phenyl group,
(4) a phenyl lower alkyl group,
(5) a hydroxy-substituted lower alkyl group,
(6) a cycloalkyl group,
(7) an amino lower alkyl group optionally having 1 or 2 substituents selected from the group consisting of an amino lower alkylcarbonyl group and a lower alkylcarbonyl group,
(8) a pyrrolidinyl group optionally having an amino lower alkylcarbonyl group,
(9) an alkoxy group,
(10) a lower alkoxy lower alkoxy lower alkyl group,
(11) a lower alkoxy lower alkoxy lower alkoxy lower alkyl group,
(12) a phenyl lower alkoxy group,
(13) an amino group optionally having 1 or 2 substituents selected from the group consisting of an alkyl group, a hydroxy-substituted lower alkyl group and a phenyl lower alkyl group,
(14) a morpholino group,
(15) a piperazinyl group optionally having a lower alkyl group,
(16) a piperidyl group optionally having a piperidyl group, or
(17) a cycloalkyloxy group;
provided when

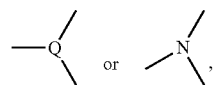

then
$R^2$ is not a hydrogen,
or a salt thereof.
Item 2. The heterocyclic compound according to Item 1, which is represented by the formula (II)

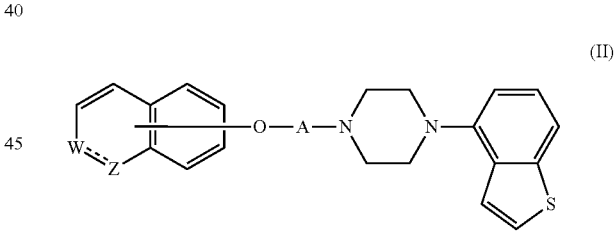

wherein each symbol is as defined in Item 1, or a salt thereof.
Item 3. The heterocyclic compound according to Item 1, which is represented by the formula (III)

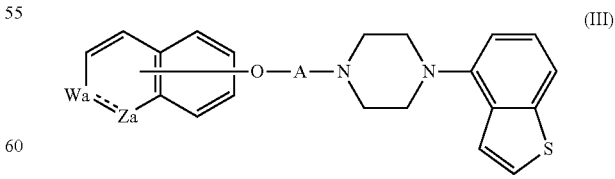

wherein

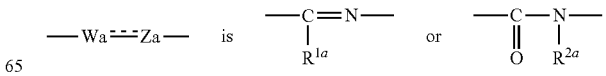

wherein
R$^{1a}$ is the following group

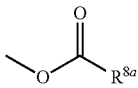

wherein
R$^{8a}$ is
(1) an alkyl group,
(2) a cycloalkyl group,
(3) a lower alkoxy group,
(4) a cycloalkyloxy group,
(5) a lower alkoxy lower alkoxy group,
(6) an amino group optionally having 1 or 2 substituents selected from the group consisting of an alkyl group and a hydroxy-substituted lower alkyl group, or
(7) the following group

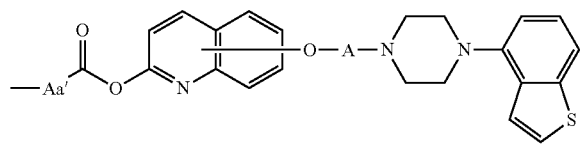

wherein Aa' is an alkylene group, and other symbol is as defined in Item 1, or
the following group

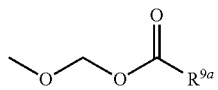

wherein
R$^{9a}$ is
(1) an alkyl group,
(2) a hydroxy-substituted lower alkyl group,
(3) a cycloalkyl group,
(4) a lower alkoxy group,
(5) a cycloalkyloxy group,
(6) a lower alkoxy lower alkoxy group,
(7) a phenyloxy group,
(8) an amino group optionally having 1 or 2 substituents selected from the group consisting of an alkyl group,
(9) a piperidyl group optionally having a piperidyl group,
(10) a piperazinyl group optionally having a lower alkyl group, or
(11) the following group

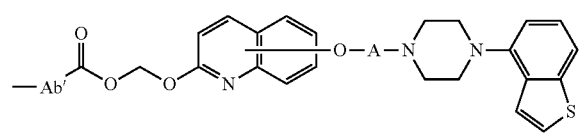

wherein Ab' is an alkylene group, and other symbol is as defined in Item 1;

R$^{2a}$ is
the following group

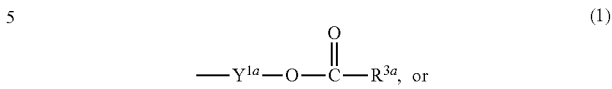

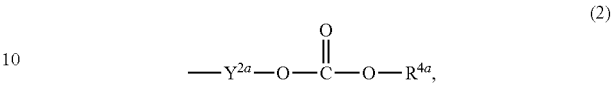

wherein
Y$^{1a}$ is a lower alkylene group,
Y$^{2a}$ is a lower alkylene group,
R$^{3a}$ is
(1) an alkyl group,
(2) a cycloalkyl group,
(3) a piperidyl group optionally having 1 or 2 substituents selected from the group consisting of a lower alkyl group,
(4) a tetrahydropyranyl group,
(5) a lower alkoxycarbonyl lower alkyl group,
(6) a lower alkoxy lower alkoxy lower alkyl group
(7) an amino lower alkyl group optionally having a lower alkylcarbonyl group, or
(8) the following group

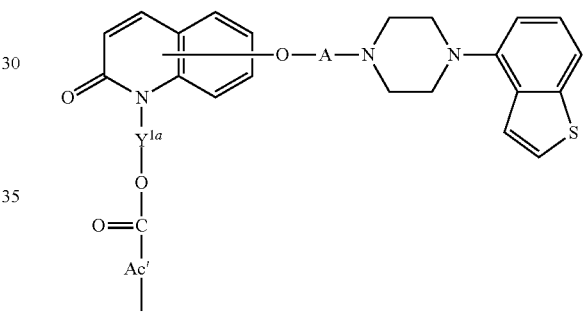

wherein Ac' is an alkylene group, Y$^{1a}$ is a lower alkylene group and other symbols are as defined in Item 1,
R$^{4a}$ is
(1) an alkyl group, or
(2) a cycloalkyl group; and
A is a lower alkylene group,
or a salt thereof.
Item 4. The heterocyclic compound according to Item 2, wherein R$^1$ is
the following group

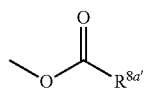

wherein
R$^{8a'}$ is
(1) an alkyl group,
(2) a cycloalkyl group,
(3) a lower alkoxy group,
(4) a cycloalkyloxy group,
(5) a lower alkoxy lower alkoxy group, or
(6) an amino group optionally having 1 or 2 substituents selected from the group consisting of an alkyl group and a hydroxy-substituted lower alkyl group, or the following group

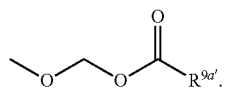

wherein
$R^{9a'}$ is
(1) an alkyl group,
(2) a hydroxy-substituted lower alkyl group,
(3) a cycloalkyl group,
(4) a lower alkoxy group,
(5) a cycloalkyloxy group,
(6) a lower alkoxy lower alkoxy group,
(7) a phenyloxy group,
(8) an amino group optionally having 1 or 2 substituents selected from the group consisting of an alkyl group,
(9) a piperidyl group optionally having a piperidyl group, or
(10) a piperazinyl group optionally having a lower alkyl group;
$R^2$ is
the following group

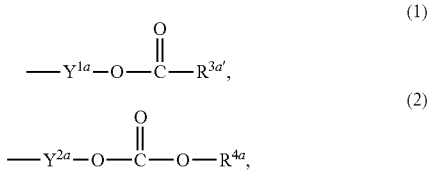

wherein
$Y^{1a}$ is a lower alkylene group,
$Y^{2a}$ is a lower alkylene group,
$R^{3a'}$ is
(1) an alkyl group,
(2) a cycloalkyl group
(3) a piperidyl group optionally having 1 or 2 substituents selected from the group consisting of a lower alkyl group,
(4) a tetrahydropyranyl group,
(5) a lower alkoxycarbonyl lower alkyl group,
(6) a lower alkoxy lower alkoxy lower alkyl group
(7) an amino lower alkyl group optionally having a lower alkylcarbonyl group,
$R^{4a}$ is
(1) an alkyl group, or
(2) a cycloalkyl group;
or a salt thereof.

Item 5. A pharmaceutical composition comprising the heterocyclic compound according to Item 1 or a pharmaceutically acceptable salt thereof, and a pharmaceutically acceptable diluent and/or a carrier.

Item 6. A prophylactic and/or therapeutic agent for a central neurological disease, comprising the heterocyclic compound according to Item 1 or a pharmaceutically acceptable salt thereof as an active ingredient.

Item 7. The agent according to Item 6, wherein the central neurological disease is selected from the group consisting of schizophrenia, treatment-resistant, refractory or chronic schizophrenia, emotional disturbance, psychotic disorder, mood disorder, bipolar disorder, mania, depression, endogenous depression, major depression, melancholic and treatment-resistant depression, dysthymic disorder, cyclothymic disorder, anxiety disorder, somatoform disorder, factitious disorder, dissociative disorder, sexual disorder, eating disorder, sleep disorder, adjustment disorder, substance-related disorder, anhedonia, delirium, Alzheimer's disease, Parkinson disease, cognitive impairment, cognitive impairment associated with neurodegenerative diseases, cognitive impairment caused by neurodegenerative diseases, cognitive impairment in schizophrenia, cognitive impairment caused by treatment-resistant, refractory or chronic schizophrenia, vomiting, motion sickness, obesity, migraine, pain, mental retardation, autistic disorder, Tourette's disorder, tic disorder, attention deficit hyperactivity disorder, conduct disorder and Down's syndrome.

Item 8. Use of the heterocyclic compound according to Item 1 or a pharmaceutically acceptable salt thereof as a medicament.

Item 9. A method of preventing and/or treating a central neurological disease, comprising administering the heterocyclic compound according to Item 1 or a pharmaceutically acceptable salt thereof to a human or an animal.

Item 10. The method according to Item 9, wherein the central neurological disease is selected from the group consisting of schizophrenia, treatment-resistant, refractory or chronic schizophrenia, emotional disturbance, psychotic disorder, mood disorder, bipolar disorder, mania, depression, endogenous depression, major depression, melancholic and treatment-resistant depression, dysthymic disorder, cyclothymic disorder, anxiety disorder, somatoform disorder, factitious disorder, dissociative disorder, sexual disorder, eating disorder, sleep disorder, adjustment disorder, substance-related disorder, anhedonia, delirium, Alzheimer's disease, Parkinson disease, cognitive impairment, cognitive impairment associated with neurodegenerative diseases, cognitive impairment caused by neurodegenerative diseases, cognitive impairment in schizophrenia, cognitive impairment caused by treatment-resistant, refractory or chronic schizophrenia, vomiting, motion sickness, obesity, migraine, pain, mental retardation, autistic disorder, Tourette's disorder, tic disorder, attention deficit hyperactivity disorder, conduct disorder and Down's syndrome.

Item 11. A method of producing a heterocyclic compound represented by the formula (I)

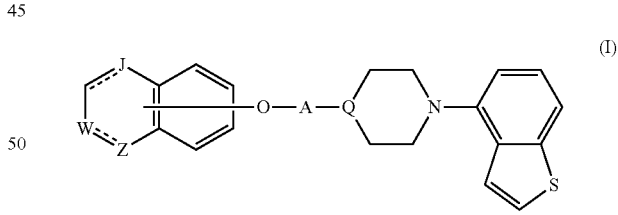

wherein each symbol is as defined in Item 1,
or a salt thereof, comprising reacting a compound represented by the formula

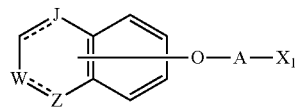

wherein $X_1$ is a halogen atom or a group that causes a substitution reaction similar to that by a halogen atom, and other symbols are as defined in Item 1, or a salt thereof, with a compound represented by

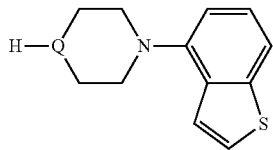

wherein Q is as defined in Item 1, or a salt thereof.

BRIEF DESCRIPTION OF DRAWINGS

FIG. 1 is a graph showing the transition of blood concentration of test preparations 1, 2 and 3 after administration.

DESCRIPTION OF EMBODIMENTS

Each group shown in the aforementioned formula (I) is specifically as follows.

Lower means, unless otherwise specified, a group having 1 to 6 (preferably 1-4) carbon atoms.

As the halogen atom, a fluorine atom, a chlorine atom, a bromine atom and an iodine atom can be mentioned.

As the alkyl group, a straight chain or branched chain alkyl group having a carbon number of 1-30 (preferably 1-20) can be mentioned. More specific examples thereof include methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 1-methylhexyl, 2-methylhexyl, 3-methylhexyl, 4-methylhexyl, 5-methylhexyl, 1-propylbutyl, 1,1-dimethylpentyl, 4,4-dimethylpentyl, 1-pentylhexyl, n-octyl, 1-methylheptyl, 2-methylheptyl, 3-methylheptyl, 4-methylheptyl, 5-methylheptyl, 6-methylheptyl, 1,1-dimethylheptyl, 1-propylpentyl, 2-ethylhexyl, 5,5-dimethylhexyl, n-nonyl, 3-methyloctyl, 4-methyloctyl, 5-methyloctyl, 6-methyloctyl, 1-propylhexyl, 2-ethylheptyl, 6,6-dimethylheptyl, n-decyl, 1-methylnonyl, 3-methylnonyl, 8-methylnonyl, 3-ethyloctyl, 3,7-dimethyloctyl, 7,7-dimethyloctyl, n-undecyl, 1,1-dimethylundecyl, 4,8-dimethylnonyl, dodecyl, tridecyl, tetradecyl, pentadecyl, 3,7,11-trimethyldodecyl, hexadecyl, 4,8,12-trimethyltridecyl, 1-methylpentadecyl, 14-methylpentadecyl, 13,13-dimethyltetradecyl, heptadecyl, 15-methylhexadecyl, octadecyl, 1-methylheptadecyl, nonadecyl, icosyl, 3,7,11,15-tetramethylhexadecyl, henicosyl, docosyl, tricosyl, tetracosyl, pentacosyl, hexacosyl, heptacosyl, octacosyl, nonacosyl, triacontyl group and the like.

As the lower alkyl group, a linear or branched chain alkyl group having a carbon number of 1-6 can be mentioned. More specific examples thereof include methyl, ethyl, n-propyl, isopropyl, n-butyl, isobutyl, tert-butyl, sec-butyl, n-pentyl, 1-methylbutyl, 2-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, 1,2,2-trimethylpropyl, 3,3-dimethylbutyl group and the like.

As the alkenyl group, a straight chain or branched chain alkenyl group having 1-10 double bonds and a carbon number of 2-30 can be mentioned, including both a trans form and a cis form. More specific examples thereof include ethenyl (vinyl), 1-propenyl, 2-propenyl, 1-methyl-1-propenyl, 2-methyl-1-propenyl, 2-methyl-2-propenyl, 2-propenyl, 2-butenyl, 1-butenyl, 3-butenyl, 2-pentenyl, 1-pentenyl, 3-pentenyl, 4-pentenyl, 1,3-butadienyl, 1,3-pentadienyl, 2-pentene-4-ynyl, 2-hexenyl, 1-hexenyl, 5-hexenyl, 3-hexenyl, 4 hexenyl, 3,3-dimethyl-1-propenyl, 2-ethyl-1-propenyl, 1,3,5-hexatrienyl, 1,3-hexadienyl, 1,4-hexadienyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icocenyl group and the like.

As the lower alkenyl group, a straight chain or branched chain alkenyl group having 1-3 double bonds and a carbon number of 2-6 can be mentioned, including both a trans form and a cis form. More specific examples thereof include vinyl, 1-propenyl, 2-propenyl, 1-methyl-1-propenyl, 2-methyl-1-propenyl, 2-methyl-2-propenyl, 2-propenyl, 2-butenyl, 1-butenyl, 3-butenyl, 2-pentenyl, 1-pentenyl, 3-pentenyl, 4-pentenyl, 1,3-butadienyl, 1,3-pentadienyl, 2-pentene-4-ynyl, 2-hexenyl, 1-hexenyl, 5-hexenyl, 3-hexenyl, 4-hexenyl, 3,3-dimethyl-1-propenyl, 2-ethyl-1-propenyl, 1,3,5-hexatrienyl, 1,3-hexadienyl, 1,4-hexadienyl group and the like.

As the cycloalkyl group, cyclo C3-C20 alkyl group having 3-20 carbon atoms can be mentioned. More specific examples thereof include monocycloalkyl such as cyclopropyl group, cyclobutyl group, cyclopentyl group, cyclohexyl group, cycloheptyl group, cyclooctyl group, cyclodecyl group, cyclododecyl group and the like, bicycloalkyl, tricycloalkyl, polycycloalkyl and the like. As the bicycloalkyl, norbornyl, pinanyl, bicyclo[2,2,2]octyl group and the like can be mentioned, and as the tricycloalkyl and polycycloalkyl, adamantyl group and the like can be mentioned.

As the cycloalkyloxy group, a cyclo C3-C20 alkyl having 3-20 carbon atoms-oxy group can be mentioned. More specific examples thereof include monocycloalkyloxy such as cyclopropyloxy group, cyclobutyloxy group, cyclopentyloxy group, cyclohexyloxy group, cycloheptyloxy group, cyclooctyloxy group, cyclodecyloxy group, cyclododecyloxy group and the like, bicycloalkyloxy, tricycloalkyloxy, polycycloalkyloxy and the like. As the cycloalkyloxy, norbornyloxy, pinanyloxy, bicyclo[2,2,2]octyloxy group and the like can be mentioned, and as the tricycloalkyloxy and polycycloalkyloxy, adamantyloxy group and the like can be mentioned.

As the lower alkoxy group, a straight chain or branched chain alkoxy group having a carbon number of 1-6 can be mentioned. More specific examples thereof include methoxy, ethoxy, n-propoxy, isopropoxy, n-butoxy, isobutoxy, tert-butoxy, sec-butoxy, n-pentyloxy, isopentyloxy, neopentyloxy, n-hexyloxy, isohexyloxy, 3-methylpentyloxy group and the like.

As the halogen-substituted lower alkyl group, the aforementioned lower alkyl group, which is substituted by 1-7, more preferably 1-3, halogen atoms can be mentioned. More specific examples thereof include fluoromethyl, difluoromethyl, trifluoromethyl, chloromethyl, dichloromethyl, trichloromethyl, bromomethyl, dibromomethyl, dichlorofluoromethyl, 2,2-difluoroethyl, 2,2,2-trifluoroethyl, pentafluoroethyl, 2-fluoroethyl, 2-chloroethyl, 3,3,3-trifluoropropyl, heptafluoropropyl, 2,2,3,3,3-pentafluoropropyl, heptafluoroisopropyl, 3-chloropropyl, 2-chloropropyl, 3-bromopropyl, 4,4,4-trifluorobutyl, 4,4,4,3,3-pentafluorobutyl, 4-chlorobutyl, 4-bromobutyl, 2-chlorobutyl, 5,5,5-trifluoropentyl, 5-chloropentyl, 6,6,6-trifluorohexyl, 6-chlorohexyl, perfluorohexyl group and the like.

As the hydroxy-substituted lower alkyl group, the aforementioned lower alkyl group, which is substituted by 1-7, more preferably 1-3, hydroxy groups can be mentioned. More specific examples thereof include hydroxymethyl, 2-hydroxyethyl, 1,1-dimethyl-2-hydroxyethyl, 3-hydroxypropyl, 4-hydroxybutyl, 2-hydroxybutyl, 5-hydroxypentyl, 1-hydroxypentyl, 6-hydroxyhexyl and the like.

As the cycloalkyl lower alkyl group, the aforementioned lower alkyl group (preferably a straight chain or branched chain alkyl group having a carbon number of 1-6), which has 1-3, preferably 1, cycloalkyl group mentioned above can be mentioned. It may be substituted with a lower alkyl group on the cycloalkyl group. Specific examples of the cycloalkyl lower alkyl group include cyclopropylmethyl, cyclohexylmethyl, 2-cyclopropylethyl, 1-cyclobutylethyl, cyclopentylmethyl, 3-cyclopentylpropyl, 4-cyclohexylbutyl, 5-cycloheptylpentyl, 6-cyclooctylhexyl, 1,1-dimethyl-2-cyclohexylethyl, 2-methyl-3-cyclopropylpropyl group and the like.

As the amino lower alkyl group, the aforementioned lower alkyl group (preferably a straight chain or branched chain alkyl group having a carbon number of 1-6), which has 1-5, preferably 1-3, amino group can be mentioned. Specific examples of the amino lower alkyl group include aminomethyl, diaminomethyl, triaminomethyl, 1-aminoethyl, 2-aminoethyl, 1-aminopropyl, 2-aminopropyl, 3-aminopropyl, 4-aminobutyl, 5-aminopentyl, 6-aminohexyl, 1-amino-2-methylethyl, 1-aminobutyl, 1-amino-2-methylpropyl, 1-amino-2,2-dimethylethyl, 1-amino-2-methylbutyl, 1-amino-3-methylbutyl, 1-aminohexyl, 1-amino-2-methylpentyl group and the like.

As the phenyl lower alkyl group, the aforementioned lower alkyl group, which has 1-3, preferably 1, phenyl group can be mentioned. It may be substituted with a lower alkyl group on the phenyl group. Specific examples of the phenyl lower alkyl group include benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, diphenylmethyl, 2,2-diphenylethyl group and the like.

As the furyl lower alkyl group, the aforementioned lower alkyl group, which has 1-3, preferably 1, furyl group can be mentioned. It may be substituted with a lower alkyl group on the furyl group. Specific examples of the furyl lower alkyl group include (2-furyl)methyl, 2-(3-furyl)ethyl, 1-(2-furyl)ethyl, 3-(3-furyl)propyl, 4-(2-furyl)butyl, 5-(3-furyl)pentyl, 6-(2-furyl)hexyl, 1,1-dimethyl-2-(3-furyl)ethyl, 2-methyl-3-(2-furyl)propyl group and the like.

As the pyridyl lower alkyl group, the aforementioned lower alkyl group, which has 1-3, preferably 1, pyridyl group can be mentioned. It may be substituted with a lower alkyl group on the pyridyl group. Specific examples of the pyridyl lower alkyl group include (4-pyridyl)methyl, 1-(3-pyridyl)ethyl, 2-(2-pyridyl)ethyl, 3-(2-pyridyl)propyl, 4-(3-pyridyl)butyl, 5-(4-pyridyl)pentyl, 6-(2-pyridyl)hexyl, 1,1-dimethyl-2-(3-pyridyl)ethyl, 2-methyl-3-(4-pyridyl)propyl group and the like.

As the lower alkoxy lower alkyl group, the aforementioned lower alkyl group (preferably a straight chain or branched chain alkyl group having a carbon number of 1-6), which has 1-3, preferably 1, lower alkoxy group (preferably a straight chain or branched chain alkoxy group having a carbon number of 1-6) mentioned above can be mentioned. Specific examples of the lower alkoxy lower alkyl group include methoxymethyl, ethoxymethyl, propoxymethyl, hexyloxymethyl, methoxyethyl, ethoxyethyl, propoxyethyl, isopropoxymethyl, butoxy methyl, tert-butoxy methyl, pentyloxymethyl, hexyloxymethyl group and the like.

As the lower alkoxycarbonyl group, a straight chain or branched chain alkoxycarbonyl group having a carbon number of 1-6, wherein the lower alkoxy moiety is the aforementioned lower alkoxy group can be mentioned. More specific examples thereof include methoxycarbonyl, ethoxycarbonyl, n-propoxycarbonyl, isopropoxycarbonyl, n-butoxycarbonyl, isobutoxycarbonyl, tert-butoxycarbonyl, sec-butoxycarbonyl, n-pentyloxycarbonyl, neopentyloxy, n-hexyloxycarbonyl, isohexyloxycarbonyl, 3-methylpentyloxycarbonyl group and the like.

As the lower alkylcarbonyl group, a straight chain or branched chain alkylcarbonyl group having a carbon number of 1-6, wherein the lower alkyl moiety is the aforementioned lower alkyl group can be mentioned. More specific examples thereof include acetyl, propionyl, butyryl, isobutyryl, valeryl, isovaleryl, pivaloyl and the like.

As the amino lower alkylcarbonyl group, the aforementioned lower alkylcarbonyl group having 1-5, preferably 1 or 2, amino groups, can be mentioned. More specific examples thereof include aminomethylcarbonyl, 2-aminoethylcarbonyl, 1-aminoethylcarbonyl, 3-aminopropylcarbonyl, 4-aminobutylcarbonyl, 5-aminopentylcarbonyl, 6-aminohexylcarbonyl, 1,1-dimethyl-2-aminoethylcarbonyl, 2-methyl-3-aminopropylcarbonyl group and the like.

As the lower alkoxycarbonyl lower alkyl group, the aforementioned lower alkyl group (preferably straight chain or branched chain alkyl group having a carbon number of 1-6), which has 1-3, preferably 1, lower alkoxycarbonyl group (e.g., methoxycarbonyl, ethoxycarbonyl, n-propoxycarbonyl, isopropoxycarbonyl, n-butoxycarbonyl, isobutoxycarbonyl, tert-butoxycarbonyl, sec-butoxycarbonyl, n-pentyloxycarbonyl, neopentyloxy, n-hexyloxycarbonyl, isohexyloxycarbonyl, 3-methylpentyloxycarbonyl group etc.) can be mentioned. Specific examples of the lower alkoxycarbonyl lower alkyl group include methoxycarbonylmethyl group, ethoxycarbonylmethyl group, propoxycarbonylmethyl group, isopropoxycarbonylmethyl group, butoxycarbonylmethyl group, isobutoxycarbonylmethyl group, sec-butoxycarbonylmethyl group, tert-butoxycarbonylmethyl group, 2-methoxycarbonylethyl group, 2-ethoxycarbonylethyl group, 2-propoxycarbonylethyl group, 3-methoxycarbonylpropyl group, 3-ethoxycarbonylpropyl group, 4-methoxycarbonylbutyl group, 4-ethoxycarbonylbutyl group and the like.

As the lower alkoxy lower alkoxy group, the aforementioned lower alkoxy group (preferably straight chain or branched chain alkoxy group having a carbon number of 1-6), which has 1-3, preferably 1, lower alkoxy group (preferably straight chain or branched chain alkoxy group having a carbon number of 1-6) mentioned above can be mentioned. Specific examples of the lower alkoxy lower alkoxy group include methoxymethoxy, ethoxymethoxy, propoxymethoxy, hexyloxymethoxy, methoxyethoxy, ethoxyethoxy, propoxyethoxy, isopropoxymethoxy, butoxymethoxy, tert-butoxymethoxy, pentyloxymethoxy, hexyloxymethoxy group and the like.

As the phenyl lower alkoxy lower alkoxy group, the aforementioned lower alkoxy lower alkoxy group having 1-3, preferably 1, phenyl group can be mentioned. Specific examples of the phenyl lower alkoxy lower alkoxy group include benzyloxymethoxy, 2-phenylethoxymethoxy, 1-phenylethoxymethoxymethoxy, 3-phenylpropoxymethoxy, 4-phenylbutoxymethoxy, 1,1-dimethyl-2-phenylethoxymethoxy, 5-phenylpentyloxymethoxy, 6-phenylhexyloxymethoxy, 2-benzyloxyethoxy, 3-benzyloxypropoxy, 4-benzyloxybutoxy, 1,1-dimethyl-2-benzyloxyethoxy, 5-benzyloxypentoxy, 6-benzyloxyhexyloxy, 2-methyl-3-benzyloxypropoxy group and the like.

As the lower alkoxy lower alkoxy lower alkyl group, the aforementioned lower alkyl group (preferably straight chain or branched chain alkyl group having a carbon number of 1-6), which has 1-3, preferably 1, lower alkoxy lower alkoxy group mentioned above can be mentioned. Specific examples of the lower alkoxy lower alkoxy lower alkyl group include methoxymethoxymethyl, 3-(3-methoxypropoxy)propyl, ethoxymethoxymethyl, 3-(3-ethoxypropoxy)propyl, 4-(4-ethoxybutoxy)butyl, 5-(5-isopropoxypentyloxy)pentyl, 6-(6-propoxyhexyloxy)hexyl, 1,1-dimethyl-2-(2-butoxyethoxy)ethyl, 2-methyl-3-(3-tert-butoxypropoxy)propyl, 2-(2-pentyloxyethoxy)ethyl, hexyloxymethoxymethyl group and the like.

As the lower alkoxy lower alkoxy lower alkoxy lower alkyl group, the aforementioned lower alkoxy lower alkyl group having 1-3, preferably 1, lower alkoxy lower alkoxy group mentioned above can be mentioned. Specific examples of the lower alkoxy lower alkoxy lower alkoxy lower alkyl group include methoxyethoxyethoxyethyl, ethoxyethoxyethoxyethyl group and the like.

As the phenyl lower alkoxy group, the aforementioned lower alkoxy group having 1-3, preferably 1, phenyl group can be mentioned. Specific examples of the phenyl lower alkoxy group include benzyloxy, 2-phenylethoxy, 1-phenylethoxy, 3-phenylpropoxy, 4-phenylbutoxy, 1,1-dimethyl-2-phenylethoxy, 5-phenylpentyloxy, 6-phenylhexyloxy, 2-benzyloxy, 3-benzyloxy, 4-benzyloxy, 1,1-dimethyl-2-benzyloxy; 5-benzyloxy, 6-benzyloxy, 2-methyl-3-benzyloxy group and the like.

As the phosphono lower alkoxy group, the aforementioned lower alkoxy group (preferably straight chain or branched chain alkoxy group having a carbon number of 1-6), which has 1-3, preferably 1, phosphono group can be mentioned. Specific examples of the phosphono lower alkoxy group include phosphonomethoxy, phosphonoethoxy, phosphonopropoxy, phosphonobutoxy, phosphonopentyloxy, phosphonohexyloxy group and the like.

As the piperidyl group optionally having a lower alkyl group, a piperidyl group optionally having 1-3, preferably 1, lower alkyl group mentioned above can be mentioned. Specific examples of the piperidyl group optionally having a lower alkyl group include piperidyl, 2-methylpiperidyl, 3-methylpiperidyl, 2-ethylpiperidyl, 3-ethylpiperidyl group and the like.

As the halogen-substituted piperidyl group, a piperidyl group substituted by 1-7, more preferably 1-3, halogen atoms can be mentioned. More specific examples thereof include fluoropiperidyl, difluoropiperidyl, chloropiperidyl, dichloropiperidyl, bromopiperidyl, dibromopiperidyl group and the like.

The tri-lower alkylsilyl group is a silyl group substituted by 3 lower alkyl groups mentioned above. Specific examples thereof include trimethylsilyl, ethyldimethylsilyl, n-propyldimethylsilyl, tert-butyldimethylsilyl, triethylsilyl, methyldiethylsilyl, dimethylethylsilyl, triisopropylsilyl group and the like.

As the lower alkylene group, a straight chain or branched chain alkylene group having a carbon number of 1-6 can be mentioned. More specific examples thereof include methylene, ethylene, trimethylene, 2-methyltrimethylene, 3-methyltetramethylene, 2,2-dimethyltrimethylene, 1-methyltrimethylene, methylmethylene, ethylmethylene, tetramethylene, pentamethylene, hexamethylene group and the like.

As the alkylene group, a straight chain or branched chain alkylene group having a carbon number of 1-30 can be mentioned. More specific examples thereof include methylene, ethylene, trimethylene, tetramethylene, hexamethylene, heptamethylene, octamethylene, decamethylene, undecamethylene, dodecamethylene, tridecamethylene, tetradecamethylene, hexadecamethylene, octadecamethylene, tricosamethylene, hexacosamethylene, triacontamethylene, 1-methylethylene, 2-ethyltrimethylene, 1-methylheptamethylene, 2-methylheptamethylene, 1-butylhexamethylene, 2-methyl-5-ethylheptamethylene, 2,3,6-trimethylheptamethylene, 6-ethyldecamethylene, 7-methyltetradecamethylene, 7-ethylhexadecamethylene, 7,12-dimethyloctadecamethylene, 8,11-dimethyloctadecamethylene, 7,10-dimethyl-7-ethylhexadecamethylene, 1-octadecylethylene, 9,10-dioctyloctadecamethylene, 8,9-dinonylhexadecamethylene, ethenylene, 1-octadecenylethylene, 7,11-octadecadienylene, 7-ethenyl-9-hexadecamethylene, 7,12-dimethyl-7,11-octadecadienylene, 8,11-dimethyl-7,11-octadecadienylene, 9,10-dioctyl-7,11-octadecadienylene, 8,9-dinonyl-6,10-hexadecadienylene group and the like.

When the heterocyclic compound represented by the formula (I) is a cation, it is preferably present as a salt together with anion. The anion includes a halogen ion (e.g., Cl—, I—) and the like.

In the formula (I),

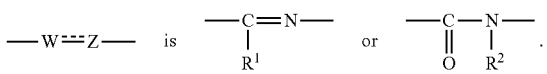

$R^1$ is preferably the following group

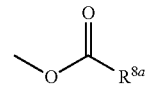

wherein
$R^{8a}$ is
(1) an alkyl group,
(2) a cycloalkyl group,
(3) a lower alkoxy group,
(4) a cycloalkyloxy group,
(5) a lower alkoxy lower alkoxy group,
(6) an amino group optionally having 1 or 2 substituents selected from the group consisting of an alkyl group and a hydroxy-substituted lower alkyl group, or
(7) the following group

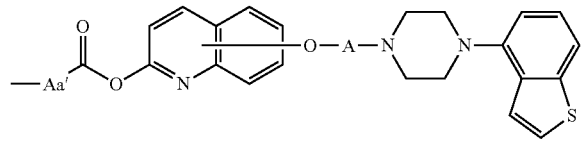

wherein Aa' is an alkylene group and A is a lower alkylene group, or
the following group

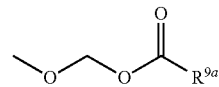

wherein
$R^{9a}$ is
(1) an alkyl group,
(2) a hydroxy-substituted lower alkyl group, (3) a cycloalkyl group,
(4) a lower alkoxy group,
(5) a cycloalkyloxy group,
(6) a lower alkoxy lower alkoxy group,
(7) a phenyloxy group,
(8) an amino group optionally having 1 or 2 substituents selected from the group consisting of an alkyl group,
(9) a piperidyl group optionally having a piperidyl group,
(10) a piperazinyl group optionally having a lower alkyl group, or
(11) the following group

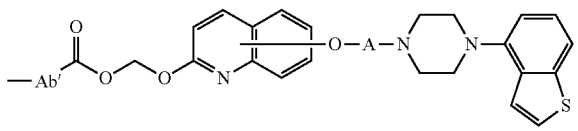

wherein Ab' is an alkylene group and A is a lower alkylene group,
more preferably,
the following group

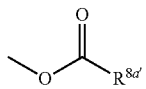

wherein
R$^{8a'}$ is
(1) an alkyl group,
(2) a cycloalkyl group,
(3) a lower alkoxy group,
(4) a cycloalkyloxy group,
(5) a lower alkoxy lower alkoxy group, or
(6) an amino group optionally having 1 or 2 substituents selected from the group consisting of an alkyl group and a hydroxy-substituted lower alkyl group, or the following group

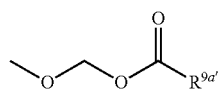

wherein
R$^{9a'}$ is
(1) an alkyl group,
(2) a hydroxy-substituted lower alkyl group,
(3) a cycloalkyl group,
(4) a lower alkoxy group,
(5) a cycloalkyloxy group,
(6) a lower alkoxy lower alkoxy group,
(7) a phenyloxy group,
(8) an amino group optionally having 1 or 2 substituents selected from the group consisting of an alkyl group,
(9) a piperidyl group optionally having a piperidyl group, or
(10) a piperazinyl group optionally having a lower alkyl group.

As R$^2$,
the following group

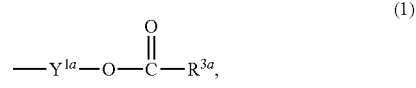

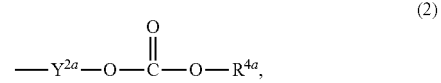

wherein
Y$^{1a}$ is a lower alkylene group,
Y$^{2a}$ is a lower alkylene group,
R$^{3a}$ is
(1) an alkyl group,
(2) a cycloalkyl group,
(3) a piperidyl group optionally having 1 or 2 substituents selected from the group consisting of a lower alkyl group,
(4) a tetrahydropyranyl group,
(5) a lower alkoxycarbonyl lower alkyl group,
(6) a lower alkoxy lower alkoxy lower alkyl group,
(7) an amino lower alkyl group optionally having a lower alkylcarbonyl group, or
(8) the following group

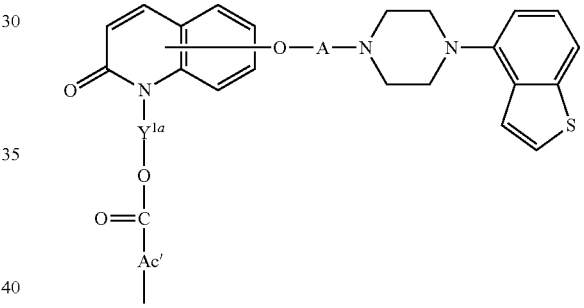

wherein Ac' is an alkylene group, Y$^{1a}$ is a lower alkylene group and A is a lower alkylene group,
R$^{4a}$ is
(1) an alkyl group, or
(2) a cycloalkyl group is preferable, more preferably, R$^2$ is the following group

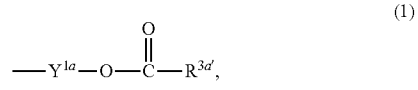

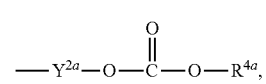

wherein
Y$^{1a}$ is a lower alkylene group,
Y$^{2a}$ is a lower alkylene group,
R$^{3a'}$ is
(1) an alkyl group,
(2) a cycloalkyl group,
(3) a piperidyl group optionally having 1 or 2 substituents selected from the group consisting of a lower alkyl group,
(4) a tetrahydropyranyl group, (5) a lower alkoxycarbonyl lower alkyl group,
(6) a lower alkoxy lower alkoxy lower alkyl group, or
(7) an amino lower alkyl group optionally having a lower alkylcarbonyl group, $R^{4a}$ is
(1) an alkyl group, or
(2) a cycloalkyl group.

The heterocyclic compound represented by the formula (I) is preferably a heterocyclic compound represented by the following formula (II)

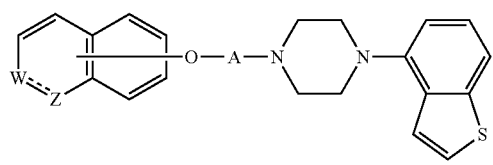

(II)

wherein each symbol is as defined in the present specification. More preferably, it is a heterocyclic compound represented by the following formula (III)

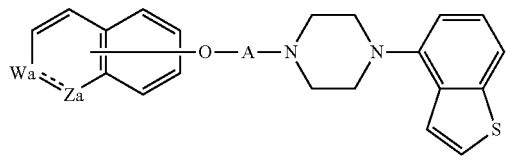

(III)

wherein each symbol is as defined In the present specification.

That is, in the formula (I),

-----J shown at the 3-position and the 4-position of the bicyclic heterocycle skeleton containing Z and W is preferably —CH═CH—, and

in the monocyclic heterocycle containing Q is preferably

A heterocyclic compound represented by the above-mentioned formula (I) (hereinafter sometimes to be referred to as compound (I)) can be produced by various methods. For example, it can be produced by a method shown by the following reaction scheme.

[Reaction scheme-1]

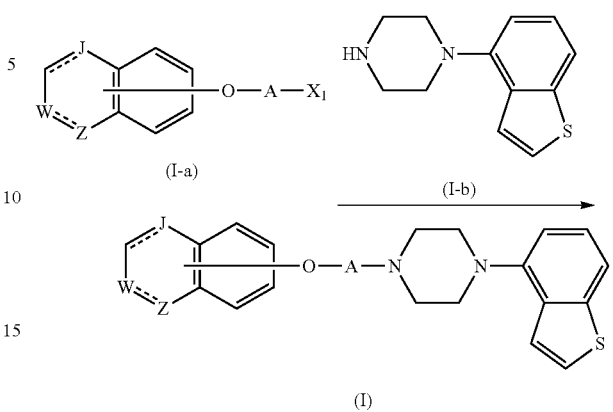

wherein each symbol is as defined above.

In the formula (I-a), the halogen atom for $X_1$ is as defined above.

Examples of the group that causes a substitution reaction similar to that by a halogen atom include a lower alkanesulfonyloxy group, an arylsulfonyloxy group, an aralkylsulfonyloxy group and the like.

Specific examples of the lower alkanesulfonyloxy group for $X_1$ include a straight chain or branched chain alkanesulfonyloxy group having a carbon number of 1-6 such as methanesulfonyloxy, ethanesulfonyloxy, n-propanesulfonyloxy, isopropanesulfonyloxy, n-butanesulfonyloxy, tert-butanesulfonyloxy, n-pentanesulfonyloxy, n-hexanesulfonyloxy group and the like.

Examples of the arylsulfonyloxy group for $X_1$ include phenylsulfonyloxy, naphthylsulfonyloxy group and the like, which optionally have, as a substituent on the phenyl ring, 1-3 groups selected from the group consisting of a straight chain or branched chain alkyl group having a carbon number of 1-6, a straight chain or branched chain alkoxy group having a carbon number of 1-6, a nitro group and a halogen atom. Specific examples of the above-mentioned phenylsulfonyloxy group optionally having substituent(s) include phenylsulfonyloxy, 4-methylphenylsulfonyloxy, 2 methylphenylsulfonyloxy, 4-nitrophenylsulfonyloxy, 4-methoxyphenylsulfonyloxy, 2-nitrophenylsulfonyloxy, 3-chlorophenylsulfonyloxy group and the like. Specific examples of the naphthylsulfonyloxy group include α-naphthylsulfonyloxy, β-naphthylsulfonyloxy group and the like.

Examples of the aralkylsulfonyloxy group for $X_1$ include a straight chain or branched chain alkanesulfonyloxy group having a carbon number of 1-6 and substituted by a phenyl group, which optionally have, as a substituent on the phenyl ring, 1-3 groups selected from the group consisting of a straight chain or branched chain alkyl group having a carbon number of 1-6, a straight chain or branched chain alkoxy group having a carbon number of 1-6, a nitro group and a halogen atom, a straight chain or branched chain alkanesulfonyloxy group having a carbon number of 1-6 and substituted by a naphthyl group and the like. Specific examples of the above-mentioned alkanesulfonyloxy group substituted by a phenyl group include benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy group and the like. Specific examples of the above-mentioned alkanesulfonyloxy group substituted by a naphthyl group include α-naphthylmethylsulfonyloxy, β-naphthylmethylsulfonyloxy group and the like.

The reaction of a compound represented by the formula (I-a) and a compound represented by the formula (I-b) is performed without solvent or in an inert solvent, in the presence or absence of a basic compound.

Examples of the inert solvent include water; ethers such as dioxane, tetrahydrofuran, diethyl ether, diethylene glycol dimethylether, ethylene glycol dimethylether and the like; aromatic hydrocarbons such as benzene, toluene, xylene and the like; lower alcohols such as methanol, ethanol, isopropanol and the like; ketones such as acetone, methylethyl ketone and the like; polar solvents such as N,N-dimethylformamide (DMF), dimethyl sulfoxide (DMSO), hexamethylphosphoric acid triamide, acetonitrile and the like.

As the basic compound, known ones can be widely used and, for example, alkali metal hydroxide such as sodium hydroxide, potassium hydroxide, cesium hydroxide, lithium hydroxide and the like; alkali metal carbonate such as sodium carbonate, potassium carbonate, cesium carbonate, lithium carbonate and the like; alkali metal hydrogen carbonate such as lithium hydrogen carbonate, sodium hydrogen carbonate, potassium hydrogen carbonate and the like; alkali metal such as sodium, potassium and the like; inorganic base such as sodium amide, sodium hydride, potassium hydride and the like, and alkali metal alcoholates such as sodium methoxide, sodium ethoxide, potassium methoxide, potassium ethoxide and the like; organic base such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO) and the like.

One kind alone from these basic compounds is used, or two or more kinds thereof are mixed and used.

The amount of the basic compound to be used is generally 0.5-10-fold mol, preferably 0.5-6-fold mol, relative to the compound of the formula (I-a).

The above-mentioned reaction can be performed by adding, as necessary, an alkali metal iodide such as potassium iodide, sodium iodide and the like as a reaction promoter.

The proportion of the compound of the formula (I-a) and the compound of the formula (I-b) to be used in the above-mentioned reaction scheme-1 is generally at least 0.5-fold mol, preferably about 0.5- to 5-fold mol, of the latter relative to the former.

The above-mentioned reaction is performed generally at room temperature–200° C., preferably room temperature–150° C., and completes in about 1-30 hr.

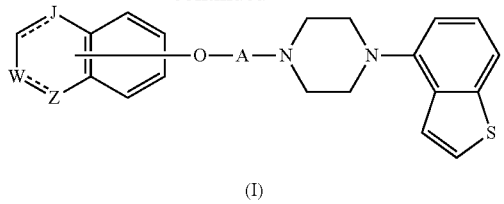

(I)

wherein $X_2$ is a hydroxyl group, a halogen atom or a group that causes a substitution reaction similar to that by a halogen atom, and other symbols are as defined above.

The halogen atom or group that causes a substitution reaction similar to that by a halogen atom for $X_2$ is as defined above.

The reaction of a compound represented by the formula (I-c) and a compound represented by the formula (I-d) is performed under the reaction conditions similar to those of the reaction of a compound represented by the formula (I-a) and a compound represented by the formula (I-b) in the aforementioned reaction scheme-1.

When compound (I-d) wherein $X_2$ is a hydroxyl group is used, the reaction of compound (I-c) and compound (I-d) can also be performed in a suitable solvent, in the presence of a condensing agent.

Specific examples of the solvent to be used here include water; halogenated hydrocarbons such as chloroform, dichloromethane, dichloroethane, carbon tetrachloride and the like; aromatic hydrocarbons such as benzene, toluene, xylene and the like; ethers such as diethyl ether, diisopropyl ether, tetrahydrofuran, dimethoxyethane and the like; esters such as methyl acetate, ethyl acetate, isopropyl acetate and the like; alcohols such as methanol, ethanol, isopropanol, propanol, butanol, 3-methoxy-1-butanol, ethylcellosolve, methylcellosolve and the like; aprotic polar solvent such as acetonitrile, pyridine, acetone, DMF, DMSO, hexamethylphosphoric acid triamide and the like, and a mixed solvent thereof and the like.

As the condensing agent, a mixture of azocarboxylate such as diethylazodicarboxylate and the like and phosphorus compound such as triphenylphosphine and the like, and the like can be mentioned.

The amount of the condensing agent to be used is generally at least an equimolar amount, preferably equimole to 2-fold molar amount, relative to compound (I-c).

The amount of compound (I-d) to be used is generally at least an equimolar amount, preferably equimole to 2-fold molar amount, relative to compound (I-c).

This reaction preferably proceeds generally at 0-200° C., preferably about 0-150° C., and generally completes in about 1-10 hr.

The compound of the formula (I-a) to be used as a starting material is produced, for example, by the method shown in the following reaction scheme-3, and the compound represented by the formula (I-d) is produced, for example, by the method shown in the following reaction scheme-4.

[Reaction scheme-2]

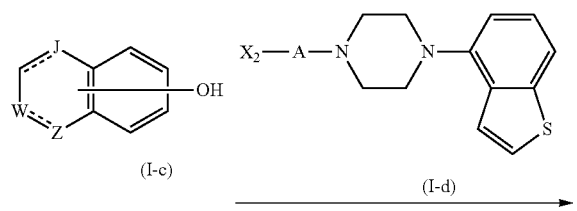

[Reaction scheme-3]

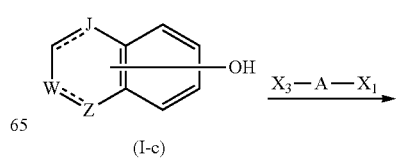

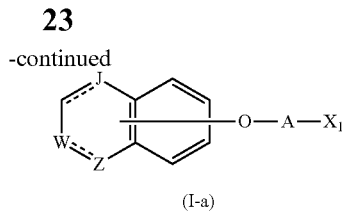

(I-a)

wherein $X_3$ is a hydroxyl group, a halogen atom or a group that causes a substitution reaction similar to that by a halogen atom, and other symbols are as defined above.

The halogen atom or group that causes a substitution reaction similar to that by a halogen atom for $X_3$ is as defined above.

The reaction of a compound represented by the formula (I-c) and a compound represented by $X_3$-A-$X_1$ is performed under the reaction conditions similar to those of the reaction of a compound represented by the formula (I-c) and a compound represented by the formula (I-d) in the aforementioned reaction scheme-2.

[Reaction scheme-4]

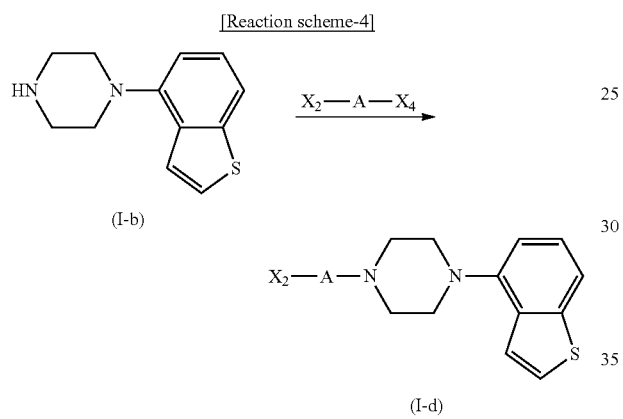

wherein $X_4$ is a hydroxyl group, a halogen atom or a group that causes a substitution reaction similar to that by a halogen atom, and other symbols are as defined above.

The halogen atom or group that causes a substitution reaction similar to that by a halogen atom for $X_4$ is as defined above.

The reaction of a compound represented by the formula (I-b) and a compound represented by $X_2$-A-$X_4$ is performed under the reaction conditions similar to those of the reaction of a compound represented by the formula (I-a) and a compound represented by the formula (I-b) in the aforementioned to reaction scheme-1. Both the compound of the formula (I-b) and a compound represented by $X_2$-A-$X_4$ are easily-available known compounds.

[Reaction scheme-5]

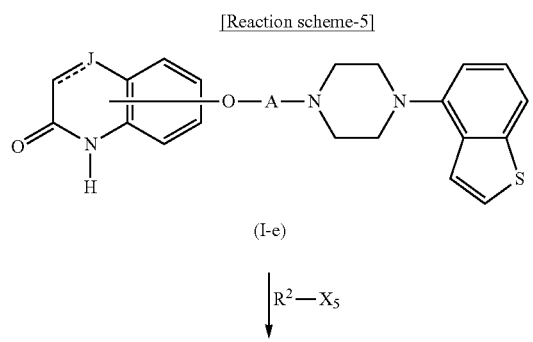

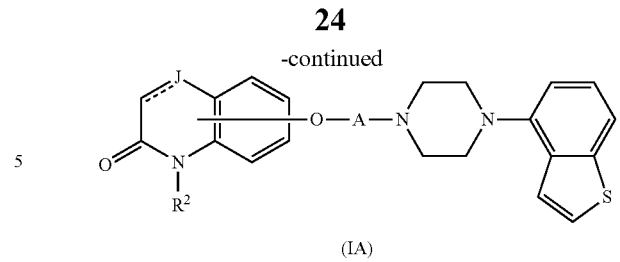

(IA)

wherein $X_5$ is a halogen atom or a group that causes a substitution reaction similar to that by a halogen atom, and other symbols are as defined above.

The halogen atom or group that causes a substitution reaction similar to that by a halogen atom for $X_5$ is as defined above.

The reaction of a compound represented by the formula (I-e) and a compound represented by $R^2$—$X_5$ is performed under the reaction conditions similar to those of the reaction of a compound represented by the formula (I-a) and a compound represented by the formula (I-b) in the aforementioned reaction scheme-1.

When

in the monocyclic heterocycle containing Q is

wherein $R^{2'}$ is as defined above,
the compound can be synthesized in the same manner as in the below-mentioned Example 383.

A compound wherein $R^8$ is

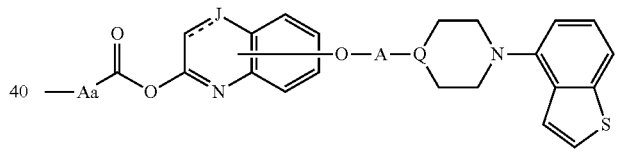

wherein each symbol is as defined above,
a compound wherein $R^9$ is

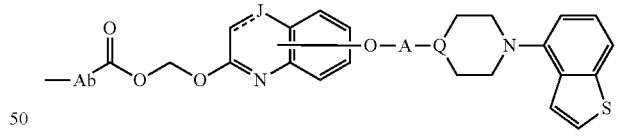

wherein each symbol is as defined above, and
a compound wherein $R^3$ is

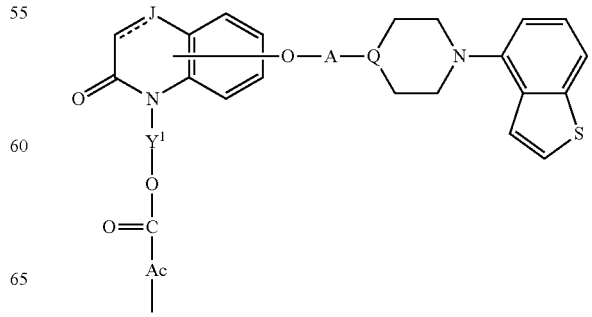

wherein each symbol is as defined above,
can be synthesized by a combination of the methods described in the below mentioned Example 14 and Example 22.

A compound (I) having a hydroxyl group on the bicyclic heterocycle skeleton containing Z and W is produced by treating a compound (I) having a methoxy group on the skeleton in a suitable solvent or without solvent, in the presence of an acid.

Examples of the solvent used here include aromatic hydrocarbons such as benzene, toluene, xylene and the like; ethers such as diethyl ether, tetrahydrofuran, dioxane, monoglyme, diglyme and the like; halogenated hydrocarbons such as dichloromethane, dichloroethane, chloroform, carbon tetrachloride and the like; fatty acid such as acetic acid and the like; esters such as ethyl acetate, methyl acetate and the like; ketones such as acetone, methyl ethyl ketone and the like; acetonitrile, pyridine, DMF, DMSO, hexamethylphosphoric acid triamide and a mixed solvent thereof and the like.

Examples of the acid include mineral acid such as hydrobromic acid, hydrochloric acid, conc. sulfuric acid and the like, fatty acid such as formic acid, acetic acid and the like, organic acid such as p-toluenesulfonic acid and the like, Lewis acid such as aluminum chloride, zinc chloride, iron chloride, tin chloride, boron trifluoride, boron tribromide and the like, iodide such as sodium iodide, potassium iodide and the like, a mixture of the above-mentioned Lewis acid and to iodide and the like.

Such acid is preferably used in an amount of generally 0.1- to 15-fold molar amount, preferably 0.5- to 10-fold molar amount, relative to compound (I). When the reaction is performed without solvent, an acid is generally used in an excess amount.

This reaction is performed generally at 0-150° C., preferably about 0-100° C., and generally completes in about 0.5-75 hr.

The starting compound used for each of the above-mentioned reaction schemes may be a preferable salt, and the object compound obtained in each reaction may form a preferable salt. The preferable salt thereof may be similar to the preferable salts of compound (I) shown below.

The preferable salt of compound (I) is a pharmaceutically acceptable salt and, for example, metal salts such as alkali metal salt (e.g., sodium salt, potassium salt etc.), alkaline earth metal salt (e.g., calcium salt, magnesium salt etc.) and the like; salts with inorganic bases such as ammonium salt, alkali metal carbonate (e.g., lithium carbonate, potassium carbonate, sodium carbonate, cesium carbonate etc.), alkali metal hydrogen carbonate (e.g., lithium hydrogen carbonate, sodium hydrogen carbonate, potassium hydrogen carbonate etc.), alkali metal hydroxide (e.g., lithium hydroxide, sodium hydroxide, potassium hydroxide, cesium hydroxide etc.) and the like; salts with organic bases such as tri(lower)alkylamine (e.g., trimethylamine, triethylamine, N-ethyldiisopropylamine etc.), pyridine, quinoline, piperidine, imidazole, picoline, dimethylaminopyridine, dimethylaniline, N-(lower)alkyl-morpholine (e.g., N-methylmorpholine etc.), 1,5-diazabicyclo[4.3.0]nonene-5 (DBN), 1,8-diazabicyclo[5.4.0]undecene-7 (DBU), 1,4-diazabicyclo[2.2.2]octane (DABCO) and the like; salts with inorganic acids such as hydrochloride, hydrobromide, hydroiodide, sulfate, nitrate, phosphate and the like; salts with organic acids such as formate, acetate, propionate, oxalate, malonate, succinate, fumarate, maleate, lactate, malate, citrate, tartrate, carbonate, picrate, methanesulfonate, ethanesulfonate, p-toluenesulfonate, glutamate, pamoate and the like; and the like can be mentioned.

In the following, compound (I) and a salt thereof are sometimes to be generically referred to as the compound of the present invention.

In addition, a compound wherein a solvate (e.g., hydrate, ethanolate etc.) is added to a starting material or object compound shown in each reaction scheme is also encompassed in each formula. As a preferable solvate, hydrate can be mentioned.

Each object compound obtained in each of the above-mentioned reaction schemes can be isolated and purified from the reaction mixture by for example, cooling the reaction mixture, applying an isolation operation of filtration, concentration, extraction and the like to separate a crude reaction product, and applying a general purification operation such as column chromatography, recrystallization and the like.

Compound (I) naturally encompasses isomers such as a geometric isomer, a stereoisomer, an optical isomer and the like.

Compound (I) usable in the present invention is also encompasses same compounds labeled with the isotope, wherein one or plural atoms is(are) replaced by one or plural atoms having a particular atomic mass or mass number. Examples of the isotope that can be incorporated into compound (I) include hydrogen, carbon, nitrogen, oxygen, sulfur, fluorine and chlorine isotopes such as $^2H$, $^3H$, $^{13}C$, $^{14}C$, $^{15}N$, $^{18}O$, $^{17}O$, $^{18}F$, $^{36}Cl$ and the like. Compound (I) labeled with particular isotope, which contains the above-mentioned isotope and/or other isotope of other atom, for example, compound (I) incorporating a radioactive isotope such as $^3H$, $^{14}C$ and the like, is useful for drug tissue distribution assay and/or substrate tissue distribution assay. Tritiated (i.e., $^3H$) or carbon-14 (i.e., $^{14}C$) isotope are particularly preferred because of easiness of preparation and detectability. Furthermore, substitution with a heavier isotope such as deuterium (i.e., $^2H$) and the like is expected to provide improved metabolic stability and particular therapeutic advantage attributable to increased in vivo half-time or decreased amount of necessary administration. An isotope-labeled compound of compound (I) can be generally prepared according to the method disclosed in WO2006/112464, by substituting a non-isotope-labeled reagent with an easily available isotope-labeled reagent.

Compound (I) may be a pharmaceutically acceptable cocrystal or a cocrystal salt. Here, the cocrystal or cocrystal salt means a crystalline substance, which is constituted from two or more kinds of specific solids each having different physical properties (e.g., structure, melting point, heat of fusion and the like) at room temperature. The cocrystal and cocrystal salt can be produced by applying a cocrystallization method known per se.

Compound (I) and a salt thereof are used in the form of a general pharmaceutical preparation. Such preparation is prepared using a diluent or excipient generally used such as filler, extender, binder, humidifying agent, disintegrant, surface activating agent, lubricant and the like. The pharmaceutical preparation can have various forms depending on the treatment object, and representative examples include tablet, pill, powder, liquid, suspension, emulsion, granule, capsule, suppository, injection (liquid, suspension etc.) and the like.

For formulation of a tablet, various ones conventionally known as a carrier in this field can be widely used. Examples thereof include excipients such as lactose, sucrose, sodium chloride, glucose, urea, starch, calcium carbonate, kaolin, crystalline cellulose, silicic acid and the like, binders such as water, ethanol, propanol, simple syrup, glucose solution, starch solution, gelatin solution, carboxymethylcellulose, shellac, methylcellulose, potassium phosphate, polyvinylpyrrolidone and the like, disintegrants such as dry starch, sodium alginate, agar powder, laminaran powder, sodium hydrogen carbonate, calcium carbonate, polyoxyethylene sorbitan fatty acid esters, sodium lauryl sulfate, stearic acid monoglyceride, starch, lactose and the like, disintegration inhibitors such as sucrose, stearin, cacao butter, hydrogenation oil and the like, absorption promoters such as quaternary ammonium base, sodium lauryl sulfate and the like, moisturizers such as glycerol, starch and the like, adsorbent such as starch, lactose, kaolin, bentonite, colloidal silicic acid and the like, lubricants such as purified talc, stearate, boric acid powder, polyethylene glycol and the like; and the like. Where necessary, the tablet can take the form of a tablet having a general coating, for example, sugar-coated tablet, gelatin-coated tablet, enteric tablet, film-coated tablet or double-compressed tablet, or multi-layer tablet.

For formulation of a pill, various ones conventionally known as a carrier in this field can be widely used. Examples thereof include excipients such as glucose, lactose, starch, cacao butter, hydrogenated vegetable oil, kaolin, talc and the like, binders such as gum arabic powder, tragacanth powder, gelatin, ethanol and the like, disintegrants such as laminaran, agar and the like; and the like.

For formulation of a suppository, various ones conventionally known as a carrier in this field can be widely used. Examples thereof include polyethylene glycol, cacao butter, higher alcohol, higher alcohol esters, gelatin, semisynthetic glyceride and the like.

A capsule is prepared by a conventional method by generally mixing an active ingredient compound with various carriers mentioned above and filling the mixture in a hard gelatin capsule, a soft capsule and the like.

For formulation of an injection, a liquid, an emulsion and a suspension are preferably sterilized and isotonic with blood. For formulation into such form, various ones conventionally known as a diluent in this field can be widely used. Examples thereof include water, ethyl alcohol, macrogol, propylene glycol, ethoxylated isostearyl alcohol, polyoxylated isostearyl alcohol, polyoxyethylene sorbitan fatty acid esters and the like.

In this case, sodium chloride, glucose or glycerol in an amount sufficient for the preparation of an isotonic solution may be contained in a pharmaceutical preparation, or general solubilizing agent, buffering agent, soothing agent and the like may be further added. Where necessary, colorant, preservative, fragrant material, flavor, sweetening agent and the like and other pharmaceutical products may be further contained in the pharmaceutical preparation.

The amount of compound (I) or a salt thereof to be contained in the pharmaceutical preparation of the present invention is not particularly limited and is appropriately selected from a wide range. It is generally about 1-70 wt %, preferably about 1-30 wt %, of the preparation composition.

The administration method of the pharmaceutical preparation of the present invention is not particularly limited, and a method suitable for various dosage forms, age, sex and other conditions of patients, level of disease and the like is employed for administration. For example, tablet, pill, liquid, suspension, emulsion, granule and capsule are orally administered. An injection is intravenously administered singly or as a mixture with a general fluid replacement such as glucose, amino acid and the like. Where necessary, it is administered singly by intramuscular, intradermal, subcutaneous or intraperitoneal administration. A suppository is intrarectally administered.

While the dose of the pharmaceutical preparation of the present invention is appropriately selected according to use, age, sex and other conditions of patients, level of disease and the like, the amount of the active ingredient compound is generally about 0.1-10 mg per day and per 1 kg body weight. The active ingredient compound in the range of about 1-200 mg is desirably contained in a unit administration form of preparation.

Effect of the Invention

The compound of the present invention has a $D_2$ receptor partial agonist effect, a $5\text{-}HT_{2A}$ receptor antagonist effect and a serotonin uptake inhibitory effect (or serotonin reuptake inhibitory effect).

The $D_2$ receptor partial agonist effect suppresses dopaminergic (DA) neurotransmission when it is enhanced, and accelerates the DAergic neurotransmission when it is lowered and thus has a function to stabilize the DA neurotransmission to a normal state (dopamine system stabilizer). According to this function, excellent clinically improving effect on the abnormal DA neurotransmission (enhancement and lowering), for example, improving effect on positive and negative symptoms, improving effect on cognitive impairment, improving effect on depressive symptom etc. are developed without causing side effects (see Michio Toru: Clinical Psychiatry, vol. 46, pages 855-864 (2004), Tetsuro Kikuchi and Tsuyoshi Hirose: Brain Science, vol. 25, pages 579-583 (2004), and Harrison, T. S. and Perry, C. M.: Drugs 64: 1715-1736, 2004).

$5\text{-}HT_{2A}$ receptor antagonist effect reduces extrapyramidal side effects, develops superior clinical effects, and is effective, for example, for improvement of negative symptoms, improvement of cognitive impairment, improvement of depressive symptom, improvement of insomnia and the like (see Jun Ishigooka and Ken Inada: Japanese Journal of Clinical Psychopharmacology, vol. 4, pages 1653-1664 (2001), Mitsukuni Murasaki Japanese Journal of Clinical Psychopharmacology, vol. 1, pages 5-22 (1998), Pullar, I. A. et al.: Eur. J. Pharmacol., 407: 39-46, 2000, and Meltzer, H.Y. et al.: Prog. Neuro-psychopharmacol. Biol. Psychiatry 27: 1159-1172, 2003).

Serotonin uptake inhibitory effect (or serotonin reuptake inhibitory effect) is effective, for example, for improvement of depressive symptom (see Mitsukuni Murasaki: Japanese Journal of Clinical Psychopharmacology, vol. 1, pages 5-22 (1998)).

The compound of the present invention is excellent in all of these three effects, or remarkably excellent in one or two of these effects.

In addition, some of the compounds of the present invention have $\alpha_1$ receptor antagonist effect in addition to the above-mentioned effects. The $\alpha_1$ receptor antagonist effect is effective for improving positive symptoms of schizophrenia (see Svensson, T. H.: Prog. Neuro-psychopharmacol. Biol. Psychiatry 27: 1145-1158, 2003).

Therefore, the compound of the present invention has a wide treatment spectrum for and excellent clinical effect on schizophrenia and other central nervous system diseases.

Accordingly, the compound, the medicament, and pharmaceutical composition of the present invention are extremely effective for the improvement of various central nervous system disorders including schizophrenia, treatment-resistant, refractory or chronic schizophrenia, emotional disturbance, psychotic disorder, mood disorder, bipolar disorder (e.g., bipolar disorder type I and bipolar disorder type II), mania, depression, endogenous depression, major depression, melancholic and treatment-resistant depression, dysthymic disorder, cyclothymic disorder, anxiety disorder (e.g., panic attack, panic disorder, agoraphobia, social phobia, obsessive-compulsive disorder, post-traumatic stress disorder, generalized anxiety disorder, acute stress disorder, etc.), somatoform disorder (e.g., hysteria, somatization disorder, conversion disorder, pain disorder, hypochondriasis, etc.), factitious disorder, dissociative disorder, sexual disorder (e.g., sexual dysfunction, sexual desire disorder, sexual arousal disorder, erectile dysfunction, etc.), eating disorder (e.g., anorexia nervosa, bulimia nervosa, etc.), sleep disorder, adjustment disorder, substance-related disorder (e.g., alcohol abuse, alcohol intoxication and drug addiction, stimulant intoxication, narcotism, etc.), anhedonia (e.g., anhedonia, anhedonia, iatrogenic anhedonia, anhedonia of a psychic or mental cause, anhedonia associated with depression, anhedonia associated with schizophrenia, etc.), delirium, cognitive impairment, cognitive impairment associated with Alzheimer's disease, Parkinson's disease, and other neurodegenerative diseases, cognitive impairment caused by Alzheimer's disease, Parkinson's disease and associated neurodegenerative diseases, cognitive impairment in schizophrenia, cognitive impairment caused by treatment-resistant, refractory or chronic schizophrenia, vomiting, motion sickness, obesity, migraine, pain, mental retardation, autistic disorder (autism), Tourette's disorder, tic disorder, attention deficit hyperactivity disorder, conduct disorder, Down's syndrome and the like.

Moreover, the compound of the present invention scarcely shows side effects and is superior in the tolerability and safety.

Furthermore, the compound of the present invention is markedly superior in the solubility in oil such as sesame oil and benzyl benzoate, and can be applied to an oil injection. An oil preparation of the compound of the present invention shows superior blood concentration sustainability. Since the compound of the present invention changes, in blood, to a compound (compound (1)) disclosed in patent document 1, the compound of the present invention is also superior in the long-term maintenance of the blood concentration of compound (1) having desired efficacy.

In addition, the compound of the present invention is easily crystallized, superior in the operability, and also superior in the chemical stability.

In addition, the compound (I) of the present invention can exert effects such as decreasing the amount of administration, improving side effects, enhancing therapeutic efficacy or the like which could not attained by conventional treatment by administering with at least one clinically used drug(s) selected from the group consisting of (1) mood stabilizers, (2) serotonin reuptake inhibitors, (3) norepinephrine reuptake inhibitors, (4) serotonin and norepinephrine reuptake inhibitors and (5) antidepressants.

The present invention is explained in more detail in the following by referring to Reference Example, Example and Experimental Example, which are not to be construed as limitative.

REFERENCE EXAMPLE 1

Synthesis of 7-(tert-butyldimethylsilanyloxy)-1-hydroxymethyl-3,4-dihydro-1H-quinolin-2-one

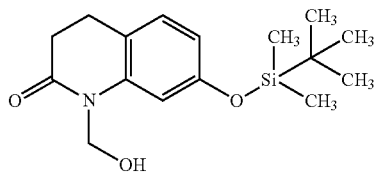 [SMILES: CC(C)(C)[Si](C)(C)Oc1ccc2c(c1)N(CO)C(=O)CC2]

7-(tert-Butyl-dimethylsilanyloxy)-3,4-dihydro-1H-quinolin-2-one (830 mg) was suspended in DMF (13 ml), formaldehyde (4.3 ml) and triethylamine (0.083 ml) were added, and the mixture was stirred at 80° C. overnight. After cooling to room temperature, water was added, and the mixture was extracted with ethyl acetate, dried over sodium sulfate, and purified by moderate-pressure silica gel column chromatography (hexane:ethyl acetate=2:1) to give the title compound (36 mg) as white crystals.

REFERENCE EXAMPLE 2

Synthesis of acetic acid 7-(tert-butyldimethylsilanyloxy)-2-oxo-3,4-dihydro-2H-quinolin-1-ylmethyl ester

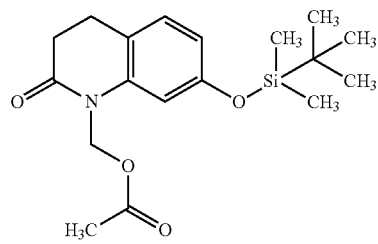

To a solution of 7-(tert-butyldimethylsilanyloxy)-1-hydroxymethyl-3,4-dihydro-1H-quinolin-2-one (37 mg) obtained in Reference Example 1 in dichloromethane were added pyridine (0.049 ml) and acetyl chloride (0.022 ml) and the mixture was stirred at room temperature overnight, and concentrated under reduced pressure. The residue was purified by moderate-pressure silica gel column chromatography (hexane:ethyl acetate=2:1) to give the title compound (26 mg) as a colorless oil.

$^1$H-NMR (CDCl$_3$) δ: 0.20 (s, 6H), 0.99 (s, 9H), 2.10 (s, 3H), 2.65-2.72 (m, 2H), 2.83-2.89 (m, 2H), 5.89 (brs, 2H), 6.51-6.56 (m, 2H), 6.99-7.04 (m, 1H)

REFERENCE EXAMPLE 3

Synthesis of 7-(4-chlorobutoxy)-1-hydroxymethyl-3,4-dihydro-1H-quinolin-2-one

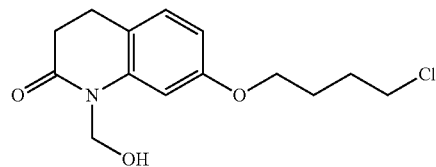 [SMILES: O=C1CCc2ccc(OCCCCCl)cc2N1CO]

The compound was synthesized in the same manner as in Reference Example 1.

REFERENCE EXAMPLE 4

Synthesis of acetic acid 7-(4-chlorobutoxy)-2-oxo-3,4-dihydro-2H-quinolin-1-ylmethyl ester

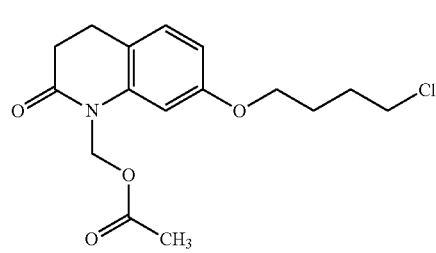 [SMILES: CC(=O)OCN1C(=O)CCc2ccc(OCCCCCl)cc21]

The compound was synthesized in the same manner as in Reference Example 2.

$^1$H-NMR (CDCl$_3$) δ: 1.90-2.03 (m, 4H), 2.12 (s, 3H), 2.64-2.72 (m, 2H), 2.84-2.90 (m, 2H), 3.63 (t, J=6.2 Hz, 2H), 3.99 (t, J=5.7 Hz, 2H), 5.91 (brs, 2H), 6.58 (dd, J=2.3, 8.2 Hz, 1H), 6.62 (d, J=2.3 Hz, 1H), 7.08 (d, J=8.2 Hz, 1H)

REFERENCE EXAMPLE 5

Synthesis of 7-benzyloxy-1-hydroxymethyl-3,4-dihydro-1H-quinolin-2-one

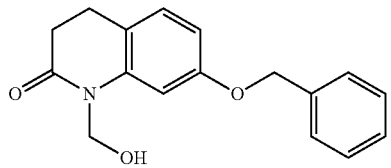 [SMILES: O=C1CCc2ccc(OCc3ccccc3)cc2N1CO]

The compound was synthesized in the same manner as in Reference Example 1.

REFERENCE EXAMPLE 6

Synthesis of tetradecanoic acid 7-benzyloxy-2-oxo-3,4-dihydro-2H-quinolin-1-ylmethyl ester

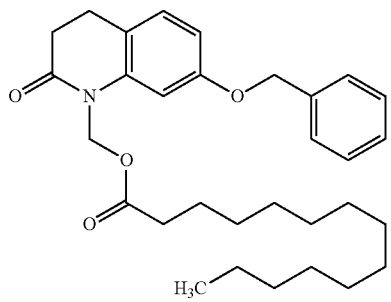 [SMILES: CCCCCCCCCCCCCC(=O)OCN1C(=O)CCc2ccc(OCc3ccccc3)cc21]

The compound was synthesized in the same manner as in Reference Example 2.

REFERENCE EXAMPLE 7

Synthesis of tetradecanoic acid 7-hydroxy-2-oxo-3,4-dihydro-2H-quinolin-1-ylmethyl ester

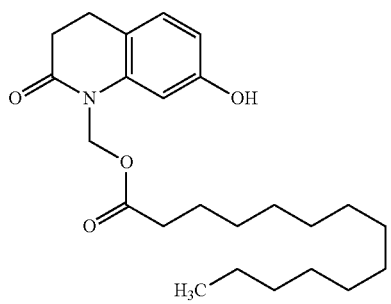 [SMILES: CCCCCCCCCCCCCC(=O)OCN1C(=O)CCc2ccc(O)cc21]

To a solution of tetradecanoic acid 7-benzyloxy-2-oxo-3,4-dihydro-2H-quinolin-1-ylmethyl ester (528 mg) obtained in Reference Example 6 in ethanol (10 ml) was added 10% palladium carbon (53 mg), and the mixture was substituted with hydrogen and stirred at room temperature for 2.5 hr. The catalyst was filtered off, and the residue was concentrated under reduced pressure and purified by moderate-pressure silica gel column chromatography (ethyl acetate). After concentration under reduced pressure, the residue was recrystallized from hexane-ethyl acetate to give the title compound (209 mg) as a white powder.

$^1$H-NMR (CDCl$_3$) δ: 0.88 (t, J=6.8 Hz, 3H), 1.20-1.35 (m, 20H), 1.58-1.68 (m, 2H), 2.35 (t, J=7.6 Hz, 2H), 2.65-2.71 (m, 2H), 2.82-2.88 (m, 2H), 5.05 (brs, 1H), 5.90 (brs, 2H), 6.53 (dd, J=2.4, 8.1 Hz, 1H), 6.56 (d, J=2.4 Hz, 1H), 7.03 (d, J=8.1 Hz, 1H)

REFERENCE EXAMPLE 8

Synthesis of acetic acid 7-(4-chlorobutoxy)-2-oxo-2H-quinolin-1-ylmethyl ester

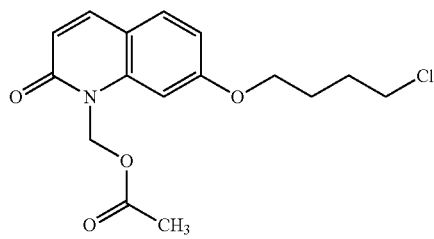

Acetic acid 7-(4-chlorobutoxy)-2-oxo-3,4-dihydro-2H-quinolin-1-ylmethyl ester (339 mg) obtained in Reference Example 4 was dissolved in tetrahydrofuran (10 ml), 2,3-dichloro-5,6-dicyano-1,4-benzoquinone (DDQ) (709 mg) was added, and the mixture was stirred at room temperature for 2 days. To the reaction mixture was added aqueous sodium hydrogen carbonate solution and the mixture was stirred, filtered, and the filtrate was extracted with methylene chloride, dried over sodium sulfate, and concentrated under reduced pressure, and the residue was purified by moderate-pressure silica gel column chromatography (ethyl acetate) and concentrated under reduced pressure to give the title compound (299 mg) as a colorless oil.

$^1$H-NMR (CDCl$_3$) δ: 1.94-2.04 (m, 4H), 2.13 (s, 3H), 3.60-3.68 (m, 2H), 4.05-4.12 (m, 2H), 6.32 (brs, 2H), 6.53 (d, J=9.5 Hz, 1H), 6.83 (dd, J=2.2, 8.6 Hz, 1H), 6.89 (d, J=2.2 Hz, 1H), 7.46 (d, J=8.6 Hz, 1H), 7.63 (d, J=9.5 Hz, 1H)

REFERENCE EXAMPLE 9

Synthesis of tetradecanoic acid 7-hydroxy-2-oxo-2H-quinolin-1-ylmethyl ester

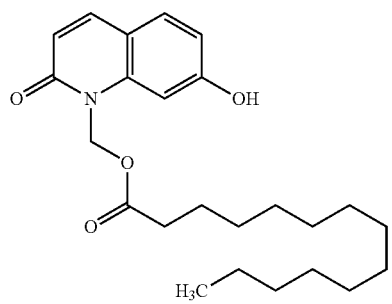

The compound was synthesized in the same manner as in Reference Example 8.

$^1$H-NMR (CDCl$_3$) δ: 0.88 (t, J=6.8 Hz, 3H), 1.17-1.32 (m, 20H), 1.55-1.70 (m, 2H), 2.35 (t, J=7.6 Hz, 2H), 6.31 (brs, 2H), 6.52 (d, J=9.5 Hz, 1H), 6.55-6.68 (m, 1H), 6.78-6.82 (m, 1H), 6.84-6.87 (m, 1H), 7.43 (d, J=8.5 Hz, 1H), 7.63 (d, J=9.5 Hz, 1H)

REFERENCE EXAMPLE 10

Synthesis of (2-butoxy ethoxy)-acetic acid 7-benzyloxy-2-oxo-3,4-dihydro-2H-quinolin-1-ylmethyl ester

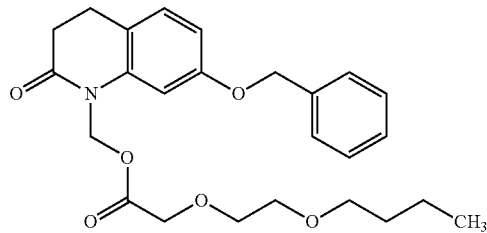 [SMILES: CCCCOCCOCC(=O)OCN1C(=O)CCc2ccc(OCc3ccccc3)cc21]

To a solution (20 ml) of 7-benzyloxy-1-hydroxymethyl-3,4-dihydro-1H-quinolin-2-one (760 mg) obtained in Reference Example 5, (2-butoxy ethoxy)acetic acid (473 mg), 1-(3 dimethylaminopropyl)-3-ethylcarbodiimide hydrochloride (771 mg) in methylene chloride was added 4-dimethylaminopyridine (65.5 mg), and the mixture was stirred at room temperature overnight. Water was added to the reaction mixture, and the mixture was extracted with ethyl acetate. This was purified by moderate-pressure silica gel column chromatography (hexane:ethyl acetate=1:0 to 0:1), and concentrated under reduced pressure to give the title compound (765 mg) as a colorless oil.

$^1$H-NMR (CDCl$_3$) δ: 0.90 (t, J=7.4 Hz, 3H), 1.29-1.40 (m, 2H), 1.50-1.59 (m, 2H), 2.64-2.71 (m, 2H), 2.82-2.90 (m, 2H), 3.44 (t, J=6.7 Hz, 2H), 3.57-3.63 (m, 2H), 3.70-3.75 (m, 2H), 4.18 (s, 2H), 5.06 (s, 2H), 5.95 (brs, 2H), 6.64-6.70 (m, 2H), 7.07 (d, J=8.0 Hz, 1H), 7.30-7.45 (m, 5H)

REFERENCE EXAMPLE 11

Synthesis of (2-butoxy ethoxy)-acetic acid 7-hydroxy-2-oxo-3,4-dihydro-2H-quinolin-1-ylmethyl ester

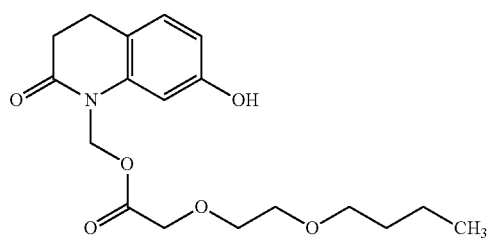 [SMILES: CCCCOCCOCC(=O)OCN1C(=O)CCc2ccc(O)cc21]

The compound was synthesized in the same manner as in Reference Example 7.

$^1$H-NMR (CDCl$_3$) δ: 0.90 (t, J=7.4 Hz, 3H), 1.29-1.40 (m, 2H), 1.52-1.61 (m, 2H), 2.64-2.72 (m, 2H), 2.81-2.88 (m, 2H), 3.49 (t, J=6.8 Hz, 2H), 3.62-3.67 (m, 2H), 3.71-3.76 (m, 2H), 4.19 (s, 2H), 5.98 (brs, 2H), 6.42-6.53 (m, 1H), 6.57 (dd, J=2.3, 8.1 Hz, 1H), 6.65 (d, J=2.3 Hz, 1H), 7.02 (d, J=8.1 Hz, 1H)

REFERENCE EXAMPLE 12

Synthesis of undec-10-enoic acid 7-(4-chlorobutoxy)-2-oxo-3,4-dihydro-2H-quinolin-1-ylmethyl ester

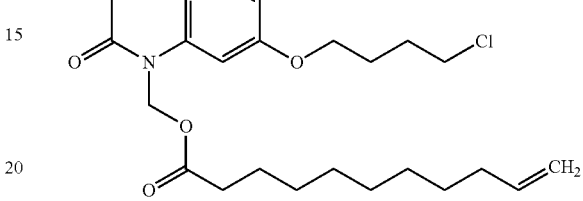

The compound was synthesized in the same manner as in Reference Example 10.

$^1$H-NMR (CDCl$_3$) δ: 1.23-1.40 (m, 10H), 1.57-1.68 (m, 2H), 1.90-2.07 (m, 6H), 2.35 (t, J=7.5 Hz, 2H), 2.65-2.71 (m, 2H), 2.83-2.89 (m, 2H), 3.62 (t, J=6.2 Hz, 2H), 3.98 (t, J=6.8 Hz, 2H), 4.90-4.95 (m, 1H), 4.95-5.02 (m, 1H), 5.74-5.86 (m, 1H), 5.91 (brs, 2H), 6.58 (dd, J=2.3, 8.1 Hz, 1H), 6.61 (d, J=2.3 Hz, 1H), 7.07 (d, J=8.1 Hz, 1H)

REFERENCE EXAMPLE 13

Synthesis of tetradecanoic acid 7-(4-chlorobutoxy)-2-oxo-2H-quinolin-1-ylmethyl ester

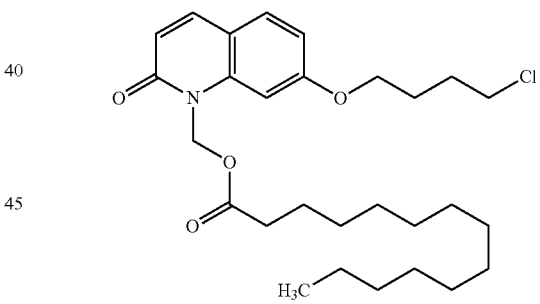

To a solution (5 ml) of tetradecanoic acid 7-hydroxy-2-oxo-2H-quinolin-1-ylmethyl ester (208 mg) obtained in Reference Example 9 in dimethylformamide were added 1-bromo-4-chlorobutane (0.358 ml) and potassium carbonate (107 mg) and the mixture was stirred at room temperature for 2 days. To the reaction mixture was added aqueous ammonium chloride solution, and the mixture was extracted with ethyl acetate. This was dried over sodium sulfate, and concentrated to give a crude product. The crude product was purified by silica gel column chromatography (hexane:ethyl acetate=1:0 to 2:1) to give the title compound (216 mg) as a white powder.

$^1$H-NMR (CDCl$_3$) δ: 0.88 (t, J=6.9 Hz, 3H), 1.18-1.33 (m, 20H), 1.56-1.67 (m, 2H), 1.94-2.04 (m, 4H), 2.36 (t, J=8.5 Hz, 2H), 3.61-3.66 (m, 2H), 4.04-4.10 (m, 2H), 6.33 (brs, 2H), 6.53 (d, J=9.4 Hz, 1H), 6.82 (dd, J=2.2, 8.6 Hz, 1H), 6.88 (d, J=2.2 Hz, 1H), 7.45 (d, J=8.6 Hz, 1H), 7.63 (d, J=9.4 Hz, 1H)

REFERENCE EXAMPLE 14

Synthesis of (2-butoxy-ethoxy)-acetic acid 7-hydroxy-2-oxo-2H-quinolin-1-ylmethyl ester

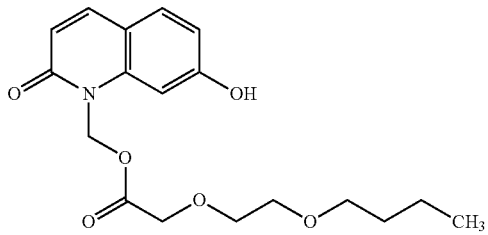 [SMILES: CCCCOCCOCC(=O)OCn1c(=O)ccc2ccc(O)cc21]

The compound was synthesized in the same manner as in Reference Example 8.

$^1$H-NMR (CDCl$_3$) δ: 0.88 (t, J=7.3 Hz, 3H), 1.22-1.38 (m, 2H), 1.48-1.59 (m, 2H), 3.40-3.50 (m, 2H), 3.58-3.64 (m, 2H), 3.67-3.73 (m, 2H), 4.18 (s, 2H), 6.39 (brs, 2H), 6.50 (d, J=9.4 Hz, 1H), 6.81-6.87 (m, 1H), 6.90-6.94 (m, 1H), 7.42 (d, J=8.5 Hz, 1H), 7.64 (d, J=9.5 Hz, 1H)

REFERENCE EXAMPLE 15

Synthesis of docosanoic acid 7-(4-chlorobutoxy)-2-oxo-3,4-dihydro-2H-quinolin-1-ylmethyl ester

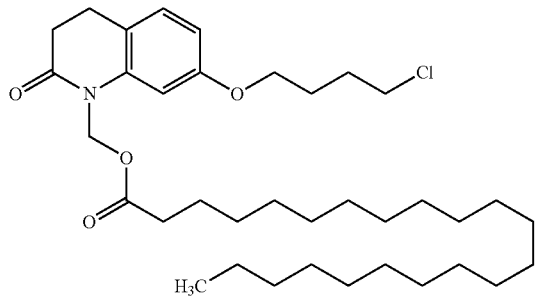 [SMILES: CCCCCCCCCCCCCCCCCCCCCC(=O)OCN1C(=O)CCc2ccc(OCCCCCl)cc21]

The compound was synthesized in the same manner as in Reference Example 12.

$^1$H-NMR (CDCl$_3$) δ: 0.88 (t, J=6.8 Hz, 3H), 1.19-1.35 (m, 36H), 1.58-1.68 (m, 2H), 1.89-2.03 (m, 4H), 2.35 (t, J=7.6 Hz, 2H), 2.64-2.72 (m, 2H), 2.82-2.90 (m, 2H), 3.62 (t, J=6.2 Hz, 2H), 3.98 (t, J=5.6 Hz, 2H), 5.91 (brs, 2H), 6.58 (dd, J=2.3, 8.2 Hz, 1H), 6.60 (d, J=2.3 Hz, 1H), 7.07 (d, J=8.2 Hz, 1H)

REFERENCE EXAMPLE 16

Synthesis of undec-10-enoic acid 7-(4-chlorobutoxy)-2-oxo-2H-quinolin-1-ylmethyl ester

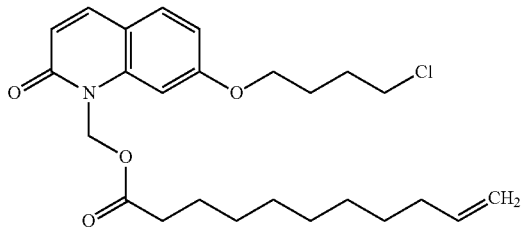 [SMILES: C=CCCCCCCCCC(=O)OCn1c(=O)ccc2ccc(OCCCCCl)cc21]

The compound was synthesized in the same manner as in Reference Example 8.

$^1$H-NMR (CDCl$_3$) δ: 1.20-1.39 (m, 10H), 1.57-1.67 (m, 2H), 1.95-2.05 (m, 6H), 2.36 (t, J=7.5 Hz, 2H), 3.61-3.66 (m, 2H), 4.04-4.10 (m, 2H), 4.90-4.95 (m, 1H), 4.95-5.01 (m, 1H), 5.74-5.85 (m, 1H), 6.33 (brs, 2H), 6.52 (d, J=9.5 Hz, 1H), 6.83 (dd, J=2.2, 8.6 Hz, 1H), 6.88 (d, J=2.2 Hz, 1H), 7.45 (d, J=8.6 Hz, 1H), 7.62 (d, J=9.5 Hz, 1H)

REFERENCE EXAMPLE 17

Synthesis of 7-(4-bromobutoxy)-4,4-dimethyl-3,4-dihydro-1H-quinolin-2-one

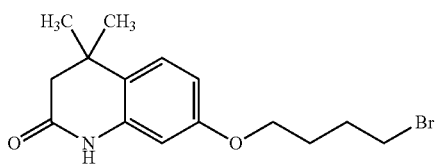 [SMILES: CC1(C)CC(=O)Nc2cc(OCCCCBr)ccc21]

To a solution (20 ml) of 7-hydroxy-4,4-dimethyl-3,4-dihydro-1H-quinolin-2-one (0.4 g) in DMF were added 1,4-dibromobutane (0.75 ml) and potassium carbonate (0.35 g) and the mixture was stirred at 60° C. for 6 hr. After cooling to room temperature, water was added to the reaction mixture and the mixture was extracted with ethyl acetate. The organic layer was washed with water, dried over magnesium sulfate, and concentrated under reduced pressure. The residue was purified by silica gel column chromatography (dichloromethane:methanol=100:1→50:1) to give the title compound (0.6 g) as a colorless solid.

$^1$H-NMR (CDCl$_3$) δ: 1.30 (6H, s), 1.88-1.98 (2H, m), 2.02-2.10 (2H, m), 2.47 (2H, s), 3.48 (2H, t, J=6.6 Hz), 3.97 (2H, t, J=6.0 Hz), 6.32 (1H, d, J=2.5 Hz), 6.57 (1H, dd, J=8.5, 2.5 Hz), 7.18 (1H, d, J=8.5 Hz), 8.11 (1H, brs)

REFERENCE EXAMPLE 18

Synthesis of 7-[4-(4-benzo[b]thiophen-4-ylpiperazin-1-yl)butoxy]-4,4-dimethyl-3,4-dihydro-1H-quinolin-2-one

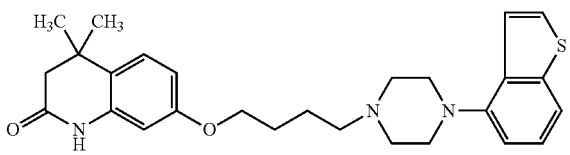 [SMILES: CC1(C)CC(=O)Nc2cc(OCCCCN3CCN(c4cccc5sccc45)CC3)ccc21]

To a solution (20 ml) of 7-(4-bromobutoxy)-4,4-dimethyl-3,4-dihydro-1H-quinolin-2-one (0.6 g) obtained in Reference Example 17 in DMF were added 1-benzo[b]thiophen-4-ylpiperazine hydrochloride (0.52 g) and potassium carbonate (0.64 g) and the mixture was stirred at 60° C. for 6 hr. After cooling to room temperature, water was added to the reaction mixture and the mixture was extracted with ethyl acetate. The organic layer was washed with water, dried over magnesium sulfate, and concentrated under reduced pressure. The residue was purified by silica gel column chromatography (dichloromethane:methanol=100:1→50:1) and crystallized from ethanol to give the title compound (0.33 g) as a white powder.

¹H-NMR (CDCl₃) δ: 1.30 (6H, s), 1.68-1.78 (2H, m), 1.80-1.90 (2H, m), 2.46 (2H, s), 2.52 (2H, t, J=7.4 Hz), 2.72 (4H, m), 3.19 (4H, m), 3.98 (2H, t, J=6.2 Hz), 6.30 (1H, d, J=2.5 Hz), 6.59 (1H, dd, J=8.5, 2.5 Hz), 6.90 (1H, d, J=7.2 Hz), 7.18 (1H, d, J=8.5 Hz), 7.27 (1H, t, J=7.8 Hz), 7.36-7.44 (2H, m), 7.55 (1H, d, J=8.1 Hz), 7.69 (1H, brs)

REFERENCE EXAMPLE 19

Synthesis of iodomethyldodecanoate

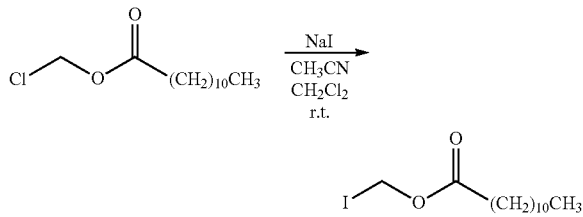

To a solution of chloromethyl dodecanoate[61413-67-0] (800 mg) in dichloromethane (10 ml) and acetonitrile (10 ml) was added sodium iodide (1.45 g), and the mixture was stirred at room temperature for 3 days. The solvent was evaporated under reduced pressure, water was added, and the mixture was extracted with dichloromethane, and dried over Na₂SO₄. The solvent was evaporated under reduced pressure to give iodomethyldbdecanoate (1.05 g).
oil: brown ¹H-NMR (CDCl₃) δ ppm: 0.88 (3H, t, J=7.0 Hz), 1.20-1.40 (16H, m), 1.50-1.70 (2H, m), 2.30-2.40 (2H, m), 5.91 (2H, s)

EXAMPLE 1

Synthesis of 7-[4-(4-benzo[b]thiophen-4-ylpiperazin-1-yl)butoxy]-1-hydroxymethyl-3,4-dihydro-1H-quinolin-2-one

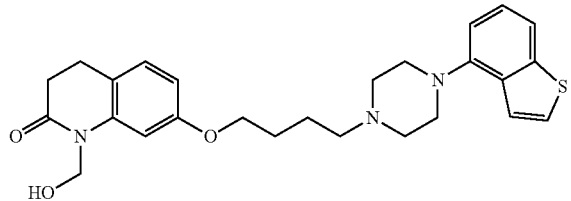 [SMILES: O=C1CCc2ccc(OCCCCN3CCN(c4cccc5sccc45)CC3)cc2N1CO]

To a solution of 7-[4-(4-benzo[b]thiophen-4-ylpiperazin-1-yl)butoxy]-3,4-dihydro-1H-quinolin-2-one (1 g) synthesized in the same manner as in WO2006/112464 (Example 11) in DMF (10 ml) were added 37% aqueous formalin solution (3.7 ml) and triethylamine (0.05 ml), and the mixture was heated at 80° C. for 20 hr. Water was added to the reaction mixture, and the mixture was extracted with ethyl acetate, and dried over magnesium sulfate. The solvent was evaporated under reduced pressure and the residue was purified by silica gel column chromatography (dichloromethane:methanol=30:1) to give a mixture (1 g, 3:2) of 7-[4-(4-benzo[b]thiophen-4-ylpiperazin-1-yl)butoxy]-1-hydroxymethyl-3,4-dihydro-1H-quinolin-2-one and 7-[4-(4-benzo[b]thiophen-4-ylpiperazin-1-yl)butoxy]-3,4-dihydro-1H-quinolin-2-one.

¹H-NMR (CDCl₃) δ: 1.68-1.80 (2H, m), 1.80-1.90 (2H, m), 2.48-2.55 (2H, m), 2.58-2.66 (2H, m), 2.66-2.78 (4H, m), 2.78-2.85 (1.2H, m), 2.86-2.92 (0.8H, m), 3.14-3.25 (4H, m), 3.94-4.40 (2H, m), 5.36 (1.2H, s), 6.31 (0.4H, d, J=2.3 Hz), 6.53 (0.4H, dd, J=2.4, 8.3 Hz), 6.58 (0.6H, dd, J=2.4, 8.2 Hz), 6.86 (0.6H, d, J=2.4 Hz), 6.89 (1H, d, J=7.2 Hz), 7.20-7.80 (1H, m), 7.27 (1H, t, J=8.4 Hz), 7.36-7.44 (2H, m), 7.55 (1H, d, J=8.0 Hz), 7.74-7.80 (0.4H, br)

EXAMPLE 2

Synthesis of 7-[4-(4-benzo[b]thiophen-4-ylpiperazin-1-yl)butoxy]-1-benzyloxymethyl-1H-quinolin-2-one

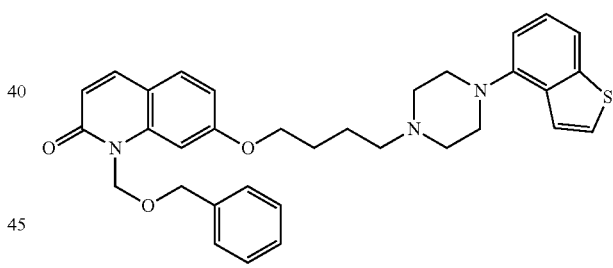

EXAMPLE 3

Synthesis of 7-[4-(4-benzo[b]thiophen-4-ylpiperazin-1-yl)butoxy]-2-benzyloxymethoxy-quinoline

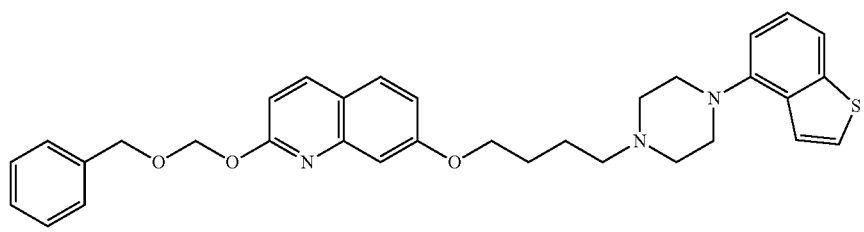 [SMILES: c1ccc(COCOc2ccc3ccc(OCCCCN4CCN(c5cccc6sccc56)CC4)cc3n2)cc1]

7-[4-(4-Benzo[b]thiophen-4-ylpiperazin-1-yl)butoxy]-1H-quinolin-2-one (1.0 g, 2.31 mmol) synthesized in the same manner as in WO2006/112464 (Example 1) was suspended in tetrahydrofuran (THF) (20 ml) and, under a nitrogen atmosphere, sodium hydride (55% oil) (0.15 g, 3.44 mmol) was added and the mixture was stirred with heating under reflux for 30 min. The mixture was ice-cooled, benzylchloromethylether (0.48 ml, 3.46 mmol) was added, and the mixture was stirred at room temperature for 3 hr. To the reaction mixture was added ice water to discontinue the reaction, and the mixture was extracted with ethyl acetate. The organic layer was dried over sodium sulfate, and concentrated under reduced pressure. The residue was purified by moderate-pressure silica gel column chromatography (hexane:ethyl acetate=100:0 to 0:100). The first fraction was concentrated under reduced pressure to give 7-[4-(4-benzo[b]thiophen-4-ylpiperazin-1-yl)butoxy]-2-benzyloxymethoxy-quinoline (0.15 g) as a colorless oil.

$^1$H-NMR (CDCl$_3$) δ: 1.73-1.83 (2H, m), 1.88-1.97 (2H, m), 2.54 (2H, t, J=7.5 Hz), 2.66-2.79 (4H, m), 3.15-3.25 (4H, m), 4.14 (2H, t, J=6.5 Hz), 4.83 (2H, s), 5.78 (2H, s), 6.80 (1H, d, J=8.5 Hz), 6.89 (1H, dd, J=0.5 Hz, J=7.5 Hz), 7.04 (1H, dd, J=2.5 Hz, J=9.0 Hz), 7.21 (1H, d, J=2.5 Hz), 7.24-7.43 (8H, m), 7.54 (1H, d, J=8.0 Hz), 7.60 (1H, d, J=8.0 Hz), 7.94 (1H, d, J=8.5 Hz)

The second fraction was concentrated to dryness under reduced pressure to give 7-[4-(4-benzo[b]thiophen-4-ylpiperazin-1-yl)butoxy]-1-benzyloxymethyl-1H-quinolin-2-one (0.86 g) as a white amorphous solid.

$^1$H-NMR (CDCl$_3$) δ: 1.71-1.81 (2H, m), 1.85-1.94 (2H, m), 2.52 (2H, t, J=7.5 Hz), 2.64-2.78 (4H, m), 3.13-3.25 (4H, m), 4.09 (2H, t, J=6.0 Hz), 4.67 (2H, s), 5.84 (2H, s), 6.50 (1H, d, J=9.5 Hz), 6.83 (1H, dd, J=2.5 Hz, J=8.5 Hz), 6.89 (1H, dd, J=0.5 Hz, J=7.5 Hz), 7.10 (1H, d, J=2.0 Hz), 7.22-7.46 (9H, m), 7.55 (1H, d, J=8.0 Hz), 7.60 (1H, d, J=9.5 Hz)

EXAMPLE4

Synthesis of 7-[4-(4-benzo[b]thiophen-4-ylpiperazin-1-yl)butoxy]-1-benzyloxymethyl-3,4-dihydro-1H-quinolin-2-one

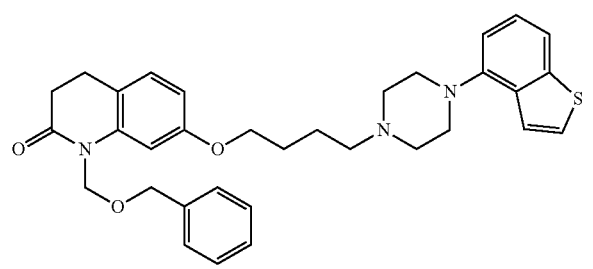 [SMILES: O=C1CCc2ccc(OCCCCN3CCN(c4cccc5sccc45)CC3)cc2N1COCc1ccccc1]

7-[4-(4-Benzo[b]thiophen-4-ylpiperazin-1-yl)butoxy]-3,4-dihydro-1H-quinolin-2-one (1.0 g, 2.30 mmol) synthesized in the same manner as in WO2006/112464 (Example 11) was suspended in tetrahydrofuran (THF) (20 ml) and, under a nitrogen atmosphere, sodium hydride (55% oil) (0.15 g, 3.44 mmol) was added, and the mixture was stirred with heating under reflux for 30 min. The mixture was ice-cooled, benzylchloromethylether (0.48 ml, 3.46 mmol) was added, and the mixture was stirred at room temperature for 3 hr. To the reaction mixture was added ice water to discontinue the reaction, and the mixture was extracted with ethyl acetate. The organic layer was dried over sodium sulfate, and concentrated under reduced pressure. The residue was purified by moderate-pressure silica gel column chromatography (hexane:ethyl acetate=100:0 to 0:100) and concentrated under reduced pressure to give the title compound (yield 0.95 g, 74%) as a pale-yellow oil.

$^1$H-NMR (CDCl$_3$) δ: 1.68-1.90 (4H, m), 2.51 (2H, t, J=7.5 Hz), 2.59-2.76 (6H, m), 2.78-2.85 (2H, m), 3.13-3.24 (4H, m), 3.98 (2H, t, J=6.0 Hz), 4.66 (2H, s), 5.44 (2H, s), 6.08 (1H, dd, J=2.5 Hz, J=8.0 Hz), 6.89 (1H, dd, J=0.5 Hz, J=7.5 Hz), 7.00 (1H, d, J=2.5 Hz), 7.03 (1H, d, J=8.0 Hz), 7.23-7.43 (8H, m), 7.55 (1H, d, J=8.0 Hz)

EXAMPLE5

Synthesis of carbonic acid 7-[4-(4-benzo[b]thiophen-4-ylpiperazin-1-yl)butoxy]-2-oxo-3,4-dihydro-2H-quinolin-1-ylmethyl ester phenyl ester

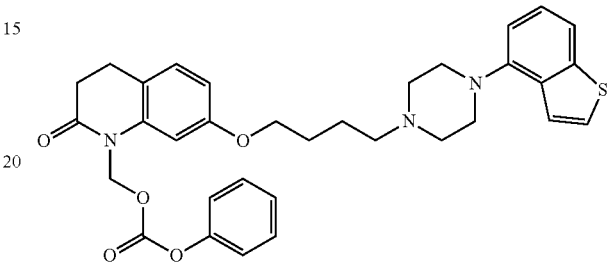

7-[4-(4-Benzo[b]thiophen-4-ylpiperazin-1-yl)butoxy]-3,4-dihydro-1H-quinolin-2-one (1.0 g, 2.30 mmol) synthesized in the same manner as in WO2006/112464 (Example 11) was suspended in tetrahydrofuran (THF) (20 ml) and, under a nitrogen atmosphere, sodium hydride (55% oil) (0.11 g, 2.52 mmol) was added, and the mixture was stirred with heating under reflux for 30 min. The mixture was cooled to −70° C., chloromethylphenylcarbonate (0.64 g, 3.43 mmol) was added, and to the mixture was stirred at −70° C. for 3 hr. Water was added to the reaction mixture to discontinue the reaction, and the mixture was extracted with ethyl acetate. The organic layer was dried over sodium sulfate, and concentrated under reduced pressure. The residue was purified by moderate-pressure silica gel column chromatography (hexane:ethyl acetate-100:0 to 0:100) and concentrated under reduced pressure to give the title compound (yield 0.95 g, 74%) as a colorless oil.

$^1$H-NMR (CDCl$_3$) δ: 1.69-1.91 (4H, m), 2.52 (2H, t, J=7.5 Hz), 2.64-2.77 (6H, m), 2.85-2.92 (2H, m), 3.14-3.24 (4H, m), 4.01 (2H, t, J=6.5 Hz), 6.06 (2H, s), 6.62 (1H, dd, J=2.5 Hz, J=8.5 Hz), 6.75 (1H, d, J=2.5 Hz), 6.86-6.91 (1H, m), 7.09 (1H, d, J=8.5 Hz), 7.19-7.29 (5H, m), 7.34-7.44 (3H, m), 7.55 (1H, d, J=8.0 Hz)

EXAMPLE6

Synthesis of 7-[4-(4-benzo[b]thiophen-4-ylpiperazin-1-yl)butoxy]-1-(tert-butyldimethylsilanyloxymethyl)-3,4-dihydro-1H-quinolin-2-one

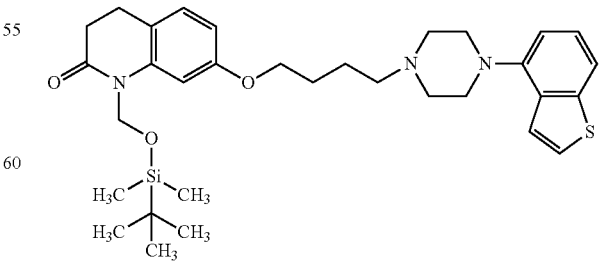

To a solution (15 ml) of 7-[4-(4-benzo[b]thiophen-4-ylpiperazin-1-yl)butoxy]-3,4-dihydro-1H-quinolin-2-one (1.5 g) synthesized in the same manner as in WO2006/112464 (Example 11) in dimethylformamide (DMF) were added 37% aqueous formalin solution (5.5 ml) and a catalytic amount of triethylamine (0.08 ml) and the mixture was stirred at 80° C. for 20 hr. After cooling to room temperature, and water was added to the reaction mixture. The obtained insoluble material was collected by filtration, dried, and dissolved in dichloromethane (15 ml). Imidazole (0.313 g) and tert-butylchlorodimethylsilane (0.519 g) were added, and the mixture was stirred at room temperature for 1.5 hr. Methanol was added, and the mixture was concentrated. This was purified by moderate-pressure silica gel column chromatography (hexane:ethyl acetate=1:0 to 2:1) to give the title compound (yield 550 mg, 41.3%) as a colorless amorphous solid.

$^1$H-NMR (CDCl$_3$) δ: 0.14 (6H, s), 0.90 (9H, s), 1.70-1.80 (2H, m), 1.80-1.92 (2H, m), 2.42 (2H, t, J=7.5 Hz), 2.58-2.64 (2H, m), 2.68-2.76 (4H, m), 2.78-2.84 (2H, m), 3.14-3.24 (4H, m), 4.00 (2H, t, J=6.3 Hz), 5.45 (2H, s), 6.58 (1H, dd, J=8.2 Hz, 2.5 Hz), 6.76 (1H, dd, J=7.6 Hz, 0.6 Hz), 7.00-7.04 (2H, m), 7.27 (1H, t, J=7.8 Hz), 7.36-7.42 (2H, m), 7.54 (1H, d, J=8.1 Hz)

EXAMPLE 7

Synthesis of carbonic acid 7-[4-(4-benzo[b]thiophen-4-ylpiperazin-1-yl)butoxy]-2-oxo-2H-quinolin-1-ylmethyl ester phenyl ester

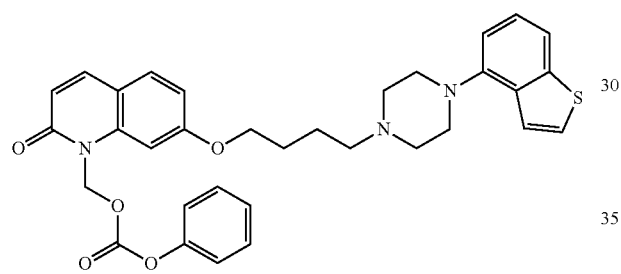

Using 7-[4-(4-benzo[b]thiophen-4-ylpiperazin-1-yl)butoxy]-1H-quinolin-2-one synthesized in the same manner as in WO2006/112464 (Example 1) and in the same manner as in Example 5, the title compound was obtained.

$^1$H-NMR (CDCl$_3$) δ: 1.71-1.80 (2H, m), 1.85-1.95 (2H, m), 2.53 (2H, t, J=7.5 Hz), 2.65-2.76 (4H, m), 3.14-3.23 (4H, m), 4.08-4.14 (2H, m), 6.46 (2H, brs), 6.53 (1H, d, J=9.5 Hz), 6.84-6.91 (2H, m), 6.97 (1H, d, J=2.0 Hz), 7.18-7.30 (4H, m), 7.35-7.43 (4H, m), 7.47 (1H, d, J=8.5 Hz), 7.55 (1H, d, J=8.0 Hz), 7.64 (1H, d, J=9.5 Hz)

EXAMPLE 8

Synthesis of 7-[4-(4-benzo[b]thiophen-4-ylpiperazin-1-yl)butoxy]-1-(tetrahydropyran-2-yloxymethyl)-3,4-dihydro-1H-quinolin-2-one

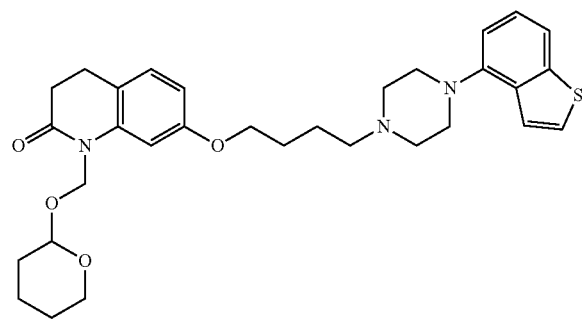 [SMILES: O=C1CCc2ccc(OCCCCN3CCN(c4cccc5sccc45)CC3)cc2N1COC1CCCCO1]

A solution of 7-[4-(4-benzo[b]thiophen-4-yl-piperazin-1-yl)-butoxy]-1-hydroxymethyl-3,4-dihydro-1H-quinolin-2-one (0.26 g), which is a mixture with 7-[4-(4-benzo[b]thiophen-4-ylpiperazin-1-yl)butoxy]-3,4-dihydro-1H-quinolin-2-one, was suspended in dichloromethane (10 ml), 3,4-dihydro-2H-pyran (0.08 ml) was added, p-toluenesulfonic acid hydrate (0.11 g) was added with stirring under ice-cooling, and the mixture was stirred at room temperature overnight. With stirring under ice-cooling, aqueous sodium hydrogen carbonate solution was added to the reaction mixture, and the mixture was extracted with dichloromethane, and dried over magnesium sulfate. The solvent was evaporated under reduced pressure and the residue was purified by silica gel column chromatography (dichloromethane:methanol=60:1) to give 7-[4-(4-benzo[b]thiophen-4-ylpiperazin-1-yl)butoxy]-1-(tetrahydro-2H-pyran-2-yloxy)methyl-3,4-dihydro-1H-quinolin-2-one (180 mg).

$^1$H-NMR (CDCl$_3$) δ: 1.50-1.80 (10H, m), 2.40-2.90 (6H, m), 2.72 (4H, brs), 3.20 (4H, brs), 3.40-4.00 (2H, m), 4.01 (2H, t, J=6.2 Hz), 4.90-5.30 (3H, m), 6.58 (1H, dd, J=8.2 Hz, 2.4 Hz), 6.90 (1H, d, J=7.6 Hz), 6.95 (1H, d, J=2.4 Hz), 7.04 (1H, d, J=8.2 Hz), 7.27 (1H, t, J=7.9 Hz), 7.36-7.44 (2H, m), 7.55 (1H, d, J=8.1 Hz)

EXAMPLE 9

Synthesis of piperidine-1-carboxylic acid 7-[4-(4-benzo[b]thiophen-4-ylpiperazin-1-yl)butoxy]-2-oxo-3,4-dihydro-2H-quinolin-1-ylmethyl ester

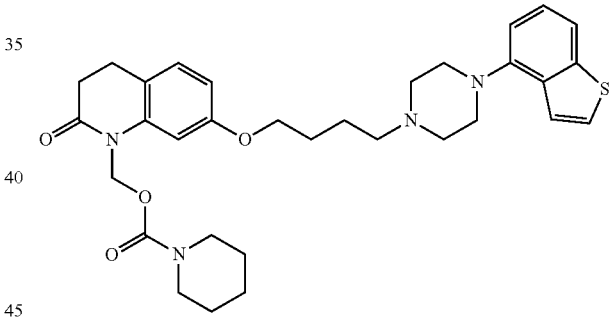

To a solution (3 ml) of carbonic acid 7-[4-(4-benzo[b]thiophen-4-ylpiperazin-1-yl)butoxy]-2-oxo-3,4-dihydro-2H-quinolin-1-ylmethyl ester phenyl ester (0.29 g) synthesized in the same manner as in Example 5 in THF were added piperidine (0.5 ml) and 1,8-diazabicyclo[5.4.0]undec-7-ene (DBU) (0.05 ml), and the mixture was stirred at room temperature for 16 hr. Water was added and the reaction mixture was extracted with ethyl acetate, dried over sodium sulfate, and concentrated under reduced pressure. The residue was purified by moderate-pressure basic silica gel column chromatography (hexane:ethyl acetate=1:0 to 1:1) to remove phenol, and concentrated under reduced pressure. The residue was purified by moderate-pressure silica gel column chromatography (hexane:ethyl acetate=1:0 to 0:1) to give the title compound (yield 0.21 g, 74%) as a colorless oil.

$^1$H-NMR (CDCl$_3$) δ: 1.40-1.62 (6H, m), 1.69-1.90 (4H, m), 2.52 (2H, t, J=7.5 Hz), 2.62-2.79 (6H, m), 2.81-2.90 (2H, m), 3.13-3.26 (4H, m), 3.31-3.51 (4H, m), 3.99 (2H, t, J=6.0 Hz), 5.93 (2H, s), 6.59 (1H, dd, J=2.5 Hz, 8.0 Hz), 6.78 (1H, d, J=2.5 Hz), 6.86-6.92 (1H, m), 7.05 (1H, d, J=8.5 Hz), 7.23-7.30 (1H, m), 7.38 (1H, d, J=5.5 Hz), 7.41 (1H, dd, J=0.5 Hz, 5.5 Hz), 7.54 (1H, d, J=8.0 Hz)

EXAMPLE 10

Synthesis of piperidine-1-carboxylic acid 7-[4-(4-benzo[b]thiophen-4-ylpiperazin-1-yl)butoxy]-2-oxo-2H-quinolin-1-ylmethyl ester

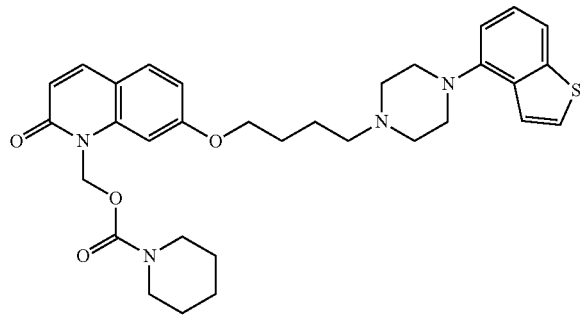 [SMILES: O=C(OCn1c(=O)ccc2ccc(OCCCCN3CCN(c4cccc5sccc45)CC3)cc21)N1CCCCC1]

To a solution (5 ml) of carbonic acid 7-[4-(4-benzo[b]thiophen-4-ylpiperazin-1-yl)butoxy]-2-oxo-2H-quinolin-1-ylmethyl ester phenyl ester (0.44 g) synthesized in the same manner as in Example 7 in THF was added piperidine (0.76 ml), and the mixture was stirred at room temperature for 3.5 days. Water was added to the reaction mixture and the mixture was extracted with ethyl acetate, dried over sodium sulfate, and concentrated under reduced pressure. The residue was purified by moderate-pressure basic silica gel column chromatography (hexane:ethyl acetate=1:0 to 1:1) to give the title compound (0.44 g, yield quantitative) as a colorless amorphous solid.

$^1$H-NMR (CDCl$_3$) δ: 1.38-1.61 (6H, m), 1.72-1.82 (2H, m), 1.85-1.96 (2H, m), 2.54 (2H, t, J=7.5 Hz), 2.66-2.80 (4H, m), 3.14-3.25 (4H, m), 3.29-3.52 (4H, m), 4.10 (2H, t, J=6.0 Hz), 6.36 (2H, s), 6.52 (1H, d, J=9.5 Hz), 6.83 (1H, dd, J=2.0 Hz, 8.5 Hz), 6.89 (1H, d, J=7.5 Hz), 7.12 (1H, t, J=2.0 Hz), 7.23-7.31 (1H, m), 7.37-7.46 (3H, m), 7.55 (1H, d, J=8.0 Hz), 7.62 (1H, d, J=9.5 Hz)

EXAMPLE 11

Synthesis of benzoic acid 7-[4-(4-benzo[b]thiophen-4-ylpiperazin-1-yl)butoxy]-2-oxo-3,4-dihydro-2H-quinolin-1-ylmethyl ester

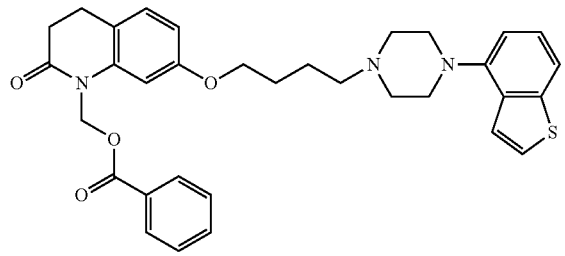

Sodium hydride (55% oil) (0.15 g, 2.52 mmol) was suspended in tetrahydrofuran (THF) (20 ml) and, under a nitrogen atmosphere, 7-[4-(4-benzo[b]thiophen-4-ylpiperazin-1-yl)butoxy]-3,4-dihydro-1H-quinolin-2-one (1.0 g, 2.30 mmol) synthesized in the same manner as in WO2006/112464 (Example 11) was added, and the mixture was stirred with heating under reflux for 25 min. The mixture was cooled to 0° C., chloromethyl benzoate (0.627 g, 3.67 mmol) was added, and the mixture was stirred at room temperature for 2.5 hr. Under ice-cooling, aqueous ammonium chloride was added to the reaction mixture to discontinue the reaction, and the mixture was extracted with ethyl acetate. The organic layer was dried over sodium sulfate, and concentrated under reduced pressure. The residue was purified by moderate-pressure silica gel column chromatography (hexane:ethyl acetate=1:0 to 2:3) and concentrated under reduced pressure to give the title compound (yield 1.132 g, 86.55%) as a colorless amorphous solid.

$^1$H-NMR (CDCl$_3$) δ: 1.64-1.75 (m, 2H), 1.77-1.86 (m, 2H), 2.44-2.51 (m, 2H), 2.61-2.77 (m, 6H), 2.87-2.93 (m, 2H), 3.11-3.22 (m, 4H), 3.97 (t, J=6.3 Hz, 2H), 6.17 (brs, 2H), 6.61 (dd, J=2.4, 8.3 Hz, 1H), 6.74 (d, J=2.4 Hz, 1H), 6.84-6.91 (m, 1H), 7.09 (d, J=8.3 Hz, 1H), 7.27 (dd, =7.7, 7.7 Hz, 1H), 7.37-7.46 (m, 4H), 7.51-7.58 (m, 2H), 8.00-8.07 (m, 2H)

EXAMPLE 12

Synthesis of benzoic acid 7-[4-(4-benzo[b]thiophen-4-ylpiperazin-1-yl)butoxy]-2-oxo-2H-quinolin-1-ylmethyl ester

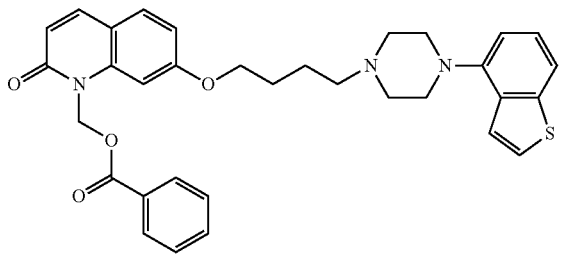

Using 7-[4-(4-benzo[b]thiophen-4-ylpiperazin-1-yl)butoxy]-1H-quinolin-2-one synthesized in the same manner as in WO2006/112464 (Example 1) and in the same manner as in Example 11, the title compound was obtained.

$^1$H-NMR (CDCl$_3$) δ: 1.67-1.78 (m, 2H), 1.81-1.91 (m, 2H), 2.45-2.53 (m, 2H), 2.63-2.75 (m, 4H), 3.11-3.22 (m, 4H), 4.07 (t, J=6.3 Hz, 2H), 6.56 (d, J=9.5 Hz, 1H), 6.59 (brs, 2H), 6.84 (dd, J=2.2, 8.6 Hz, 1H), 6.86-6.90 (m, 1H), 6.98 (d, J=2.2 Hz, 1H), 7.27 (dd, J=7.8, 7.8 Hz, 1H), 7.37-7.44 (m, 4H), 7.46 (d, J=8.6 Hz, 1H), 7.51-7.59 (m, 2H), 7.65 (d, J=9.5 Hz, 1H), 8.02-8.07 (m, 2H)

EXAMPLE 13

Synthesis of cyclopentanecarboxylic acid 7-[4-(4-benzo[b]thiophen-4-ylpiperazin-1-yl)butoxy]-2-oxo-3,4-dihydro-2H-quinolin-1-ylmethyl ester

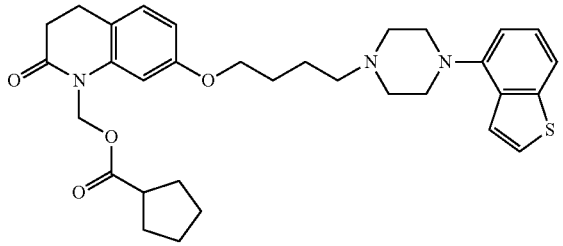

To a solution (20 ml) of 7-[4-(4-benzo[b]thiophen-4-ylpiperazin-1-yl)butoxy]-1-hydroxymethyl-3,4-dihydro-1H-quinolin-2-one (962 mg, 2.066 mmol) synthesized in the same manner as in Example 1, cyclopentanecarboxylic acid (0.448 ml, 4.13 mmol), 2-chloro-1,3-dimethylimidazolium chloride (768 mg, 4.55 mmol) in methylene chloride was added triethylamine (1.267 ml, 9.09 mmol), and the mixture was stirred at room temperature for 1 hr. 2-Chloro-1,3-dimethylimidazolium chloride (768 mg, 4.55 mmol) was added, and the mixture was heated under reflux for 1 hr. After cooling to room temperature, water was added to the reaction mixture, and the mixture was extracted with ethyl acetate. This was purified by moderate-pressure basic silica gel column (hexane:ethyl acetate=1:3) and concentrated under reduced pressure to give the title compound (yield 261 mg, 22.49%) as a colorless oil.

$^1$H-NMR (CDCl$_3$) δ: 1.50-1.63 (m, 2H), 1.63-1.79 (m, 4H), 1.79-1.95 (m, 6H), 2.52 (t, J=7.4 Hz, 2H), 2.64-2.83 (m, 7H), 2.83-2.89 (m, 2H), 3.13-3.25 (m, 4H), 3.98 (d, J=6.2 Hz, 2H), 5.91 (brs, 2H), 6.57-6.61 (m, 2H), 6.89 (d, J=7.6 Hz, 1H), 7.04-7.09 (m, 1H), 7.27 (dd, J=7.8, 7.8 Hz, 1H), 7.36-7.43 (m, 2H), 7.54 (d, J=8.0 Hz, 1H)

EXAMPLE 14

Synthesis of cyclohexanecarboxylic acid 7-[4-(4-benzo[b]thiophen-4-ylpiperazin-1-yl)butoxy]-2-oxo-3,4-dihydro-2H-quinolin-1-ylmethyl ester

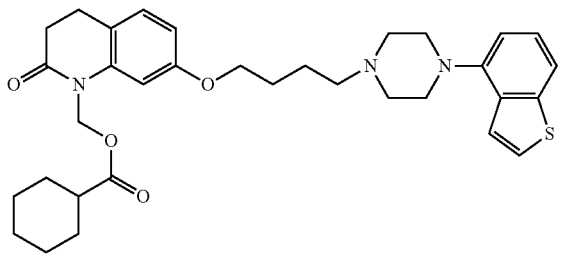 [SMILES: O=C(OCN1C(=O)CCc2ccc(OCCCCN3CCN(c4cccc5sccc45)CC3)cc21)C1CCCCC1]

To a solution (15 ml) of 7-[4-(4-benzo[b]thiophen-4-ylpiperazin-1-yl)butoxy]-1-hydroxymethyl-3,4-dihydro-1H-quinolin-2-one (550 mg) synthesized in the same manner as in Example 1 in dichloromethane was added pyridine (0.287 ml), cyclohexanecarbonyl chloride (0.158 ml) with stirring under ice-cooling and the mixture was stirred at room temperature overnight. Water was added to the reaction mixture and the to mixture was extracted with ethyl acetate. The organic layer was dried over sodium sulfate, and concentrated under reduced pressure. The residue was purified by moderate-pressure silica gel column chromatography (hexane:ethyl acetate=1:0 to 1:3), and concentrated under reduced pressure. The residue was purified by basic silica gel column chromatography, and concentrated to dryness under reduced pressure to give the title compound (yield 172 mg, 25.3%) as a colorless amorphous solid.

$^1$H-NMR (CDCl$_3$) δ: 1.15-1.32 (m, 3H), 1.40-1.53 (m, 2H), 1.57-1.65 (m, 1H), 1.68-1.79 (m, 4H), 1.81-1.96 (m, 4H), 2.36 (tt, J=3.6, 11.2 Hz, 1H), 2.52 (t, J=7.5 Hz, 2H), 2.65-2.76 (m, 6H), 2.83-2.90 (m, 2H), 3.15-3.24 (m, 4H), 3.98 (t, J=6.2 Hz, 2H), 5.91 (brs, 2H), 6.56-6.63 (m, 2H), 6.87-6.92 (m, 1H), 7.05-7.09 (m, 1H), 7.27 (dd, J=7.7, 7.7 Hz, 1H), 7.37-7.43 (m, 2H), 7.55 (d, J=8.0 Hz, 1H)

EXAMPLE 15

Synthesis of 2,2-dimethylpropionic acid 7-[4-(4-benzo[b]thiophen-4-ylpiperazin-1-yl)butoxy]-2-oxo-3,4-dihydro-2H-quinolin-1-ylmethyl ester

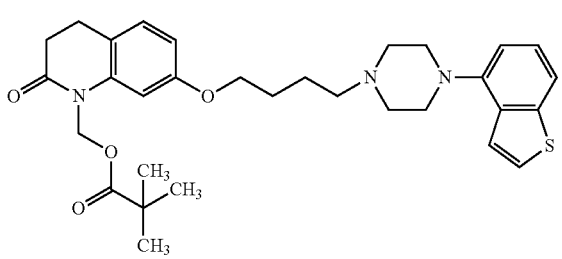 [SMILES: CC(C)(C)C(=O)OCN1C(=O)CCc2ccc(OCCCCN3CCN(c4cccc5sccc45)CC3)cc21]

In the same manner as in Example 11, the title compound was obtained.

$^1$H-NMR (CDCl$_3$) δ: 1.22 (s, 9H), 1.68-1.90 (m, 4H), 2.48-2.55 (m, 2H), 2.65-2.76 (m, 6H), 2.82-2.89 (m, 2H), 3.13-3.24 (m, 4H), 3.97 (t, J=6.2 Hz, 2H), 5.90 (s, 2H), 6.57-6.62 (m, 2H), 6.87-6.92 (m, 1H), 7.07 (d, J=8.1 Hz, 1H), 7.27 (dd, J=7.7, 7.7 Hz, 1H), 7.37-7.43 (m, 2H), 7.55 (d, J=8.1 Hz, 1H)

EXAMPLE 16

Synthesis of N-butyl-N-methylcarbamic acid 7-[4-(4-benzo[b]thiophen-4-ylpiperazin-1-yl)butoxy]-2-oxo-3,4-dihydro-2H-quinolin-1-ylmethyl ester

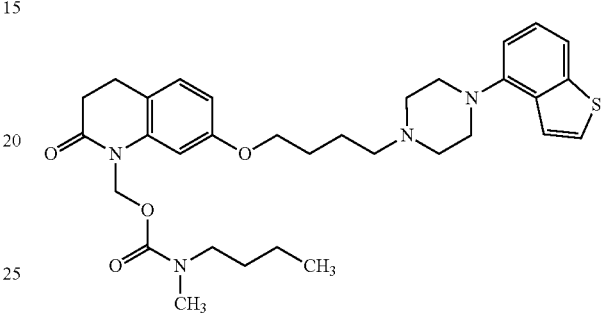

Using carbonic acid 7-[4-(4-benzo[b]thiophen-4-ylpiperazin-1-yl)butoxy]-2-oxo-3,4-dihydro-2H-quinolin-1-ylmethyl ester phenyl ester synthesized in the same manner as in Example 5 and in the same manner as in Example 10, the title compound was obtained.

$^1$H-NMR (CDCl$_3$) δ: {0.82 (t, J=7.0 Hz), 0.94 (t, J=7.0 Hz) total 3H (1:1)}, 1.14-1.58 (4H, m), 1.64-1.91 (4H, m), 2.52 (2H, t, J=7.5 Hz), 2.63-2.78 (6H, m), 2.81-2.96 (5H, m), 3.13-3.33 (6H, m), 3.99 (2H, t, J=6.0 Hz), 5.92 (2H, s), 6.59 (1H, dd, J=2.0 Hz, 8.0 Hz), 6.77 (1H, d, J=6.0 Hz), 6.89 (1H, d, J=7.5 Hz), 7.06 (1H, d, J=8.0 Hz), 7.27 (1H, dd, J=8.0 Hz, 8.0 Hz), 7.38 (1H, d, J=5.5 Hz), 7.41 (1H, d, J=7.5 Hz), 7.55 (1H, d, J=8.0 Hz)

EXAMPLE 17

Synthesis of N-decylcarbamic acid 7-[4-(4-benzo[b]thiophen-4-ylpiperazin-1-yl)butoxy]-2-oxo-3,4-dihydro-2H-quinolin-1-ylmethyl ester

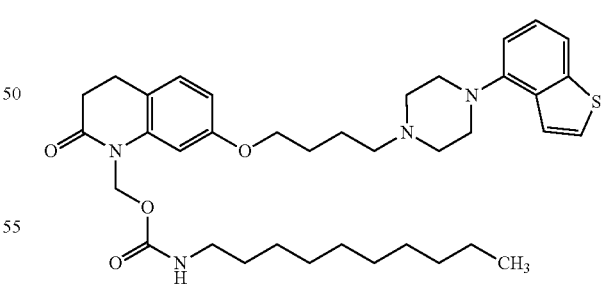

Using carbonic acid 7-[4-(4-benzo[b]thiophen-4-ylpiperazin-1-yl)butoxy]-2-oxo-3,4-dihydro-2H-quinolin-1-ylmethyl ester phenyl ester synthesized in the same manner as in Example 5 and in the same manner as in Example 10, the title compound was obtained.

$^1$H-NMR (CDCl$_3$) δ: 0.87 (3H, t, J=7.0 Hz), 1.16-1.34 (14H, m), 1.42-1.53 (2H, m), 1.69-1.89 (4H, m), 2.52 (2H, t, J=7.5 Hz), 2.62-2.77 (6H, m), 2.80-2.88 (2H, m), 3.12-3.25 (6H, m), 4.00 (2H, t, J=6.0 Hz), 4.85 (1H, t, J=5.5 Hz), 5.91 (2H, s), 6.59 (1H, dd, J=2.0 Hz, 8.0 Hz), 6.79 (1H, d, J=2.0

Hz), 6.86-6.91 (1H, m), 7.05 (1H, d, J=8.0 Hz), 7.27 (1H, dd, J=8.0 Hz, 8.0 Hz), 7.36-7.44 (2H, m), 7.54 (1H, d, J=8.0 Hz)

EXAMPLE 18

Synthesis of 2,2-dimethylpropionic acid 7-[4-(4-benzo[b]thiophen-4-ylpiperazin-1-yl)butoxy]-2-oxo-2H-quinolin-1-ylmethyl ester

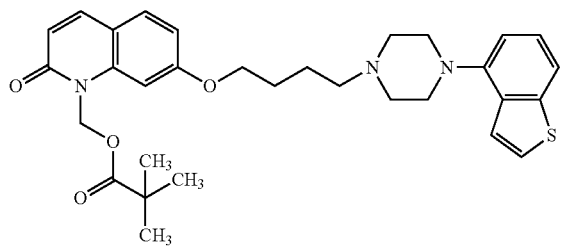 [SMILES: CC(C)(C)C(=O)OCn1c(=O)ccc2ccc(OCCCCN3CCN(c4cccc5sccc45)CC3)cc21]

Using 7-[4-(4-benzo[b]thiophen-4-ylpiperazin-1-yl)butoxy]-1H-quinolin-2-one synthesized in the same manner as in WO2006/112464 (Example 1) and in the same manner as in Example 11, the title compound was obtained.

$^1$H-NMR (CDCl$_3$) δ: 1.20 (s, 9H), 1.71-1.81 (m, 2H), 1.85-1.95 (m, 2H), 2.54 (t, J=7.5 Hz, 2H), 2.67-2.78 (m, 4H), 3.15-3.24 (m, 4H), 4.06 (t, J=6.2 Hz, 2H), 6.33 (brs, 2H), 6.52 (d, J=9.5 Hz, 1H), 6.80 (d, J=2.2 Hz, 1H), 6.84 (dd, J=2.2, 8.6 Hz, 1H), 6.88-6.91 (m, 1H), 7.27 (dd, J=7.8, 7.8 Hz, 1H), 7.37-7.43 (m, 2H), 7.45 (d, J=8.6 Hz, 1H), 7.55 (d, J=8.1 Hz, 1H), 7.63 (d, J=9.5 Hz, 1H)

EXAMPLE 19

Synthesis of butyric acid 7-[4-(4-benzo[b]thiophen-4-ylpiperazin-1-yl)butoxy]-2-oxo-3,4-dihydro-2H-quinolin-1-ylmethyl ester

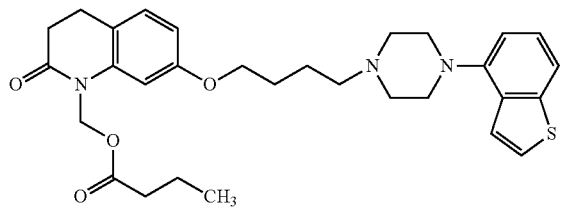

In the same manner as in Example 11, the title compound was obtained.

$^1$H-NMR (CDCl$_3$) δ: 0.96 (t, J=7.4 Hz, 3H), 1.63-1.79 (m, 4H), 1.80-1.90 (m, 2H), 2.35 (t, J=7.4 Hz, 2H), 2.52 (t, J=7.4 Hz, 2H), 2.64-2.77 (m, 6H), 2.82-2.90 (m, 2H), 3.14-3.25 (m, 4H), 3.99 (t, J=6.2 Hz, 2H), 5.92 (brs, 2H), 6.57-6.63 (m, 2H), 6.87-6.92 (m, 1H), 7.07 (d, J=8.1 Hz, 1H), 7.27 (dd, J=7.8, 7.8 Hz, 1H), 7.37-7.44 (m, 2H), 7.55 (d, J=8.0 Hz, 1H)

EXAMPLE 20

Synthesis of butyric acid 7-[4-(4-benzo[b]thiophen-4-ylpiperazin-1-yl)butoxy]-2-oxo-2H-quinolin-1-ylmethyl ester

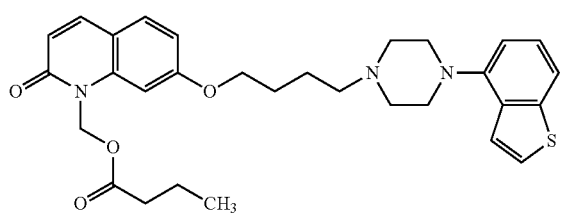 [SMILES: CCCC(=O)OCn1c(=O)ccc2ccc(OCCCCN3CCN(c4cccc5sccc45)CC3)cc21]

Using 7-[4-(4-benzo[b]thiophen-4-ylpiperazin-1-yl)butoxy]-1H-quinolin-2-one synthesized in the same manner as in WO2006/112464 (Example 1) and in the same manner as in Example 11, the title compound was obtained.

$^1$H-NMR (CDCl$_3$) δ: 0.94 (t, J=7.4 Hz, 3H), 1.62-1.72 (m, 2H), 1.72-1.82 (m, 2H), 1.86-1.96 (m, 2H), 2.35 (t, J=7.4 Hz, 2H), 2.54 (t, J=7.4 Hz, 2H), 2.65-2.78 (m, 4H), 3.13-3.25 (m, 4H), 4.08 (t, J=6.2 Hz, 2H), 6.34 (brs, 2H), 6.52 (d, J=9.5 Hz, 1H), 6.84 (dd, J=2.2, 8.6 Hz, 1H), 6.86-6.91 (m, 2H), 7.27 (dd, J=7.8, 7.8 Hz, 1H), 7.37-7.43 (m, 2H), 7.45 (d, J=8.6 Hz, 1H), 7.55 (d, J=8.0 Hz, 1H), 7.63 (d, J=9.5 Hz, 1H)

EXAMPLE 21

Synthesis of dodecanoic acid 7-[4-(4-benzo[b]thiophen-4-ylpiperazin-1-yl)butoxy]-2-oxo-3,4-dihydro-2H-quinolin-1-ylmethyl ester

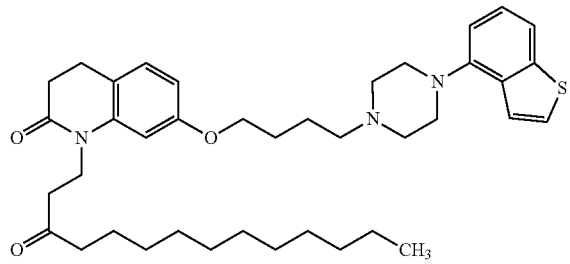

In the same manner as in Example 14, the title compound was obtained.

$^1$H-NMR (CDCl$_3$) δ: 0.87 (3H, t, J=6.8 Hz), 1.20-1.36 (16H, m), 1.58-1.69 (2H, m), 1.69-1.80 (2H, m), 1.80-1.90 (2H, m), 2.36 (2H, t, J=7.6 Hz), 2.52 (2H, t, J=7.4 Hz), 2.64-2.76 (6H, m), 2.82-2.90 (2H, m), 3.14-3.26 (4H, br), 3.98 (2H, t, J=6.2 Hz), 5.92 (2H, brs), 6.56-6.64 (2H, m), 6.89 (1H, d, J=7.6 Hz), 7.07 (1H, d, J=8.1 Hz), 7.27 (1H, t, J=7.8 Hz), 7.40 (2H, dd, J=5.6, 12.6 Hz), 7.55 (1H, d, J=8.0 Hz)

EXAMPLE 22

Synthesis of dodecanoic acid 7-[4-(4-benzo[b]thiophen-4-ylpiperazin-1-yl)butoxy]-2-oxo-2H-quinolin-1-ylmethyl ester

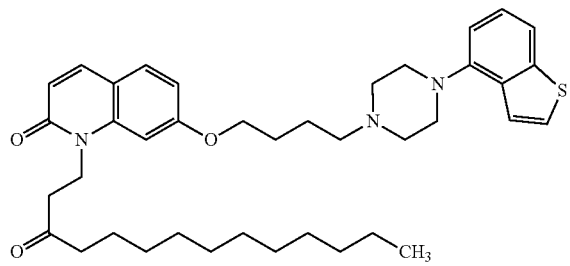 [SMILES: CCCCCCCCCCCC(=O)CCn1c(=O)ccc2ccc(OCCCCN3CCN(c4cccc5sccc45)CC3)cc21]

To a solution (5 ml) of dodecanoic acid 7-[4-(4-benzo[b]thiophen-4-ylpiperazin-1-yl)butoxy]-2-oxo-3,4-dihydro-2H-quinolin-1-ylmethyl ester (150 mg) synthesized in the same manner as in Example 21 in THF was added trifluoroacetic acid (TFA) (0.11 ml), then to a solution (3 ml) of 2,3-dichloro-5,6-dicyano-1,4-benzoquinone (DDQ) (0.27 g) in THF was added, and the mixture was stirred at room temperature for 3 days. To the reaction mixture were added water and sodium carbonate, and the mixture was extracted with dichloromethane, dried over sodium sulfate, and concentrated under reduced pressure. The residue was purified by preparative thin layer chromatography (ethyl acetate) to give the title compound (yield 50 mg, 33.4%) as a brown oil.

$^1$H-NMR (CDCl$_3$) δ: 0.87 (3H, t, J=6.9 Hz), 1.20-1.34 (16H, m), 1.55-1.68 (2H, m), 1.72-1.82 (2H, m), 1.85-1.94 (2H, m), 2.36 (2H, t, J=7.5 Hz), 2.50-2.60 (2H, m), 2.73 (4H, m), 3.20 (4H, m), 4.08 (2H, t, J=5.3 Hz), 6.34 (2H, brs), 6.52 (1H, d, J=9.5 Hz), 6.84 (1H, dd, J=2.2, 8.5 Hz), 6.86-6.92 (2H, m), 7.24-7.30 (1H, m), 7.40 (2H, dd, J=5.6, 10.9 Hz), 7.45 (1H, d, J=8.6 Hz), 7.55 (1H, d, J=8.0 Hz), 7.62 (1H, d, J=9.5 Hz)

EXAMPLE23

Synthesis of hexadecanoic acid 7-[4-(4-benzo[b]thiophen-4-ylpiperazin-1-yl)butoxy]-2-oxo-3,4-dihydro-2H-quinolin-1-ylmethyl ester

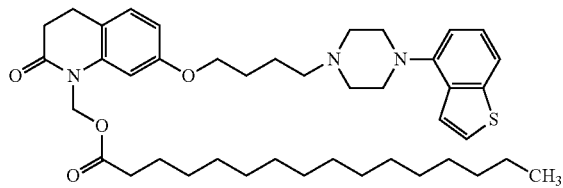 [SMILES: CCCCCCCCCCCCCCCC(=O)OCN1C(=O)CCc2ccc(OCCCCN3CCN(c4cccc5sccc45)CC3)cc21]

In the same manner as in Example 14, the title compound was obtained.

$^1$H-NMR (CDCl$_3$) δ: 0.88 (t, J=6.8, 3H), 1.18-1.34 (m, 26H), 1.57-1.80 (m, 4H), 1.80-1.90 (m, 2H), 2.36 (t, J=7.5 Hz, 2H), 2.53 (t, J=7.5 Hz, 2H), 2.63-2.77 (m, 6H), 2.83-2.89 (m, 2H), 3.15-3.25 (m, 2H), 3.98 (t, J=6.2 Hz, 2H), 5.92 (brs, 2H), 6.59 (dd, J=2.3, 8.1 Hz, 1H), 6.62 (d, J=2.3 Hz, 1H), 6.87-6.92 (m, 1H), 7.07 (d, J=8.1 Hz, 1H), 7.27 (dd, J=7.8, 7.8 Hz, 1H), 7.37-7.43 (m, 2H), 7.55 (d, J=8.0 Hz, 1H)

EXAMPLE24

Synthesis of octanoic acid 7-[4-(4-benzo[b]thiophen-4-ylpiperazin-1-yl)butoxy]-2-oxo-3,4-dihydro-2H-quinolin-1-ylmethyl ester

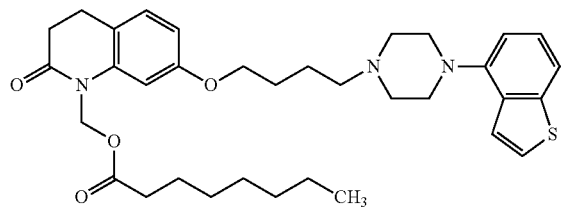

In the same manner as in Example 14, the title compound was obtained.

$^1$H-NMR (CDCl$_3$) δ: 0.86 (t, J=6.9 Hz, 3H), 1.19-1.35 (m, 8H), 1.59-1.68 (m, 2H), 1.69-1.80 (m, 2H), 1.80-1.90 (m, 2H), 2.36 (t, J=7.5 Hz, 2H), 2.53 (t, J=7.5 Hz, 2H), 2.65-2.78 (m, 6H), 2.83-2.89 (m, 2H), 3.14-3.24 (m, 4H), 3.98 (t, J=6.2 Hz, 2H), 5.92 (brs, 2H), 6.60 (dd, J=2.2, 8.1 Hz, 1H), 6.62 (d, J=2.2, 1H), 6.88-6.92 (m, 1H), 7.07 (d, J=8.1 Hz, 1H), 7.27 (dd, J=7.8, 7.8 Hz, 1H), 7.37-7.43 (m, 2H), 7.55 (d, J=8.1 Hz, 1H)

EXAMPLE25

Synthesis of phenylacetic acid 7-[4-(4-benzo[b]thiophen-4-ylpiperazin-1-yl)butoxy]-2-oxo-3,4-dihydro-2H-quinolin-1-ylmethyl ester

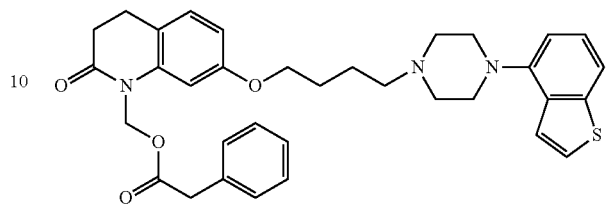

In the same manner as in Example 14, the title compound was obtained.

$^1$H-NMR (CDCl$_3$) δ: 1.62-1.86 (m, 4H), 2.52 (t, J=7.4 Hz, 2H), 2.65-2.77 (m, 6H), 2.82-2.88 (m, 2H), 3.14-3.25 (m, 4H), 3.68 (s, 2H), 3.85 (t, J=6.2 Hz, 2H), 5.94 (brs, 2H), 6.51 (d, J=2.3 Hz, 1H), 6.58 (dd, J=2.3, 8.2 Hz, 1H), 6.88-6.92 (m, 1H), 7.06 (d, J=8.2 Hz, 1H), 7.23-7.34 (m, 6H), 7.37-7.43 (m, 2H), 7.55 (d, J=8.1 Hz, 1H)

EXAMPLE26

Synthesis of phenylacetic acid 7-[(4-(4-benzo[b]thiophen-4-ylpiperazin-1-yl)butoxy]-2-oxo-2H-quinolin-1-ylmethyl ester

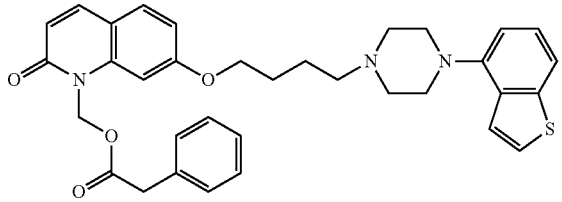 [SMILES: O=C(Cc1ccccc1)OCn1c(=O)ccc2ccc(OCCCCN3CCN(c4cccc5sccc45)CC3)cc21]

Using 7-[(4-(4-benzo[b]thiophen-4-ylpiperazin-1-yl)butoxy]-1H-quinolin-2-one synthesized in the same manner as in WO2006/112464 (Example 1) and in the same manner as in Example 11, the title compound was obtained.

$^1$H-NMR (CDCl$_3$) δ: 1.65-1.88 (m, 4H), 2.52 (t, J=7.4 Hz, 2H), 2.64-2.78 (m, 4H), 3.14-3.25 (m, 4H), 3.67 (s, 2H), 3.87 (t, J=6.2 Hz, 2H), 6.35 (brs, 2H), 6.52 (d, J=9.5 Hz, 1H), 6.72 (d, J=2.1 Hz, 1H), 6.82 (dd, J=2.1, 8.6 Hz, 1H), 6.84-6.92 (m, 1H), 7.22-7.31 (m, 6H), 7.37-7.46 (m, 3H), 7.55 (d, J=8.0 Hz, 1H), 7.63 (d, J=9.5 Hz, 1H)

EXAMPLE27

Synthesis of N-butylcarbamic acid 7-[4-(4-benzo[b]thiophen-4-ylpiperazin-1-yl)butoxy]-2-oxo-3,4-dihydro-2H-quinolin-1-ylmethyl ester

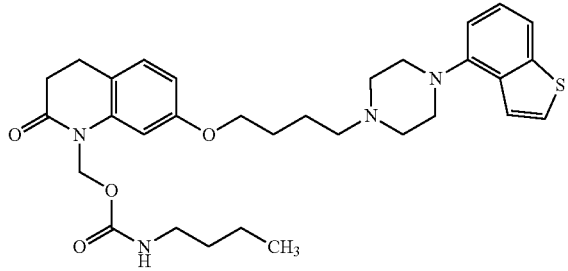

Using carbonic acid 7-[4-(4-benzo[b]thiophen-4-ylpiperazin-1-yl)butoxy]-2-oxo-3,4-dihydro-2H-quinolin-1-ylmethyl ester phenyl ester synthesized in the same manner as in Example 5 and in the same manner as in Example 10, the title compound was obtained.

$^1$H-NMR (CDCl$_3$) δ: 0.92 (3H, t, J=7.5 Hz), 1.24-1.40 (2H, m), 1.43-1.53 (2H, m), 1.69-1.80 (2H, m), 1.81-1.91 (2H, m), 2.53 (2H, t, J=7.5 Hz), 2.64-2.77 (6H, m), 2.82-2.89 (2H, m), 3.13-3.27 (6H, m), 4.00 (2H, t, J=6.0 Hz), 4.74-4.82 (1H, m), 5.92 (2H, s), 6.59 (1H, dd, J=2.0 Hz, 8.0 Hz), 6.79 (1H, d, J=6.0 Hz), 6.89 (1H, d, J=7.5 Hz), 7.05 (1H, d, J=8.0 Hz), 7.24-7.30 (1H, m), 7.38 (1H, d, J=5.5 Hz), 7.41 (1H, d, J=5.5 Hz), 7.55 (1H, d, J=8.0 Hz)

EXAMPLE 28

Synthesis of N,N-dibutylcarbamic acid 7-[4-(4-benzo[b]thiophen-4-ylpiperazin-1-yl)butoxy]-2-oxo-3,4-dihydro-2H-quinolin-1-ylmethyl ester

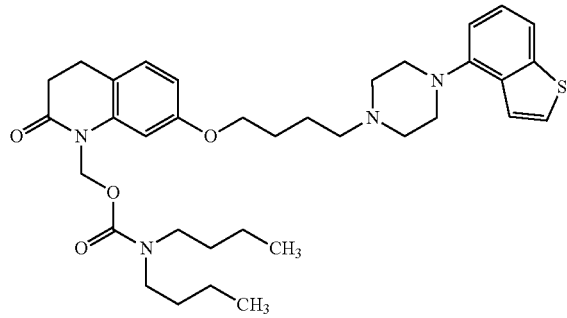

Using carbonic acid 7-[4-(4-benzo[b]thiophen-4-ylpiperazin-1-yl)butoxy]-2-oxo-3,4-dihydro-2H-quinolin-1-ylmethyl ester phenyl ester synthesized in the same manner as in Example 5 and in the same manner as in Example 10, the title compound was obtained.

$^1$H-NMR (CDCl$_3$) δ: 0.80 (3H, t, J=7.0 Hz), 0.93 (3H, t, J=7.0 Hz), 1.13-1.58 (8H, m), 1.68-1.90 (4H, m), 2.52 (2H, t, J=7.5 Hz), 2.62-2.78 (6H, m), 2.80-2.89 (2H, m), 3.09-3.30 (8H, m), 3.98 (2H, t, J=6.0 Hz), 5.93 (2H, s), 6.59 (1H, dd, J=2.5 Hz, 8.5 Hz), 6.76 (1H, d, J=2.5 Hz), 6.90 (1H, d, J=7.5 Hz), 7.06 (1H, d, J=8.5 Hz), 7.24-7.30 (1H, m), 7.38 (1H, d, J=5.5 Hz), 7.41 (1H, d, J=5.5 Hz), 7.55 (1H, d, J=8.0 Hz)

EXAMPLE 29

Synthesis of N-cyclohexylmethylcarbamic acid 7-[4-(4-benzo[b]thiophen-4-ylpiperazin-1-yl)butoxy]-2-oxo-3,4-dihydro-2H-quinolin-1-ylmethyl ester

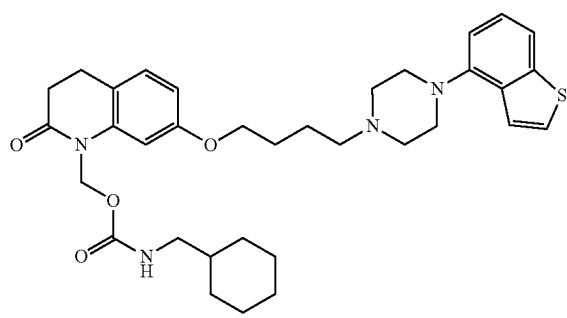 [SMILES: O=C(NCC1CCCCC1)OCN1C(=O)CCc2ccc(OCCCCN3CCN(c4cccc5sccc45)CC3)cc21]

Using carbonic acid 7-[4-(4-benzo[b]thiophen-4-ylpiperazin-1-yl)butoxy]-2-oxo-3,4-dihydro-2H-quinolin-1-ylmethyl ester phenyl ester synthesized in the same manner as in Example 5 and in the same manner as in Example 10, the title compound was obtained.

$^1$H-NMR (CDCl$_3$) δ: 0.81-0.98 (2H, m), 1.07-1.30 (3H, m), 1.36-1.50 (1H, m), 1.59-1.80 (7H, m), 1.81-1.91 (2H, m), 2.53 (2H, t, J=7.5 Hz), 2.63-2.78 (6H, m), 2.81-2.89 (2H, m), 3.05 (2H, J=6.5 Hz), 3.14-3.24 (4H, m), 4.00 (2H, t, J=6.0 Hz), 4.84 (1H, t, J=5.5 Hz), 5.92 (2H, s), 6.59 (1H, dd, J=2.5 Hz, 8.5 Hz), 6.80 (1H, d, J=2.0 Hz), 6.87-6.92 (1H, m), 7.05 (1H, d, J=8.5 Hz), 7.24-7.30 (1H, m), 7.37-7.44 (2H, m), 7.55 (1H, d, J=8.0 Hz)

EXAMPLE 30

Synthesis of octanoic acid 7-[4-(4-benzo[b]thiophen-4-ylpiperazin-1-yl)butoxy]-2-oxo-2H-quinolin-1-ylmethyl ester

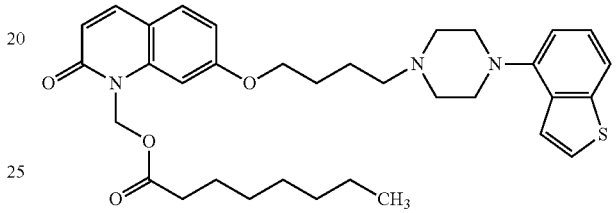

In the same manner as in Example 22, the title compound was obtained.

$^1$H-NMR (CDCl$_3$) δ: 0.85 (t, J=6.9 Hz, 3H), 1.16-1.33 (m, 8H), 1.57-1.68 (m, 2H), 1.74-1.96 (m, 4H), 2.36 (t, J=7.5 Hz, 2H), 2.52-2.63 (m, 2H), 2.69-2.85 (m, 4H), 3.15-3.29 (m, 4H), 4.08 (t, J=6.2 Hz, 2H), 6.34 (brs, 2H), 6.52 (d, J=9.5 Hz, 1H), 6.84 (dd, J=2.1, 8.6 Hz, 1H), 6.86-6.92 (m, 2H), 7.27 (dd, J=7.8, 7.8 Hz, 1H), 7.37-7.42 (m, 2H), 7.45 (d, J=8.6 Hz, 1H), 7.55 (d, J=8.0 Hz, 1H), 7.62 (d, J=9.5 Hz, 1H)

EXAMPLE 31

Synthesis of icosanoic acid 7-[4-(4-benzo[b]thiophen-4-ylpiperazin-1-yl)butoxy]-2-oxo-3,4-dihydro-2H-quinolin-1-ylmethyl ester

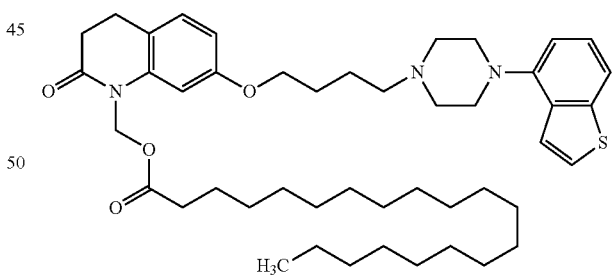

To a solution (6 ml) of arachidic acid (1048 mg, 3.35 mmol) in 1,2-dichloroethane was added thionyl chloride (1.217 ml, 16.77 mmol), and the mixture was heated under reflux, and concentrated under reduced pressure to give acid chloride. To a solution (15 ml) of 7-[4-(4-benzo[b]thiophen-4-ylpiperazin-1-yl)butoxy]-1-hydroxymethyl-3,4-dihydro-1H-quinolin-2-one (781 mg, 1.677 mmol) synthesized in the same manner as in Example 1 in dichloromethane were added pyridine (1.357 ml, 16.77 mmol) and the above-mentioned acid chloride, and the mixture was stirred at room temperature for 3 hr. The organic layer was dried over sodium sulfate, and concentrated under reduced pressure. The residue was purified by moderate-pressure silica gel column chromatography (hexane:ethyl acetate=1:0 to 1:1), and concentrated under reduced pressure. The residue was purified by basic silica gel column chromatography (hexane:ethyl acetate=1:0 to 1:1), and concentrated to dryness under reduced pressure to give the title compound (yield 856 mg, 67%) as a colorless oil.

$^1$H-NMR (CDCl$_3$) δ: 0.88 (t, J=6.8 Hz, 3H), 1.19-1.35 (m, 32H), 1.57-1.68 (m, 2H), 1.69-1.79 (m, 2H), 1.80-1.90 (m, 2H), 2.36 (t, J=7.6 Hz, 2H), 2.52 (t, J=7.5 Hz, 2H), 2.64-2.77 (m, 6H), 2.83-2.89 (m, 2H), 3.14-3.25 (m, 4H), 3.98 (t, J=6.2 Hz, 2H), 5.92 (brs, 2H), 6.60 (dd, J=2.3, 8.1 Hz, 1H), 6.62 (d, J=2.3 Hz, 1H), 6.87-6.92 (m, 1H), 7.07 (d, J=8.1 Hz, 1H), 7.27 (dd, J=7.8, 7.8 Hz, 1H), 7.37-7.43 (m, 2H), 7.55 (d, J=8.1 Hz, 1H)

EXAMPLE 32

Synthesis of cyclohexanecarboxylic acid 7-[4-(4-benzo[b]thiophen-4-ylpiperazin-1-yl)butoxy]-2-oxo-2H-quinolin-1-ylmethyl ester

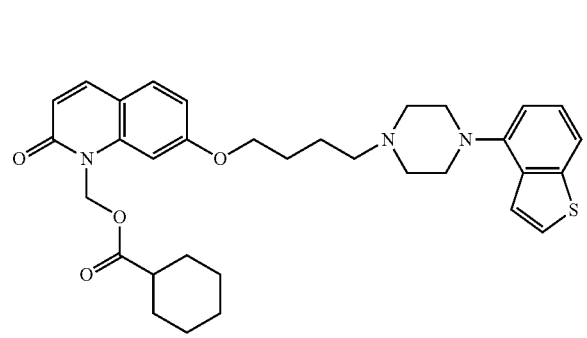 [SMILES: O=C(OCn1c(=O)ccc2ccc(OCCCCN3CCN(c4cccc5sccc45)CC3)cc21)C1CCCCC1]

Using 7-[4-(4-benzo[b]thiophen-4-ylpiperazin-1-yl)butoxy]-1H-quinolin-2-one synthesized in the same manner as in WO2006/112464 (Example 1) and in the same manner as in Example 11, the title compound was obtained.

$^1$H-NMR (CDCl$_3$) δ: 1.14-1.31 (m, 3H), 1.39-1.52 (m, 2H), 1.54-1.65 (m, 1H), 1.67-1.82 (m, 4H), 1.84-1.95 (m, 4H), 2.31-2.41 (m, 1H), 2.54 (t, J=7.6 Hz, 2H), 2.65-2.79 (m, 4H), 3.13-3.25 (m, 4H), 4.07 (t, J=6.2 Hz, 2H), 6.33 (brs, 2H), 6.52 (d, J=9.5 Hz, 1H), 6.81-6.86 (m, 2H), 6.89 (d, J=7.6 Hz, 1H), 7.27 (dd, J=7.8, 7.8 Hz, 1H), 7.37-7.47 (m, 3H), 7.55 (d, J=8.0 Hz, 1H), 7.62 (d, J=9.5 Hz, 1H)

EXAMPLE 33

Synthesis of (Z)-octadec-9-enoic acid 7-[4-(4-benzo[b]thiophen-4-ylpiperazin-1-yl)butoxy]-2-oxo-3,4-dihydro-2H-quinolin-1-ylmethyl ester

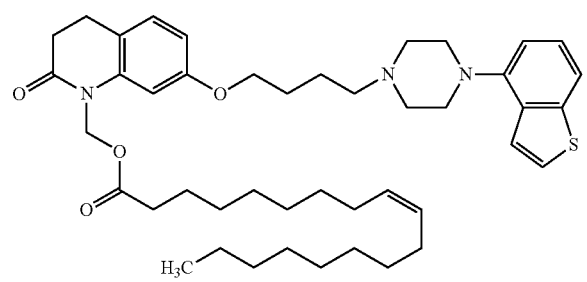

In the same manner as in Example 14, the title compound was obtained.

$^1$H-NMR (CDCl$_3$) δ: 0.87 (t, J=6.8 Hz, 3H), 1.20-1.36 (m, 20H), 1.58-1.68 (m, 2H), 1.69-1.79 (m, 2H), 1.80-1.90 (m, 2H), 1.93-2.07 (m, 4H), 2.36 (t, J=7.5 Hz, 2H), 2.52 (t, J=7.5 Hz, 2H), 2.64-2.79 (m, 6H), 2.83-2.90 (m, 2H), 3.14-3.25 (m, 4H), 3.99 (t, J=6.3 Hz, 2H), 5.28-5.40 (m, 2H), 5.92 (brs, 2H), 6.60 (dd, J=2.3, 8.1 Hz, 1H), 6.62 (d, J=2.3 Hz, 1H), 6.87-6.92 (m, 1H), 7.07 (d, J=8.1 Hz, 1H), 7.27 (t, J=7.8 Hz, 1H), 7.37-7.43 (m, 2H), 7.55 (d, J=8.0 Hz, 1H)

EXAMPLE 34

Synthesis of N-decylcarbamic acid 7-[4-(4-benzo[b]thiophen-4-ylpiperazin-1-yl)butoxy]-2-oxo-2H-quinolin-1-ylmethyl ester

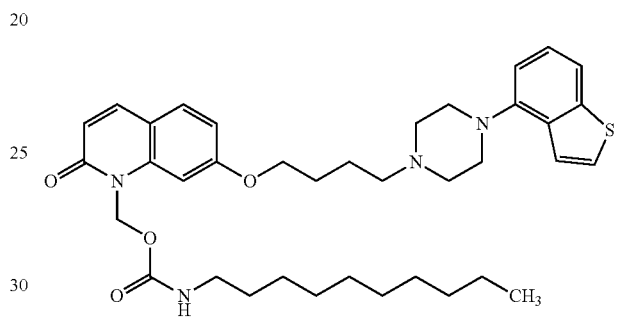

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

$^1$H-NMR (CDCl$_3$) δ: 0.87 (3H, t, J=7.0 Hz), 1.16-1.35 (12H, m), 1.42-1.53 (4H, m), 1.72-1.83 (2H, m), 1.86-1.95 (2H, m), 2.54 (2H, t, J=7.5 Hz), 2.67-2.80 (4H, m), 3.13-3.28 (6H, m), 4.11 (2H, t, J=6.0 Hz), 4.87 (1H, t, J=5.5 Hz), 6.33 (2H, s), 6.51 (1H, d, J=9.5 Hz), 6.83 (1H, dd, J=2.0 Hz, J=8.5 Hz), 6.87-6.92 (1H, m), 7.16 (1H, d, J=1.5 Hz), 7.24-7.30 (1H, m), 7.36-7.45 (3H, m), 7.55 (1H, d, J=8.0 Hz), 7.62 (1H, d, J=9.5 Hz)

EXAMPLE 35

Synthesis of N-butylcarbamic acid 7-[4-(4-benzo[b]thiophen-4-ylpiperazin-1-yl)butoxy]-2-oxo-2H-quinolin-1-ylmethyl ester

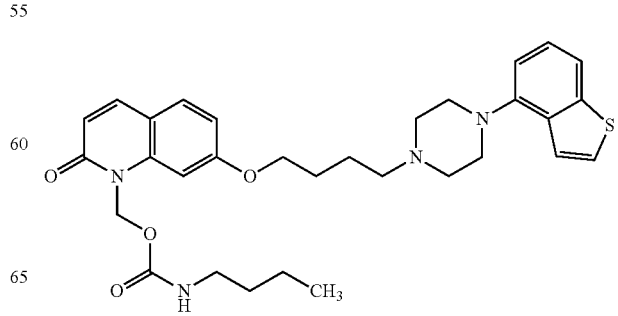

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

$^1$H-NMR (CDCl$_3$) δ: 0.91 (3H, t, J=7.5 Hz), 1.28-1.39 (2H, m), 1.43-1.53 (2H, m), 1.73-1.82 (2H, m), 1.87-1.95 (2H, m), 2.54 (2H, t, J=7.5 Hz), 2.67-2.78 (4H, m), 3.15-3.24 (6H, m), 4.11 (2H, t, J=6.0 Hz), 4.88 (1H, t, J=5.5 Hz), 6.32 (2H, s), 6.51 (1H, d, J=9.5 Hz), 6.83 (1H, dd, J=2.0 Hz, J=8.5 Hz), 6.89 (1H, d, J=7.5 Hz), 7.15 (1H, d, J=1.5 Hz), 7.24-7.30 (1H, m), 7.37-7.45 (3H, m), 7.55 (1H, d, J=8.0 Hz), 7.61 (1H, d, J=9.5 Hz)

EXAMPLE 36

Synthesis of N-butyl-N-methylcarbamic acid 7-[4-(4-benzo[b]thiophen-4-ylpiperazin-1-yl)butoxy]-2-oxo-2H-quinolin-1-ylmethyl ester

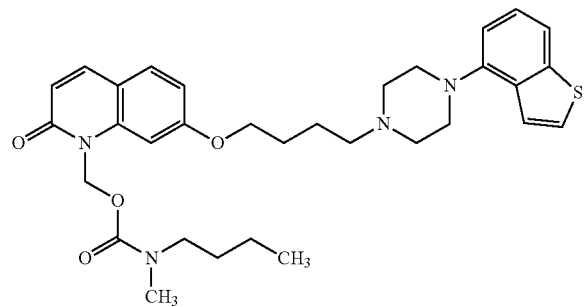 [SMILES: CCCCN(C)C(=O)OCn1c(=O)ccc2ccc(OCCCCN3CCN(c4cccc5sccc45)CC3)cc21]

Using carbonic acid 7-[(4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

$^1$H-NMR (CDCl$_3$) δ: {0.87 (t, J=7.5 Hz), 0.94 (t, J=7.5 Hz) total 3H (1:1)}, 1.08-1.19 (1H, m), 1.26-1.43 (2H, m), 1.47-1.57 (1H, m), 1.72-1.83 (2H, m), 1.85-1.95 (2H, m), 2.54 (2H, t, J=7.5 Hz), 2.66-2.79 (4H, m), {2.82 (s), 2.92 (s) total 3H (1:1)}, 3.12-3.25 (5H, m), 3.30 (1H, t, J=7.5 Hz), 4.10 (2H, t, J=6.0 Hz), 6.35 (2H, s), 6.52 (1H, dd, J=1.5 Hz, J=9.5 Hz), 6.83 (1H, dd, J=1.5 Hz, J=8.5 Hz), 6.89 (1H, d, J=7.5 Hz), 7.10 (1H, d, J=16.5 Hz), 7.25-7.30 (1H, m), 7.37-7.45 (3H, m), 7.55 (1H, d, J=8.0 Hz), 7.62 (1H, d, J=9.5 Hz)

EXAMPLE 37

Synthesis of cyclopentanecarboxylic acid 7-[4-(4-benzo[b]thiophen-4-ylpiperazin-1-yl)butoxy]-2-oxo-2H-quinolin-1-ylmethyl ester

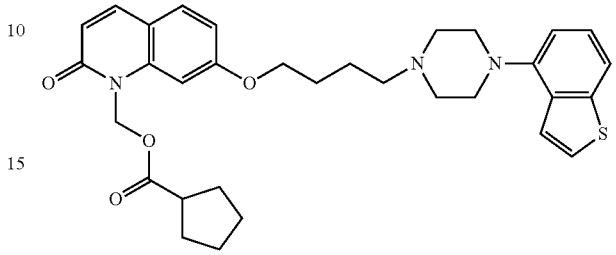

To a solution (10 ml) of cyclopentanecarboxylic acid 7-[4-(4-benzo[b]thiophen-4-ylpiperazin-1-yl)butoxy]-2-oxo-3,4-dihydro-2H-quinolin-1-ylmethyl ester (252 mg) synthesized in the same manner as in Example 13 in THF was added 2,3-dichloro-5,6-dicyano-1,4-benzoquinone (DDQ) (509 mg), and the mixture was stirred at room temperature stirred for 2 days. To the reaction mixture were added water and sodium carbonate, and the mixture was extracted with dichloromethane, dried over sodium sulfate, and concentrated under reduced pressure. The residue was purified by moderate-pressure silica gel column chromatography (hexane:ethyl acetate=1:0 to 0:1) and further by NH silica gel column chromatography (hexane:ethyl acetate=1:0 to 0:1) to give the title compound (yield 38 mg, 15%) as a colorless amorphous solid.

$^1$H-NMR (CDCl$_3$) δ: 1.50-1.62 (m, 2H), 1.62-1.95 (m, 10H), 2.54 (t, J=7.5 Hz, 2H), 2.67-2.83 (m, 5H), 3.14-3.25 (m, 4H), 4.07 (t, J=6.2 Hz, 2H), 6.33 (brs, 2H), 6.52 (d, J=9.5 Hz, 1H), 6.81-6.86 (m, 2H), 6.89 (d, J=7.4 Hz, 1H), 7.27 (t, J=7.9, 7.9 Hz, 1H), 7.37-7.47 (m, 3H), 7.55 (d, J=7.9 Hz, 1H), 7.62 (d, J=9.5 Hz, 1H)

EXAMPLE 38

Synthesis of N-octadecylcarbamic acid 7-[4-(4-benzo[b]thiophen-4-ylpiperazin-1-yl)butoxy]-2-oxo-2H-quinolin-1-ylmethyl ester

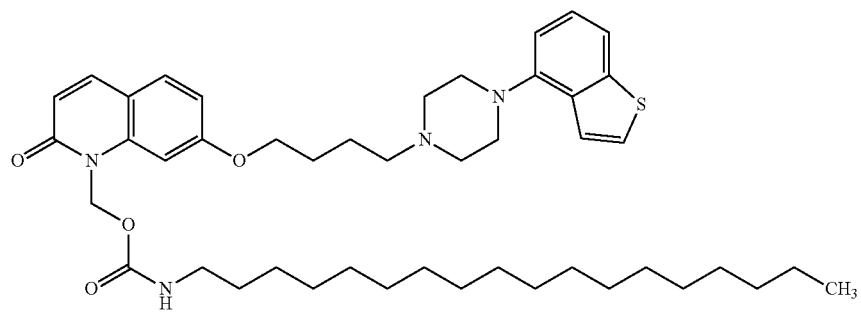 [SMILES: CCCCCCCCCCCCCCCCCCNC(=O)OCn1c(=O)ccc2ccc(OCCCCN3CCN(c4cccc5sccc45)CC3)cc21]

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

¹H-NMR (CDCl₃) δ: 0.88 (3H, t, J=7.0 Hz), 1.13-1.34 (30H, m), 1.43-1.53 (2H, m), 1.73-1.83 (2H, m), 1.85-1.965 (2H, m), 2.54 (2H, t, J=7.5 Hz), 2.66-2.79 (4H, m), 3.13-3.25 (6H, m), 4.12 (2H, t, J=6.0 Hz), 4.85 (1H, t, J=5.5 Hz), 6.33 (2H, s), 6.52 (1H, d, J=9.5 Hz), 6.83 (1H, dd, J=2.0 Hz, J=8.5 Hz), 6.89 (1H, d, J=7.5 Hz), 7.16 (1H, d, J=1.5 Hz), 7.24-7.30 (1H, m), 7.36-7.45 (3H, m), 7.55 (1H, d, J=8.0 Hz), 7.62 (1H, d, J=9.5 Hz)

EXAMPLE39

Synthesis of (Z)-octadec-9-enoic acid 7-[4-(4 benzo[b]thiophen-4-ylpiperazin-1-yl)butoxy]-2-oxo-2H-quinolin-1-ylmethyl ester

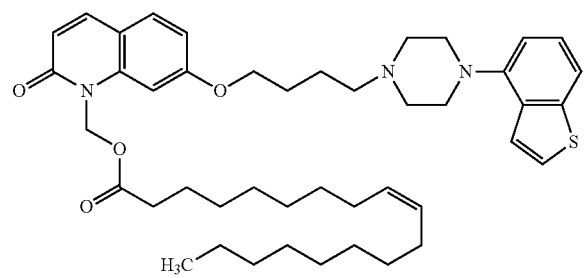

Using 7-[4-(4-benzo[b]thiophen-4-ylpiperazin-1-yl)butoxy]-1H-quinolin-2-one synthesized in the same manner as in WO2006/112464 (Example 1) and in the same manner as in Example 11, the title compound was obtained. ¹H-NMR (CDCl₃) δ: 0.87 (t, J=6.8 Hz, 3H), 1.18-1.35 (m, 20H), 1.57-1.68 (m, 2H), 1.72-1.82 (m, 2H), 1.86-2.04 (m, 6H), 2.36 (t, J=7.4 Hz, 2H), 2.52 (t, J=7.4 Hz, 2H), 2.67-2.79 (m, 4H), 3.14-3.24 (m, 4H), 4.08 (t, J=6.2 Hz, 2H), 5.26-5.39 (m, 2H), 6.34 (brs, 2H), 6.52 (d, J=9.5 Hz, 1H), 6.84 (dd, J=152.2, 8.6 Hz, 1H), 6.86-6.91 (m, 2H), 7.27 (t, J=7.9 Hz, 1H), 7.37-7.43 (m, 2H), 7.45 (d, J=8.6 Hz, 1H), 7.55 (d, J=8.0 Hz, 1H), 7.62 (d, J=9.5 Hz, 1H)

EXAMPLE40

Synthesis of 2-pentylheptanoic acid 7-[4-(4-benzo[b]thiophen-4-ylpiperazin-1-yl)butoxy]-2-oxo-3,4-dihydro-2H-quinolin-1-ylmethyl ester

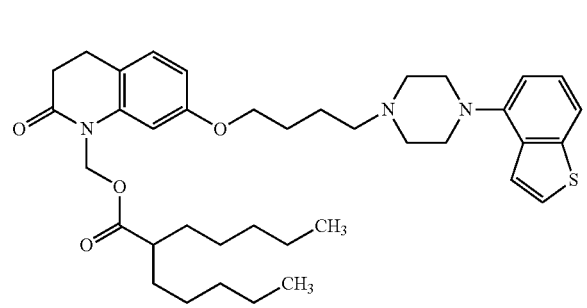 [SMILES: CCCCCC(CCCCC)C(=O)OCN1C(=O)CCc2ccc(OCCCCN3CCN(c4cccc5sccc45)CC3)cc21]

In the same manner as in Example 31, the title compound was obtained.

¹H-NMR (CDCl₃) δ: 0.85 (t, 6H), 1.17-1.31 (m, 12H), 1.37-1.49 (m, 2H), 1.55-1.78 (m, 4H), 1.79-1.89 (m, 2H), 2.32-2.41 (m, 1H), 2.52 (t, J=7.4 Hz, 2H), 2.64-2.77 (m, 6H), 2.82-2.89 (m, 2H), 3.13-3.24 (m, 4H), 3.97 (t, J=6.2 Hz, 2H), 5.94 (brs, 2H), 6.59 (dd, J=2.3, 8.2 Hz, 1H), 6.63 (d, J=2.3 Hz, 1H), 6.87-6.92 (m, 1H), 7.06 (d, J=8.2 Hz, 1H), 7.27 (dd, J=7.8, 7.8 Hz, 1H), 7.37-7.43 (m, 2H), 7.55 (d, J=8.0 Hz, 1H),

EXAMPLE41

Synthesis of icosanoic acid 7-[4-(4-benzo[b]thiophen-4-ylpiperazin-1-yl)butoxy]-2-oxo-2H-quinolin-1-ylmethyl ester

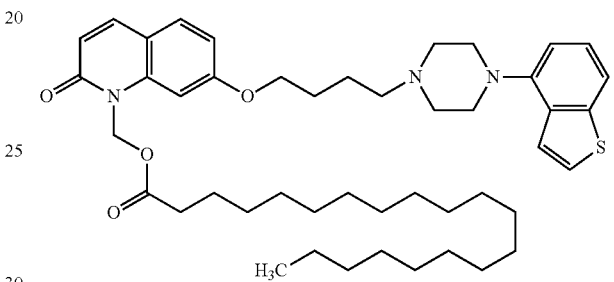

In the same manner as in Example 22, the title compound was obtained.

¹H-NMR (CDCl₃) δ: 0.88 (t, J=6.8 Hz, 3H), 1.18-1.33 (m, 32H), 1.58-1.67 (m, 2H), 1.72-1.82 (m, 2H), 1.86-1.96 (m, 2H), 2.36 (t, J=7.5 Hz, 2H), 2.54 (t, J=7.5 Hz, 2H), 2.67-2.77 (m, 4H), 3.14-3.24 (m, 4H), 4.08 (t, J=6.2 Hz, 2H), 6.34 (brs, 2H), 6.52 (d, J=9.5 Hz, 1H), 6.84 (dd, J=2.1, 8.6 Hz, 1H), 6.86-6.91 (m, 2H), 7.27 (dd, J=7.9, 7.9 Hz, 1H), 7.36-7.43 (m, 2H), 7.44 (d, J=8.6 Hz, 1H), 7.55 (d, J=8.0 Hz, 1H), 7.62 (d, J=9.5 Hz, 1H)

EXAMPLE42

Synthesis of hexadecanoic acid 7-[4-(4-benzo[b]thiophen-4-ylpiperazin-1-yl)butoxy]-2-oxo-2H-quinolin-1-ylmethyl ester

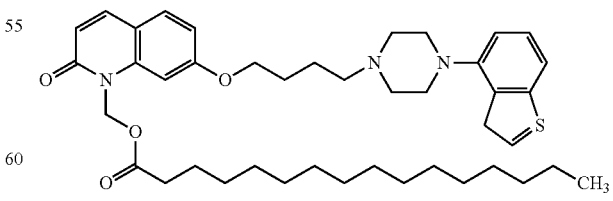

In the same manner as in Example 22, the title compound was obtained.

¹H-NMR (CDCl₃) δ: 0.87 (t, J=6.8 Hz, 3H), 1.18-1.32 (m, 24H), 1.58-1.67 (m, 2H), 1.72-1.95 (m, 4H), 2.36 (t, J=7.5 Hz, 2H), 2.54 (t, J=7.5 Hz, 2H), 2.66-2.78 (m, 4H), 3.14-3.24 (m, 4H), 4.08 (t, J=6.2 Hz, 2H), 6.34 (brs, 2H), 6.52 (d, J=9.5 Hz, 1H), 6.84 (dd, J=2.2, 8.6 Hz, 1H), 6.86-6.91 (m, 2H), 7.27 (dd, J=7.8, 7.8 Hz, 1H), 7.36-7.43 (m, 2H), 7.44 (d, J=9.5 Hz, 1H), 7.55 (d, J=8.6 Hz, 1H), 7.62 (d, J=9.5 Hz, 1H)

EXAMPLE 43

Synthesis of N-pentadecylcarbamic acid 7-[4-(4-benzo[b]thiophen-4-ylpiperazin-1-yl)butoxy]-2-oxo-2H-quinolin-1-ylmethyl ester

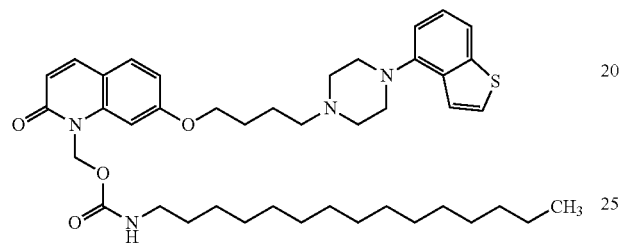

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

¹H-NMR (CDCl₃) δ: 0.88 (3H, t, J=7.0 Hz), 1.16-1.33 (24H, m), 1.42-1.53 (2H, m), 1.72-1.83 (2H, m), 1.86-1.95 (2H, m), 2.54 (2H, t, J=7.5 Hz), 2.67-2.78 (4H, m), 3.14-3.24 (6H, m), 4.11 (2H, t, J=6.0 Hz), 4.86 (1H, t, J=5.5 Hz), 6.33 (2H, s), 6.51 (1H, d, J=9.5 Hz), 6.83 (1H, dd, J=2.0 Hz, J=8.5 Hz), 6.89 (1H, d, J=7.5 Hz), 7.39 (1H, d, J=1.5 Hz), 7.24-7.29 (1H, m), 7.37-7.44 (3H, m), 7.55 (1H, d, J=8.0 Hz), 7.61 (1H, d, J=9.5 Hz)

EXAMPLE 44

Synthesis of N-methyl-N-octadecylcarbamic acid 7-[4-(4-benzo[b]thiophen-4-ylpiperazin-1-yl)butoxy]-2-oxo-2H-quinolin-1-ylmethyl ester

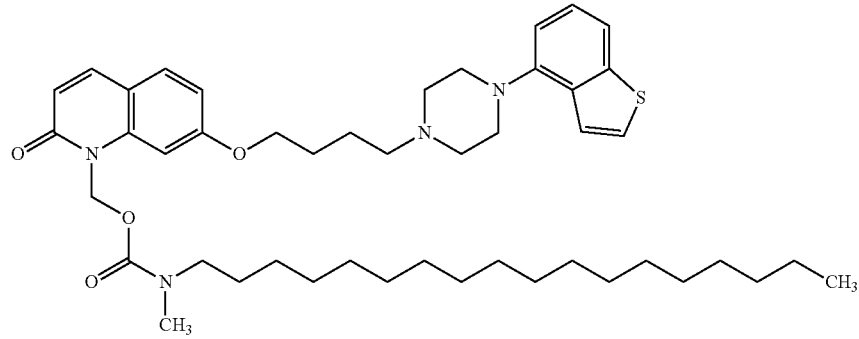 [SMILES: CCCCCCCCCCCCCCCCCCN(C)C(=O)OCn1c(=O)ccc2ccc(OCCCCN3CCN(c4cccc5sccc45)CC3)cc21]

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

¹H-NMR (CDCl₃) δ: 0.88 (3H, t, J=7.0 Hz), 1.01-1.32 (30H, m), 1.33-1.43 (1H, m), 1.47-1.58 (1H, m), 1.72-1.83 (2H, m), 1.85-1.95 (2H, m), 2.54 (2H, t, J=7.5 Hz), 2.66-2.78 (4H, m), {2.82 (s), 2.93 (s) total 3H (1:1)}, 3.12-3.24 (5H, m), 3.25-3.32 (1H, m), 4.09 (2H, t, J=5.5 Hz), 6.36 (2H, s), 6.52 (1H, dd, J=2.0 Hz, J=9.5 Hz), 6.83 (1H, d, J=8.5 Hz), 6.89 (1H, d, J=7.5 Hz), 7.10 (1H, d, J=17.5 Hz), 7.24-7.30 (1H, m), 7.36-7.46 (3H, m), 7.55 (1H, d, J=8.0 Hz), 7.66 (1H, dd, J=4.0 Hz, J=9.5 Hz)

EXAMPLE 45

Synthesis of N,N-dibutylcarbamic acid 7-[4-(4-benzo[b]thiophen-4-ylpiperazin-1-yl)butoxy]-2-oxo-2H-quinolin-1-ylmethyl ester

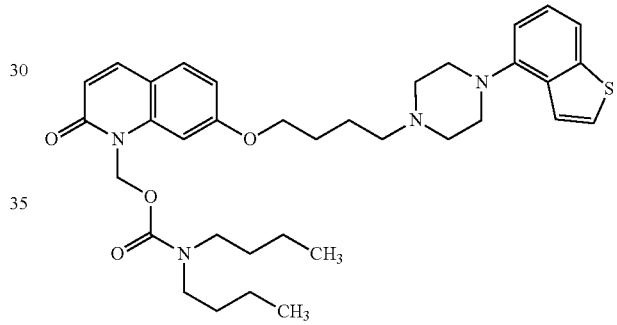

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

¹H-NMR (CDCl₃) δ: 0.72 (3H, t, J=7.5 Hz), 0.93 (3H, t, J=7.5 Hz), 1.06-1.19 (2H, m), 1.24-1.42 (4H, m), 1.48-1.59

(2H, m), 1.72-1.83 (2H, m), 1.85-1.95 (2H, m), 2.54 (2H, t, J=7.5 Hz), 2.65-2.83 (4H, m), 3.12 (2H, t, J=7.5 Hz), 3.15-3.23 (4H, m), 3.26 (2H, J=7.5 Hz), 4.09 (2H, t, J=6.0 Hz), 6.36 (2H, s), 6.51 (1H, d, J=9.5 Hz), 6.83 (1H, dd, J=2.0 Hz, J=8.5 Hz), 6.90 (1H, d, J=7.5 Hz), 7.07 (1H, d, J=2.0 Hz), 7.25-7.31 (1H, m), 7.37-7.45 (3H, m), 7.55 (1H, d, J=8.0 Hz), 7.61 (1H, d, J=9.5 Hz)

EXAMPLE 46

Synthesis of N-methylcarbamic acid 7-[4-(4-benzo[b]thiophen-4-ylpiperazin-1-yl)butoxy]-2-oxo-3,4-dihydro-2H-quinolin-1-ylmethyl ester

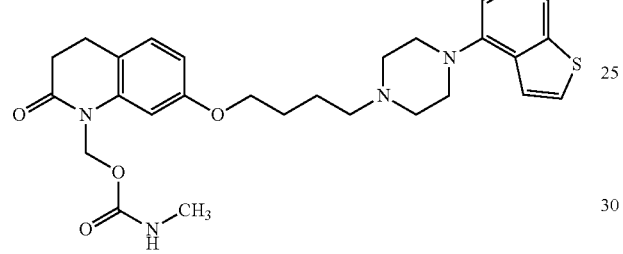

Using carbonic acid 7-[4-(4-benzo[b]thiophen-4-ylpiperazin-1-yl)butoxy]-2-oxo-3,4-dihydro-2H-quinolin-1-ylmethyl ester phenyl ester synthesized in the same manner as in Example 5 and in the same manner as in Example 10, the title compound was obtained.

$^1$H-NMR (CDCl$_3$) δ: 1.70-1.80 (2H, m), 1.81-1.91 (2H, m), 2.53 (2H, t, J=7.5 Hz), 2.63-2.77 (6H, m), 2.79-2.89 (5H, m), 3.14-3.24 (4H, m), 4.00 (2H, t, J=6.0 Hz), 4.75 (1H, d, J=4.0 Hz), 5.92 (2H, s), 6.59 (1H, dd, J=2.5 Hz, 8.5 Hz), 6.78 (1H, d, J=2.5 Hz), 6.90 (1H, d, J=7.5 Hz), 7.06 (1H, d, J=8.5 Hz), 7.24-7.30 (1H, m), 7.38 (1H, d, J=5.5 Hz), 7.41 (1H, d, J=5.5 Hz), 7.55 (1H, d, J=8.0 Hz)

EXAMPLE 47

Synthesis of N,N-dimethylcarbamic acid 7-[4-(4-benzo[b]thiophen-4-ylpiperazin-1-yl)butoxy]-2-oxo-3,4-dihydro-2H-quinolin-1-ylmethyl ester

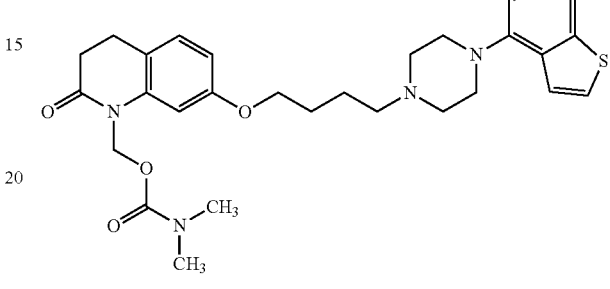

Using carbonic acid 7-[4-(4-benzo[b]thiophen-4-ylpiperazin-1-yl)butoxy]-2-oxo-3,4-dihydro-2H-quinolin-1-ylmethyl ester phenyl ester synthesized in the same manner as in Example 5 and in the same manner as in Example 10, the title compound was obtained.

$^1$H-NMR (CDCl$_3$) δ: 1.69-1.79 (2H, m), 1.81-1.90 (2H, m), 2.52 (2H, t, J=7.5 Hz), 2.64-2.77 (6H, m), 2.83-2.91 (2H, m), 2.88 (3H, s), 2.95 (3H, s), 3.14-3.24 (4H, m), 4.00 (2H, t, J=6.5 Hz), 5.92 (2H, s), 6.59 (1H, dd, J=2.5 Hz, 8.5 Hz), 6.78 (1H, d, J=2.5 Hz), 6.90 (1H, d, J=7.5 Hz), 7.06 (1H, d, J=8.5 Hz), 7.24-7.30 (1H, m), 7.38 (1H, d, J=5.5 Hz), 7.42 (1H, d, J=5.5 Hz), 7.55 (1H, d, J=8.0 Hz)

EXAMPLE 48

Synthesis of octadecanoic acid 7-[4-(4-benzo[b]thiophen-4-ylpiperazin-1-yl)butoxy]-2-oxo-3,4-dihydro-2H-quinolin-1-ylmethyl ester

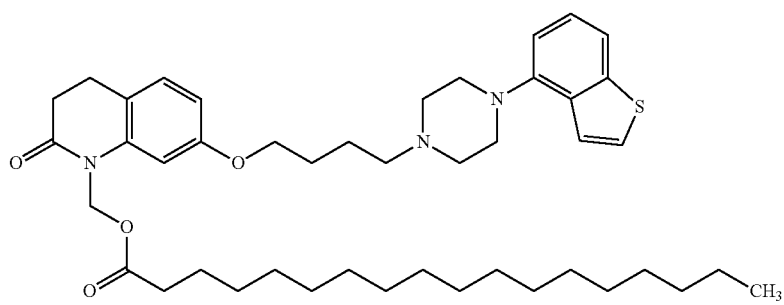 [SMILES: CCCCCCCCCCCCCCCCCC(=O)OCN1C(=O)CCc2ccc(OCCCCN3CCN(c4cccc5sccc45)CC3)cc21]

To a solution (20 ml) of 7-[4-(4-benzo[b]thiophen-4-ylpiperazin-1-yl)butoxy]-1-hydroxymethyl-3,4-dihydro-1H-quinolin-2-one (640 mg, 2.066 mmol) synthesized in the same manner as in Example 1, stearic acid (587 mg, 2.062 mmol), 1-(3-dimethylaminopropyl)-3-ethylcarbodiimide hydrochloride (395 mg, 2.062 mmol) in methylene chloride was added 4-dimethylaminopyridine (33.6 mg, 0.275 mmol), and the mixture was stirred at room temperature overnight. Water was added to the reaction mixture, and the mixture was extracted with ethyl acetate. This was purified by moderate-pressure silica gel column chromatography (hexane:ethyl acetate=1:0 to 0:1) and further by basic silica gel column chromatography (hexane:ethyl acetate=1:0 to 0:1) and concentrated under reduced pressure to give the title compound (yield 649 mg, 64.5%) as a colorless oil.

$^1$H-NMR (CDCl$_3$) δ: 0.88 (t, J=6.9 Hz, 3H), 1.18-1.35 (m, 28H), 1.59-1.68 (m, 2H), 1.69-1.79 (m, 2H), 1.80-1.90 (m, 2H), 2.36 (t, J=7.5 Hz, 2H), 2.52 (t, J=7.4 Hz, 2H), 2.65-2.76 (m, 6H), 2.83-2.90 (m, 2H), 3.14-3.24 (m, 4H), 3.98 (t, J=6.2 Hz, 2H), 5.92 (brs, 2H), 6.60 (dd, J=2.2, 8.1 Hz, 1H), 6.62 (d, J=2.2 Hz, 1H), 6.87-6.92 (m, 1H), 7.07 (d, J=8.1 Hz, 1H), 7.27 (dd, J=7.8, 7.8 Hz, 1H), 7.37-7.43 (m, 2H), 7.55 (d, J=8.0 Hz, 1H)

EXAMPLE 49

Synthesis of carbonic acid 7-[4-(4-benzo[b]thiophen-4-ylpiperazin-1-yl)butoxy]-2-oxo-3,4-dihydro-2H-quinolin-1-ylmethyl ester ethyl ester

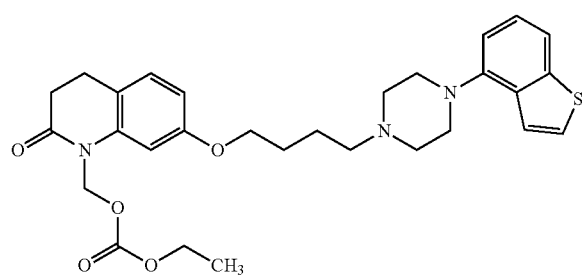 [SMILES: CCOC(=O)OCN1C(=O)CCc2ccc(OCCCCN3CCN(c4cccc5sccc45)CC3)cc21]

In the same manner as in Example 14, the title compound was obtained.

$^1$H-NMR (CDCl$_3$) δ: 1.32 (3H, t, J=7.2 Hz), 1.70-1.80 (2H, m), 1.80-1.90 (2H, m), 2.52 (2H, t, J=7.4 Hz), 2.65-2.73 (2H, m), 2.72 (4H, m), 2.86 (2H, t, J=7.2 Hz), 3.14-3.24 (4H, br), 4.00 (2H, t, J=6.2 Hz), 4.25 (2H, q, J=7.2 Hz), 5.94 (2H, brs), 6.59 (1H, dd, J=2.3, 8.3 Hz), 6.69 (1H, d, J=2.3 Hz), 6.90 (1H, d, J=7.6 Hz), 7.06 (1H, d, J=8.1 Hz), 7.27 (1H, t, J=7.8 Hz), 7.37-7.43 (2H, m), 7.55 (1H, d, J=8.1 Hz)

EXAMPLE 50

Synthesis of carbonic acid 7-[4-(4-benzo[b]thiophen-4-ylpiperazin-1-yl)butoxy]-2-oxo-2H-quinolin-1-ylmethyl ester ethyl ester

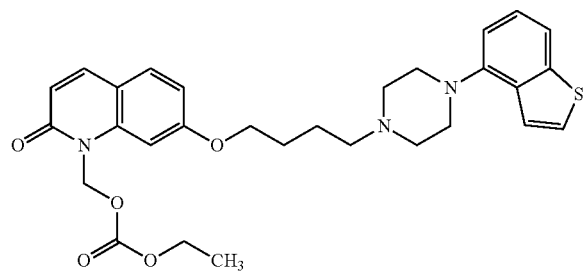 [SMILES: CCOC(=O)OCn1c(=O)ccc2ccc(OCCCCN3CCN(c4cccc5sccc45)CC3)cc21]

In the same manner as in Example 22, the title compound was obtained.

$^1$H-NMR (CDCl$_3$) δ: 1.31 (3H, t, J=7.1 Hz), 1.72-1.84 (2H, m), 1.84-1.96 (2H, m), 2.56 (2H, t, J=7.4 Hz), 2.70-2.80 (4H, m), 3.16-3.26 (4H, m), 4.10 (2H, t, J=6.2 Hz), 4.26 (2H, q, J=7.1 Hz), 6.35 (2H, brs), 6.50 (1H, d, J=9.5 Hz), 6.84 (1H, dd, J=2.2, 8.6 Hz), 6.88-6.95 (2H, m), 7.27 (1H, t, J=7.8 Hz), 7.37-7.41 (2H, m), 7.44 (1H, d, J=8.6 Hz), 7.55 (1H, d, J=8.0 Hz), 7.61 (1H, d, J=9.5 Hz)

EXAMPLE 51

Synthesis of N-ethylcarbamic acid 7-[4-(4-benzo[b]thiophen-4-ylpiperazin-1-yl)butoxy]-2-oxo-3,4-dihydro-2H-quinolin-1-ylmethyl ester

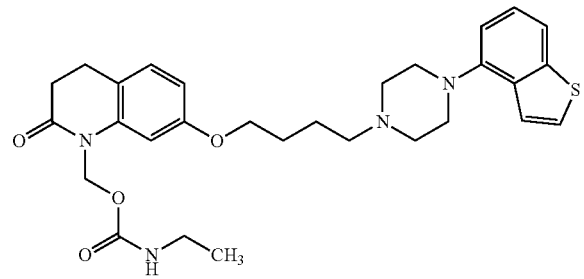 [SMILES: CCNC(=O)OCN1C(=O)CCc2ccc(OCCCCN3CCN(c4cccc5sccc45)CC3)cc21]

Using carbonic acid 7-[4-(4-benzo[b]thiophen-4-ylpiperazin-1-yl)butoxy]-2-oxo-3,4-dihydro-2H-quinolin-1-ylmethyl ester phenyl ester synthesized in the same manner as in Example 5 and in the same manner as in Example 10, the title compound was obtained.

$^1$H-NMR (CDCl$_3$) δ: 1.14 (3H, t, J=7.0 Hz), 1.69-1.80 (2H, m), 1.81-1.90 (2H, m), 2.52 (2H, t, J=7.5 Hz), 2.61-2.79 (6H, m), 2.81-2.90 (2H, m), 3.09-3.31 (6H, m), 4.00 (2H, t, J=6.0 Hz), 4.73-4.84 (1H, m), 5.92 (2H, s), 6.59 (1H, dd, J=2.5 Hz, 8.5 Hz), 6.79 (1H, d, J=2.0 Hz), 6.90 (1H, d, J=7.5 Hz), 7.06 (1H, d, J=8.5 Hz), 7.24-7.30 (1H, m), 7.37-7.44 (2H, m), 7.55 (1H, d, J=8.0 Hz)

EXAMPLE 52

Synthesis of N,N-diethylcarbamic acid 7-[4-(4-benzo[b]thiophen-4-ylpiperazin-1-yl)butoxy]-2-oxo-3,4-dihydro-2H-quinolin-1-ylmethyl ester

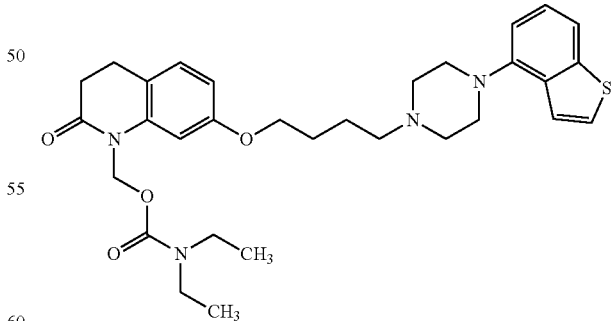

Using carbonic acid 7-[4-(4-benzo[b]thiophen-4-ylpiperazin-1-yl)butoxy]-2-oxo-3,4-dihydro-2H-quinolin-1-ylmethyl ester phenyl ester synthesized in the same manner as in Example 5 and in the same manner as in Example 10, the title compound was obtained.

$^1$H-NMR (CDCl$_3$) δ: 1.00-1.19 (6H, m), 1.66-1.79 (2H, m), 1.80-1.91 (2H, m), 2.52 (2H, t, J=7.5 Hz), 2.63-2.78 (6H, m), 2.82-2.90 (2H, m), 3.14-3.38 (8H, m), 3.99 (2H, t, J=6.0 Hz), 5.93 (2H, s), 6.59 (1H, dd, J=2.5 Hz, 8.5 Hz), 6.77 (1H, d, J=2.5 Hz), 6.90 (1H, d, J=7.5 Hz), 7.06 (1H, d, J=8.5 Hz), 7.24-7.30 (1H, m), 7.38 (1H, d, J=5.5 Hz), 7.41 (1H, d, J=5.5 Hz), 7.55 (1H, d, J=8.0 Hz)

EXAMPLE 53

Synthesis of N-methylcarbamic acid 7-[4-(4-benzo[b]thiophen-4-ylpiperazin-1-yl)butoxy]-2-oxo-2H-quinolin-1-ylmethyl ester

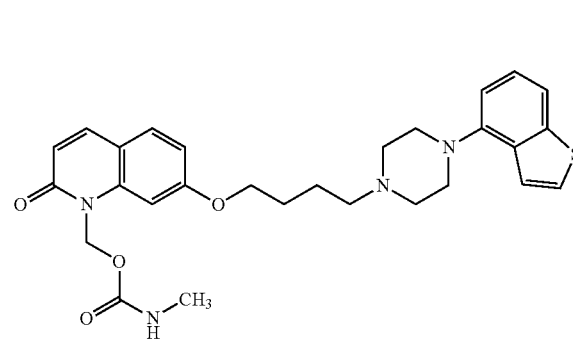

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

¹H-NMR (CDCl₃) δ: 1.73-1.84 (2H, m), 1.85-1.96 (2H, m), 2.55 (2H, t, J=7.5 Hz), 2.66-2.78 (4H, m), {2.82 (s), 2.84 (s) total 3H (1:1)}, 3.13-3.26 (4H, m), 4.12 (2H, t, J=6.0 Hz), 4.76-4.86 (1H, m), 6.33 (2H, s), 6.51 (1H, d, J=9.5 Hz), 6.83 (1H, dd, J=2.0 Hz, J=8.5 Hz), 6.89 (1H, d, J=7.5 Hz), 7.15 (1H, d, J=2.0 Hz), 7.24-7.31 (1H, m), 7.37-7.46 (3H, m), 7.55 (1H, d, J=8.0 Hz), 7.62 (1H, d, J=9.5 Hz)

EXAMPLE 54

Synthesis of 2-pentylheptanoic acid 7-[4-(4-benzo[b]thiophen-4-ylpiperazin-1-yl)butoxy]-2-oxo-2H-quinolin-1-ylmethyl ester

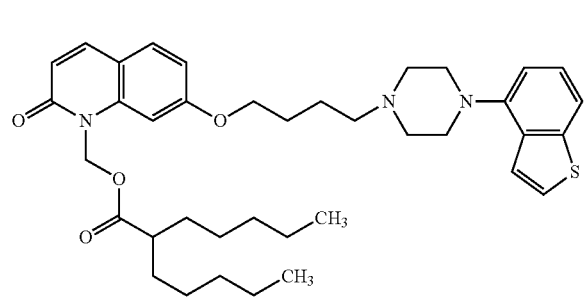 [SMILES: CCCCCC(CCCCC)C(=O)OCn1c(=O)ccc2ccc(OCCCCN3CCN(c4cccc5sccc45)CC3)cc21]

In the same manner as in Example 22, the title compound was obtained.

¹H-NMR (CDCl₃) δ: 0.80 (t, J=6.5 Hz, 6H), 1.13-1.24 (m, 12H), 1.37-1.48 (m, 2H), 1.54-1.66 (m, 2H), 1.71-1.81 (m, 2H), 1.85-1.95 (m, 2H), 2.33-2.43 (m, 1H), 2.54 (t, J=7.4 Hz, 2H), 2.64-2.79 (m, 4H), 3.13-3.26 (m, 4H), 4.07 (t, J=6.2 Hz, 2H), 6.36 (brs, 2H), 6.52 (d, J=9.5 Hz, 1H), 6.83 (dd, J=2.1, 8.6 Hz, 1H), 6.87-6.93 (m, 2H), 7.27 (dd, J=7.8, 7.8 Hz, 1H), 7.37-7.43 (m, 2H), 7.44 (d, J=8.6 Hz, 1H), 7.55 (d, J=8.0 Hz, 1H), 7.62 (d, J=9.5 Hz, 1H)

EXAMPLE 55

Synthesis of N-ethylcarbamic acid 7-[4-(4-benzo[b]thiophen-4-ylpiperazin-1-yl)butoxy]-2-oxo-2H-quinolin-1-ylmethyl ester

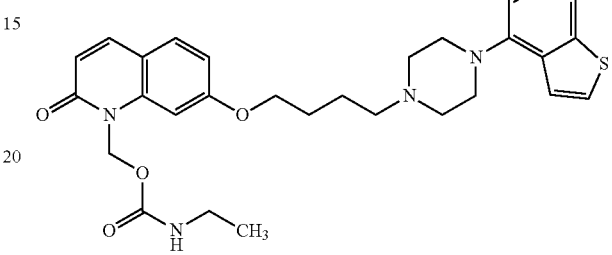

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

¹H-NMR (CDCl₃) δ: 1.14 (3H, t, J=7.0 Hz), 1.72-1.82 (2H, m), 1.85-1.95 (2H, m), 2.54 (2H, t, J=7.5 Hz), 2.66-2.78 (4H, m), 3.13-3.30 (6H, m), 4.12 (2H, t, J=6.0 Hz), 4.80-4.89 (1H, m), 6.33 (2H, s), 6.51 (1H, d, J=9.5 Hz), 6.83 (1H, dd, J=2.0 Hz, J=8.5 Hz), 6.87-6.92 (1H, m), 7.13-7.17 (1H, m), 7.24-7.30 (1H, m), 7.37-7.45 (3H, m), 7.55 (1H, d, J=8.0 Hz), 7.62 (1H, d, J=9.5 Hz)

EXAMPLE 56

Synthesis of N,N-dimethylcarbamic acid 7-[4-(4-benzo[b]thiophen-4-ylpiperazin-1-yl)butoxy]-2-oxo-2H-quinolin-1-ylmethyl ester

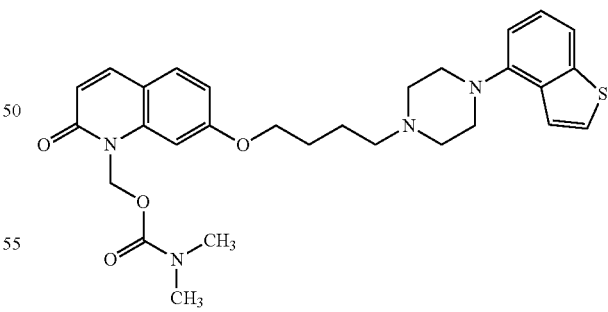

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

¹H-NMR (CDCl₃) δ: 1.72-1.82 (2H, m), 1.86-1.95 (2H, m), 2.54 (2H, t, J=7.5 Hz), 2.67-2.78 (4H, m), 2.86 (3H, s), 2.96 (3H, s), 3.15-3.24 (4H, m), 4.10 (2H, t, J=6.0 Hz), 6.35 (2H, s), 6.52 (1H, d, J=9.5 Hz), 6.83 (1H, dd, J=2.0 Hz, J=8.5

Hz), 6.89 (1H, d, J=7.5 Hz), 7.12 (1H, d, J=2.0 Hz), 7.24-7.31 (1H, m), 7.37-7.45 (3H, m), 7.55 (1H, d, J=8.0 Hz), 7.62 (1H, d, J=9.5 Hz)

EXAMPLE 57

Synthesis of N,N-diethylcarbamic acid 7-[4-(4-benzo[b]thiophen-4-ylpiperazin-1-yl)butoxy]-2-oxo-2H-quinolin-1-ylmethyl ester

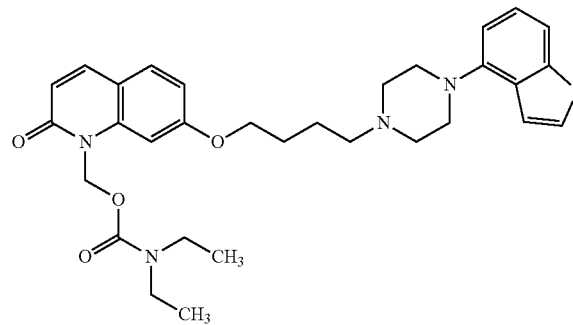

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

$^1$H-NMR (CDCl$_3$) δ: 1.01 (3H, t, J=7.0 Hz), 1.15 (3H, t, J=7.0 Hz), 1.72-1.82 (2H, m), 1.84-1.95 (2H, m), 2.54 (2H, t, J=7.5 Hz), 2.64-2.808 (4H, m), 3.11-3.26 (6H, m), 3.34 (2H, q, J=7.0 Hz), 4.09 (2H, t, J=6.0 Hz), 6.36 (2H, s), 6.52 (1H, d, J=9.5 Hz), 6.83 (1H, dd, J=2.0 Hz, J=8.5 Hz), 6.87-6.92 (1H, m), 7.09 (1H, d, J=2.0 Hz), 7.24-7.31 (1H, m), 7.37-7.46 (3H, m), 7.55 (1H, d, J=8.0 Hz), 7.62 (1H, d, J=9.5 Hz)

EXAMPLE 58

Synthesis of hexanoic acid 7-[4-(4-benzo[b]thiophen-4-ylpiperazin-1-yl)butoxy]-2-oxo-2H-quinolin-1-ylmethyl ester

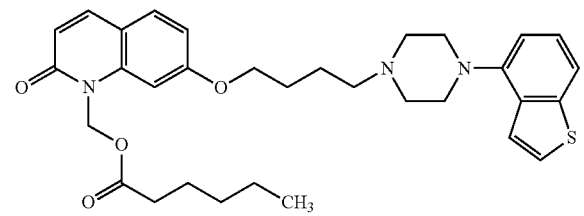 [SMILES: CCCCCC(=O)OCn1c(=O)ccc2ccc(OCCCCN3CCN(c4cccc5sccc45)CC3)cc21]

Using 7-[4-(4-benzo[b]thiophen-4-ylpiperazin-1-yl)butoxy]-1H-quinolin-2-one synthesized in the same manner as in WO2006/112464 (Example 1) and in the same manner as in Example 11, the title compound was obtained.

$^1$H-NMR (CDCl$_3$) δ: 0.85 (t, J=6.8 Hz, 3H), 1.25-1.33 (m, 4H), 1.58-1.69 (m, 2H), 1.70-1.85 (m, 2H), 1.85-1.95 (m, 2H), 2.36 (t, J=7.5 Hz, 2H), 2.54 (t, J=7.4 Hz, 2H), 2.67-2.78 (m, 4H), 3.15-3.25 (m, 4H), 4.08 (t, J=6.2 Hz, 2H), 6.34 (brs, 2H), 6.52 (d, J=9.5 Hz, 1H), 6.84 (dd, J=2.2, 8.6 Hz, 1H), 6.84-6.92 (m, 2H), 7.27 (dd, J=7.8, 7.8 Hz, 1H), 7.37-7.43 (m, 2H), 7.45 (d, J=8.6 Hz, 1H), 7.55 (d, J=8.1 Hz, 1H), 7.62 (d, J=9.5 Hz, 1H)

EXAMPLE 59

Synthesis of decanoic acid 7-[4-(4-benzo[b]thiophen-4-ylpiperazin-1-yl)butoxy]-2-oxo-2H-quinolin-1-ylmethyl ester

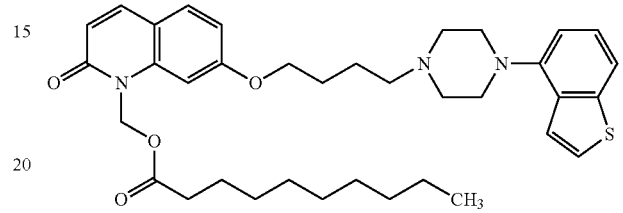

Using 7-[4-(4-benzo[b]thiophen-4-ylpiperazin-1-yl)butoxy]-1H-quinolin-2-one synthesized in the same manner as in WO2006/112464 (Example 1) and in the same manner as in Example 11, the title compound was obtained.

$^1$H-NMR (CDCl$_3$) δ: 0.86 (t, J=6.8 Hz, 3H), 1.17-1.32 (m, 12H), 1.57-1.68 (m, 2H), 1.72-1.82 (m, 2H), 1.85-1.95 (m, 2H), 2.36 (t, J=7.5 Hz, 2H), 2.54 (t, J=7.5 Hz, 2H), 2.65-2.78 (m, 4H), 3.13-3.25 (m, 4H), 4.08 (t, J=6.2 Hz, 2H), 6.34 (brs, 2H), 6.52 (d, J=9.5 Hz, 1H), 6.84 (d, J=2.2, 8.6 Hz, 1H), 6.86-6.92 (m, 2H), 7.27 (dd, J=7.8, 7.8 Hz, 1H), 7.37-7.43 (m, 2H), 7.45 (d, J=8.6 Hz, 1H), 7.55 (d, J=8.0 Hz, 1H), 7.62 (d, J=9.5 Hz, 1H)

EXAMPLE 60

Synthesis of octadecanoic acid 7-[4-(4-benzo[b]thiophen-4-ylpiperazin-1-yl)butoxy]-2-oxo-2H-quinolin-1-ylmethyl ester

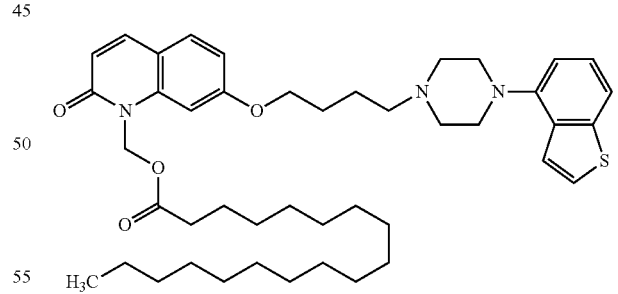

In the same manner as in Example 22, the title compound was obtained.

$^1$H-NMR (CDCl$_3$) δ: 0.88 (t, J=6.8 Hz, 3H), 1.18-1.33 (m, 28H), 1.58-1.67 (m, 2H), 1.72-1.82 (m, 2H), 1.85-1.95 (m, 2H), 2.36 (t, J=7.5 Hz, 2H), 2.54 (t, J=7.5 Hz, 2H), 2.66-2.79 (m, 4H), 3.14-3.25 (m, 4H), 4.08 (t, J=6.2 Hz, 2H), 6.34 (brs, 2H), 6.52 (d, J=9.5 Hz, 1H), 6.84 (dd, J=2.2, 8.6 Hz, 1H), 6.87-6.91 (m, 2H), 7.27 (dd, J=7.8, 7.8 Hz, 1H), 7.37-7.43 (m, 2H), 7.45 (d, J=8.6 Hz, 1H), 7.55 (d, J=8.0 Hz, 1H), 7.62 (d, J=9.5 Hz, 1H)

EXAMPLE 61

Synthesis of acetic acid 7-[4-(4-benzo[b]thiophen-4-ylpiperazin-1-yl)butoxy]-2-oxo-2H-quinolin-1-ylmethyl ester

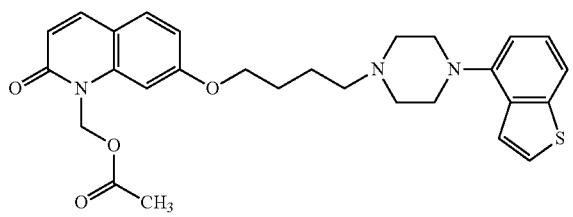 [SMILES: CC(=O)OCn1c(=O)ccc2ccc(OCCCCN3CCN(c4cccc5sccc45)CC3)cc21]

Acetic acid 7-(4-chlorobutoxy)-2-oxo-2H-quinolin-1-ylmethyl ester (299 mg), 1-benzo[b]thiophen-4-ylpiperazine hydrochloride (235 mg), potassium carbonate (319 mg) and sodium iodide (152 mg) were suspended in DMF (5 ml), and this was stirred at 70° C. for 3 hr and further at 80° C. for 4 hr. After cooling to room temperature, to the reaction mixture was added aqueous ammonium chloride solution, and the mixture was extracted with ethyl acetate, dried over sodium sulfate, and concentrated under reduced pressure. The residue was purified by moderate-pressure silica gel column chromatography (hexane:ethyl acetate=1:0 to 1:9) and further by basic silica gel column chromatography, and concentrated under reduced pressure to give the title compound (132 mg) as a colorless amorphous solid.

$^1$H-NMR (CDCl$_3$) δ: 1.73-1.83 (m, 2H), 1.84-1.95 (m, 2H), 2.13 (s, 3H), 2.54 (t, J=7.4 Hz, 2H), 2.68-2.77 (m, 4H), 3.15-3.24 (m, 4H), 4.09 (t, J=6.3 Hz, 2H), 6.33 (brs, 2H), 6.52 (d, J=9.5 Hz, 1H), 6.85 (dd, J=2.2, 8.6 Hz, 1H), 6.87-6.92 (m, 2H), 7.27 (dd, J=7.8, 7.8 Hz, 1H), 7.37-7.43 (m, 2H), 7.45 (d, J=8.6 Hz, 1H), 7.55 (d, J=8.1 Hz, 1H), 7.63 (d, J=9.5 Hz, 1H)

EXAMPLE 62

Synthesis of N-benzylcarbamic acid 7-[4-(4-benzo[b]thiophen-4-ylpiperazin-1-yl)butoxy]-2-oxo-2H-quinolin-1-ylmethyl ester

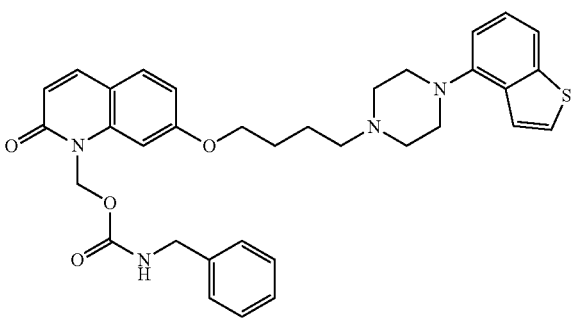 [SMILES: O=C(NCc1ccccc1)OCn1c(=O)ccc2ccc(OCCCCN3CCN(c4cccc5sccc45)CC3)cc21]

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

$^1$H-NMR (CDCl$_3$) δ: 1.69-1.80 (2H, m), 1.82-1.92 (2H, m), 2.52 (2H, t, J=7.5 Hz), 2.64-2.77 (4H, m), 3.11-3.24 (4H, m), 4.07 (2H, t, J=6.0 Hz), 4.41 (2H, t, J=6.0 Hz), 5.26 (1H, t, J=6.0 Hz), 6.37 (2H, s), 6.51 (1H, d, J=9.5 Hz), 6.83 (1H, dd, J=2.0 Hz, J=8.5 Hz), 6.88 (1H, d, J=7.0 Hz), 7.15 (1H, d, J=1.5 Hz), 7.23-7.34 (6H, m), 7.38 (1H, d, J=5.5 Hz), 7.41 (1H, d, J=5.5 Hz), 7.43 (1H, d, J=8.5 Hz), 7.55 (1H, d, J=8.0 Hz), 7.61 (1H, d, J=9.5 Hz)

EXAMPLE 63

Synthesis of N-cyclohexylmethylcarbamic acid 7-[4-(4-benzo[b]thiophen-4-ylpiperazin-1-yl)butoxy]-2-oxo-2H-quinolin-1-ylmethyl ester

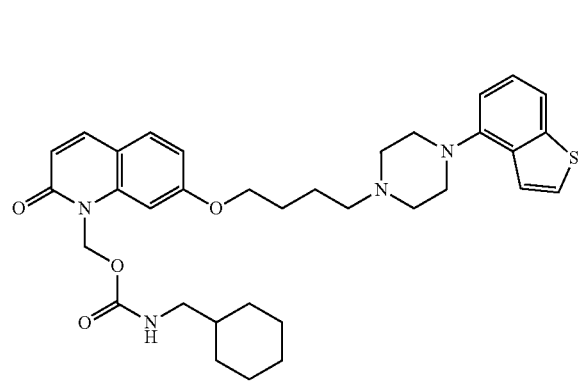 [SMILES: O=C(NCC1CCCCC1)OCn1c(=O)ccc2ccc(OCCCCN3CCN(c4cccc5sccc45)CC3)cc21]

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

$^1$H-NMR (CDCl$_3$) δ: 0.83-0.97 (2H, m), 1.02-1.28 (3H, m), 1.36-1.50 (1H, m), 1.54-1.84 (7H, m), 1.86-1.96 (2H, m), 2.54 (2H, t, J=7.5 Hz), 2.65-2.81 (4H, m), 3.05 (2H, t, J=6.5 Hz), 3.13-3.27 (4H, m), 4.11 (2H, t, J=6.0 Hz), 4.90 (1H, t, J=6.0 Hz), 6.33 (2H, s), 6.51 (1H, d, J=9.5 Hz), 6.83 (1H, dd, J=2.0 Hz, J=8.5 Hz), 6.89 (1H, d, J=7.5 Hz), 7.16 (1H, d, J=2.0 Hz), 7.24-7.30 (1H, m), 7.37-7.45 (3H, m), 7.55 (1H, d, J=8.0 Hz), 7.62 (1H, d, J=9.5 Hz)

EXAMPLE 64

Synthesis of {7-[4-(4-benzo[b]thiophen-4-ylpiperazin-1-yl)butoxy]-2-oxo-2H-quinolin-1-ylmethoxycarbonylamino}acetic acid methyl ester

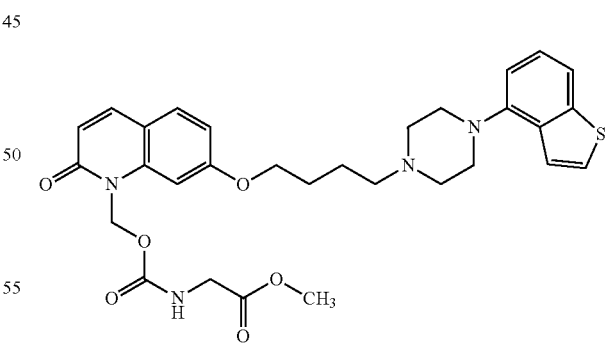

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

$^1$H-NMR (CDCl$_3$) δ: 1.73-1.84 (2H, m), 1.86-1.94 (2H, m), 2.54 (2H, t, J=7.5 Hz), 2.66-2.81 (4H, m), 3.12-3.27 (4H, m), 3.74 (3H, s), 4.00 (2H, d, J=5.5 Hz), 4.11 (2H, t, J=6.0 Hz), 5.34-5.44 (1H, m), 6.36 (2H, s), 6.51 (1H, d, J=9.5 Hz), 6.84 (1H, dd, J=2.0 Hz, J=8.5 Hz), 6.87-6.92 (1H, m), 7.09

(1H, d, J=2.0 Hz), 7.25-7.30 (1H, m), 7.37-7.46 (3H, m), 7.55 (1H, d, J=8.0 Hz), 7.62 (1H, d, J=9.5 Hz)

EXAMPLE 65

Synthesis of tetradecanoic acid 7-[4-(4-benzo[b]thiophen-4-ylpiperazin-1-yl)butoxy]-2-oxo-2H-quinolin-1-ylmethyl ester

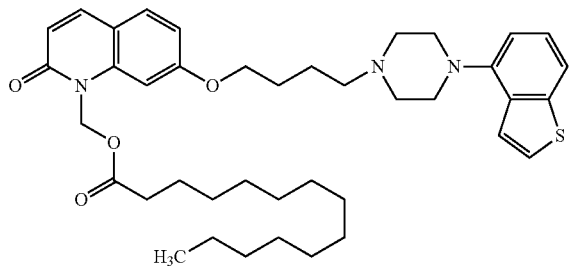 [SMILES: CCCCCCCCCCCCCC(=O)OCn1c(=O)ccc2ccc(OCCCCN3CCN(c4cccc5sccc45)CC3)cc21]

In the same manner as in Example 61, the title compound was obtained.

$^1$H-NMR (CDCl$_3$) δ: 0.87 (t, J=6.8 Hz, 3H), 1.18-1.33 (m, 20H), 1.58-1.68 (m, 2H), 1.72-1.82 (m, 2H), 1.84-1.95 (m, 2H), 2.36 (t, J=7.5 Hz, 2H), 2.54 (t, J=7.5 Hz, 2H), 2.66-2.79 (m, 4H), 3.13-3.25 (m, 4H), 4.08 (t, J=6.2 Hz, 2H), 6.34 (brs, 2H), 6.52 (d, J=9.5 Hz, 1H), 6.84 (dd, J=2.2, 8.6 Hz, 1H), 6.87-6.91 (m, 2H), 7.27 (dd, J=7.8, 7.8 Hz, 1H), 7.37-7.43 (m, 2H), 7.45 (d, J=8.6 Hz, 1H), 7.55 (d, J=8.1 Hz, 1H), 7.62 (d, J=9.5 Hz, 1H)

EXAMPLE 66

Synthesis of 7-[4-(4-benzo[b]thiophen-4-ylpiperazin-1-yl)butoxy]-1-(2,2,2-trifluoroethoxymethyl)-3,4-dihydro-1H-quinolin-2-one

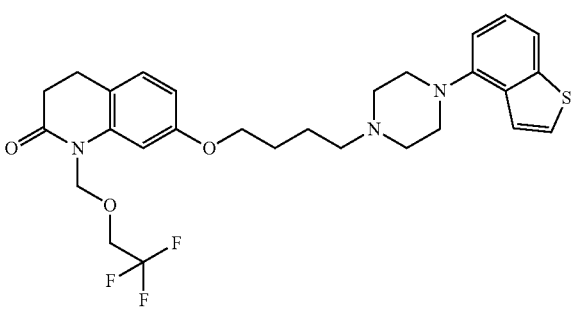 [SMILES: O=C1CCc2ccc(OCCCCN3CCN(c4cccc5sccc45)CC3)cc2N1COCC(F)(F)F]

2,2,2-Trifluoroethanol (0.10 ml) was dissolved in anhydrous THF (3 ml) under a nitrogen atmosphere and sodium hydride (about 55% oil) (60 mg) was added under ice-cooling. The reaction mixture was stirred at room temperature for 30 min under a nitrogen atmosphere. The obtained solution was ice-cooled again and, under a nitrogen atmosphere, a solution (3 ml) of carbonic acid 7-[4-(4-benzo[b]thiophen-4-ylpiperazin-1-yl)butoxy]-2-oxo-3,4-dihydro-2H-quinolin-1-ylmethyl ester phenyl ester (0.25 g) obtained in Example 5 in anhydrous THF was added using a cannula. The reaction mixture was stirred at room temperature for 18 hr under a nitrogen atmosphere. To the reaction mixture was added ice water to discontinue the reaction, and the mixture was extracted with ethyl acetate. The organic layer was dried over sodium sulfate, and concentrated by filtration. The obtained residue was purified by silica gel column chromatography (ethyl acetate) to give the title compound (90 mg) as a colorless oil.

$^1$H-NMR (CDCl$_3$) δ: 1.69-1.93 (4H, m), 2.47-2.56 (2H, m), 2.64-2.76 (6H, m), 2.80-2.87 (2H, m), 3.13-3.25 (4H, m), 3.93-4.14 (4H, m), 5.42 (2H, s), 6.61 (1H, dd, J=2.5 Hz, J=8.5 Hz), 6.86-6.91 (2H, m), 7.05 (1H, d, J=8.5 Hz), 7.24-7.28 (1H, m), 7.37 (1H, d, J=5.5 Hz), 7.41 (1H, d, J=5.5 Hz), 7.54 (1H, d, J=8.0 Hz)

EXAMPLE 67

Synthesis of morpholine-4-carboxylic acid 7-[4-(4-benzo[b]thiophen-4-ylpiperazin-1-yl)butoxy]-2-oxo-2H-quinolin-1-ylmethyl ester

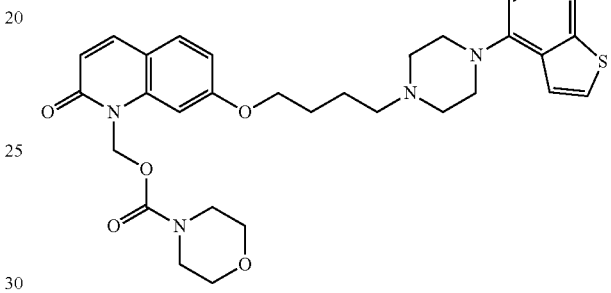

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

$^1$H-NMR (CDCl$_3$) δ: 1.72-1.82 (2H, m), 1.87-1.96 (2H, m), 2.54 (2H, t, J=7.5 Hz), 2.66-2.80 (4H, m), 3.16-3.34 (4H, m), 3.37-3.73 (8H, m), 4.10 (2H, d, J=6.0 Hz), 6.37 (2H, s), 6.52 (1H, d, J=9.5 Hz), 6.84 (1H, dd, J=2.0 Hz, J=8.5 Hz), 6.89 (1H, d, J=7.5 Hz), 7.09 (1H, d, J=2.5 Hz), 7.24-7.30 (1H, m), 7.37-7.43 (2H, m), 7.45 (1H, d, J=8.5 Hz), 7.55 (1H, d, J=8.0 Hz), 7.63 (1H, d, J=9.5 Hz)

EXAMPLE 68

Synthesis of decanoic acid 7-[4-(4-benzo[b]thiophen-4-ylpiperazin-1-yl)butoxy]-2-oxo-3,4-dihydro-2H-quinolin-1-ylmethyl ester

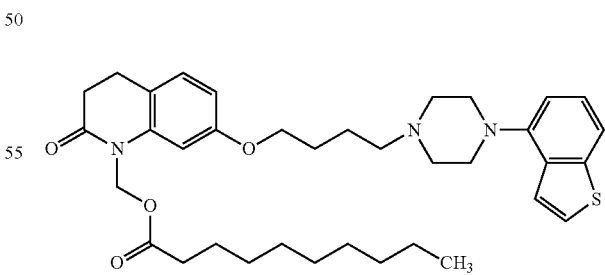

In the same manner as in Example 11, the title compound was obtained.

$^1$H-NMR (CDCl$_3$) δ: 0.87 (t, J=6.8 Hz, 3H), 1.20-1.34 (m, 12H), 1.58-1.68 (m, 2H), 1.69-1.80 (m, 2H), 1.80-1.90 (m, 2H), 2.36 (t, J=7.6 Hz, 2H), 2.52 (t, J=7.5 Hz, 2H), 2.64-2.77 (m, 6H), 2.83-2.89 (m, 2H), 3.13-3.24 (m, 4H), 3.98 (t, J=6.2 Hz, 2H), 5.92 (brs, 2H), 6.60 (dd, J=2.2, 8.1 Hz, 1H), 6.62 (d, J=2.2 Hz, 1H), 6.87-6.92 (m, 1H), 7.07 (d, J=8.1 Hz, 1H), 7.27 (dd, J=7.9, 7.9 Hz, 1H), 7.37-7.43 (m, 2H), 7.55 (d, J=8.0 Hz, 1H)

EXAMPLE 69

Synthesis of 7-[4-(4-benzo[b]thiophen-4-ylpiperazin-1-yl)butoxy]-2-oxo-2H-quinolin-1-ylmethyl benzyloxycarbamate

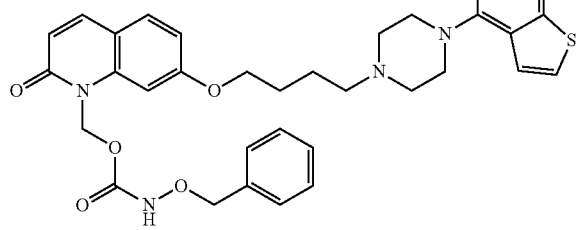

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

$^1$H-NMR (CDCl$_3$) δ: 1.67-1.79 (2H, m), 1.81-1.92 (2H, m), 2.49 (2H, t, J=7.5 Hz), 2.60-2.74 (4H, m), 3.07-3.21 (4H, m), 4.05 (2H, d, J=6.0 Hz), 4.85 (2H, s), 6.37 (2H, s), 6.46 (1H, d, J=9.5 Hz), 6.80-6.88 (2H, m), 7.03 (1H, d, J=2.0 Hz), 7.23-7.45 (9H, m), 7.54 (1H, d, J=8.0 Hz), 7.58 (1H, d, J=9.5 Hz), 8.11 (1H, s)

EXAMPLE 70

Synthesis of hexanoic acid 7-[4-(4-benzo[b]thiophen-4-ylpiperazin-1-yl)butoxy]-2-oxo-3,4-dihydro-2H-quinolin-1-ylmethyl ester

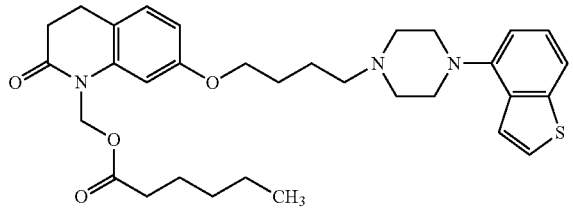

In the same manner as in Example 11, the title compound was obtained.

$^1$H-NMR (CDCl$_3$) δ: 0.88 (t, J=6.9 Hz, 3H), 1.26-1.34 (m, 4H), 1.59-1.69 (m, 2H), 1.69-1.80 (m, 2H), 1.80-1.90 (m, 2H), 2.36 (t, J=7.5 Hz, 2H), 2.53 (t, J=7.4 Hz, 2H), 2.64-2.77 (m, 6H), 2.83-2.89 (m, 2H), 3.14-3.24 (m, 4H), 3.98 (t, J=6.2 Hz, 2H), 5.92 (brs, 2H), 6.60 (dd, J=2.2, 8.1 Hz, 1H), 6.62 (d, J=2.2 Hz, 1H), 6.88-6.92 (m, 1H), 7.07 (d, J=8.1 Hz, 1H), 7.27 (dd, J=7.8, 7.8 Hz, 1H), 7.37-7.43 (m, 2H), 7.55 (d, J=8.0 Hz, 1H)

EXAMPLE 71

Synthesis of N-cyclohexylcarbamic acid 7-[4-(4-benzo[b]thiophen-4-ylpiperazin-1-yl)butoxy]-2-oxo-2H-quinolin-1-ylmethyl ester

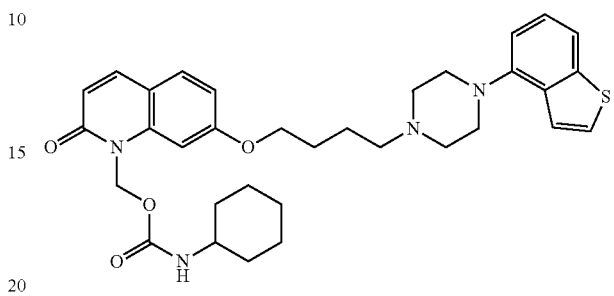

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

$^1$H-NMR (CDCl$_3$) δ: 1.02-1.22 (3H, m), 1.24-1.41 (2H, m), 1.52-1.97 (9H, m), 2.54 (2H, t, J=7.5 Hz), 2.64-2.82 (4H, m), 3.11-3.28 (4H, m), 3.45-3.59 (1H, m), 4.11 (2H, t, J=6.0 Hz), 4.83 (1H, d, J=8.0 Hz), 6.31 (2H, s), 6.50 (1H, d, J=9.5 Hz), 6.83 (1H, dd, J=2.0 Hz, J=8.5 Hz), 6.89 (1H, d, J=7.5 Hz), 7.14 (1H, brs), 7.24-7.30 (1H, m), 7.36-7.45 (3H, m), 7.55 (1H, d, J=8.0 Hz), 7.60 (1H, d, J=9.5 Hz)

EXAMPLE 72

Synthesis of carbonic acid 7-[4-(4-benzo[b]thiophen-4-ylpiperazin-1-yl)butoxy]-2-oxo-3,4-dihydro-2H-quinolin-1-ylmethyl ester methyl ester

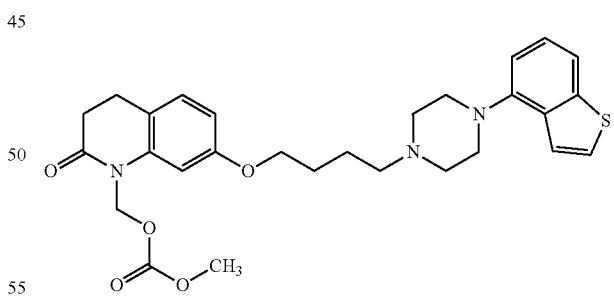

In the same manner as in Example 14, the title compound was obtained.

$^1$H-NMR (CDCl$_3$) δ: 1.68-1.80 (2H, m), 1.80-1.90 (2H, m), 2.52 (2H, t, J=7.4 Hz), 2.64-2.78 (6H, m), 2.86 (2H, t, J=7.0 Hz), 3.14-3.24 (4H, br), 3.83 (3H, s), 4.00 (2H, t, J=6.2 Hz), 5.95 (2H, brs), 6.59 (1H, dd, J=2.4, 8.2 Hz), 6.69 (1H, d, J=2.2 Hz), 6.90 (1H, d, J=7.4 Hz), 7.06 (1H, d, J=8.2 Hz), 7.27 (1H, t, J=7.8 Hz), 7.36-7.44 (2H, m), 7.55 (1H, d, J=8.0 Hz)

EXAMPLE 73

Synthesis of ({7-[4-(4-benzo[b]thiophen-4-ylpiperazin-1-yl)butoxy]-2-oxo-2H-quinolin-1-ylmethoxycarbonyl}methylamino)acetic acid methyl ester

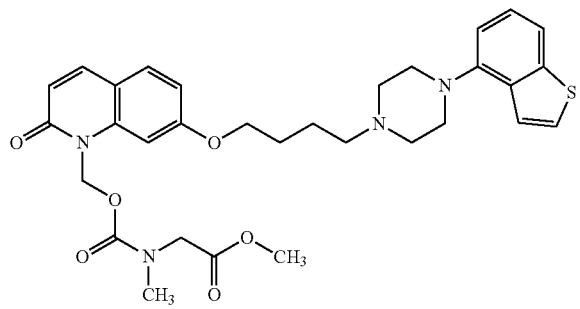 [SMILES: COC(=O)CN(C)C(=O)OCn1c(=O)ccc2ccc(OCCCCN3CCN(c4cccc5sccc45)CC3)cc21]

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

$^{1}$H-NMR (CDCl$_3$) δ: 1.72-1.83 (2H, m), 1.85-1.97 (2H, m), 2.50-2.60 (2H, m), 2.66-2.81 (4H, m), {2.92 (s), 3.02 (s) total 3H (1:1)}, 3.14-3.27 (4H, m), {3.53 (s), 3.74 (s) total 3H (1:1)}, 3.91 (1H, s), 4.06 (1H, s), 4.07-4.17 (2H, m), 6.33 (1H, s), 6.38 (1H, s), {6.50 (d, J=9.5 Hz), 6.52 (d, J=9.5 Hz total 1H (1:1)}, 6.80-6.86 (1H, m), {6.88 (brs), 6.90 (brs) total 1H (1:1)}, {6.98 (d, J=2.0 Hz), 7.06 (d, J=2.0 Hz) total 1H (1:1)}, 7.24-7.30 (1H, m), 7.37-7.46 (3H, m), 7.55 (1H, d, J=8.0 Hz), {7.61 (d, J=9.5 Hz), 7.63 (d, J=9.0 Hz) total 1H (1:1)}

EXAMPLE 74

Synthesis of undec-10-enoic acid 7-[4-(4-benzo[b]thiophen-4-ylpiperazin-1-yl)butoxy]-2-oxo-2H-quinolin-1-ylmethyl ester

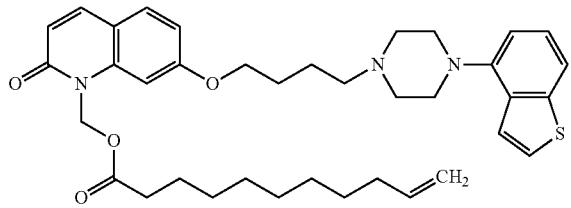 [SMILES: C=CCCCCCCCCC(=O)OCn1c(=O)ccc2ccc(OCCCCN3CCN(c4cccc5sccc45)CC3)cc21]

In the same manner as in Example 61, the title compound was obtained.

$^{1}$H-NMR (CDCl$_3$) δ: 1.19-1.38 (m, 10H), 1.58-1.67 (m, 2H), 1.72-1.82 (m, 2H), 1.86-1.95 (m, 2H), 1.97-2.06 (m, 2H), 2.36 (t, J=7.5 Hz, 2H), 2.54 (t, J=7.5 Hz, 2H), 2.66-2.79 (m, 4H), 3.15-3.24 (m, 4H), 4.08 (t, J=6.2 Hz, 2H), 4.88-4.94 (m, 1H), 4.94-5.02 (m, 1H), 5.73-5.85 (m, 1H), 6.34 (brs, 2H), 6.52 (d, J=9.5 Hz, 1H), 6.84 (dd, J=2.2, 8.6 Hz, 1H), 6.87-6.91 (m, 2H), 7.27 (dd, J=7.8, 7.8 Hz, 1H), 7.37-7.43 (m, 2H), 7.45 (d, J=8.6 Hz, 1H), 7.55 (d, J=8.1 Hz, 1H), 7.62 (d, J=9.5 Hz, 1H)

EXAMPLE 75

Synthesis of N-octadecylcarbamic acid 7-[4-(4-benzo[b]thiophen-4-ylpiperazin-1-yl)butoxy]-2-oxo-3,4-dihydro-2H-quinolin-1-ylmethyl ester

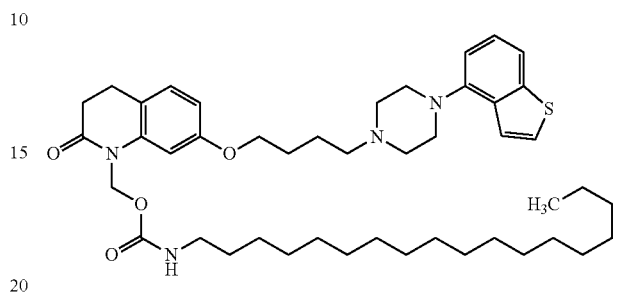

In the same manner as in Example 9, the title compound was obtained.

$^{1}$H-NMR (CDCl$_3$) δ: 0.88 (3H, t, J=7.0 Hz), 1.16-1.35 (30H, m), 1.42-1.54 (2H, m), 1.70-1.80 (2H, m), 1.81-1.90 (2H, m), 2.52 (2H, t, J=7.5 Hz), 2.62-2.78 (6H, m), 2.81-2.90 (2H, m), 3.12-3.27 (6H, m), 4.00 (2H, t, J=6.0 Hz), 4.79 (1H, t, J=5.5 Hz), 5.92 (2H, s), 6.59 (1H, dd, J=2.5 Hz, 8.0 Hz), 6.80 (1H, d, J=2.0 Hz), 6.89 (1H, d, J=7.5 Hz), 7.05 (1H, d, J=8.0 Hz), 7.24-7.30 (1H, m), 7.38 (1H, d, J=5.5 Hz), 7.41 (1H, d, J=5.5 Hz), 7.55 (1H, d, J=8.0 Hz)

EXAMPLE 76

Synthesis of N-pentadecylcarbamic acid 7-[4-(4-benzo[b]thiophen-4-ylpiperazin-1-yl)butoxy]-2-oxo-3,4-dihydro-2H-quinolin-1-ylmethyl ester

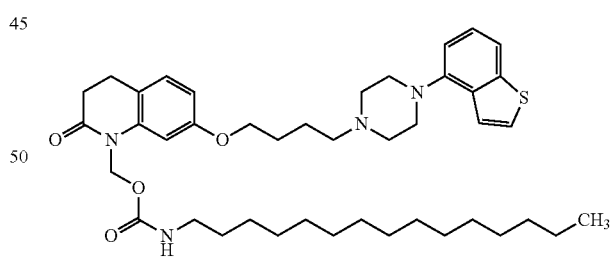

In the same manner as in Example 9, the title compound was obtained.

$^{1}$H-NMR (CDCl$_3$) δ: 0.88 (3H, t, J=7.0 Hz), 1.16-1.35 (24H, m), 1.43-1.53 (2H, m), 1.69-1.80 (2H, m), 1.81-1.90 (2H, m), 2.53 (2H, t, J=7.5 Hz), 2.63-2.77 (6H, m), 2.81-2.90 (2H, m), 3.14-3.25 (6H, m), 4.00 (2H, t, J=6.0 Hz), 4.80 (1H, t, J=5.5 Hz), 5.92 (2H, s), 6.59 (1H, dd, J=2.5 Hz, 8.0 Hz), 6.80 (1H, d, J=2.0 Hz), 6.89 (1H, d, J=7.5 Hz), 7.05 (1H, d, J=8.0 Hz), 7.24-7.30 (1H, m), 7.38 (1H, d, J=5.5 Hz), 7.41 (1H, dd, J=0.5 Hz, J=5.5 Hz), 7.55 (1H, d, J=8.0 Hz)

EXAMPLE 77

Synthesis of 2-methylbutyric acid 7-[4-(4-benzo[b]thiophen-4-ylpiperazin-1-yl)butoxy]-2-oxo-3,4-dihydro-2H-quinolin-1-ylmethyl ester

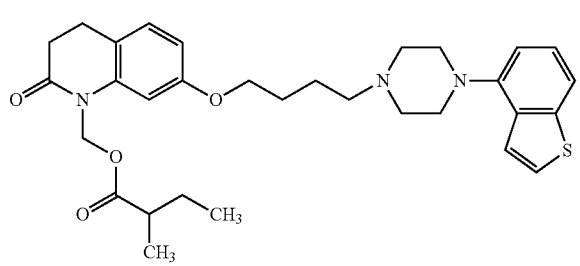 [SMILES: CCC(C)C(=O)OCN1C(=O)CCc2ccc(OCCCCN3CCN(c4cccc5sccc45)CC3)cc21]

In the same manner as in Example 48, the title compound was obtained.

$^1$H-NMR (CDCl$_3$) δ: 0.91 (t, J=7.4 Hz, 3H), 1.17 (d, J=7.0 Hz, 3H), 1.42-1.55 (m, 1H), 1.64-1.92 (m, 5H), 2.43 (m, 1H), 2.52 (t, J=7.5 Hz, 2H), 2.64-2.79 (m, 6H), 2.83-2.90 (m, 2H), 3.14-3.25 (m, 4H), 3.98 (t, J=6.2 Hz, 2H), 5.92 (brs, 2H), 6.57-6.63 (m, 2H), 6.90 (d, J=7.4 Hz, 1H), 7.07 (d, J=8.3 Hz, 1H), 7.27 (dd, J=7.8 Hz, 7.8 Hz, 1H), 7.37-7.43 (m, 2H), 7.55 (d, J=8.0 Hz, 1H)

EXAMPLE 78

Synthesis of 2-methylhexanoic acid 7-[4-(4-benzo[b]thiophen-4-ylpiperazin-1-yl)butoxy]-2-oxo-3,4-dihydro-2H-quinolin-1-ylmethyl ester

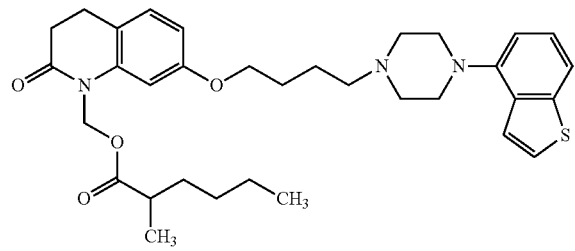

In the same manner as in Example 48, the title compound was obtained.

$^1$H-NMR (CDCl$_3$) δ: 0.86 (t, J=6.9 Hz, 3H), 1.16 (d, J=7.0 Hz, 3H), 1.23-1.32 (m, 4H), 1.36-1.48 (m, 1H), 1.58-1.79 (m, 3H), 1.79-1.89 (m, 2H), 2.43-2.56 (m, 3H), 2.64-2.77 (m, 6H), 2.83-2.90 (m, 2H), 3.14-3.25 (m, 4H), 3.98 (t, J=6.2 Hz, 2H), 5.92 (brs, 2H), 6.57-6.62 (m, 2H), 6.90 (d, J=7.5 Hz, 1H), 7.07 (d, J=8.0 Hz, 1H), 7.27 (dd, J=7.8, 7.8 Hz, 1H), 7.38 (d, J=5.6 Hz, 1H), 7.41 (d, J=5.6 Hz, 1H), 7.55 (d, J=8.0 Hz, 1H)

EXAMPLE 79

Synthesis of N-methyl-N-octadecylcarbamic acid 7-[4-(4-benzo[b]thiophen-4-ylpiperazin-1-yl)butoxy]-2-oxo-3,4-dihydro-2H-quinolin-1-ylmethyl ester

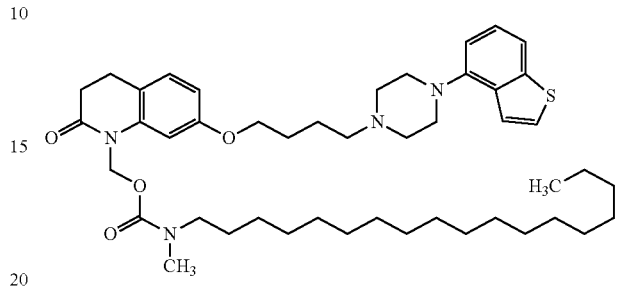

In the same manner as in Example 9, the title compound was obtained.

$^1$H-NMR (CDCl$_3$) δ: 0.88 (3H, t, J=7.0 Hz), 1.10-1.34 (30H, m), 1.38-1.57 (2H, m), 1.68-1.90 (4H, m), 2.52 (2H, t, J=7.5 Hz), 2.63-2.79 (6H, m), 2.81-2.95 (5H, m), 3.13-3.31 (6H, m), 3.99 (2H, t, J=5.5 Hz), 5.93 (2H, s), 6.59 (1H, d, J=8.0 Hz), 6.77 (1H, d, J=8.0 Hz), 6.89 (1H, d, J=7.5 Hz), 7.06 (1H, d, J=8.0 Hz), 7.24-7.31 (1H, m), 7.36-7.43 (2H, m), 7.55 (1H, d, J=8.0 Hz)

EXAMPLE 80

Synthesis of N-benzylcarbamic acid 7-[4-(4-benzo[b]thiophen-4-ylpiperazin-1-yl)butoxy]-2-oxo-3,4-dihydro-2H-quinolin-1-ylmethyl ester

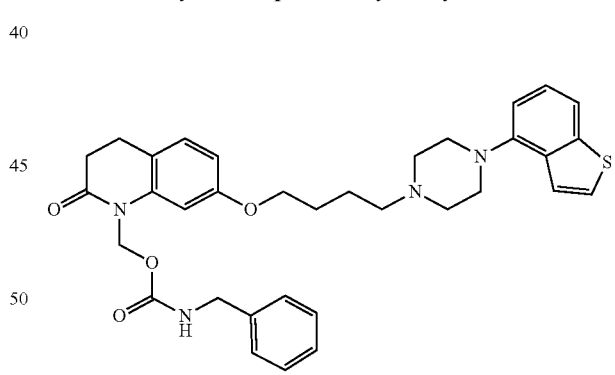

Using carbonic acid 7-[4-(4-benzo[b]thiophen-4-ylpiperazin-1-yl)butoxy]-2-oxo-3,4-dihydro-2H-quinolin-1-ylmethyl ester phenyl ester synthesized in the same manner as in Example 5 and in the same manner as in Example 10, the title compound was obtained.

$^1$H-NMR (CDCl$_3$) δ: 1.69-1.89 (4H, m), 2.51 (2H, t, J=7.5 Hz), 2.63-2.77 (6H, m), 2.86 (2H, t, J=7.5 Hz), 3.13-3.25 (4H, m), 3.98 (2H, t, J=6.0 Hz), 4.40 (2H, t, J=6.0 Hz), 5.10-5.18 (1H, m), 5.97 (2H, s), 6.59 (1H, dd, J=2.5 Hz, J=8.5 Hz), 6.80 (1H, d, J=2.0 Hz), 6.89 (1H, d, J=7.5 Hz), 7.06 (1H, d, J=8.5 Hz), 7.23-7.35 (6H, m), 7.37-7.43 (2H, m), 7.55 (1H, d, J=8.0 Hz)

EXAMPLE 81

Synthesis of 2-methylpentanoic acid 7-[4-(4-benzo[b]thiophen-4-ylpiperazin-1-yl)butoxy]-2-oxo-3,4-dihydro-2H-quinolin-1-ylmethyl ester

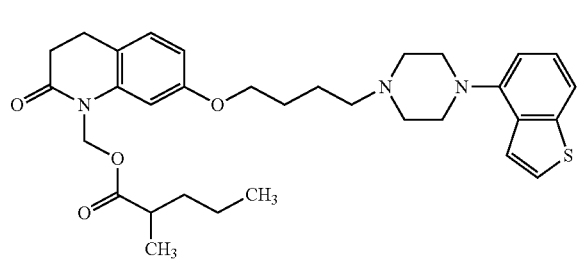 [SMILES: CCCC(C)C(=O)OCN1C(=O)CCc2ccc(OCCCCN3CCN(c4cccc5sccc45)CC3)cc21]

In the same manner as in Example 48, the title compound was obtained.

$^1$H-NMR (CDCl$_3$) δ: 0.88 (t, J=7.2 Hz, 3H), 1.16 (d, J=7.0 Hz, 3H), 1.28-1.46 (m, 3H), 1.61-1.68 (m, 1H), 1.68-1.79 (m, 2H), 1.79-1.90 (m, 2H), 2.45-2.56 (m, 3H), 2.64-2.78 (m, 6H), 2.82-2.90 (m, 2H), 3.12-3.25 (m, 4H), 3.98 (t, J=6.2 Hz, 2H), 5.92 (brs, 2H), 6.56-6.62 (m, 2H), 6.90 (d, J=7.6 Hz, 1H), 7.04-7.10 (m, 1H), 7.27 (dd, J=7.8, 7.8 Hz, 1H), 7.38 (d, J=5.5 Hz, 1H), 7.41 (d, J=5.5 Hz, 1H), 7.55 (d, J=8.0 Hz, 1H)

EXAMPLE 82

Synthesis of tetradecanoic acid 7-[4-(4-benzo[b]thiophen-4-ylpiperazin-1-yl)butoxy]-2-oxo-3,4-dihydro-2H-quinolin-1-ylmethyl ester

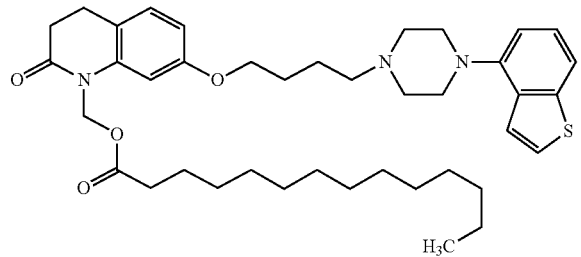 [SMILES: CCCCCCCCCCCCCC(=O)OCN1C(=O)CCc2ccc(OCCCCN3CCN(c4cccc5sccc45)CC3)cc21]

In the same manner as in Example 14, the title compound was obtained.

$^1$H-NMR (CDCl$_3$) δ: 0.87 (t, J=6.8 Hz, 3H), 1.20-1.33 (m, 20H), 1.57-1.68 (m, 2H), 1.69-1.79 (m, 2H), 1.80-1.90 (m, 2H), 2.36 (t, J=7.6 Hz, 2H), 2.52 (t, J=7.5 Hz, 2H), 2.65-2.77 (m, 6H), 2.83-2.90 (m, 2H), 3.14-3.24 (m, 4H), 3.98 (t, J=6.2 Hz, 2H), 5.92 (brs, 2H), 6.60 (dd, J=2.2, 8.1 Hz, 1H), 6.62 (d, J=2.2 Hz, 1H), 6.90 (d, J=9.0 Hz, 1H), 7.07 (d, J=8.1 Hz, 1H), 7.24-7.30 (m, 1H), 7.38 (d, J=5.6 Hz, 1H), 7.41 (d, J=5.6 Hz, 1H), 7.55 (d, J=8.0 Hz, 1H)

EXAMPLE 83

Synthesis of N-cyclohexylcarbamic acid 7-[4-(4-benzo[b]thiophen-4-ylpiperazin-1-yl)butoxy]-2-oxo-3,4-dihydro-2H-quinolin-1-ylmethyl ester

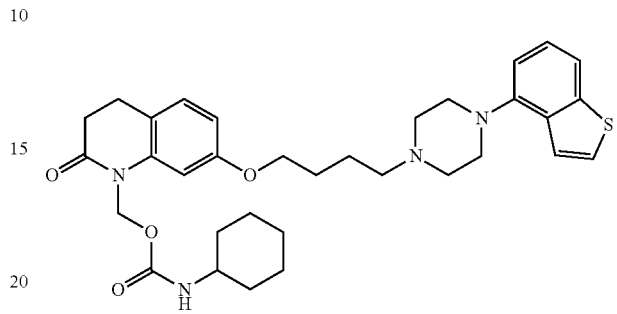

In the same manner as in Example 9, the title compound was obtained.

$^1$H-NMR (CDCl$_3$) δ: 1.05-1.21 (4H, m), 1.25-1.43 (2H, m), 1.63-1.93 (8H, m), 2.52 (2H, t, J=7.5 Hz), 2.63-2.78 (6H, m), 2.81-2.90 (2H, m), 3.14-3.26 (4H, m), 3.46-3.58 (1H, m), 4.00 (2H, t, J=6.0 Hz), 4.71 (1H, d, J=8.0 Hz), 5.91 (2H, s), 6.59 (1H, dd, J=2.0 Hz, J=8.0 Hz), 6.79 (1H, d, J=2.0 Hz), 6.90 (1H, dd, J=0.5 Hz, J=7.5 Hz), 7.05 (1H, d, J=8.0 Hz), 7.24-7.31 (1H, m), 7.38 (1H, d, J=5.5 Hz), 7.41 (1H, dd, J=0.5 Hz, J=5.5 Hz), 7.55 (1H, d, J=8.0 Hz)

EXAMPLE 84

Synthesis of 2,2-dimethylhexanoic acid 7-[4-(4-benzo[b]thiophen-4-ylpiperazin-1-yl)butoxy]-2-oxo-3,4-dihydro-2H-quinolin-1-ylmethyl ester

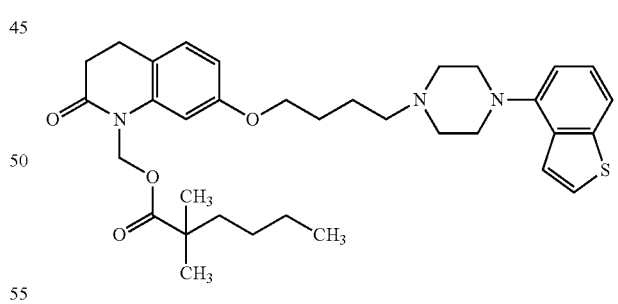

In the same manner as in Example 48, the title compound was obtained.

$^1$H-NMR (CDCl$_3$) δ: 0.84 (t, J=6.9 Hz, 3H), 1.14-1.29 (m, 4H), 1.17 (s, 6H), 1.47-1.54 (m, 2H), 1.68-1.78 (m, 2H), 1.79-1.89 (m, 2H), 2.52 (t, J=7.5 Hz, 2H), 2.65-2.76 (m, 6H), 2.83-2.89 (m, 2H), 3.15-3.23 (m, 4H), 3.97 (d, J=6.3 Hz, 2H), 5.91 (brs, 2H), 6.57-6.62 (m, 2H), 6.88-6.92 (m, 1H), 7.07 (d, J=8.2 Hz, 1H), 7.27 (dd, J=7.8, 7.8 Hz, 1H), 7.37-7.43 (m, 2H), 7.55 (d, J=8.0 Hz, 1H)

EXAMPLE 85

Synthesis of acetic acid 7-[4-(4-benzo[b]thiophen-4-ylpiperazin-1-yl)butoxy]-2-oxo-3,4-dihydro-2H-quinolin-1-ylmethyl ester

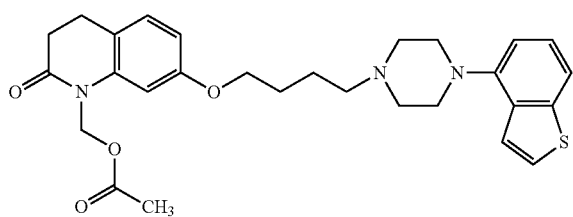

In the same manner as in Example 48, the title compound was obtained.

$^1$H-NMR (CDCl$_3$) δ: 1.64-1.80 (m, 2H), 1.80-1.90 (m, 2H), 2.12 (s, 3H), 2.53 (t, J=7.3 Hz, 2H), 2.65-2.77 (m, 6H), 2.83-2.90 (m, 2H), 3.13-3.24 (m, 4H), 3.99 (t, J=6.2 Hz, 2H), 5.91 (brs, 2H), 6.60 (dd, J=2.3, 8.2 Hz, 1H), 6.63 (d, J=2.3 Hz, 1H), 6.90 (d, J=7.5 Hz, 1H), 7.07 (d, J=8.2 Hz, 1H), 7.24-7.30 (m, 1H), 7.38 (d, J=5.6 Hz, 1H), 7.41 (d, J=5.6 Hz, 1H), 7.55 (d, J=8.0 Hz, 1H)

EXAMPLE 86

Synthesis of morpholine-4-carboxylic acid 7-[4-(4-benzo[b]thiophen-4-ylpiperazin-1-yl)butoxy]-2-oxo-3,4-dihydro-2H-quinolin-1-ylmethyl ester

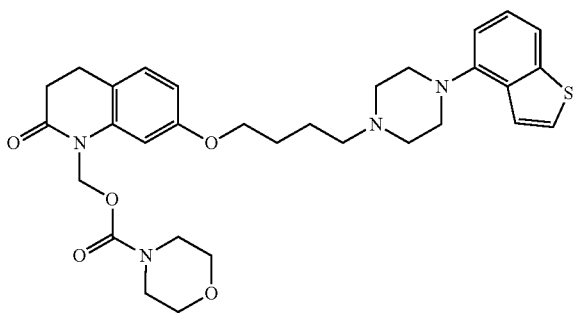

Using carbonic acid 7-[4-(4-benzo[b]thiophen-4-ylpiperazin-1-yl)butoxy]-2-oxo-3,4-dihydro-2H-quinolin-1-ylmethyl ester phenyl ester synthesized in the same manner as in Example 5 and in the same manner as in Example 10, the title compound was obtained.

$^1$H-NMR (CDCl$_3$) δ: 1.69-1.79 (2H, m), 1.81-1.90 (2H, m), 2.53 (2H, t, J=7.5 Hz), 2.64-2.78 (6H, m), 2.83-2.90 (2H, m), 3.13-3.25 (4H, m), 3.38-3.55 (4H, m), 3.56-3.74 (4H, m), 4.00 (2H, t, J=6.5 Hz), 5.94 (2H, s), 6.60 (1H, dd, J=2.5 Hz, J=8.5 Hz), 6.74 (1H, d, J=2.5 Hz), 6.90 (1H, d, J=7.5 Hz), 7.07 (1H, d, J=8.5 Hz), 7.24-7.30 (1H, m), 7.39 (1H, d, J=5.5 Hz), 7.41 (1H, dd, J=0.5 Hz, J=5.5 Hz), 7.55 (1H, d, J=8.0 Hz)

EXAMPLE 87

Synthesis of 2-methylbutyric acid 7-[4-(4-benzo[b]thiophen-4-ylpiperazin-1-yl)butoxy]-2-oxo-2H-quinolin-1-ylmethyl ester

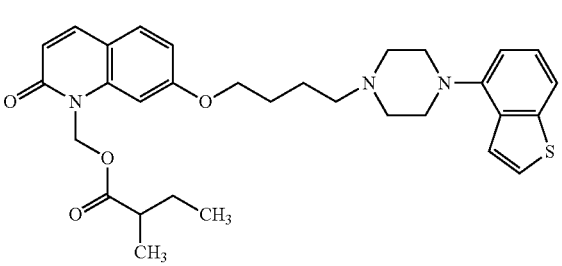 [SMILES: CCC(C)C(=O)OCn1c(=O)ccc2ccc(OCCCCN3CCN(c4cccc5sccc45)CC3)cc21]

In the same manner as in Example 22, the title compound was obtained.

$^1$H-NMR (CDCl$_3$) δ: 0.89 (t, J=7.5 Hz, 3H), 1.16 (d, J=7.0 Hz, 3H), 1.42-1.54 (m, 1H), 1.60-1.81 (m, 3H), 1.85-1.95 (m, 2H), 2.44 (dt, J=7.0, 7.0 Hz, 1H), 2.54 (t, J=7.5 Hz, 2H), 2.64-2.79 (m, 4H), 3.15-3.25 (m, 4H), 4.07 (t, J=6.2 Hz, 2H), 6.34 (brs, 2H), 6.52 (d, J=9.5 Hz, 1H), 6.81-6.87 (m, 2H), 6.87-6.92 (m, 1H), 7.27 (dd, J=7.8, 7.8 Hz, 1H), 7.37-7.43 (m, 2H), 7.45 (d, J=8.3 Hz, 1H), 7.55 (d, J=8.0 Hz, 1H), 7.63 (d, J=9.5 Hz, 1H)

EXAMPLE 88

Synthesis of 2-methylhexanoic acid 7-[4-(4-benzo[b]thiophen-4-ylpiperazin-1-yl)butoxy]-2-oxo-2H-quinolin-1-ylmethyl ester

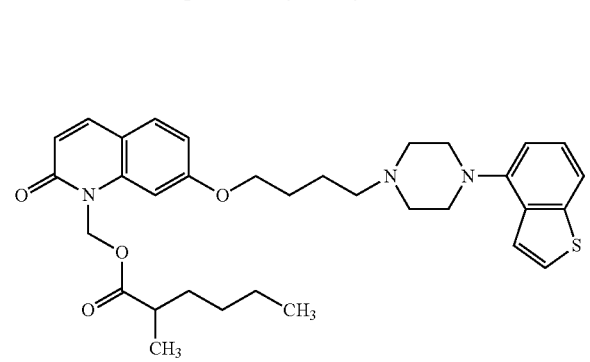 [SMILES: CCCCC(C)C(=O)OCn1c(=O)ccc2ccc(OCCCCN3CCN(c4cccc5sccc45)CC3)cc21]

In the same manner as in Example 22, the title compound was obtained.

$^1$H-NMR (CDCl$_3$) δ: 0.81 (t, J=7.0 Hz, 3H), 1.15 (d, J=7.0 Hz, 3H), 1.18-1.29 (m, 4H), 1.35-1.47 (m, 1H), 1.59-1.81 (m, 3H), 1.85-1.94 (m, 2H), 2.44-2.58 (m, 3H), 2.65-2.80 (m, 4H), 3.13-3.25 (m, 4H), 4.07 (t, J=6.2 Hz, 2H), 6.34 (brs, 2H), 6.52 (d, J=9.5 Hz, 1H), 6.81-6.87 (m, 2H), 6.87-6.92 (m, 1H), 7.27 (dd, J=7.9, 7.9 Hz, 1H), 7.37-7.43 (m, 2H), 7.45 (d, J=8.4 Hz, 1H), 7.55 (d, J=8.0 Hz, 1H), 7.62 (d, J=9.5 Hz, 1H)

EXAMPLE 89

Synthesis of {7-[4-(4-benzo[b]thiophen-4-ylpiperazin-1-yl)butoxy]-2-oxo-3,4-dihydro-2H-quinolin-1-ylmethoxycarbonylamino}acetic acid methyl ester

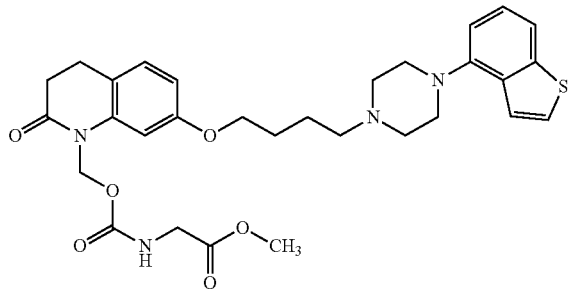 [SMILES: COC(=O)CNC(=O)OCN1C(=O)CCc2ccc(OCCCCN3CCN(c4cccc5sccc45)CC3)cc21]

In the same manner as in Example 9, the title compound was obtained.

¹H-NMR (CDCl₃) δ: 1.70-1.79 (2H, m), 1.81-1.90 (2H, m), 2.53 (2H, t, J=7.5 Hz), 2.64-2.77 (6H, m), 2.82-2.89 (2H, m), 3.14-3.24 (4H, m), 3.75 (3H, s), 3.97-4.05 (4H, m), 4.34 (1H, t, J=5.0 Hz), 5.95 (2H, s), 6.60 (1H, dd, J=2.0 Hz, J=8.5 Hz), 6.77 (1H, d, J=2.0 Hz), 6.89 (1H, d, J=7.5 Hz), 7.06 (1H, d, J=8.5 Hz), 7.24-7.31 (1H, m), 7.38 (1H, d, J=5.5 Hz), 7.41 (1H, d, J=5.5 Hz), 7.55 (1H, d, J=8.0 Hz)

EXAMPLE 90

Synthesis of ({7-[4-(4-benzo[b]thiophen-4-ylpiperazin-1-yl)butoxy]-2-oxo-3,4-dihydro-2H-quinolin-1-ylmethoxycarbonyl}methylamino)acetic acid methyl ester

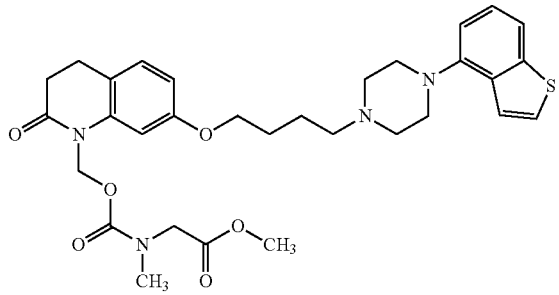

In the same manner as in Example 9, the title compound was obtained.

¹H-NMR (CDCl₃) δ: 1.70-1.79 (2H, m), 1.81-1.91 (2H, m), 2.49-2.57 (2H, m), 2.63-2.78 (6H, m), 2.81-2.90 (2H, m), {3.64 (s), 3.75 (s) total 3H (1:1)}, 3.14-3.25 (4H, m), {3.64 (s), 3.75 (s) total 3H (1:1)}, 3.93 (s, 1H), 3.97-4.04 (2H, m), 4.06 (1H, s), 5.91 (1H, s), 5.96 (1H, s), 6.56-6.63 (1H, m), {6.68 (d, J=2.0 Hz), 6.77 (d, J=2.0 Hz) total 1H (1:1)}, 6.90 (1H, d, J=7.5 Hz), 7.06 (1H, dd, J=8.0 Hz, J=8.0 Hz), 7.24-7.31 (1H, m), 7.38 (1H, d, J=5.5 Hz), 7.41 (1H, d, J=5.5 Hz), 7.55 (1H, d, J=8.0 Hz)

EXAMPLE 91

Synthesis of pentadecanoic acid 7-[4-(4-benzo[b]thiophen-4-ylpiperazin-1-yl)butoxy]-2-oxo-3,4-dihydro-2H-quinolin-1-ylmethyl ester

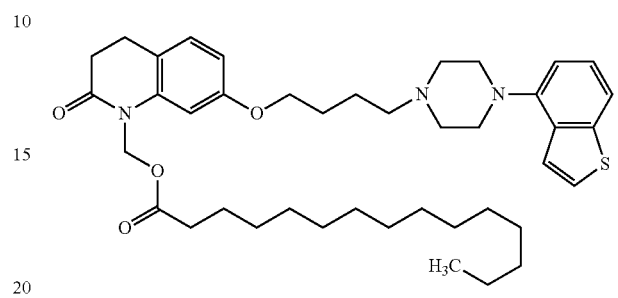

In the same manner as in Example 48, the title compound was obtained.

¹H-NMR (CDCl₃) δ: 0.87 (t, J=6.8 Hz, 3H), 1.17-1.35 (m, 22H), 1.55-1.68 (m, 2H), 1.69-1.80 (m, 2H), 1.80-1.90 (m, 2H), 2.36 (t, J=7.6 Hz, 2H), 2.52 (t, J=7.5 Hz, 2H), 2.64-2.76 (m, 6H), 2.83-2.89 (m, 2H), 3.13-3.24 (m, 4H), 3.98 (t, J=6.2 Hz, 2H), 5.92 (brs, 2H), 6.59 (dd, J=2.3, 8.2 Hz, 1H), 6.62 (d, J=2.3 Hz, 1H), 6.87-6.92 (m, 1H), 7.07 (d, J=8.2 Hz, 1H), 7.27 (dd, J=7.8, 7.8 Hz, 1H), 7.37-7.43 (m, 2H), 7.55 (d, J=8.0 Hz, 1H)

EXAMPLE 92

Synthesis of 2-methylheptanoic acid 7-[4-(4-benzo[b]thiophen-4-ylpiperazin-1-yl)butoxy]-2-oxo-3,4-dihydro-2H-quinolin-1-ylmethyl ester

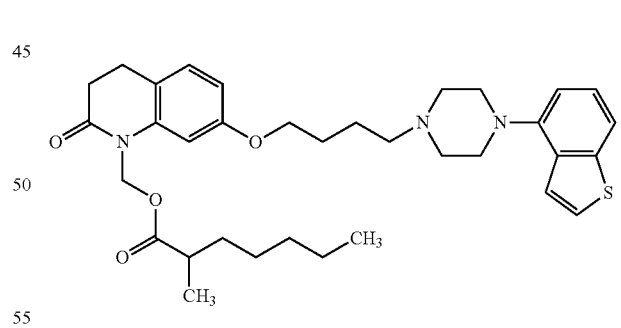

In the same manner as in Example 48, the title compound was obtained.

¹H-NMR (CDCl₃) δ: 0.85 (t, J=6.8 Hz, 3H), 1.16 (d, J=7.0 Hz, 3H), 1.19-1.34 (m, 6H), 1.34-1.47 (m, 1H), 1.60-1.79 (m, 3H), 1.79-1.90 (m, 2H), 2.42-2.56 (m, 3H), 2.64-2.78 (m, 6H), 2.82-2.90 (m, 2H), 3.12-3.26 (m, 4H), 3.97 (t, J=6.2 Hz, 2H), 5.92 (brs, 2H), 6.57-6.62 (m, 2H), 6.87-6.92 (m, 1H), 7.07 (d, J=8.1 Hz, 1H), 7.27 (dd, J=7.8, 7.8 Hz, 1H), 7.37-7.43 (m, 2H), 7.55 (d, J=8.0 Hz, 1H)

EXAMPLE 93

Synthesis of N-(3,3,3-trifluoropropyl)carbamic acid 7-[4-(4-benzo[b]thiophen-4-ylpiperazin-1-yl)butoxy]-2-oxo-3,4-dihydro-2H-quinolin-1-ylmethyl ester

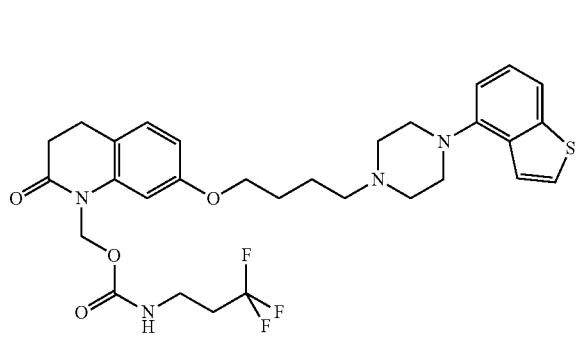 [SMILES: O=C(NCCC(F)(F)F)OCN1C(=O)CCc2ccc(OCCCCN3CCN(c4cccc5sccc45)CC3)cc21]

In the same manner as in Example 9, the title compound was obtained.

$^1$H-NMR (CDCl$_3$) δ: 1.69-1.79 (2H, m), 1.80-1.90 (2H, m), 2.29-2.43 (2H, m), 2.52 (2H, t, J=7.5 Hz), 2.61-2.77 (6H, m), 2.79-2.89 (2H, m), 3.13-3.26 (4H, m), 3.46 (2H, dt, J=6.5 Hz, J=6.5 Hz), 3.99 (2H, t, J=6.0 Hz), 5.20 (1H, t, J=6.0 Hz), 5.92 (2H, s), 6.59 (1H, dd, J=2.0 Hz, J=8.5 Hz), 6.74 (1H, d, J=2.0 Hz), 6.89 (1H, d, J=7.5 Hz), 7.05 (1H, d, J=8.5 Hz), 7.23-7.30 (1H, m), 7.38 (1H, d, J=5.5 Hz), 7.41 (1H, d, J=5.5 Hz), 7.54 (1H, d, J=8.0 Hz)

EXAMPLE 94

Synthesis of 2-methylpentanoic acid 7-[4-(4-benzo[b]thiophen-4-ylpiperazin-1-yl)butoxy]-2-oxo-2H-quinolin-1-ylmethyl ester

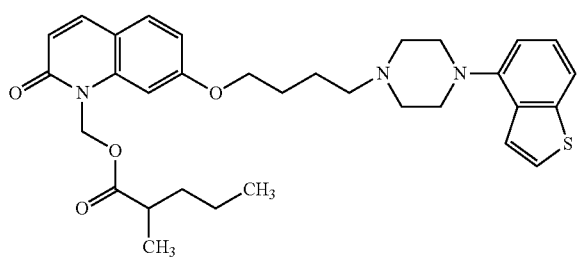 [SMILES: CCCC(C)C(=O)OCn1c(=O)ccc2ccc(OCCCCN3CCN(c4cccc5sccc45)CC3)cc21]

In the same manner as in Example 22, the title compound was obtained.

$^1$H-NMR (CDCl$_3$) δ: 0.86 (t, J=7.2 Hz, 3H), 1.15 (d, J=7.0 Hz, 3H), 1.23-1.45 (m, 3H), 1.59-1.82 (m, 3H), 1.85-1.95 (m, 2H), 2.46-2.58 (m, 3H), 2.65-2.79 (m, 4H), 3.14-3.25 (m, 4H), 4.07 (t, J=6.2 Hz, 2H), 6.34 (brs, 2H), 6.52 (d, J=9.4 Hz, 1H), 6.82-6.87 (m, 2H), 6.90 (d, J=7.6 Hz, 1H), 7.25-7.30 (m, 1H), 7.39 (d, J=5.5 Hz, 1H), 7.42 (d, J=5.5 Hz, 1H), 7.43-7.47 (m, 1H), 7.55 (d, J=8.1 Hz, 1H), 7.63 (d, J=9.5 Hz, 1H)

EXAMPLE 95

Synthesis of heptadecanoic acid 7-[4-(4-benzo[b]thiophen-4-ylpiperazin-1-yl)butoxy]-2-oxo-3,4-dihydro-2H-quinolin-1-ylmethyl ester

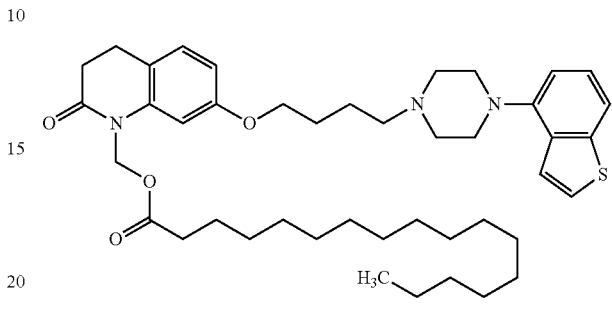

In the same manner as in Example 48, the title compound was obtained.

$^1$H-NMR (CDCl$_3$) δ: 0.88 (t, J=6.9 Hz, 3H), 1.16-1.35 (m, 26H), 1.57-1.68 (m, 2H), 1.68-1.79 (m, 2H), 1.79-1.90 (m, 2H), 2.36 (t, J=7.5 Hz, 2H), 2.52 (d, J=7.4 Hz, 2H), 2.64-2.77 (m, 6H), 2.83-2.90 (m, 2H), 3.14-3.24 (m, 4H), 3.98 (t, J=6.2 Hz, 2H), 5.92 (brs, 2H), 6.57-6.63 (m, 2H), 6.87-6.92 (m, 1H), 7.07 (d, J=8.1 Hz, 1H), 7.27 (dd, J=7.8, 7.8 Hz, 1H), 7.37-7.43 (m, 2H), 7.55 (d, J=8.0 Hz, 1H)

EXAMPLE 96

Synthesis of furan-3-carboxylic acid 7-[4-(4-benzo[b]thiophen-4-ylpiperazin-1-yl)butoxy]-2-oxo-3,4-dihydro-2H-quinolin-1-ylmethyl ester

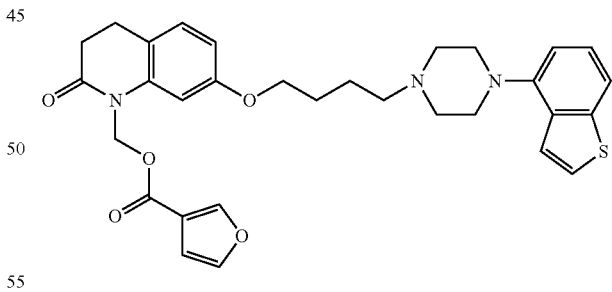

In the same manner as in Example 48, the title compound was obtained.

$^1$H-NMR (CDCl$_3$) δ: 1.64-1.77 (m, 2H), 1.78-1.88 (m, 2H), 2.50 (t, J=7.5 Hz, 2H), 2.63-2.75 (m, 6H), 2.85-2.92 (m, 2H), 3.12-3.23 (m, 4H), 3.98 (t, J=6.2 Hz, 2H), 6.09 (brs, 2H), 6.60 (dd, J=2.3, 8.3 Hz, 1H), 6.71 (d, J=2.3 Hz, 1H), 6.74-6.77 (m, 1H), 6.87-6.91 (m, 1H), 7.09 (d, J=8.3 Hz, 1H), 7.27 (dd, J=7.9, 7.9 Hz, 1H), 7.37-7.43 (m, 3H), 7.55 (d, J=7.9 Hz, 1H), 8.01-8.05 (m, 1H)

EXAMPLE 97

Synthesis of N-(2-methoxyethyl)carbamic acid 7-[4-(4-benzo[b]thiophen-4-ylpiperazin-1-yl)butoxy]-2-oxo-3,4-dihydro-2H-quinolin-1-ylmethyl ester

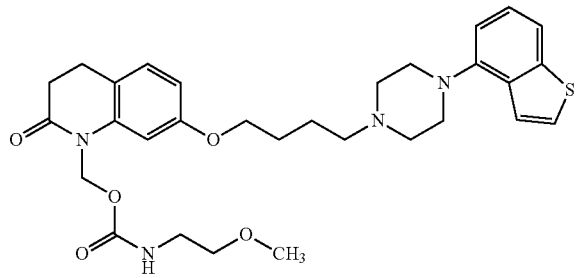

Using carbonic acid 7-[4-(4-benzo[b]thiophen-4-ylpiperazin-1-yl)butoxy]-2-oxo-3,4-dihydro-2H-quinolin-1-ylmethyl ester phenyl ester synthesized in the same manner as in Example 5 and in the same manner as in Example 10, the title compound was obtained.

$^1$H-NMR (CDCl$_3$) δ: 1.69-1.91 (4H, m), 2.53 (2H, t, J=7.5 Hz), 2.62-2.78 (6H, m), 2.81-2.91 (2H, m), 3.13-3.26 (4H, m), 3.33 (3H, s), 3.35-3.48 (4H, m), 4.00 (2H, t, J=6.0 Hz), 5.12-5.21 (1H, m), 5.92 (2H, s), 6.59 (1H, dd, J=2.0 Hz, J=8.0 Hz), 6.78 (1H, d, J=2.0 Hz), 6.90 (1H, d, J=7.5 Hz), 7.06 (1H, d, J=8.0 Hz), 7.24-7.30 (1H, m), 7.38 (1H, d, J=5.5 Hz), 7.42 (1H, d, J=5.5 Hz), 7.55 (1H, d, J=8.0 Hz)

EXAMPLE 98

Synthesis of N-furan-2-yl-N-methylcarbamic acid 7-[4-(4-benzo[b]thiophen-4-ylpiperazin-1-yl)butoxy]-2-oxo-3,4-dihydro-2H-quinolin-1-ylmethyl ester

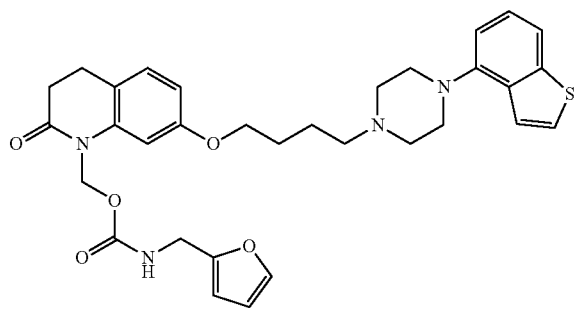 [SMILES: O=C(NCc1ccco1)OCN1C(=O)CCc2ccc(OCCCCN3CCN(c4cccc5sccc45)CC3)cc21]

Using carbonic acid 7-[4-(4-benzo[b]thiophen-4-ylpiperazin-1-yl)butoxy]-2-oxo-3,4-dihydro-2H-quinolin-1-ylmethyl ester phenyl ester synthesized in the same manner as in Example 5 and in the same manner as in Example 10, the title compound was obtained.

$^1$H-NMR (CDCl$_3$) δ: 1.69-1.90 (4H, m), 2.52 (2H, t, J=7.5 Hz), 2.62-2.77 (6H, m), 2.81-2.90 (2H, m), 3.12-3.27 (4H, m), 3.99 (2H, t, J=6.0 Hz), 4.39 (2H, d, J=6.0 Hz), 5.11-5.19 (1H, m), 5.95 (2H, s), 6.23 (1H, brs), 6.30 (1H, brs), 6.59 (1H, dd, J=2.5 Hz, J=8.0 Hz), 6.77 (1H, d, J=2.5 Hz), 6.89 (1H, d, J=7.5 Hz), 7.06 (1H, d, J=8.0 Hz), 7.24-7.30 (1H, m), 7.34 (1H, brs), 7.38 (1H, d, J=5.5 Hz), 7.41 (1H, d, J=5.5 Hz), 7.55 (1H, d, J=8.0 Hz)

EXAMPLE 99

Synthesis of 3-{7-[4-(4-benzo[b]thiophen-4-ylpiperazin-1-yl)butoxy]-2-oxo-2H-quinolin-1-ylmethoxycarbonylamino}-propionic acid ethyl ester

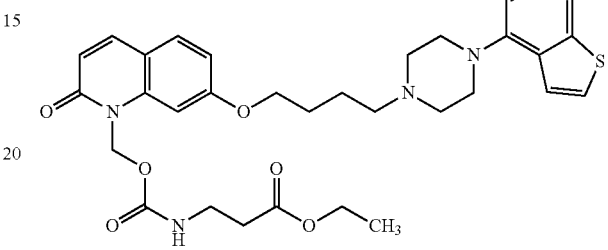

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

$^1$H-NMR (CDCl$_3$) δ: 1.23 (3H, t, J=7.0 Hz), 1.73-1.83 (2H, m), 1.86-1.96 (2H, m), 2.49-2.59 (4H, m), 2.66-2.80 (4H, m), 3.15-3.27 (4H, m), 3.45-3.53 (2H, m), 4.07-4.15 (4H, m), 5.36-5.43 (1H, m), 6.32 (2H, s), 6.51 (1H, d, J=9.5 Hz), 6.83 (1H, dd, J=2.0 Hz, J=8.5 Hz), 6.89 (1H, d, J=7.5 Hz), 7.11 (1H, d, J=2.0 Hz), 7.24-7.30 (1H, m), 7.37-7.46 (3H, m), 7.55 (1H, d, J=8.0 Hz), 7.61 (1H, d, J=9.5 Hz)

EXAMPLE 100

Synthesis of (2-butoxyethoxy)acetic acid 7-[4-(4-benzo[b]thiophen-4-ylpiperazin-1-yl)butoxy]-2-oxo-3,4-dihydro-2H-quinolin-1-ylmethyl ester

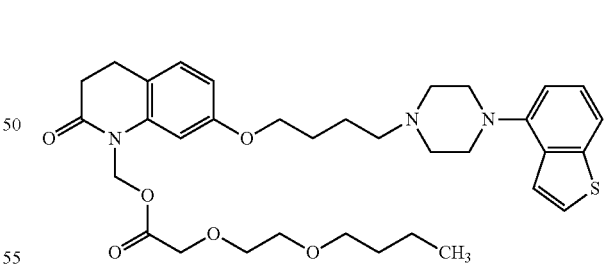

In the same manner as in Example 48, the title compound was obtained.

$^1$H-NMR (CDCl$_3$) δ: 0.90 (t, J=7.4 Hz, 3H), 1.29-1.40 (m, 2H), 1.50-1.59 (m, 2H), 1.69-1.80 (m, 2H), 1.80-1.90 (m, 2H), 2.53 (t, J=7.4 Hz, 2H), 2.64-2.77 (m, 6H), 2.83-2.90 (m, 2H), 3.13-3.24 (m, 4H), 3.45 (t, J=7.7 Hz, 2H), 3.58-3.63 (m, 2H), 3.71-3.76 (m, 2H), 3.98 (t, J=6.2 Hz, 2H), 4.22 (s, 2H), 5.99 (brs, 2H), 6.57-6.62 (m, 2H), 6.87-6.92 (m, 1H), 7.07 (d, J=7.8 Hz, 1H), 7.27 (dd, J=7.8, 7.8 Hz, 1H), 7.36-7.44 (m, 2H), 7.55 (d, J=8.0 Hz, 1H)

EXAMPLE 101

Synthesis, of 4-{7-[4-(4-benzo[b]thiophen-4-ylpiperazin-1-yl)butoxy]-2-oxo-2H-quinolin-1-ylmethoxycarbonylamino}butyric acid methyl ester

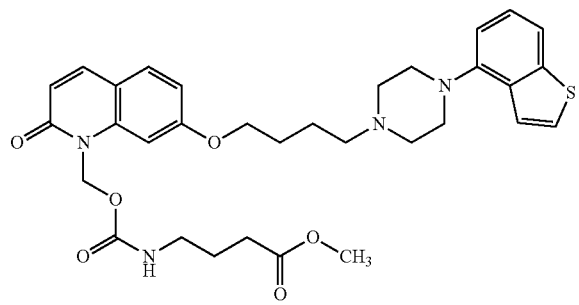 [SMILES: COC(=O)CCCNC(=O)OCn1c(=O)ccc2ccc(OCCCCN3CCN(c4cccc5sccc45)CC3)cc21]

Using carbonic acid 7-[4-(4-benzo[b]thiophen-4-ylpiperazin-1-yl)butoxy]-2-oxo-2H-quinolin-1-ylmethyl ester phenyl ester synthesized in the same manner as in Example 7 and in the same manner as in Example 9, the title compound was obtained.

$^1$H-NMR (CDCl$_3$) δ: 1.73-1.95 (6H, m), 2.36 (2H, t, J=7.0 Hz), 2.54 (2H, t, J=7.5 Hz), 2.66-2.80 (4H, m), 3.116-3.31 (6H, m), 3.64 (3H, s), 4.11 (2H, t, J=6.0 Hz) 5.06 (1H, t, J=6.0 Hz), 6.32 (2H, s), 6.51 (1H, d, J=9.5 Hz), 6.83 (1H, dd, J=2.0 Hz, J=8.5 Hz), 6.89 (1H, d, J=7.5 Hz), 7.12 (1H, d, J=1.5 Hz), 7.24-7.30 (1H, m), 7.36-7.46 (3H, m), 7.55 (1H, d, J=8.0 Hz), 7.61 (1H, d, J=9.5 Hz)

EXAMPLE 102

Synthesis of 1-methylpiperidine-4-carboxylic acid 7-[4-(4-benzo[b]thiophen-4-ylpiperazin-1-yl)butoxy]-2-oxo-3,4-dihydro-2H-quinolin-1-ylmethyl ester

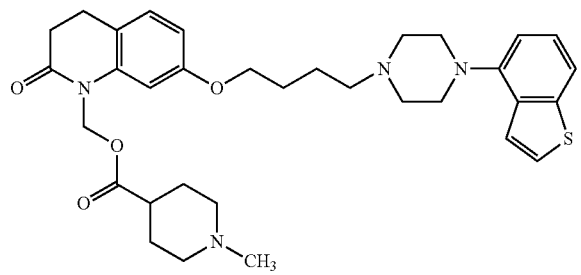 [SMILES: CN1CCC(C(=O)OCN2C(=O)CCc3ccc(OCCCCN4CCN(c5cccc6sccc56)CC4)cc32)CC1]

In the same manner as in Example 48, the title compound was obtained.

$^1$H-NMR (CDCl$_3$) δ: 1.58-2.06 (m, 10H), 2.04 (s, 3H), 2.28-2.40 (m, 1H), 2.52 (t, J=7.4 Hz, 2H), 2.63-2.82 (m, 8H), 2.82-2.90 (m, 2H), 3.14-3.25 (m, 4H), 3.97 (t, J=6.3 Hz, 2H), 5.93 (brs, 2H), 6.56-6.62 (m, 2H), 6.88-6.92 (m, 1H), 7.07 (d, J=8.1 Hz, 1H), 7.27 (dd, J=7.8, 7.8 Hz, 1H), 7.37-7.43 (m, 2H), 7.55 (d, J=8.0 Hz, 1H)

EXAMPLE 103

Synthesis of 2,2-dimethylhexanoic acid 7-[4-(4-benzo[b]thiophen-4-ylpiperazin-1-yl)butoxy]-2-oxo-2H-quinolin-1-ylmethyl ester

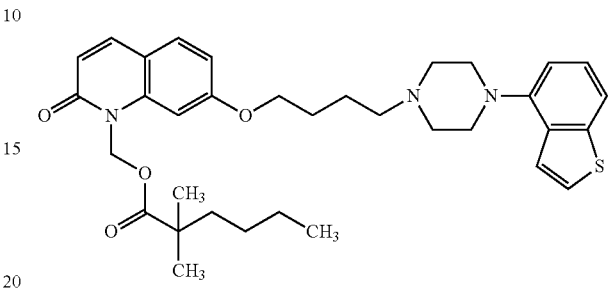

In the same manner as in Example 22, the title compound was obtained.

$^1$H-NMR (CDCl$_3$) δ: 0.77 (t, J=6.8 Hz, 3H), 1.09-1.20 (m, 10H), 1.42-1.52 (m, 2H), 1.68-1.95 (m, 4H), 2.54 (t, J=7.5 Hz, 2H), 2.66-2.78 (m, 4H), 3.14-3.25 (m, 4H), 4.07 (t, J=6.2 Hz, 2H), 6.33 (brs, 2H), 6.52 (d, J=9.5 Hz, 1H), 6.81-6.86 (m, 2H), 6.87-6.92 (m, 1H), 7.27 (dd, J=7.8, 7.8 Hz, 1H), 7.36-7.37 (m, 3H), 7.55 (d, J=8.0 Hz, 1H), 7.62 (d, J=9.5 Hz, 1H)

EXAMPLE 104

Synthesis of pentadecanoic acid 7-[4-(4-benzo[b]thiophen-4-ylpiperazin-1-yl)butoxy]-2-oxo-2H-quinolin-1-ylmethyl ester

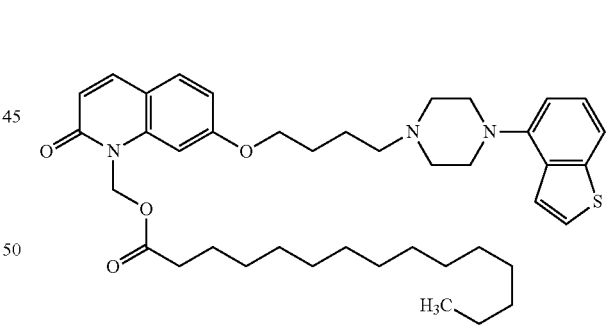

In the same manner as in Example 22, the title compound was obtained.

$^1$H-NMR (CDCl$_3$) δ: 0.87 (t, J=6.8 Hz, 3H), 1.16-1.34 (m, 22H), 1.57-1.67 (m, 2H), 1.67-1.82 (m, 2H), 1.85-1.95 (m, 2H), 2.36 (t, J=7.5 Hz, 2H), 2.54 (t, J=7.5 Hz, 2H), 2.65-2.79 (m, 4H), 3.13-3.25 (m, 4H), 4.08 (t, J=6.2 Hz, 2H), 6.34 (brs, 2H), 6.52 (d, J=9.5 Hz, 1H), 6.84 (dd, J=2.2, 8.6 Hz, 1H), 6.86-6.92 (m, 2H), 7.27 (dd, J=7.8, 7.8 Hz, 1H), 7.37-7.43 (m, 2H), 7.45 (d, J=8.6 Hz, 1H), 7.55 (d, J=8.1 Hz, 1H), 7.62 (d, J=9.5 Hz, 1H)

EXAMPLE 105

Synthesis of 4-methylpentanoic acid 7-[4-(4-benzo[b]thiophen-4-ylpiperazin-1-yl)butoxy]-2-oxo-3,4-dihydro-2H-quinolin-1-ylmethyl ester

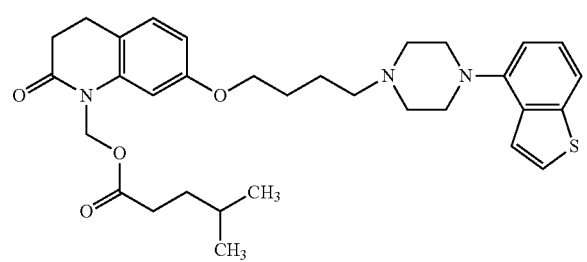 [SMILES: CC(C)CCC(=O)OCN1C(=O)CCc2ccc(OCCCCN3CCN(c4cccc5sccc45)CC3)cc21]

In the same manner as in Example 48, the title compound was obtained.

$^1$H-NMR (CDCl$_3$) δ: 0.89 (d, J=6.3 Hz, 6H), 1.51-1.63 (m, 3H), 1.69-1.80 (m, 2H), 1.80-1.90 (m, 2H), 2.33-2.40 (m, 2H), 2.52 (t, J=7.4 Hz, 2H), 2.65-2.77 (m, 6H), 2.83-2.90 (m, 2H), 3.14-3.24 (m, 4H), 3.99 (t, J=6.2 Hz, 2H), 5.91 (brs, 2H), 6.57-6.63 (m, 2H), 6.87-6.92 (m, 1H), 7.07 (d, J=8.0 Hz, 1H), 7.27 (dd, J=7.8, 7.8 Hz, 1H), 7.37-7.43 (m, 2H), 7.55 (d, J=8.1 Hz, 1H)

EXAMPLE 106

Synthesis of cycloheptanecarboxylic acid 7-[4-(4-benzo[b]thiophen-4-ylpiperazin-1-yl)butoxy]-2-oxo-3,4-dihydro-2H-quinolin-1-ylmethyl ester

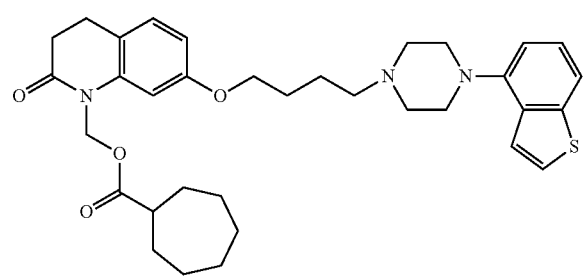 [SMILES: O=C(OCN1C(=O)CCc2ccc(OCCCCN3CCN(c4cccc5sccc45)CC3)cc21)C1CCCCCC1]

In the same manner as in Example 48, the title compound was obtained.

$^1$H-NMR (CDCl$_3$) δ: 1.40-1.59 (m, 6H), 1.64-1.79 (m, 6H), 1.80-1.90 (m, 2H), 1.90-1.99 (m, 2H), 2.48-2.59 (m, 3H), 2.64-2.78 (m, 6H), 2.82-2.90 (m, 2H), 3.14-3.23 (m, 4H), 3.98 (t, J=6.2 Hz, 2H), 5.91 (brs, 2H), 6.57-6.63 (m, 2H), 6.90 (d, J=7.3 Hz, 1H), 7.05-7.09 (m, 1H), 7.27 (dd, J=7.8, 7.8 Hz, 1H), 7.37-7.43 (m, 2H), 7.55 (d, J=8.0 Hz, 1H)

EXAMPLE 107

Synthesis of benzyloxycarbamic acid 7-[4-(4-benzo[b]thiophen-4-ylpiperazin-1-yl)butoxy]-2-oxo-3,4-dihydro-2H-quinolin-1-ylmethyl ester

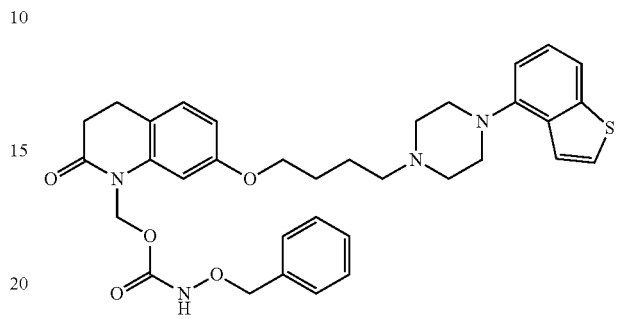

In the same manner as in Example 9, the title compound was obtained.

$^1$H-NMR (CDCl$_3$) δ: 1.67-1.89 (4H, m), 2.51 (2H, t, J=7.5 Hz), 2.61-2.76 (6H, m), 2.81-2.90 (2H, m), 3.10-3.23 (4H, m), 4.00 (2H, t, J=6.0 Hz), 4.87 (2H, s), 6.00 (2H, s), 6.60 (1H, dd, J=2.5 Hz, J=8.5 Hz), 6.73 (1H, d, J=2.5 Hz), 6.86-6.91 (1H, m), 7.07 (1H, d, J=8.5 Hz), 7.24-7.42 (8H, m), 7.55 (1H, d, J=8.0 Hz), 7.59 (1H, brs) [0598]

EXAMPLE 108

Synthesis of heptadecanoic acid 7-[4-(4-benzo[b]thiophen-4-ylpiperazin-1-yl)butoxy]-2-oxo-2H-quinolin-1-ylmethyl ester

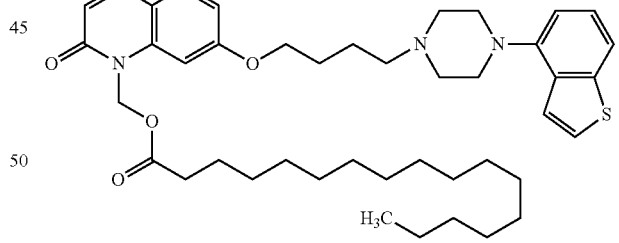

In the same manner as in Example 22, the title compound was obtained.

$^1$H-NMR (CDCl$_3$) δ: 0.87 (t, J=6.9 Hz, 3H), 1.17-1.33 (m, 26H), 1.57-1.67 (m, 2H), 1.69-1.82 (m, 2H), 1.85-1.95 (m, 2H), 2.36 (t, J=7.5 Hz, 2H), 2.54 (t, J=7.5 Hz, 2H), 2.67-2.77 (m, 4H), 3.14-3.24 (m, 4H), 4.08 (t, J=6.2 Hz, 2H), 6.34 (brs, 2H), 6.52 (d, J=9.5 Hz, 1H), 6.84 (dd, J=2.2, 8.6 Hz, 1H), 6.86-6.91 (m, 2H), 7.27 (dd, J=7.8, 7.8 Hz, 1H), 7.36-7.43 (m, 2H), 7.44 (d, J=8.6 Hz, 1H), 7.55 (d, J=8.0 Hz, 1H), 7.62 (d, J=9.5 Hz, 1H)

EXAMPLE 109

Synthesis of N-(2-methoxyethyl)carbamic acid 7-[4-(4-benzo[b]thiophen-4-ylpiperazin-1-yl)butoxy]-2-oxo-2H-quinolin-1-ylmethyl ester

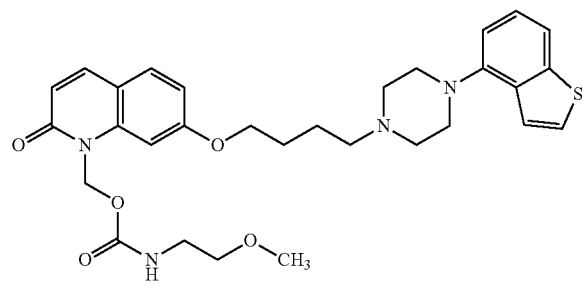 [SMILES: COCCNC(=O)OCn1c(=O)ccc2ccc(OCCCCN3CCN(c4cccc5sccc45)CC3)cc21]

In the same manner as in Example 10, the title compound was obtained.

$^1$H-NMR (CDCl$_3$) δ: 1.73-1.83 (2H, m), 1.86-1.96 (2H, m), 2.55 (2H, t, J=7.5 Hz), 2.67-2.80 (4H, m), 3.16-3.25 (4H, m), 3.32 (3H, s), 3.36-3.47 (4H, m), 4.11 (2H, d, J=6.0 Hz), 5.17-5.24 (1H, m), 6.33 (2H, s), 6.51 (1H, d, J=9.5 Hz), 6.83 (1H, dd, J=2.0 Hz, J=8.5 Hz), 6.89 (1H, d, J=7.5 Hz), 7.13 (1H, d, J=2.0 Hz), 7.24-7.30 (1H, m), 7.37-7.47 (3H, m), 7.55 (1H, d, J=8.0 Hz), 7.62 (1H, d, J=9.5 Hz)

EXAMPLE 110

Synthesis of N-furan-2-yl-N-methylcarbamic acid 7-[4-(4-benzo[b]thiophen-4-ylpiperazin-1-yl)butoxy]-2-oxo-2H-quinolin-1-ylmethyl ester

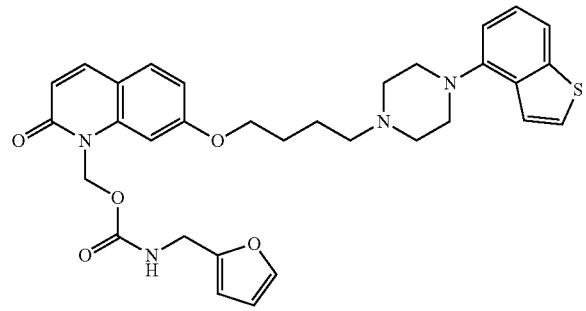 [SMILES: O=C(NCc1ccco1)OCn1c(=O)ccc2ccc(OCCCCN3CCN(c4cccc5sccc45)CC3)cc21]

In the same manner as in Example 10, the title compound was obtained.

$^1$H-NMR (CDCl$_3$) δ: 1.71-1.82 (2H, m), 1.83-1.96 (2H, m), 2.54 (2H, t, J=7.5 Hz), 2.65-2.80 (4H, m), 3.13-3.28 (4H, m), 4.10 (2H, t, J=6.0 Hz), 4.39 (2H, d, J=6.0 Hz), 5.19-5.29 (1H, m), 6.21 (1H, d, J=3.0 Hz), 6.30 (1H, d, J=3.0 Hz), 6.36 (2H, s), 6.50 (1H, d, J=9.5 Hz), 6.83 (1H, dd, J=2.0 Hz, J=8.5 Hz), 6.87-6.91 (1H, m), 7.12 (1H, d, J=1.5 Hz), 7.24-7.30 (1H, m), 7.33 (1H, brs), 7.37-7.46 (3H, m), 7.55 (1H, d, J=8.0 Hz), 7.61 (1H, d, J=9.5 Hz)

EXAMPLE 111

Synthesis of N-benzyl-N-methylcarbamic acid 7-[4-(4-benzo[b]thiophen-4-ylpiperazin-1-yl)butoxy]-2-oxo-2H-quinolin-1-ylmethyl ester

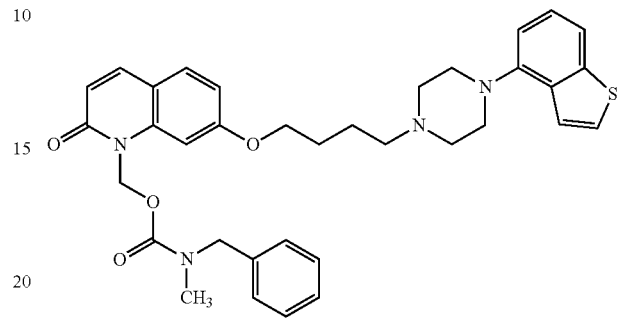

In the same manner as in Example 10, the title compound was obtained.

$^1$H-NMR (CDCl$_3$) δ: 1.69-1.79 (2H, m), 1.82-1.92 (2H, m), 2.53 (2H, t, J=7.0 Hz), 2.64-2.76 (4H, m), {2.80 (s), 2.93 (s) total 3H (1:1)}, 3.13-3.25 (4H, m), 4.02 (1H, t, J=6.0 Hz), 4.08 (1H, t, J=6.0 Hz), 4.37 (1H, s), 4.52 (1H, s), 6.41 (1H, s), 6.43 (1H, s), 6.52 (1H, dd, J=8.5 Hz, J=8.5 Hz), 6.80-6.91 (2H, m), {6.99-7.09 (m), 7.14-7.19 (m) total 3H (1:1)}, 7.21-7.35 (4H, m), 7.37-7.46 (3H, m), 7.55 (1H, d, J=8.0 Hz), 7.62 (1H, dd, J=9.0 Hz, J=9.0 Hz)

EXAMPLE 112

Synthesis of N-allylcarbamic acid 7-[4-(4-benzo[b]thiophen-4-ylpiperazin-1-yl)butoxy]-2-oxo-2H-quinolin-1-ylmethyl ester

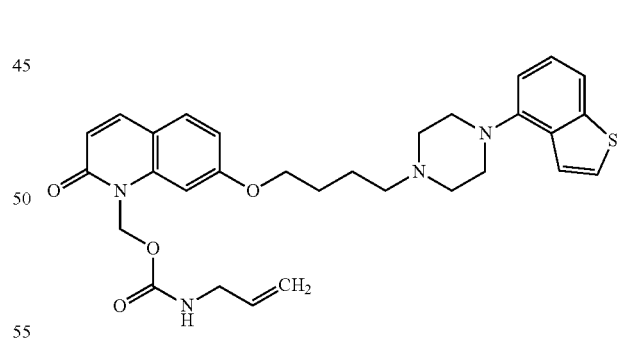

In the same manner as in Example 10, the title compound was obtained.

$^1$H-NMR (CDCl$_3$) δ: 1.73-1.83 (2H, m), 1.85-1.96 (2H, m), 2.54 (2H, t, J=7.5 Hz), 2.64-2.80 (4H, m), 3.13-3.26 (4H, m), 3.84 (2H, t, J=5.5 Hz), 4.11 (2H, t, J=6.0 Hz), 4.91-5.01 (1H, m), 5.08-5.24 (2H, m), 5.77-5.90 (1H, m), 6.35 (2H, s), 6.51 (1H, d, J=9.5 Hz), 6.84 (1H, dd, J=2.0 Hz, J=8.5 Hz), 6.89 (1H, d, J=7.5 Hz), 7.14 (1H, brs), 7.24-7.30 (1H, m), 7.37-7.47 (3H, m), 7.55 (1H, d, J=8.0 Hz), 7.62 (1H, d, J=9.5 Hz)

EXAMPLE 113

Synthesis of N-pyridin-2-yl-N-methylcarbamic acid 7-[4-(4-benzo[b]thiophen-4-ylpiperazin-1-yl)butoxy]-2-oxo-2H-quinolin-1-ylmethyl ester

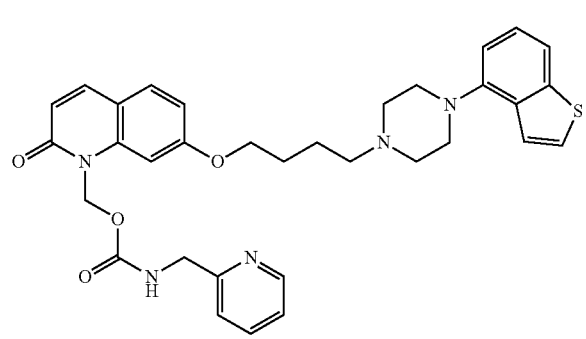 [SMILES: O=C(NCc1ccccn1)OCn1c(=O)ccc2ccc(OCCCCN3CCN(c4cccc5sccc45)CC3)cc21]

In the same manner as in Example 10, the title compound was obtained.

$^1$H-NMR (CDCl$_3$) δ: 1.64-1.81 (2H, m), 1.83-1.93 (2H, m), 2.53 (2H, t, J=7.5 Hz), 2.66-2.80 (4H, m), 3.12-3.25 (4H, m), 4.08 (2H, t, J=6.0 Hz), 4.53 (2H, d, J=5.0 Hz), 6.01 (1H, t, J=5.0 Hz), 6.38 (2H, s), 6.52 (1H, d, J=9.5 Hz), 6.83 (1H, dd, J=2.0 Hz, J=8.5 Hz), 6.88 (1H, d, J=7.5 Hz), 7.03-7.19 (2H, m), 7.21-7.30 (2H, m), 7.36-7.46 (3H, m), 7.55 (1H, d, J=8.0 Hz), 7.59-7.67 (2H, m), 8.40-8.57 (1H, m)

EXAMPLE 114

Synthesis of undec-10-enoic acid 7-[4-(4-benzo[b]thiophen-4-ylpiperazin-1-yl)butoxy]-2-oxo-3,4-dihydro-2H-quinolin-1-ylmethyl ester

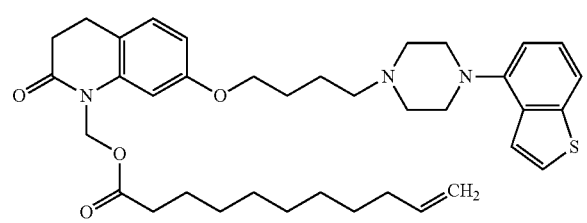 [SMILES: C=CCCCCCCCCC(=O)OCN1C(=O)CCc2ccc(OCCCCN3CCN(c4cccc5sccc45)CC3)cc21]

In the same manner as in Example 48, the title compound was obtained.

$^1$H-NMR (CDCl$_3$) δ: 1.21-1.40 (m, 10H), 1.54-1.68 (m, 2H), 1.68-1.79 (m, 2H), 1.79-1.90 (m, 2H), 1.97-2.06 (m, 2H), 2.36 (t, J=9.5 Hz, 2H), 2.52 (t, J=7.4 Hz, 2H), 2.64-2.76 (m, 6H), 2.83-2.96 (m, 2H), 3.14-3.23 (m, 4H), 3.99 (t, J=6.3 Hz, 2H), 4.89-4.94 (m, 1H), 4.94-5.02 (m, 1H), 5.73-5.86 (m, 1H), 5.92 (brs, 2H), 6.57-6.63 (m, 2H), 6.87-6.92 (m, 1H), 7.07 (d, J=8.1 Hz, 1H), 7.27 (dd, J=7.9, 7.9 Hz, 1H), 7.36-7.43 (m, 2H), 7.55 (d, J=7.9 Hz, 1H)

EXAMPLE 115

Synthesis of furan-3-carboxylic acid 7-[4-(4-benzo[b]thiophen-4-ylpiperazin-1-yl)butoxy]-2-oxo-2H-quinolin-1-ylmethyl ester

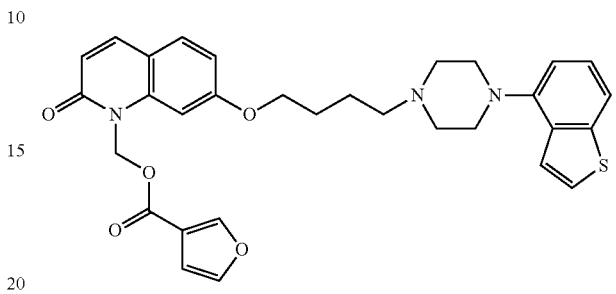

In the same manner as in Example 22, the title compound was obtained.

$^1$H-NMR (CDCl$_3$) δ: 1.67-1.81 (m, 2H), 1.81-1.97 (m, 2H), 2.52 (dd, J=7.5 Hz, 2H), 2.62-2.78 (m, 4H), 3.11-3.24 (m, 4H), 4.08 (t, J=6.2 Hz, 2H), 6.51 (brs, 2H), 6.54 (d, J=9.5 Hz, 1H), 6.74-6.77 (m, 1H), 6.84 (dd, J=2.2, 8.6 Hz, 1H), 6.89 (d, J=7.6 Hz, 1H), 6.96 (d, J=2.2 Hz, 1H), 7.27 (dd, J=7.8, 7.8 Hz, 1H), 7.37-7.43 (m, 3H), 7.46 (d, J=8.6 Hz, 1H), 7.55 (d, J=8.0 Hz, 1H), 7.64 (d, J=9.5 Hz, 1H), 8.01-8.04 (m, 1H)

EXAMPLE 116

Synthesis of N-phenethylcarbamic acid 7-[4-(4-benzo[b]thiophen-4-ylpiperazin-1-yl)butoxy]-2-oxo-2H-quinolin-1-ylmethyl ester

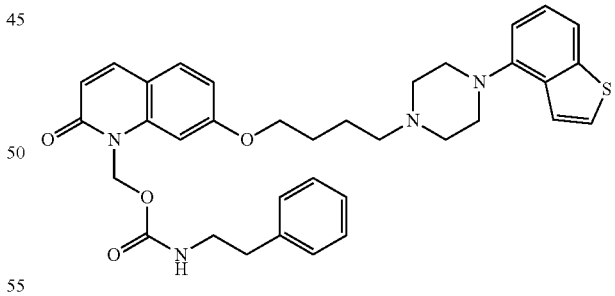

In the same manner as in Example 10, the title compound was obtained.

$^1$H-NMR (CDCl$_3$) δ: 1.71-1.82 (2H, m), 1.85-1.96 (2H, m), 2.53 (2H, t, J=7.5 Hz), 2.63-2.77 (4H, m), 2.81 (2H, t, J=7.0 Hz), 3.13-3.26 (4H, m), 3.44-3.52 (2H, m), 4.11 (2H, t, J=6.0 Hz), 4.90 (1H, t, J=5.5 Hz), 6.32 (2H, s), 6.50 (1H, d, J=9.5 Hz), 6.84 (1H, dd, J=2.0 Hz, J=8.5 Hz), 6.88 (1H, d, J=7.5 Hz), 7.12-7.34 (7H, m), 7.37-7.47 (3H, m), 7.55 (1H, d, J=8.0 Hz), 7.61 (1H, d, J=9.5 Hz)

EXAMPLE 117

Synthesis of N-isopropyl-carbamic acid 7-[4-(4 benzo[b]thiophen-4-ylpiperazin-1-yl)butoxy]-2-oxo-2H-quinolin-1-ylmethyl ester

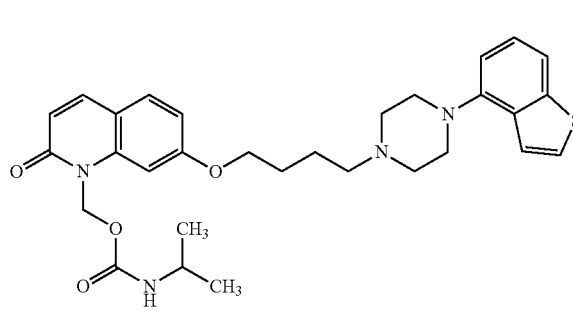

In the same manner as in Example 10, the title compound was obtained.

¹H-NMR (CDCl₃) δ: 1.15 (6H, d, J=6.5 Hz), 1.72-1.82 (2H, m), 1.85-1.94 (2H, m), 2.54 (2H, t, J=7.5 Hz), 2.66-2.78 (4H, m), 3.12-3.26 (4H, m), 3.78-3.90 (1H, m), 4.10 (2H, d, J=6.0 Hz), 4.93 (1H, d, J=7.5 Hz), 6.29 (2H, s), 6.48 (1H, d, J=9.5 Hz), 6.82 (1H, dd, J=2.0 Hz, J=8.5 Hz), 6.88 (1H, d, J=7.5 Hz), 7.13 (1H, brs), 7.26 (1H, dd, J=8.0 Hz, J=8.0 Hz), 7.35-7.44 (3H, m), 7.54 (1H, d, J=8.0 Hz), 7.57 (1H, d, J=9.5 Hz)

EXAMPLE 118

Synthesis of 2-methylheptanoic acid 7-[4-(4-benzo[b]thiophen-4-ylpiperazin-1-yl)butoxy]-2-oxo-2H-quinolin-1-ylmethyl ester

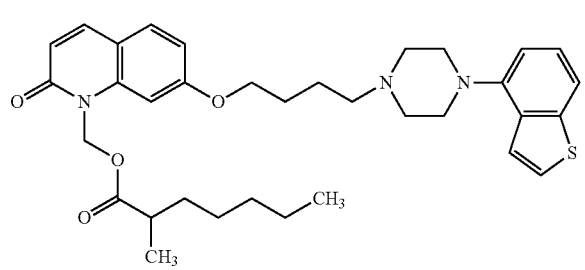

In the same manner as in Example 22, the title compound was obtained.

¹H-NMR (CDCl₃) δ: 0.81 (d, J=6.8 Hz, 3H), 1.15 (d, J=7.0 Hz, 3H), 1.17-1.30 (m, 6H), 1.35-1.46 (m, 1H), 1.58-1.71 (m, 1H), 1.71-1.82 (m, 2H), 1.82-1.98 (m, 2H), 2.43-2.58 (m, 3H), 2.66-2.79 (m, 4H), 3.14-3.25 (m, 4H), 4.07 (d, J=6.2 Hz, 2H), 6.35 (brs, 2H), 6.52 (d, J=9.5 Hz, 1H), 6.84 (dd, J=2.2, 8.5 Hz, 1H), 6.85-6.92 (m, 2H), 7.27 (dd, J=7.9, 7.9 Hz, 1H), 7.37-7.43 (m, 2H), 7.44 (d, J=8.5 Hz, 1H), 7.55 (d, J=8.0 Hz, 1H), 7.62 (d, J=9.5 Hz, 1H)

EXAMPLE 119

Synthesis of cycloheptanecarboxylic acid 7-[4-(4-benzo[b]thiophen-4-ylpiperazin-1-yl)butoxy]-2-oxo-2H-quinolin-1-ylmethyl ester

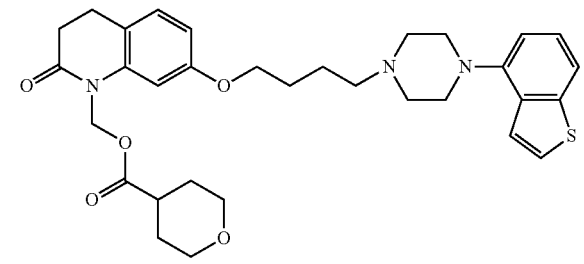 [SMILES: O=C(OCN1C(=O)CCc2ccc(OCCCCN3CCN(c4cccc5sccc45)CC3)cc21)C1CCOCC1]

In the same manner as in Example 22, the title compound was obtained.

¹H-NMR (CDCl₃) δ: 1.37-1.58 (m, 6H), 1.62-1.81 (m, 6H), 1.84-1.97 (m, 4H), 2.50-2.58 (m, 3H), 2.67-2.79 (m, 4H), 3.15-3.25 (m, 4H), 4.07 (t, J=6.2 Hz, 2H), 6.33 (brs, 2H), 6.52 (d, J=9.5 Hz, 1H), 6.82-6.86 (m, 2H), 6.87-6.92 (m, 1H), 7.27 (dd, J=8.0, 8.0 Hz, 1H), 7.37-7.43 (m, 2H), 7.43-7.47 (m, 1H), 7.55 (d, J=8.0 Hz, 1H), 7.62 (d, J=9.5 Hz, 1H)

EXAMPLE 120

Synthesis of tetrahydropyran-4-carboxylic acid 7-[4-(4-benzo[b]thiophen-4-ylpiperazin-1-yl)butoxy]-2-oxo-3,4-dihydro-2H-quinolin-1-ylmethyl ester In the same manner as in Example 48, the title compound was obtained.

¹H-NMR (CDCl₃) δ: 1.69-1.90 (m, 8H), 2.52 (t, J=7.4 Hz, 2H), 2.56-2.65 (m, 1H), 2.65-2.77 (m, 6H), 2.83-2.90 (m, 2H), 3.14-3.25 (m, 4H), 3.37-3.45 (m, 2H), 3.90-4.01 (m, 4H), 5.94 (brs, 2H), 6.57 (d, J=2.2 Hz, 1H), 6.60 (d, J=2.2, 8.2 Hz, 1H), 6.90 (d, J=7.6 Hz, 1H), 7.07 (d, J=8.2 Hz, 1H), 7.24-7.30 (m, 1H), 7.38 (d, J=5.6 Hz, 1H), 7.42 d, J=5.6 Hz, 1H), 7.55 (d, J=8.0 Hz, 1H)

EXAMPLE 121

Synthesis of malonic acid 7-[4-(4-benzo[b]thiophen-4-ylpiperazin-1-yl)butoxy]-2-oxo-3,4-dihydro-2H-quinolin-1-ylmethyl ester tert-butyl ester

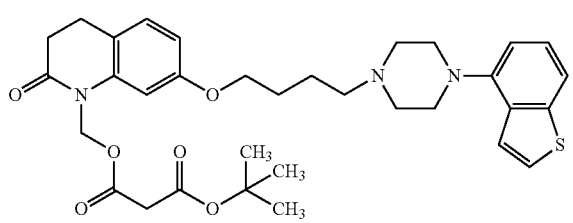 [SMILES: CC(C)(C)OC(=O)CC(=O)OCN1C(=O)CCc2ccc(OCCCCN3CCN(c4cccc5sccc45)CC3)cc21]

In the same manner as in Example 48, the title compound was obtained.

$^1$H-NMR (CDCl$_3$) δ: 1.44 (s, 9H), 1.69-1.80 (m, 2H), 1.80-1.89 (m, 2H), 2.52 (d, J=7.4 Hz, 2H), 2.64-2.79 (m, 6H), 2.83-2.90 (m, 2H), 3.14-3.25 (m, 4H), 3.35 (s, 2H), 4.01 (t, J=6.2 Hz, 2H), 5.96 (brs, 2H), 6.00 (dd, J=2.3, 8.2 Hz, 1H), 6.67 (d, J=2.3 Hz, 1H), 6.90 (d, J=7.4 Hz, 1H), 7.07 (d, J=8.2 Hz, 1H), 7.25-7.30 (m, 1H), 7.37-7.43 (m, 2H), 7.55 (d, J=8.0 Hz, 1H)

EXAMPLE 122

Synthesis of N-isobutylcarbamic acid 7-[4-(4-benzo[b]thiophen-4-ylpiperazin-1-yl)butoxy]-2-oxo-2H-quinolin-1-ylmethyl ester

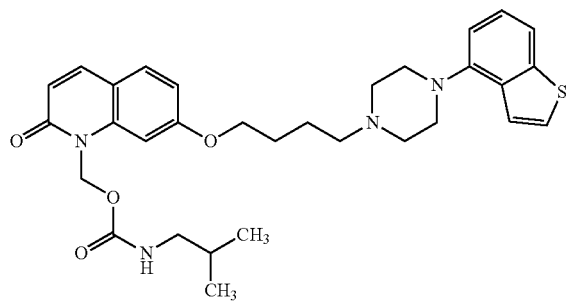

In the same manner as in Example 10, the title compound was obtained.

$^1$H-NMR (CDCl$_3$) δ: 0.86-0.93 (6H, m), 1.69-1.82 (3H, m), 1.84-1.94 (2H, m), 2.54 (2H, t, J=7.5 Hz), 2.65-2.78 (4H, m), 3.03 (2H, t, J=6.5 Hz), 3.13-3.25 (4H, m), 4.10 (2H, d, J=6.0 Hz), 5.09 (1H, t, J=6.0 Hz), 6.32 (2H, s), 6.49 (1H, d, J=9.5 Hz), 6.82 (1H, dd, J=2.0 Hz, J=8.5 Hz), 6.86-6.91 (1H, m), 7.13 (1H, d, J=2.0 Hz), 7.24-7.30 (1H, m), 7.36-7.44 (3H, m), 7.54 (1H, d, J=8.0 Hz), 7.58 (1H, d, J=9.5 Hz)

EXAMPLE 123

Synthesis of 4,4-difluoropiperidine-1-carboxylic acid 7-[4-(4-benzo[b]thiophen-4-ylpiperazin-1-yl)butoxy]-2-oxo-2H-quinolin-1-ylmethyl ester

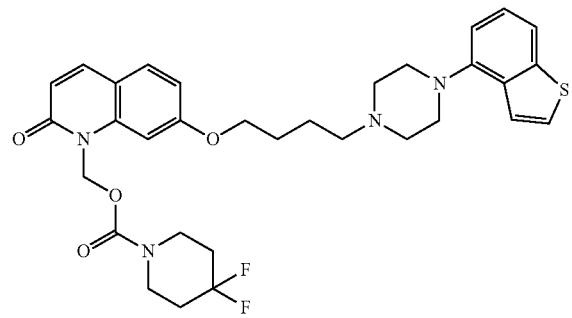 [SMILES: O=C(OCn1c(=O)ccc2ccc(OCCCCN3CCN(c4cccc5sccc45)CC3)cc21)N1CCC(F)(F)CC1]

In the same manner as in Example 48, the title compound was obtained.

$^1$H-NMR (CDCl$_3$) δ: 1.72-2.07 (8H, m), 2.54 (2H, t, J=7.5 Hz), 2.64-2.78 (4H, m), 3.13-3.25 (4H, m), 3.48-3.71 (4H, m), 4.10 (2H, d, J=6.0 Hz), 6.36 (2H, s), 6.52 (1H, d, J=9.5 Hz), 6.85 (1H, dd, J=2.0 Hz, J=8.5 Hz), 6.89 (1H, d, J=7.5 Hz), 7.06 (1H, d, J=2.0 Hz), 7.27 (1H, dd, J=8.0 Hz, J=8.0 Hz), 7.39 (1H, d, J=5.5 Hz), 7.41 (1H, d, J=5.5 Hz), 7.45 (1H, d, J=8.5 Hz), 7.55 (1H, d, J=8.0 Hz), 7.63 (1H, d, J=9.5 Hz)

EXAMPLE 124

Synthesis of 4,4,4-trifluorobutyric acid 7-[4-(4-benzo[b]thiophen-4-ylpiperazin-1-yl)butoxy]-2-oxo-3,4-dihydro-2H-quinolin-1-ylmethyl ester

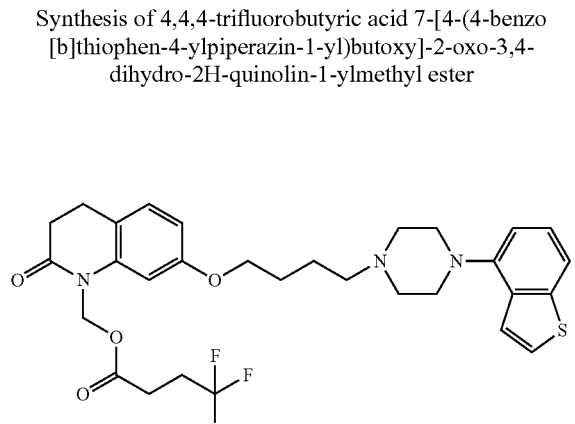

In the same manner as in Example 48, the title compound was obtained.

$^1$H-NMR (CDCl$_3$) δ: 1.69-1.80 (m, 2H), 1.80-1.90 (m, 2H), 2.43-2.57 (m, 4H), 2.62-2.77 (m, 8H), 2.83-2.90 (m, 2H), 3.13-3.24 (m, 4H), 3.99 (t, J=6.2 Hz, 2H), 5.95 (brs, 2H), 6.57-6.63 (m, 2H), 6.87-6.92 (m, 1H), 7.08 (d, J=8.1 Hz, 1H), 7.27 (dd, J=7.8, 7.8 Hz, 1H), 7.37-7.42 (m, 2H), 7.55 (d, J=8.1 Hz, 1H)

EXAMPLE 125

Synthesis of N-furan-2-ylmethyl-N-methylcarbamic acid 7-[4-(4-benzo[b]thiophen-4-ylpiperazin-1-yl)butoxy]-2-oxo-2H-quinolin-1-ylmethyl ester

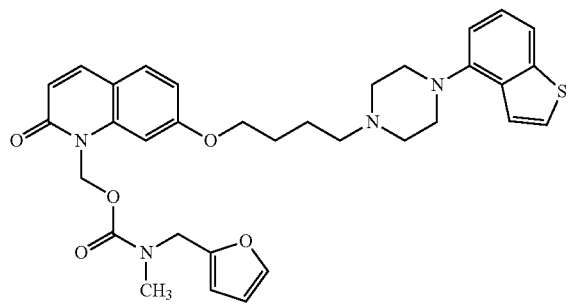 [SMILES: CN(Cc1ccco1)C(=O)OCn1c(=O)ccc2ccc(OCCCCN3CCN(c4cccc5sccc45)CC3)cc21]

In the same manner as in Example 10, the title compound was obtained.

$^1$H-NMR (CDCl$_3$) δ: 1.69-1.82 (2H, m), 1.84-1.94 (2H, m), 2.53 (2H, t, J=7.5 Hz), 2.65-2.78 (4H, m), {2.84 (s), 2.97 (s) total 3H (1:1)}, 3.13-3.26 (4H, m), 4.05 (1H, d, J=6.0 Hz), 4.10 (1H, t, J=6.0 Hz), 4.31 (1H, s), 4.49 (1H, s), {6.02 (d, J=2.5 Hz), 6.24 (d, J=2.5 Hz) total 1H (1:1)}, {6.17 (brs), 6.32 (brs) total 1H (1:1)}, 6.39 (2H, s), 6.52 (1H, d, J=9.5 Hz), 6.83 (1H, dd, J=2.0 Hz, J=8.5 Hz), 6.89 (1H, d, J=7.5 Hz), {7.02 (brs), 7.12 (brs) total 1H (1:1)}, {7.19 (brs), 7.36 (brs) total 1H (1:1)}, 7.24-7.31 (1H, m), 7.36-7.46 (3H, m), 7.55 (1H, d, J=8.0 Hz), 7.62 (1H, d, J=9.5 Hz)

EXAMPLE 126

Synthesis of 4-methylpentanoic acid 7-[4-(4-benzo[b]thiophen-4-ylpiperazin-1-yl)butoxy]-2-oxo-2H-quinolin-1-ylmethyl ester

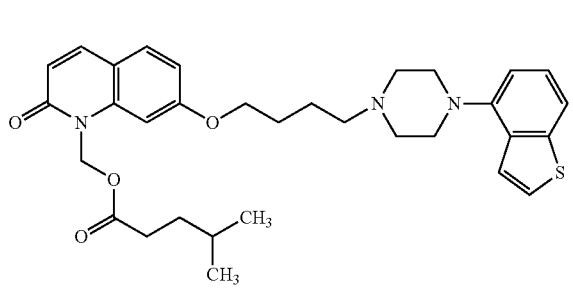 [SMILES: CC(C)CCC(=O)OCn1c(=O)ccc2ccc(OCCCCN3CCN(c4cccc5sccc45)CC3)cc21]

In the same manner as in Example 22, the title compound was obtained.

$^1$H-NMR (CDCl$_3$) δ: 0.87 (d, J=6.3 Hz, 6H), 1.50-1.62 (m, 3H), 1.70-1.82 (m, 2H), 1.86-1.95 (m, 2H), 2.33-2.40 (m, 2H), 2.54 (t, J=7.5 Hz, 2H), 2.66-2.79 (m, 4H), 3.14-3.24 (m, 4H), 4.08 (t, J=6.2 Hz, 2H), 6.33 (brs, 2H), 6.52 (d, J=9.5 Hz, 1H), 6.84 (dd, J=2.2, 8.6 Hz, 1H), 6.86-6.91 (m, 2H), 7.27 (dd, J=7.8, 7.8 Hz, 1H), 7.37-7.43 (m, 2H), 7.45 (d, J=8.6 Hz, 1H), 7.55 (d, J=8.0 Hz, 1H), 7.63 (d, J=9.5 Hz, 1H)

EXAMPLE 127

Synthesis of cyclobutanecarboxylic acid 7-[4-(4-benzo[b]thiophen-4-ylpiperazin-1-yl)butoxy]-2-oxo-3,4-dihydro-2H-quinolin-1-ylmethyl ester

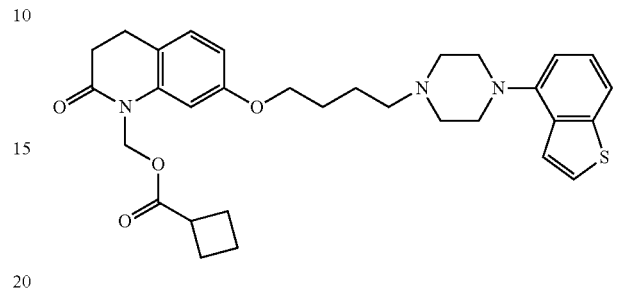

In the same manner as in Example 48, the title compound was obtained.

$^1$H-NMR (CDCl$_3$) δ: 1.68-1.79 (m, 2H), 1.80-2.03 (m, 4H), 2.15-2.25 (m, 2H), 2.25-2.37 (m, 2H), 2.52 (t, J=7.5 Hz, 2H), 2.64-2.77 (m, 6H), 2.83-2.89 (m, 2H), 3.13-3.24 (m, 5H), 3.98 (t, J=6.2 Hz, 2H), 5.92 (brs, 2H), 6.57-6.62 (m, 2H), 6.90 (d, J=7.5 Hz, 1H), 7.07 (d, J=8.4 Hz, 1H), 7.24-7.30 (m, 1H), 7.38 (d, J=5.6 Hz, 1H), 7.41 (d, J=5.6 Hz, 1H), 7.55 (d, J=8.1 Hz, 1H)

EXAMPLE 128

Synthesis of benzofuran-5-carboxylic acid 7-[4-(4-benzo[b]thiophen-4-ylpiperazin-1-yl)butoxy]-2-oxo-3,4-dihydro-2H-quinolin-1-ylmethyl ester

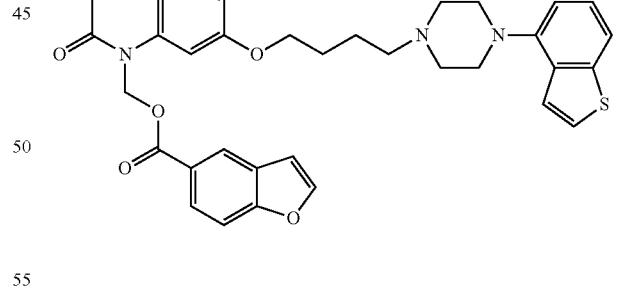

In the same manner as in Example 48, the title compound was obtained.

$^1$H-NMR (CDCl$_3$) δ: 1.62-1.74 (m, 2H), 1.75-1.86 (m, 2H), 2.46 (t, J=7.5 Hz, 2H), 2.58-2.71 (m, 4H), 2.71-2.79 (m, 2H), 2.82-2.93 (m, 2H), 3.07-3.20 (m, 4H), 3.96 (t, J=6.3 Hz, 2H), 6.19 (brs, 2H), 6.61 (dd, J=2.3, 8.3 Hz, 1H), 6.77 (d, J=2.3 Hz, 1H), 6.79-6.83 (m, 1H), 6.85-6.90 (m, 1H), 7.10 (d, J=8.3 Hz, 1H), 7.27 (dd, J=7.9, 7.9 Hz, 1H), 7.36-7.41 (m, 2H), 7.52 (d, J=8.7 Hz, 1H), 7.55 (d, J=7.9 Hz, 1H), 7.65 (d, J=2.2 Hz, 1H), 8.03 (dd, J=1.7, 8.7 Hz, 1H), 8.36 (d, J=1.7 Hz, 1H)

EXAMPLE 129

Synthesis of N-methoxycarbamic acid (7-{4-[4-(benzo[b]thiophen-4-yl)piperazin-1-yl]butoxy}-2-oxo-2H-quinolin-1-yl)methyl

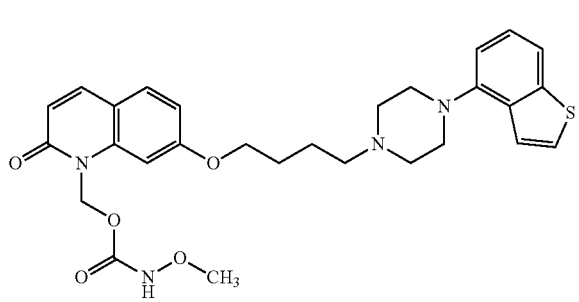 [SMILES: CONC(=O)OCn1c(=O)ccc2ccc(OCCCCN3CCN(c4cccc5sccc45)CC3)cc21]

In the same manner as in Example 10, the title compound was obtained.

$^1$H-NMR (CDCl$_3$) δ: 1.72-1.82 (2H, m), 1.84-1.95 (2H, m), 2.54 (2H, t, J=7.5 Hz), 2.65-2.79 (4H, m), 3.13-3.26 (4H, m), {3.51 (s), 3.73 (s) total 3H (1:3)}, 4.07-4.17 (2H, m), {6.33 (s), 6.39 (s) total 2H (1:3)}, 6.48-6.53 (1H, m), 6.80-6.88 (2H, m), {7.05 (d, J=2.0 Hz), 7.13 (d, J=2.0 Hz) total 1H (3:1)}, 7.24-7.30 (1H, m), 7.37-7.47 (3H, m), 7.55 (1H, d, J=8.0 Hz), {7.58 (brs), 7.83 (brs) total 1H (1:3)}, 7.62 (1H, d, J=9.5 Hz)

EXAMPLE 130

Synthesis of tetrahydropyran-4-carboxylic acid 7-[4-(4-benzo[b]thiophen-4-ylpiperazin-1-yl)butoxy]-2-oxo-2H-quinolin-1-ylmethyl ester

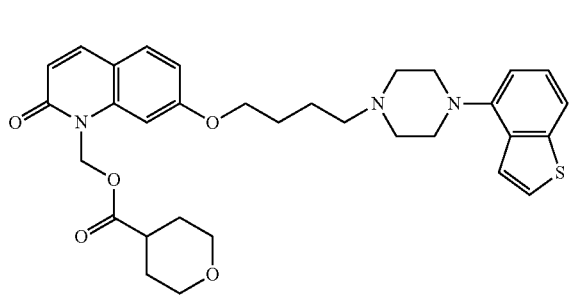

In the same manner as in Example 22, the title compound was obtained.

$^1$H-NMR (CDCl$_3$) δ: 1.71-1.95 (m, 8H), 2.54 (t, J=7.5 Hz, 2H), 2.57-2.66 (m, 1H), 2.67-2.79 (m, 4H), 3.14-3.25 (m, 4H), 3.34-3.43 (m, 2H), 3.93 (dt, J=3.6, 7.6 Hz, 2H), 4.08 (t, J=6.3 Hz, 2H), 6.35 (brs, 2H), 6.52 (d, J=9.5 Hz, 1H), 6.81-6.87 (m, 2H), 6.87-6.92 (m, 1H), 7.27 (dd, J=7.9, 7.9 Hz, 1H), 7.39 (d, J=5.5 Hz, 1H), 7.42 (d, J=5.5 Hz, 1H), 7.46 (d, J=8.4 Hz, 1H), 7.55 (d, J=7.9 Hz, 1H), 7.63 (d, J=9.5 Hz, 1H)

EXAMPLE 131

Synthesis of thiophene-2-carboxylic acid 7-[4-(4-benzo[b]thiophen-4-ylpiperazin-1-yl)butoxy]-2-oxo-3,4-dihydro-2H-quinolin-1-ylmethyl ester

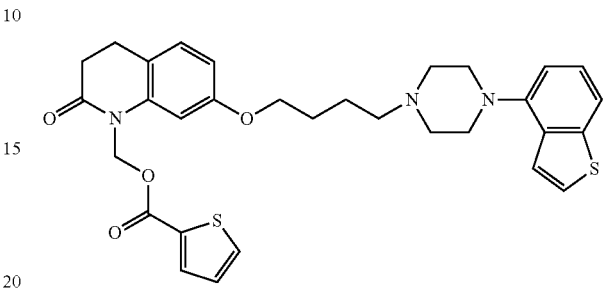

In the same manner as in Example 48, the title compound was obtained.

$^1$H-NMR (CDCl$_3$) δ: 1.66-1.76 (m, 2H), 1.77-1.89 (m, 2H), 2.50 (t, J=7.5 Hz, 2H), 2.62-2.76 (m, 6H), 2.85-2.92 (m, 2H), 3.10-3.23 (m, 4H), 3.98 (t, J=6.2 Hz, 2H), 6.14 (brs, 2H), 6.61 (dd, J=2.3, 8.2 Hz, 1H), 6.75 (d, J=2.3 Hz, 1H), 6.86-6.91 (m, 1H), 7.05-7.11 (m, 2H), 7.27 (dd, J=7.8, 7.8 Hz, 1H), 7.37-7.43 (m, 2H), 7.53-7.58 (m, 2H), 7.82 (dd, J=1.2, 3.8 Hz, 1H)

EXAMPLE 132

Synthesis of nicotinic acid 7-[4-(4-benzo[b]thiophen-4-ylpiperazin-1-yl)butoxy]-2-oxo-3,4-dihydro-2H-quinolin-1-ylmethyl ester

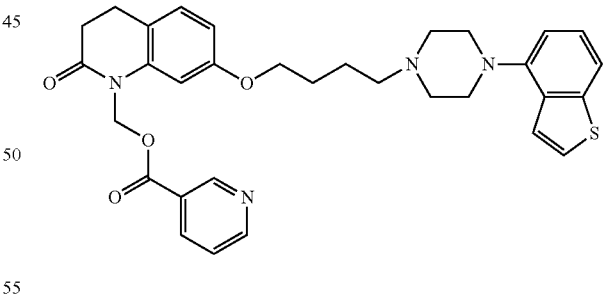

In the same manner as in Example 48, the title compound was obtained.

$^1$H-NMR (CDCl$_3$) δ: 1.64-1.76 (m, 2H), 1.77-1.88 (m, 2H), 2.49 (t, J=7.5 Hz, 2H), 2.61-2.78 (m, 6H), 2.87-2.94 (m, 2H), 3.10-3.24 (m, 4H), 3.98 (t, J=6.3 Hz, 2H), 6.19 (brs, 2H), 6.62 (dd, J=2.3, 8.3 Hz, 1H), 6.72 (d, J=2.3 Hz, 1H), 6.88 (d, J=7.5 Hz, 1H), 7.10 (d, J=8.3 Hz, 1H), 7.27 (dd, J=7.8, 7.8 Hz, 1H), 7.35-7.42 (m, 3H), 7.55 (d, J=8.0 Hz, 1H), 8.30 (ddd, J=2.0, 2.0, 8.0 Hz, 1H), 8.77 (dd, J=1.7, 4.9 Hz, 1H), 9.21-9.25 (m, 1H)

EXAMPLE 133

Synthesis of carbonic acid 7-[4-(4-benzo[b]thiophen-4-ylpiperazin-1-yl)butoxy]-2-oxo-2H-quinolin-1-ylmethyl ester 4-nitrophenyl ester

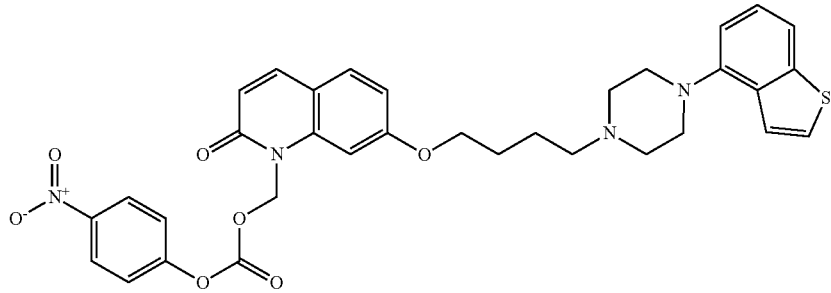 [SMILES: O=C(OCn1c(=O)ccc2ccc(OCCCCN3CCN(c4cccc5sccc45)CC3)cc21)Oc1ccc([N+](=O)[O-])cc1]

7-[4-(4-Benzo[b]thiophen-4-ylpiperazin-1-yl)butoxy]-1H-quinolin-2-one (2.0 g) was suspended in anhydrous THF (40 ml) under a nitrogen atmosphere, and sodium hydride (about 55% oil) (0.22 g) was added. The mixture was refluxed for 30 min under a nitrogen atmosphere. The obtained solution was cooled to was cooled to −70° C., and a solution (20 ml) of chloromethyl-4-nitrophenyl carbonate (1.50 g) in anhydrous THF with cannula. The reaction mixture was stirred at room temperature for 3 hr. Water was added to the reaction mixture to discontinue the reaction, and the mixture was extracted with ethyl acetate. The organic layer was dried over sodium sulfate, and concentrated by filtration. The obtained residue was purified by silica gel column chromatography (ethyl acetate) to give the component (Rf value: 0.62, ethyl acetate, 0.67 g) as a pale-yellow amorphous compound. The obtained compound was used for the next reaction step without further purification.

EXAMPLE 134

Synthesis of carbonic acid 7-[4-(4-benzo[b]thiophen-4-ylpiperazin-1-yl)butoxy]-2-oxo-2H-quinolin-1-ylmethyl ester dodecyl ester

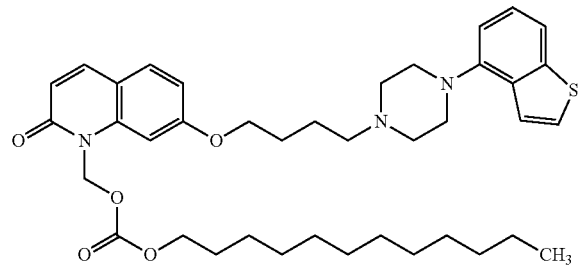 [SMILES: CCCCCCCCCCCCOC(=O)OCn1c(=O)ccc2ccc(OCCCCN3CCN(c4cccc5sccc45)CC3)cc21]

1-Dodecanol (0.10 g) was dissolved in anhydrous THF (5 ml) under a nitrogen atmosphere and sodium hydride (about 55% oil) (25 mg) was added under ice-cooling with stirring. The reaction mixture was stirred at room temperature for 30 min under a nitrogen atmosphere, and then the mixture was ice-cooled. To the mixture was added a solution (5 ml) of carbonic acid 7-[4-(4-benzo[b]thiophen-4-ylpiperazin-1-yl)butoxy]-2-oxo-2H-quinolin-1-ylmethyl ester 4-nitrophenyl ester obtained in Example 133 (0.33 g) in anhydrous THF using a cannula. Under a nitrogen atmosphere, the reaction mixture was stirred with ice-cooling for 2 hr, and at room temperature for 1 hr. Water was added to the reaction mixture to discontinue the reaction, and the mixture was extracted with ethyl acetate. The organic layer was dried over sodium sulfate, and concentrated by filtration. The obtained residue was purified by silica gel column chromatography (ethyl acetate:hexane=1:1) to give the title compound (0.14 g) as a colorless oil.

$^1$H-NMR (CDCl$_3$) δ: 0.87 (3H, t, J=7.0 Hz), 1.17-1.38 (18H, m), 1.59-1.70 (2H, m), 1.73-1.82 (2H, m), 1.86-1.95 (2H, m), 2.54 (2H, t, J=7.5 Hz), 2.69-2.78 (4H, m), 3.16-3.24 (4H, m), 4.10 (2H, t, J=6.0 Hz), 4.18 (2H, t, J=6.5 Hz), 6.35 (2H, brs), 6.50 (1H, d, J=9.5 Hz), 6.84 (1H, dd, J=2.0 Hz, J=8.5 Hz), 6.89 (1H, d, J=7.5 Hz), 6.93 (1H, d, J=2.0 Hz), 7.24-7.30 (1H, m), 7.38 (1H, d, J=5.5 Hz), 7.42 (1H, d, J=5.5 Hz), 7.44 (1H, d, J=8.5 Hz), 7.55 (1H, d, J=8.0 Hz), 7.61 (1H, d, J=9.5 Hz)

EXAMPLE 135

Synthesis of carbonic acid 7-[4-(4-benzo[b]thiophen-4-ylpiperazin-1-yl)butoxy]-2-oxo-2H-quinolin-1-ylmethyl ester decyl ester

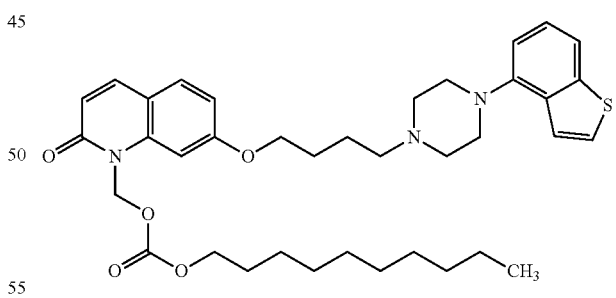

Using 7-[4-(4-benzo[b]thiophen-4-ylpiperazin-1-yl)butoxy]-1H-quinolin-2-one synthesized in the same manner as in WO2006/112464 (Example 1), and in the same manner as in Example 5, the title compound was obtained.

$^1$H-NMR (CDCl$_3$) δ: 0.87 (3H, t, J=7.0 Hz), 1.17-1.38 (14H, m), 1.62-1.70 (2H, m), 1.72-1.83 (2H, m), 1.86-1.96 (2H, m), 2.54 (2H, t, J=7.5 Hz), 2.64-2.81 (4H, m), 3.12-3.26 (4H, m), 4.07-4.13 (2H, m), 4.18 (2H, t, J=6.5 Hz), 6.35 (2H, brs), 6.50 (1H, d, J=9.5 Hz), 6.84 (1H, dd, J=2.0 Hz, J=8.5 Hz), 6.89 (1H, d, J=7.5 Hz), 6.93 (1H, d, J=2.0 Hz), 7.24-7.30

(1H, m), 7.38 (1H, d, J=5.5 Hz), 7.42 (1H, d, J=5.5 Hz), 7.44 (1H, d, J=8.5 Hz), 7.55 (1H, d, J=8.0 Hz), 7.61 (1H, d, J=9.5 Hz)

EXAMPLE 136

Synthesis of cyclobutanecarboxylic acid 7-[4-(4-benzo[b]thiophen-4-ylpiperazin-1-yl)butoxy]-2-oxo-2H-quinolin-1-ylmethyl ester

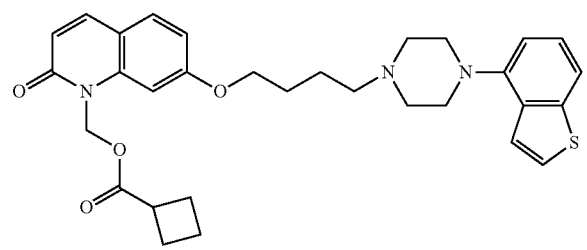

In the same manner as in Example 22, the title compound was obtained.

$^1$H-NMR (CDCl$_3$) δ: 1.66-1.84 (m, 2H), 1.84-2.05 (m, 4H), 2.14-2.24 (m, 2H), 2.24-2.36 (m, 2H), 2.55 (t, J=7.5 Hz, 2H), 2.65-2.80 (m, 4H), 3.12-3.26 (m, 5H), 4.08 (t, J=6.2 Hz, 2H), 6.34 (brs, 2H), 6.52 (d, J=9.5 Hz, 1H), 6.84 (dd, J=2.2, 8.5 Hz, 1H), 6.87 (d, J=2.2 Hz, 1H), 6.89 (d, J=7.6 Hz, 1H), 7.24-7.30 (m, 1H), 7.39 (d, J=5.6 Hz, 1H), 7.41 (d, J=5.6 Hz, 1H), 7.44 (d, J=8.5 Hz, 1H), 7.55 (d, J=8.0 Hz, 1H), 7.62 (d, J=9.5 Hz, 1H)

EXAMPLE 137

Synthesis of benzofuran-5-carboxylic acid 7-[4-(4-benzo[b]thiophen-4-ylpiperazin-1-yl)butoxy]-2-oxo-2H-quinolin-1-ylmethyl ester

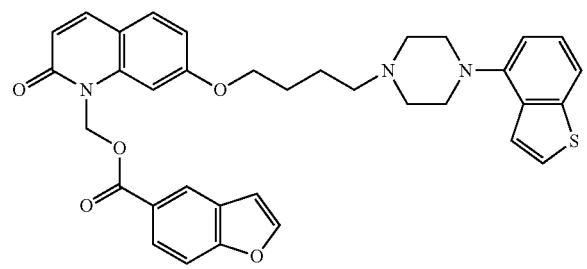 [SMILES: O=C(OCn1c(=O)ccc2ccc(OCCCCN3CCN(c4cccc5sccc45)CC3)cc21)c1ccc2occc2c1]

In the same manner as in Example 22, the title compound was obtained.

$^1$H-NMR (CDCl$_3$) δ: 1.66-1.78 (m, 2H), 1.78-1.92 (m, 2H), 2.48 (t, J=7.4 Hz, 2H), 2.59-2.74 (m, 4H), 3.10-3.20 (m, 4H), 4.07 (t, J=6.2 Hz, 2H), 6.57 (d, J=9.5 Hz, 1H), 6.61 (brs, 2H), 6.76-6.81 (m, 1H), 6.84 (dd, J=2.1, 8.6 Hz, 1H), 6.87 (d, J=7.6 Hz, 1H), 7.00-7.04 (m, 1H), 7.27 (dd, J=7.9, 7.9 Hz, 1H), 7.37-7.42 (m, 2H), 7.47 (d, J=8.6 Hz, 1H), 7.50 (d, J=8.7 Hz, 1H), 7.55 (d, J=7.9 Hz, 1H), 7.62-7.69 (m, 2H), 8.03 (dd, J=1.7, 8.7 Hz, 1H), 8.35 (d, J=1.7 Hz, 1H)

EXAMPLE 138

Synthesis of 4,4,4-trifluorobutyric acid 7-[4-(4-benzo[b]thiophen-4-ylpiperazin-1-yl)butoxy]-2-oxo-2H-quinolin-1-ylmethyl ester

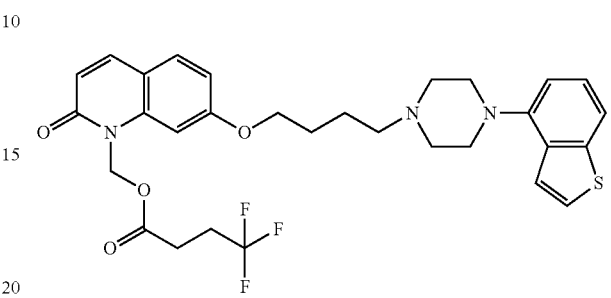

In the same manner as in Example 22, the title compound was obtained.

$^1$H-NMR (CDCl$_3$) δ: 1.68-1.82 (m, 2H), 1.86-1.96 (m, 2H), 2.43-2.58 (m, 4H), 2.62-2.69 (m, 2H), 2.69-2.79 (m, 4H), 3.14-3.26 (m, 4H), 4.08 (t, J=6.2 Hz, 2H), 6.36 (brs, 2H), 6.52 (d, J=9.5 Hz, 1H), 6.83-6.88 (m, 2H), 6.88-6.92 (m, 1H), 7.27 (dd, J=7.9, 7.9 Hz, 1H), 7.37-7.43 (m, 2H), 7.46 (d, J=8.3 Hz, 1H), 7.55 (d, J=7.9 Hz, 1H), 7.64 (d, J=9.5 Hz, 1H)

EXAMPLE 139

Synthesis of N-(3,3,3-trifluoropropyl)carbamic acid 7-[4-(4-benzo[b]thiophen-4-ylpiperazin-1-yl)butoxy]-2-oxo-2H-quinolin-1-ylmethyl ester

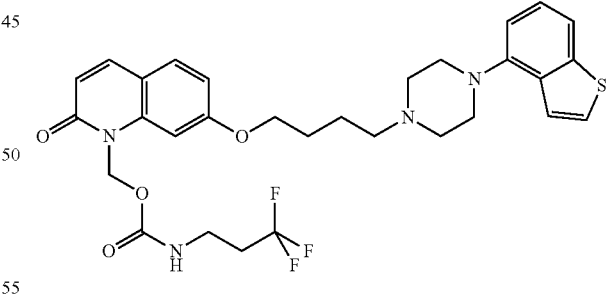

In the same manner as in Example 134, the title compound was obtained.

$^1$H-NMR (CDCl$_3$) δ: 1.72-1.95 (4H, m), 2.30-2.44 (2H, m), 2.54 (2H, t, J=7.5 Hz), 2.65-2.82 (4H, m), 3.13-3.26 (4H, m), 3.48 (2H, dt, J=6.5 Hz, J=6.5 Hz), 4.04-4.14 (2H, m), 5.32-5.39 (1H, m), 6.31 (2H, s), 6.48 (1H, d, J=9.5 Hz), 6.83 (1H, dd, J=2.0 Hz, J=8.5 Hz), 6.86-6.91 (1H, m), 7.07 (1H, d, J=2.0 Hz), 7.24-7.30 (1H, m), 7.37-7.44 (3H, m), 7.54 (1H, d, J=8.0 Hz), 7.58 (1H, d, J=9.5 Hz)

EXAMPLE 140

Synthesis of carbonic acid 7-[4-(4-benzo[b]thiophen-4-ylpiperazin-1-yl)butoxy]-2-oxo-2H-quinolin-1-ylmethyl ester (E)-3-phenyl-allyl ester

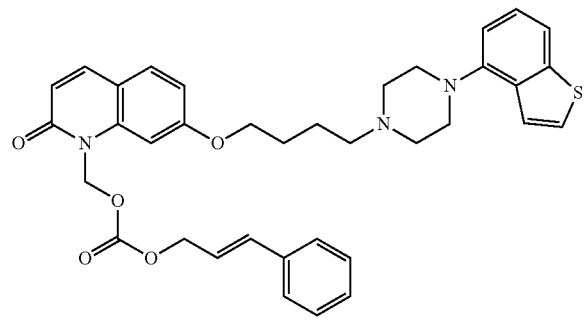 [SMILES: O=C(OC/C=C/c1ccccc1)OCn1c(=O)ccc2ccc(OCCCCN3CCN(c4cccc5sccc45)CC3)cc21]

In the same manner as in Example 134, the title compound was obtained.

$^1$H-NMR (CDCl$_3$) δ: 1.69-1.80 (2H, m), 1.82-1.94 (2H, m), 2.51 (2H, t, J=7.5 Hz), 2.63-2.77 (4H, m), 3.12-3.24 (4H, m), 4.05-4.11 (2H, m), 4.34 (1H, dd, J=1.0 Hz, J=6.5 Hz), 4.83 (1H, dd, J=1.0 Hz, J=6.5 Hz), 6.16-6.30 (1H, m), 6.38 (2H, brs), 6.50 (1H, dd, J=2.0 Hz, J=9.5 Hz), 6.57-6.70 (1H, m), 6.80-6.85 (1H, m), 6.87 (1H, brd, J=7.5 Hz), 6.93 (1H, brs), 7.20-7.46 (9H, m), 7.54 (1H, d, J=8.0 Hz), 7.59 (1H, dd, J=3.5 Hz, J=9.5 Hz)

EXAMPLE 141

Synthesis of thiophene-2-carboxylic acid 7-[4-(4-benzo[b]thiophen-4-ylpiperazin-1-yl)butoxy]-2-oxo-2H-quinolin-1-ylmethyl ester

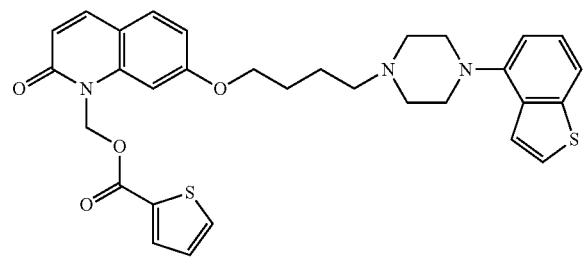

In the same manner as in Example 22, the title compound was obtained.

$^1$H-NMR (CDCl$_3$) δ: 1.66-1.82 (m, 2H), 1.84-1.93 (m, 2H), 2.52 (t, J=7.5 Hz, 2H), 2.64-2.77 (m, 4H), 3.12-3.24 (m, 4H), 4.08 (t, J=6.2 Hz, 2H), 6.52-6.60 (m, 3H), 6.84 (dd, J=2.1, 8.6 Hz, 1H), 6.89 (d, J=7.8 Hz, 1H), 7.00 (d, J=2.1 Hz, 1H), 7.07 (dd, J=3.8, 4.9 Hz, 1H), 7.27 (dd, J=7.8, 7.8 Hz, 1H), 7.38 (d, J=5.6 Hz, 1H), 7.41 (d, J=5.6 Hz, 1H), 7.45 (d, J=8.6 Hz, 1H), 7.53-7.59 (m, 2H), 7.64 (d, J=9.5 Hz, 1H), 7.82 (dd, J=1.2, 3.8 Hz, 1H)

EXAMPLE 142

Synthesis of carbonic acid 7-[4-(4-benzo[b]thiophen-4-ylpiperazin-1-yl)butoxy]-2-oxo-3,4-dihydro-2H-quinolin-1-ylmethyl ester decyl ester

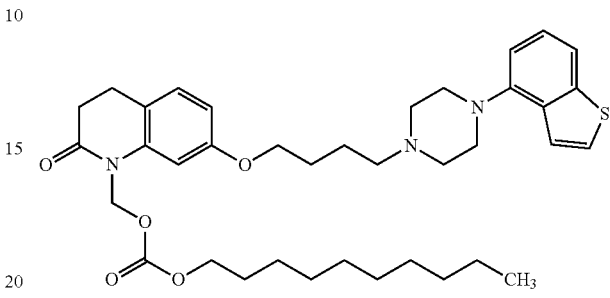

In the same manner as in Example 5, the title compound was obtained.

$^1$H-NMR (CDCl$_3$) δ: 0.87 (3H, t, J=7.0 Hz), 1.19-1.41 (14H, m), 1.62-1.80 (4H, m), 1.82-1.91 (2H, m), 2.52 (2H, t, J=7.5 Hz), 2.64-2.77 (6H, m), 2.82-2.90 (2H, m), 3.14-3.24 (4H, m), 4.00 (2H, t, J=6.0 Hz), 4.17 (2H, t, J=6.5 Hz), 5.94 (2H, s), 6.59 (1H; dd, J=2.5 Hz, J=8.5 Hz), 6.69 (1H, dd, J=2.5 Hz), 6.90 (1H, d, J=7.5 Hz), 7.06 (1H, d, J=8.5 Hz), 7.25-7.30 (1H, m), 7.38 (1H, d, J=5.5 Hz), 7.40-7.43 (1H, m), 7.55 (1H, d, J=8.0 Hz)

EXAMPLE 143

Synthesis of carbonic acid 7-[4-(4-benzo[b]thiophen-4-ylpiperazin-1-yl)butoxy]-2-oxo-3,4-dihydro-2H-quinolin-1-ylmethyl ester hexyl ester

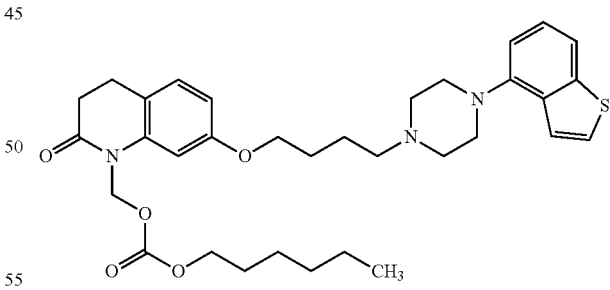

In the same manner as in Example 14, the title compound was obtained.

$^1$H-NMR (CDCl$_3$) δ: 0.88 (3H, t, J=6.9 Hz), 1.20-1.90 (12H, m), 2.52 (2H, t, J=7.4 Hz), 2.60-2.80 (6H, m), 2.83-2.88 (2H, m), 3.20 (4H, br), 4.00 (2H, t, J=6.2 Hz), 4.18 (2H, t, J=6.7 Hz), 5.94 (2H, brs), 6.59 (1H, dd, J=2.4, 8.2 Hz), 6.69 (1H, d, J=2.3 Hz), 6.90 (1H, d, J=7.6 Hz), 7.06 (1H, d, J=8.3 Hz), 7.20-7.30 (1H, m), 7.35-7.45 (2H, m), 7.55 (1H, d, J=8.0 Hz)

EXAMPLE 144

Synthesis of carbonic acid 7-[4-(4-benzo[b]thiophen-4-ylpiperazin-1-yl)butoxy]-2-oxo-3,4-dihydro-2H-quinolin-1-ylmethyl ester hexadecyl ester

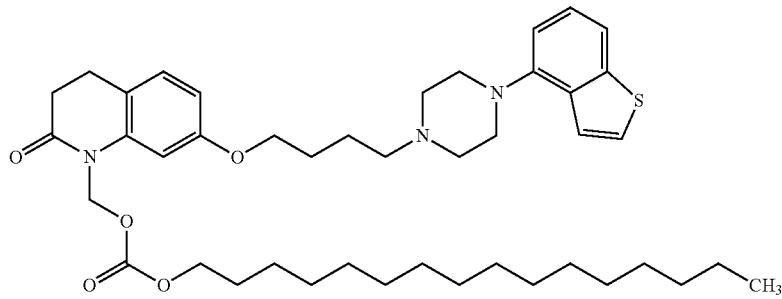 [SMILES: CCCCCCCCCCCCCCCCOC(=O)OCN1C(=O)CCc2ccc(OCCCCN3CCN(c4cccc5sccc45)CC3)cc21]

In the same manner as in Example 14, the title compound was obtained.

$^1$H-NMR (CDCl$_3$) δ: 0.88 (3H, t, J=6.8 Hz), 1.20-1.90 (32H, m), 2.53 (2H, t, J=7.4 Hz), 2.64-2.78 (6H, m), 2.80-2.90 (2H, m), 3.20 (4H, br), 4.00 (2H, t, J=6.2 Hz), 4.17 (2H, t, J=6.8 Hz), 5.94 (2H, brs), 6.59 (1H, dd, J=2.3, 8.3 Hz), 6.69 (1H, d, J=2.3 Hz), 6.89 (1H, d, J=7.6 Hz), 7.06 (1H, d, J=8.3 Hz), 7.27 (1H, t, J=7.8 Hz), 7.35-7.45 (2H, m), 7.54 (1H, d, J=8.0 Hz)

EXAMPLE 145

Synthesis of carbonic acid 7-[4-(4-benzo[b]thiophen-4-ylpiperazin-1-yl)butoxy]-2-oxo-3,4-dihydro-2H-quinolin-1-ylmethyl ester heptyl ester

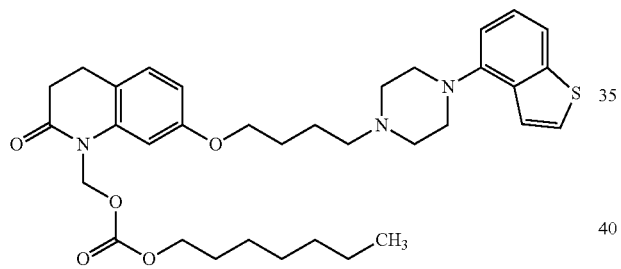

In the same manner as in Example 14, the title compound was obtained.

$^1$H-NMR (CDCl$_3$) δ: 0.87 (3H, t, J=7.0 Hz), 1.22-1.40 (6H, m), 1.52-1.90 (8H, m), 2.53 (2H, t, J=7.4 Hz), 2.64-2.78 (6H, m), 2.86 (2H, t, J=7.2 Hz), 3.20 (4H, br), 4.00 (2H, t, J=6.2 Hz), 4.17 (2H, t, J=6.8 Hz), 5.94 (2H, brs), 6.59 (1H, dd, J=2.4, 8.3 Hz), 6.69 (1H, d, J=2.3 Hz), 6.90 (1H, d, J=7.6 Hz), 7.06 (1H, d, J=8.2 Hz), 7.27 (1H, t, J=7.8 Hz), 7.35-7.45 (2H, m), 7.55 (1H, d, J=8.1 Hz)

EXAMPLE 146

Synthesis of carbonic acid 7-[4-(4-benzo[b]thiophen-4-ylpiperazin-1-yl)butoxy]-2-oxo-2H-quinolin-1-ylmethyl ester cyclohexyl ester

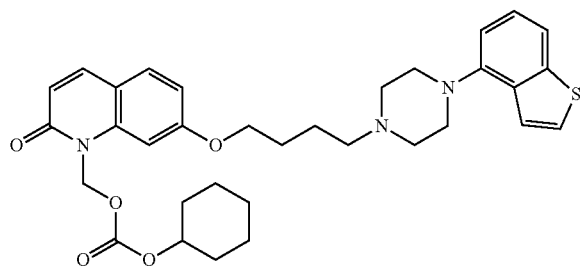 [SMILES: O=C(OCn1c(=O)ccc2ccc(OCCCCN3CCN(c4cccc5sccc45)CC3)cc21)OC1CCCCC1]

Using 7-[4-(4-benzo[b]thiophen-4-ylpiperazin-1-yl)butoxy]-1H-quinolin-2-one synthesized in the same manner as in WO2006/112464 (Example 1), and in the same manner as in Example 5, the title compound was obtained.

$^1$H-NMR (CDCl$_3$) δ: 1.17-1.28 (1H, m), 1.29-1.41 (2H, m), 1.42-1.57 (3H, m), 1.68-1.82 (4H, m), 1.84-1.98 (4H, m), 2.53 (2H, t, J=7.5 Hz), 2.64-2.80 (4H, m), 3.12-3.26 (4H, m), 4.09 (2H, t, J=6.0 Hz), 4.64-4.72 (1H, m), 6.34 (2H, s), 6.49 (1H, d, J=9.5 Hz), 6.83 (1H, dd, J=2.0 Hz, 8.5 Hz), 6.89 (1H, d, J=7.5 Hz), 6.92 (1H, d, J=2.0 Hz), 7.23-7.30 (1H, m), 7.36-7.44 (3H, m), 7.54 (1H, d, J=8.0 Hz), 7.59 (1H, d, J=9.5 Hz)

EXAMPLE 147

Synthesis of carbonic acid 7-[4-(4-benzo[b]thiophen-4-ylpiperazin-1-yl)butoxy]-2-oxo-3,4-dihydro-2H-quinolin-1-ylmethyl ester 2,2,2-trifluoro-ethyl ester

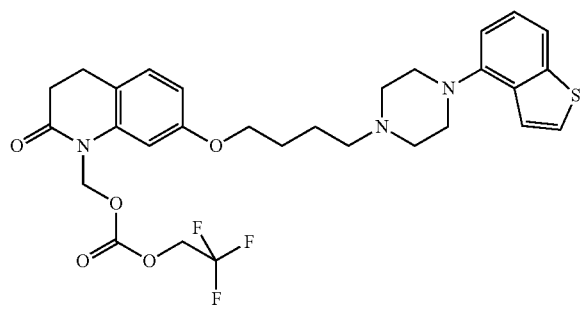 [SMILES: O=C(OCN1C(=O)CCc2ccc(OCCCCN3CCN(c4cccc5sccc45)CC3)cc21)OCC(F)(F)F]

In the same manner as in Example 5, the title compound was obtained.

$^1$H-NMR (CDCl$_3$) δ: 1.69-1.79 (2H, m), 1.81-1.90 (2H, m), 2.51 (2H, t, J=7.5 Hz), 2.63-2.76 (6H, m), 2.81-2.90 (2H, m), 3.13-3.26 (4H, m), 3.99 (2H, t, J=6.0 Hz), 4.55 (2H, q, J=8.0 Hz), 6.00 (2H, s), 6.61 (1H, dd, J=2.5 Hz, 8.0 Hz), 6.65 (1H, d, J=2.5 Hz), 6.86-6.91 (1H, m), 7.07 (1H, d, J=8.5 Hz), 7.23-7.29 (1H, m), 7.37 (1H, d, J=5.5 Hz), 7.39-7.43 (1H, m), 7.54 (1H, d, J=8.0 Hz)

EXAMPLE 148

Synthesis of malonic acid 7-[4-(4-benzo[b]thiophen-4-ylpiperazin-1-yl)butoxy]-2-oxo-2H-quinolin-1-ylmethyl ester tert-butyl ester

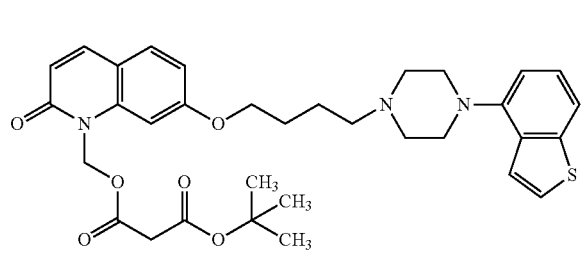 [SMILES: CC(C)(C)OC(=O)CC(=O)OCn1c(=O)ccc2ccc(OCCCCN3CCN(c4cccc5sccc45)CC3)cc21]

In the same manner as in Example 22, the title compound was obtained.

$^1$H-NMR (CDCl$_3$) δ: 1.38 (s, 9H), 1.69-1.83 (m, 2H), 1.85-1.95 (m, 2H), 2.55 (t, J=7.4 Hz, 2H), 2.67-2.79 (m, 4H), 3.14-3.25 (m, 4H), 3.35 (s, 2H), 4.13 (t, J=6.1 Hz, 2H), 6.37 (brs, 2H), 6.51 (d, J=9.5 Hz, 1H), 6.84 (dd, J=2.2, 8.6 Hz, 1H), 6.87-6.92 (m, 2H), 7.27 (dd, J=7.8, 7.8 Hz, 1H), 7.37-7.43 (m, 2H), 7.44 (d, J=8.6 Hz, 1H), 7.55 (d, J=8.0 Hz, 1H), 7.63 (d, J=9.5 Hz, 1H)

EXAMPLE 149

Synthesis of carbonic acid 7-[4-(4-benzo[b]thiophen-4-ylpiperazin-1-yl)butoxy]-2-oxo-3,4-dihydro-2H-quinolin-1-ylmethyl ester octyl ester

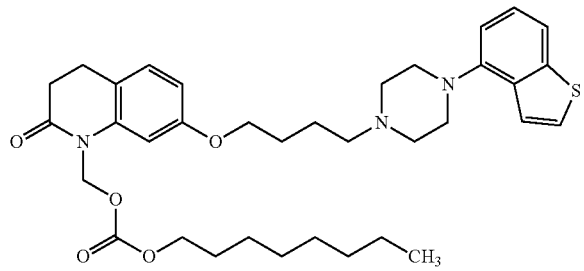 [SMILES: CCCCCCCCOC(=O)OCN1C(=O)CCc2ccc(OCCCCN3CCN(c4cccc5sccc45)CC3)cc21]

In the same manner as in Example 14, the title compound was obtained.

$^1$H-NMR (CDCl$_3$) δ: 0.87 (3H, t, J=6.8 Hz), 1.20-1.40 (8H, m), 1.60-1.90 (8H, m), 2.53 (2H, t, J=7.4 Hz), 2.64-2.78 (6H, m), 2.86 (2H, t, J=6.8 Hz), 3.20 (4H, br), 4.00 (2H, t, J=6.2 Hz), 4.17 (2H, t, J=6.8 Hz), 5.94 (2H, brs), 6.59 (1H, dd, J=2.3, 8.2 Hz), 6.69 (1H, d, J=2.3 Hz), 6.90 (1H, d, J=7.6 Hz), 7.06 (1H, d, J=8.1 Hz), 7.27 (1H, t, J=7.8 Hz), 7.36-7.44 (2H, m), 7.54 (1H, d, J=8.0 Hz)

EXAMPLE 150

Synthesis of carbonic acid 7-[4-(4-benzo[b]thiophen-4-ylpiperazin-1-yl)butoxy]-2-oxo-3,4-dihydro-2H-quinolin-1-ylmethyl ester cyclohexyl ester

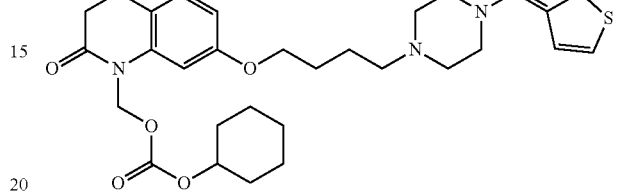

In the same manner as in Example 5, the title compound was obtained.

$^1$H-NMR (CDCl$_3$) δ: 1.17-1.28 (1H, m), 1.29-1.41 (2H, m), 1.43-1.58 (3H, m), 1.68-1.79 (4H, m), 1.80-1.89 (2H, m), 1.90-1.99 (2H, m), 2.52 (2H, t, J=7.5 Hz), 2.64-2.77 (6H, m), 2.82-2.89 (2H, m), 3.14-3.25 (4H, m), 4.00 (2H, t, J=6.0 Hz), 4.62-4.71 (1H, m), 5.94 (2H, s), 6.59 (1H, dd, J=2.5 Hz, 8.5 Hz), 6.69 (1H, d, J=2.5 Hz), 6.90 (1H, d, J=7.5 Hz), 7.06 (1H, d, J=8.5 Hz), 7.24-7.30 (1H, m), 7.38 (1H, d, J=5.5 Hz), 7.40-7.44 (1H, m), 7.55 (1H, d, J=8.0 Hz)

EXAMPLE 151

Synthesis of carbonic acid 7-[4-(4-benzo[b]thiophen-4-ylpiperazin-1-yl)butoxy]-2-oxo-3,4-dihydro-2H-quinolin-1-ylmethyl ester butyl ester

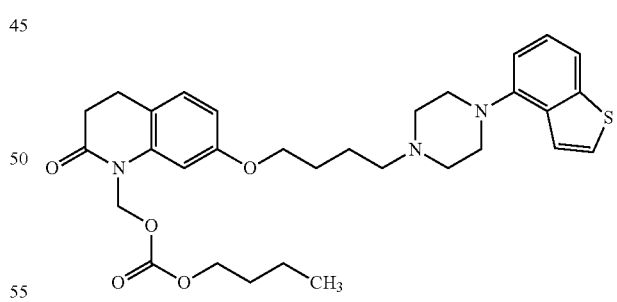

In the same manner as in Example 5, the title compound was obtained.

$^1$H-NMR (CDCl$_3$) δ: 0.93 (3H, t, J=7.4 Hz), 1.34-1.46 (2H, m), 1.60-1.90 (6H, m), 2.52 (2H, t, J=7.4 Hz), 2.64-2.76 (6H, m), 2.82-2.88 (2H, m), 3.16-3.26 (4H, br), 4.00 (2H, t, J=6.2 Hz), 4.19 (2H, t, J=6.7 Hz), 5.94 (2H, brs), 6.59 (1H, dd, J=2.3, 8.2 Hz), 6.69 (1H, d, J=2.3 Hz), 6.89 (1H, d, J=7.6 Hz), 7.06 (1H, d, J=8.0 Hz), 7.27 (1H, t, J=7.8 Hz), 7.36-7.44 (2H, m), 7.55 (1H, d, J=8.1 Hz)

EXAMPLE 152

Synthesis of N-methyl-N-pyridin-2-ylmethylcarbamic acid 7-[4-(4-benzo[b]thiophen-4-ylpiperazin-1-yl)butoxy]-2-oxo-2H-quinolin-1-ylmethyl ester

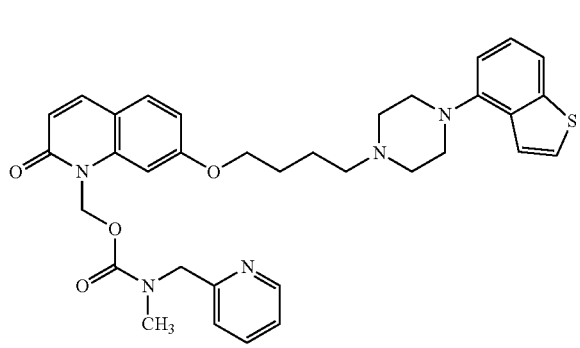 [SMILES: CN(Cc1ccccn1)C(=O)OCn1c(=O)ccc2ccc(OCCCCN3CCN(c4cccc5sccc45)CC3)cc21]

In the same manner as in Example 14, the title compound was obtained.

$^1$H-NMR (CDCl$_3$) δ: 1.68-1.81 (2H, m), 1.82-1.94 (2H, m), 2.47-2.58 (2H, m), 2.64-2.78 (4H, m), {2.91 (s), 3.06 (s) total 3H (1:1)}, 3.13-3.25 (4H, m), 4.00-4.10 (2H, m), 4.47 (1H, s), 4.65 (1H, s), 6.37 (1H, brs), 6.43 (1H, brs), {6.48 (d, J=9.5 Hz), 6.53 (d, J=9.5 Hz) total 1H (1:1)}, 6.78-6.97 (2H, m), 6.99-7.05 (1H, m), 7.13-7.21 (1H, m), 7.23-7.31 (2H, m), 7.36-7.47 (3H, m), 7.52-7.68 (3H, m), {8.38 (d, J=4.5 Hz), 8.54 (d, J=4.5 Hz) total 1H (1:1)}

EXAMPLE 153

Synthesis of thiomorpholine-4-carboxylic acid 7-[4-(4-benzo[b]thiophen-4-ylpiperazin-1-yl)butoxy]-2-oxo-2H-quinolin-1-ylmethyl ester

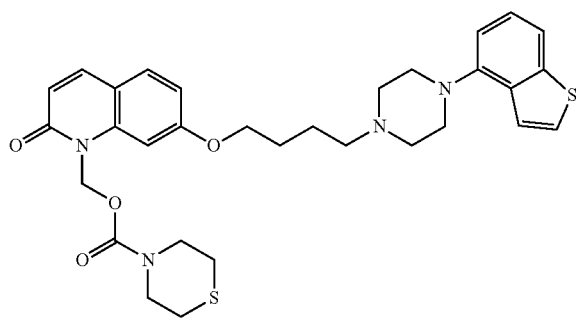

In the same manner as in Example 14, the title compound was obtained.

$^1$H-NMR (CDCl$_3$) δ: 1.72-1.82 (2H, m), 1.86-1.95 (2H, m), 2.45-2.52 (2H, m), 2.54 (2H, t, J=7.5 Hz), 2.58-2.64 (2H, m), 2.68-2.79 (4H, m), 3.15-3.26 (4H, m), 3.63-3.72 (2H, m), 3.73-3.83 (2H, m), 4.10 (2H, d, J=6.5 Hz), 6.36 (2H, s), 6.52 (1H, d, J=9.5 Hz), 6.84 (1H, dd, J=2.0 Hz, J=8.5 Hz), 6.87-6.92 (1H, m), 7.06 (1H, d, J=2.0 Hz), 7.24-7.30 (1H, m), 7.37-7.47 (3H, m), 7.55 (1H, d, J=8.0 Hz), 7.63 (1H, d, J=9.5 Hz)

EXAMPLE 154

Synthesis of dodecanoic acid 7-[4-(4-benzo[b]thiophen-4-ylpiperazin-1-yl)butoxy]-4,4-dimethyl-2-oxo-3,4-dihydro-2H-quinolin-1-ylmethyl ester

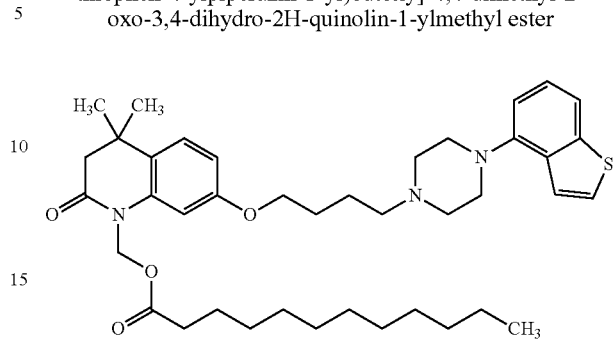

Using 7-[4-(4-benzo[b]thiophen-4-ylpiperazin-1-yl)butoxy]-4,4-dimethyl-3,4-dihydro-1H-quinolin-2-one obtained in Reference Example 18, the title compound was synthesized in the same manner as in Example 5.

$^1$H-NMR (CDCl$_3$) δ: 0.87 (3H, t, J=6.9 Hz), 1.20-1.32 (22H, m), 1.56-1.68 (2H, m), 1.68-1.80 (2H, m), 1.80-1.90 (2H, m), 2.35 (2H, t, J=7.5 Hz), 2.50-2.56 (4H, m), 2.68-2.76 (4H, m), 3.14-3.24 (4H, m), 3.99 (2H, t, J=6.2 Hz), 5.97 (2H, brs), 6.62-6.68 (2H, m), 6.89 (1H, d, J=7.6 Hz), 7.20 (1H, d, J=8.3 Hz), 7.27 (1H, t, J=7.8 Hz), 7.40 (2H, dd, J=5.6, 12.5 Hz), 7.54 (1H, d, J=8.0 Hz)

EXAMPLE 155

Synthesis of 7-[4-(4-benzo[b]thiophen-4-ylpiperazin-1-yl)butoxy]-1-hydroxymethyl-4,4-dimethyl-3,4-dihydro-1H-quinolin-2-one

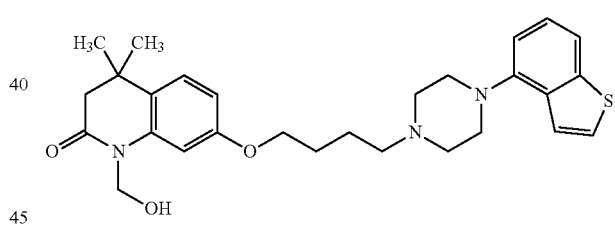

To a solution of 7-[4-(4-benzo[b]thiophen-4-ylpiperazin-1-yl)butoxy]-4,4-dimethyl-3,4-dihydro-1H-quinolin-2-one (0.4 g) obtained in Reference Example 18 in DMF (10 ml) were added 37% aqueous formalin solution (1.5 ml) and triethylamine (0.02 ml), and the mixture was heated at 80° C. for 10 hr. Water was added to the reaction mixture, and the mixture was extracted with ethyl acetate, and dried over magnesium sulfate. The solvent was evaporated under reduced pressure to give a mixture (0.46 g, 1:3) of 7-[4-(4-benzo[b]thiophen-4-ylpiperazin-1-yl)butoxy]-1-hydroxymethyl-4,4-dimethyl-3,4-dihydro-1H-quinolin-2-one and 7-[4-(4-benzo[b]thiophen-4-ylpiperazin-1-yl)butoxy]-4,4-dimethyl-3,4-dihydro-1H-quinolin-2-one.

amorphous: colorless $^1$H-NMR (CDCl$_3$) δ: 1.26 (3H, t, J=7.2 Hz), 1.27 (1.5H, s), 1.29 (4.5H, s), 1.68-1.78 (2H, m), 1.78-1.90 (2H, m), 2.46 (1.5H, s), 2.48 (0.5H, s), 2.52 (2H, t, J=7.4 Hz), 2.72 (4H, m), 3.19 (4H, m), 3.95-4.05 (2H, m), 5.41 (0.5H, s), 6.36 (0.75H, d, J=2.5 Hz), 6.58 (0.75H, dd, J=2.5, 8.5 Hz), 6.64 (0.25H, dd, J=2.4, 8.5 Hz), 6.87-6.92 (1.25H, m), 7.17 (0.75H, d, J=8.5 Hz), 7.18 (0.25H, d, J=8.5 Hz), 7.27 (1H, t, J=7.8 Hz), 7.36-7.44 (2H, m), 7.54 (1H, d, J=8.0 Hz), 8.32 (0.75H, brs)

EXAMPLE 156

Synthesis of carbonic acid 7-[4-(4-benzo[b]thiophen-4-ylpiperazin-1-yl)-butoxy]-4,4-dimethyl-2-oxo-3,4-dihydro-2H-quinolin-1-ylmethyl ester decyl ester

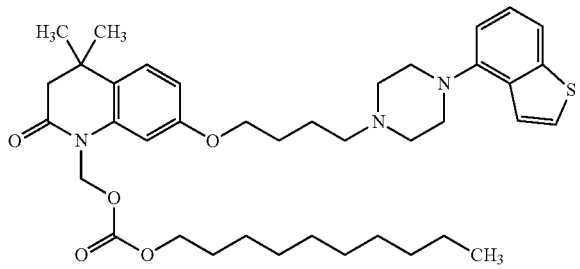

7-[4-(4-Benzo[b]thiophen-4-ylpiperazin-1-yl)butoxy]-1-hydroxymethyl-4,4-dimethyl-3,4-dihydro-1H-quinolin-2-one (460 mg), which is a mixture with 7-[4-(4-benzo[b]thiophen-4-ylpiperazin-1-yl)butoxy]-4,4-dimethyl-3,4-dihydro-1H-quinolin-2-one obtained in Example 155, was suspended in methylene chloride (10 ml), pyridine (0.06 ml) and decyl chloroformate (103 mg) were added, and the mixture was stirred under ice-cooling for 4 hr. Water was added to the reaction mixture, and the mixture was extracted with methylene chloride, and dried over magnesium sulfate. The solvent was evaporated under reduced pressure and the residue was purified by silica gel column chromatography (ethyl acetate:n-hexane=2:1) to give carbonic acid 7-[4-(4-benzo[b]thiophen-4-ylpiperazin-1-yl)-butoxy]-4,4-dimethyl-2-oxo-3,4-dihydro-2H-quinolin-1-ylmethyl ester decyl ester (108 mg).
colorless oil $^1$H-NMR (CDCl$_3$) δ: 0.87 (3H, t, J=6.8 Hz), 1.20-1.40 (20H, m), 1.62-1.70 (2H, m), 1.70-1.80 (2H, m), 1.80-1.90 (2H, m), 2.50-2.56 (4H, m), 2.73 (4H, m), 3.20 (4H, m), 4.00 (2H, t, J=6.2 Hz), 4.17 (2H, t, J=6.8 Hz), 5.99 (2H, s), 6.65 (1H, dd, J=2.4, 8.5 Hz), 6.71 (1H, d, J=2.3 Hz), 6.89 (1H, d, J=7.6 Hz), 7.20 (1H, d, J=8.4 Hz), 7.27 (1H, t, J=7.8 Hz), 7.36-7.44 (2H, m), 7.54 (1H, d, J=8.1 Hz)

EXAMPLE 157

Synthesis of carbonic acid 7-[4-(4-benzo[b]thiophen-4-ylpiperazin-1-yl)-butoxy]-4,4-dimethyl-2-oxo-3,4-dihydro-2H-quinolin-1-ylmethyl ester phenyl ester

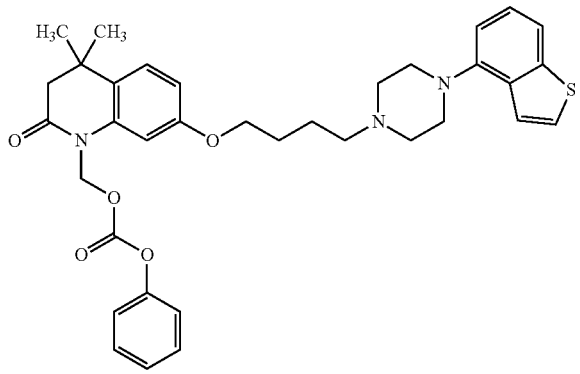 [SMILES: CC1(C)CC(=O)N(COC(=O)Oc2ccccc2)c2cc(OCCCCN3CCN(c4cccc5sccc45)CC3)ccc21]

To a solution of 7-[4-(4-benzo[b]thiophen-4-ylpiperazin-1-yl)butoxy]-4,4-dimethyl-3,4-dihydro-1H-quinolin-2-one (0.38 g) obtained in Reference Example 18 in THF (10 ml) was added 60% sodium hydride (40 mg) with stirring under ice-cooling, and the mixture was heated under reflux for 0.5 hr. Thereafter, with stirring under ice-cooling, a solution of chloromethyl phenylcarbonate (0.23 g) in THF (1 ml) was added dropwise, and the mixture was stirred at room temperature overnight. With stirring under ice-cooling, water was added to the reaction mixture, and the mixture was extracted with ethyl acetate, washed with water, and dried over magnesium sulfate. The solvent was evaporated under reduced pressure and the residue was purified by silica gel column chromatography (ethyl acetate:n-hexane=1:1) to give carbonic acid 7-[4-(4 benzo[b]thiophen-4-ylpiperazin-1-yl)-butoxy]-4,4-dimethyl-2-oxo-3,4-dihydro-2H-quinolin-1-ylmethyl ester phenyl ester (130 mg).
colorless oil $^1$H-NMR (CDCl$_3$) δ: 1.30 (6H, s), 1.68-1.90 (4H, m), 2.46-2.56 (2H, m), 2.57 (2H, s), 2.68-2.78 (4H, br), 3.14-3.24 (4H, br), 4.02 (2H, t, J=6.2 Hz), 6.11 (2H, s), 6.68 (1H, dd, J=2.4, 8.5 Hz), 6.75 (1H, d, J=2.4 Hz), 6.89 (1H, d, J=7.6 Hz), 7.16-7.46 (9H, m), 7.55 (1H, d, J=8.0 Hz).

EXAMPLE 158

Synthesis of N-decylcarbamic acid 7-[4-(4-benzo[b]thiophen-4-ylpiperazin-1-yl)-butoxy]-4,4-dimethyl-2-oxo-3,4-dihydro-2H-quinolin-1-ylmethyl ester

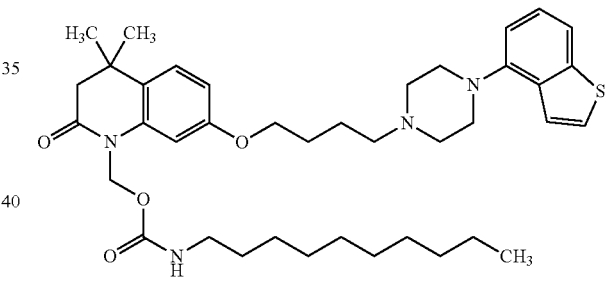

To a solution of 7-[4-(4-benzo[b]thiophen-4-ylpiperazin-1-yl)butoxy]-4,4-dimethyl-3,4-dihydro-1H-quinolin-2-one (0.21 g) obtained in Reference Example 18 in THF (10 ml) was added with stirring under ice-cooling 60% sodium hydride (27 mg), and the mixture was heated under reflux for 0.5 hr. Thereafter, with stirring under ice-cooling, a solution of chloromethyl phenylcarbonate (0.17 g) in THF (1 ml) was added dropwise, and the mixture was stirred at room temperature overnight. With stirring under ice-cooling, water was added to the reaction mixture, and the mixture was extracted with ethyl acetate, washed with water, and dried over magnesium sulfate. The solvent was evaporated under reduced pressure. To a solution of the obtained residue in THF (10 ml) was added decylamine (0.5 ml), and the mixture was stirred at room temperature overnight. With stirring under ice-cooling, water was added to the reaction mixture, and the mixture was extracted with ethyl acetate, washed with water, and dried over magnesium sulfate. The solvent was evaporated under reduced pressure and the residue was purified by silica gel column chromatography (ethyl acetate:n-hexane=2:1) to give N-decylcarbamic acid 7-[4-(4-benzo[b]thiophen-4-ylpiperazin-1-yl)-butoxy]-4,4-dimethyl-2-oxo-3,4-dihydro-2H-quinolin-1-ylmethyl ester (126 mg).

yellow oil $^1$H-NMR (CDCl$_3$) δ: 0.87 (3H, t, J=6.8 Hz), 1.18-1.34 (20H, m), 1.42-1.52 (2H, m), 1.70-1.80 (2H, m), 1.80-1.90 (2H, m), 2.48-2.56 (4H, m), 2.66-2.78 (4H, br), 3.12-3.24 (6H, m), 4.01 (2H, t, J=6.1 Hz), 4.76-4.84 (1H, m), 5.96 (2H, s), 6.64 (1H, dd, J=2.3, 8.5 Hz), 6.81 (1H, d, J=2.0 Hz), 6.89 (1H, d, J=7.6 Hz), 7.19 (1H, d, J=8.5 Hz), 7.24-7.30 (1H, m), 7.36-7.44 (2H, m), 7.55 (1H, d, J=8.0 Hz)

EXAMPLE 163

Synthesis of carbonic acid 7-[4-(4-benzo[b]thiophen-4-ylpiperazin-1-yl)butoxy]-2-oxo-2H-quinolin-1-ylmethyl ester methyl ester

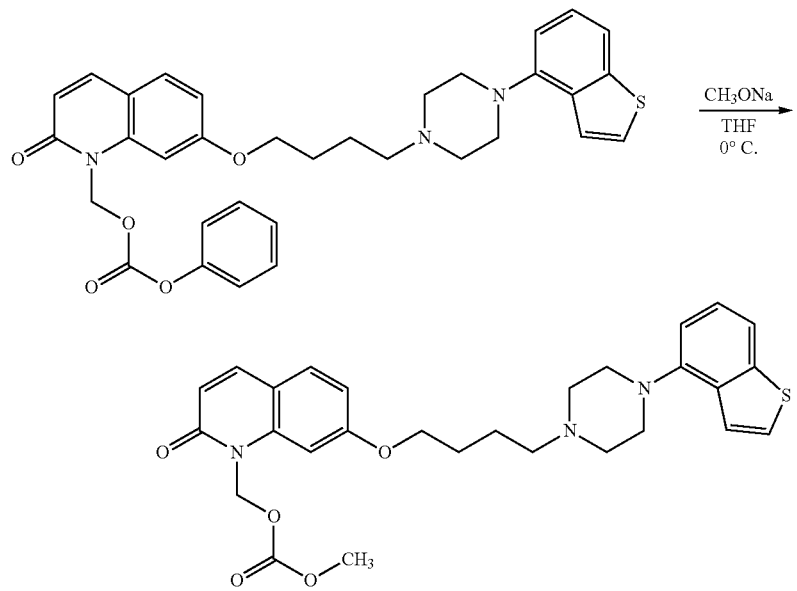

To a solution of n-hexylalcohol (50.5 mg) in tetrahydrofuran (5 ml) was added with stirring under ice-cooling 60% sodium hydride (18 mg) by small portions, and the mixture was stirred at the same temperature for 0.5 hr, to a solution of carbonic acid 7-[4-(4-benzo[b]thiophen-4-ylpiperazin-1-yl) butoxy]-2-oxo-2H-quinolin-1-ylmethyl ester phenyl ester (240 mg) in tetrahydrofuran (1 ml) was added with stirring under ice-cooling sodium methoxide (30 mg), and the mixture was stirred for 3 hr. Water was added to the reaction mixture, and the mixture was extracted with ethyl acetate, and dried over sodium sulfate. The solvent was evaporated under reduced pressure and the residue was purified by silica gel column chromatography (ethyl acetate) to give carbonic acid 7-[4-(4-benzo[b]thiophen-4-ylpiperazin-1-yl)butoxy]-2-oxo-2H-quinolin-1-ylmethyl ester methyl ester (42 mg).

oil: colorless $^1$H-NMR (CDCl$_3$) δ ppm: 1.72-1.84 (2H, m), 1.85-1.96 (2H, m), 2.55 (2H, t, J=7.4 Hz), 2.68-2.80 (4H, br), 3.14-3.26 (4H, br), 3.83 (3H, s), 4.10 (2H, t, J=6.2 Hz), 6.35 (2H, s), 6.50 (1H, d, J=9.5 Hz), 6.84 (1H, dd, J=2.2, 8.6 Hz), 6.89 (1H, d, J=7.6 Hz), 6.92 (1H, d, J=2.0 Hz), 7.27 (1H, t, J=7.8 Hz), 7.36-7.46 (3H, m), 7.50 (1H, d, J=8.0 Hz), 7.60 (1H, d, J=9.5 Hz)

EXAMPLE 165

Synthesis of carbonic acid 7-[4-(4-benzo[b]thiophen-4-ylpiperazin-1-yl)butoxy]-2-oxo-2H-quinolin-1-ylmethyl ester propyl ester

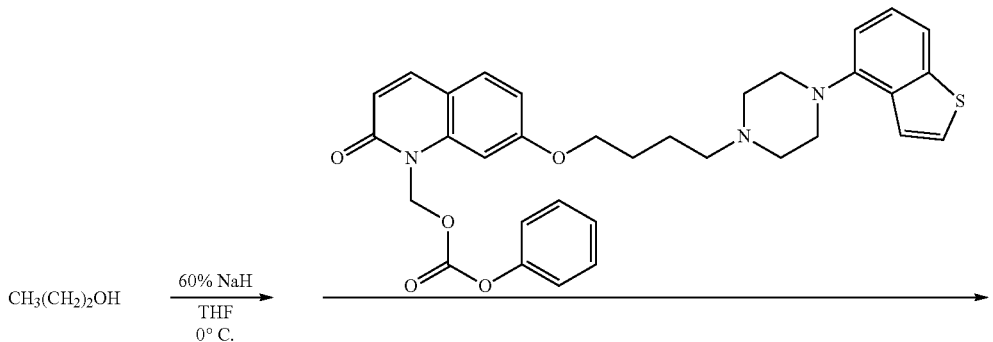

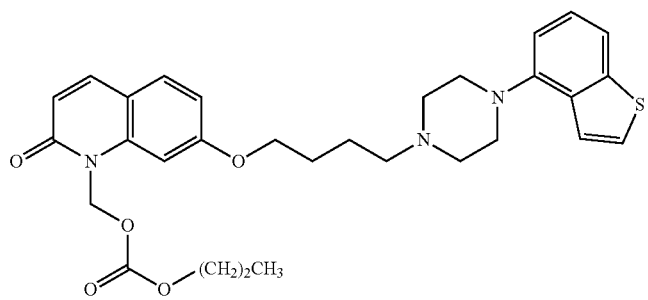 [SMILES: COC(=O)OCn1c(=O)ccc2ccc(OCCCCN3CCN(c4cccc5sccc45)CC3)cc21]

In the same manner as in Example 175, the compound was obtained (yield 78 mg, 27.5%) as a colorless oil.

$^1$H-NMR (CDCl$_3$) δ ppm: 0.94 (3H, t, J=7.4 Hz), 1.58-1.84 (4H, m), 1.84-1.96 (2H, m), 2.54 (2H, t, J=7.5 Hz), 2.66-2.80 (4H, br), 3.14-3.28 (4H, br), 4.09 (2H, t, J=6.0 Hz), 4.15 (2H, t, J=6.7 Hz), 6.34 (2H, s), 6.49 (1H, d, J=9.5 Hz), 6.83 (1H, dd, J=2.1, 8.6 Hz), 6.89 (1H, d, J=7.6 Hz), 6.93 (1H, d, J=2.0 Hz), 7.26 (1H, t, J=7.8 Hz), 7.36-7.44 (3H, m), 7.54 (1H, d, J=8.0 Hz), 7.62 (1H, d, J=9.5 Hz)

EXAMPLE 168

Synthesis of carbonic acid 7-[4-(4-benzo[b]thiophen-4-ylpiperazin-1-yl)butoxy]-2-oxo-2H-quinolin-1-ylmethyl ester butyl ester In the same manner as in Example 175, the compound was obtained (yield 47 mg, 14.3%) as a colorless oil.

$^1$H-NMR (CDCl$_3$) δ ppm: 0.92 (3H, t, J=7.4 Hz), 1.32-1.44 (2H, m), 1.60-1.70 (2H, m), 1.72-1.84 (2H, m), 1.86-1.96 (2H, m), 2.55 (2H, t, J=7.5 Hz), 2.68-2.80 (4H, br), 3.16-3.26 (4H, br), 4.06-4.15 (2H, m), 4.20 (2H, t, J=6.7 Hz), 6.35 (2H, s), 6.50 (1H, d, J=9.5 Hz), 6.84 (1H, dd, J=2.2, 8.6 Hz), 6.89 (1H, d, J=7.7 Hz), 6.93 (1H, d, J=2.1 Hz), 7.27 (1H, t, J=7.8 Hz), 7.36-7.46 (3H, m), 7.55 (1H, d, J=8.0 Hz), 7.61 (1H, d, J=9.5 Hz)

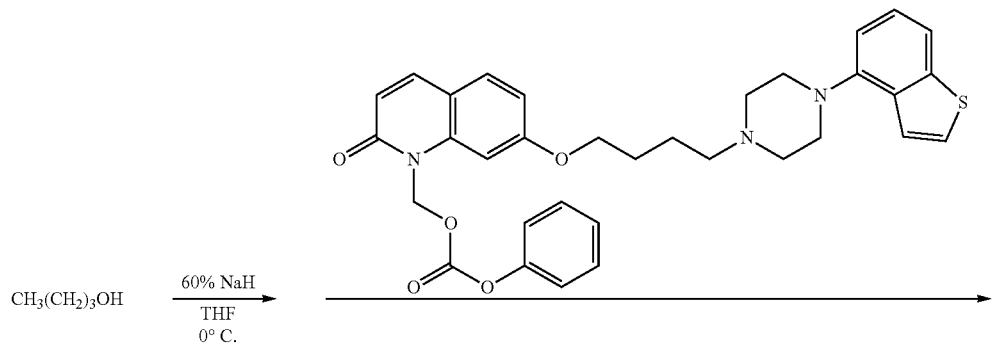

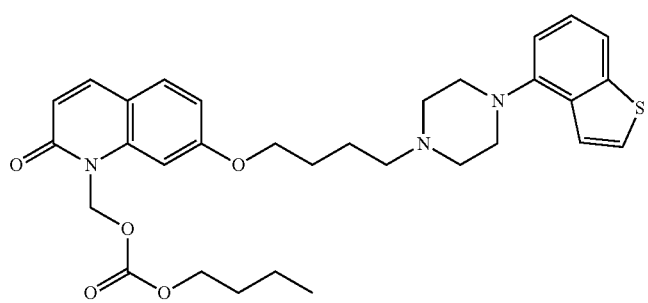 [SMILES: CCCOC(=O)OCn1c(=O)ccc2ccc(OCCCCN3CCN(c4cccc5sccc45)CC3)cc21]

EXAMPLE 170

Synthesis of carbonic acid 7-[4-(4-benzo[b]thiophen-4-ylpiperazin-1-yl)butoxy]-2-oxo-2H-quinolin-1-ylmethyl ester isobutyl ester

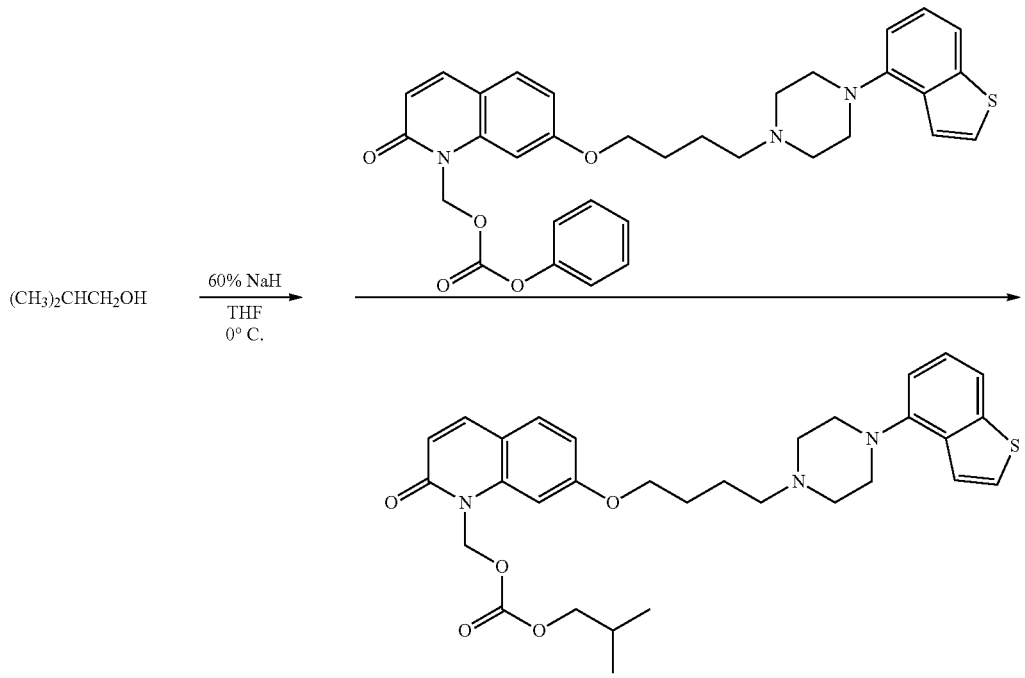

In the same manner as in Example 175, the compound was obtained (yield 48 mg, 14.6%) as a colorless oil.

$^1$H-NMR (CDCl$_3$) δ ppm: 0.94 (6H, d, J=6.7 Hz), 1.70-2.04 (5H, m), 2.55 (2H, t, J=7.4 Hz), 2.66-2.80 (4H, br), 3.14-3.24 (4H, br), 3.98 (2H, d, J=6.6 Hz), 4.10 (2H, t, J=6.2 Hz), 6.35 (2H, s), 6.51 (1H, d, J=9.5 Hz), 6.84 (1H, dd, J=2.2, 8.6 Hz), 6.89 (1H, d, J=7.6 Hz), 6.93 (1H, d, J=2.0 Hz), 7.27 (1H, t, J=7.8 Hz), 7.37-7.46 (3H, m), 7.55 (1H, d, J=8.1 Hz), 7.61 (1H, d, J=9.5 Hz)

EXAMPLE 175

Synthesis of carbonic acid 7-[4-(4-benzo[b]thiophen-4-ylpiperazin-1-yl)butoxy]-2-oxo-2H-quinolin-1-ylmethyl ester hexyl ester

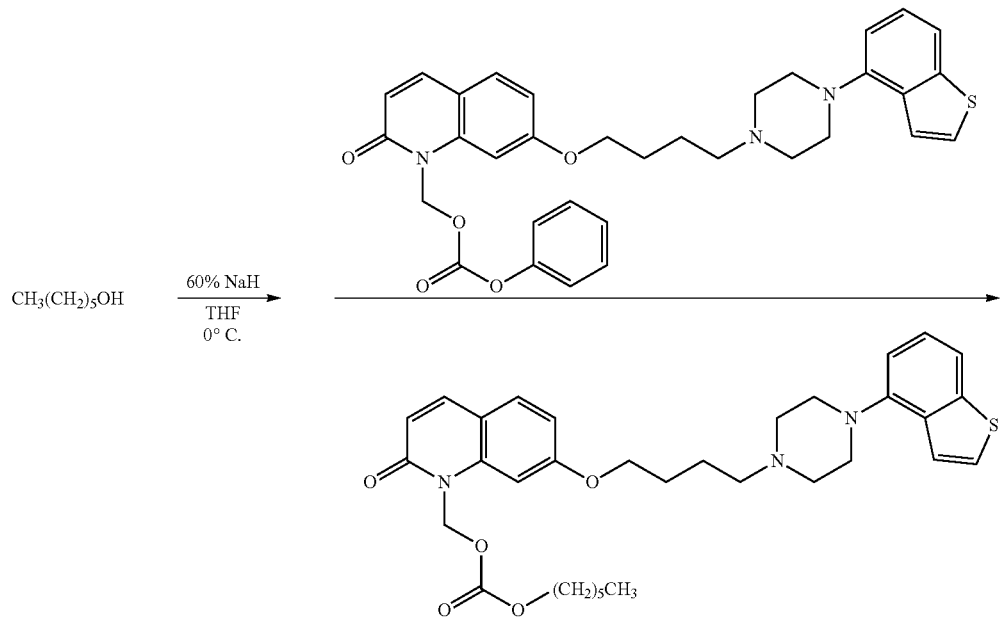

To a solution of n-hexylalcohol (50.5 mg) in tetrahydrofuran (5 ml) was added with stirring under ice-cooling 60% sodium hydride (18 mg) by small portions, and the mixture was stirred at the same temperature for 0.5 hr, a solution of carbonic acid 7-[4-(4-benzo[b]thiophen-4-ylpiperazin-1-yl)butoxy]-2-oxo-2H-quinolin-1-ylmethyl ester phenyl ester (240 mg) in tetrahydrofuran (1 ml) was added dropwise, and the mixture was stirred under ice-cooling for 3 hr. Water was added to the reaction mixture, and the mixture was extracted with ethyl acetate, and dried over sodium sulfate. The solvent was evaporated under reduced pressure and the residue was purified by silica gel column chromatography (ethyl acetate) to give carbonic acid 7-[4-(4-benzo[b]thiophen-4-ylpiperazin-1-yl)butoxy]-2-oxo-2H-quinolin-1-ylmethyl ester hexyl ester (30 mg).

oil: colorless $^1$H-NMR (CDCl$_3$) δ ppm: 0.87 (3H, t, J=6.9 Hz), 1.20-1.40 (6H, m), 1.60-1.72 (2H, m), 1.72-1.84 (2H, m), 1.84-2.00 (2H, m), 2.55 (2H, t, J=7.4 Hz), 2.65-2.82 (4H, br), 3.10-3.28 (4H, br), 4.10 (2H, t, J=6.2 Hz), 4.19 (2H, t, J=6.7 Hz), 6.35 (2H, s), 6.50 (1H, d, J=9.5 Hz), 6.84 (1H, dd, J=2.2, 8.6 Hz), 6.89 (1H, d, J=7.6 Hz), 6.93 (1H, d, J=2.1 Hz), 7.27 (1H, t, J=7.8 Hz), 7.36-7.46 (3H, m), 7.55 (1H, d, J=8.0 Hz), 7.61 (1H, d, J=9.6 Hz)

EXAMPLE 177

Synthesis of carbonic acid 7-[4-(4-benzo[b]thiophen-4-ylpiperazin-1-yl)butoxy]-2-oxo-2H-quinolin-1-ylmethyl ester nonyl ester

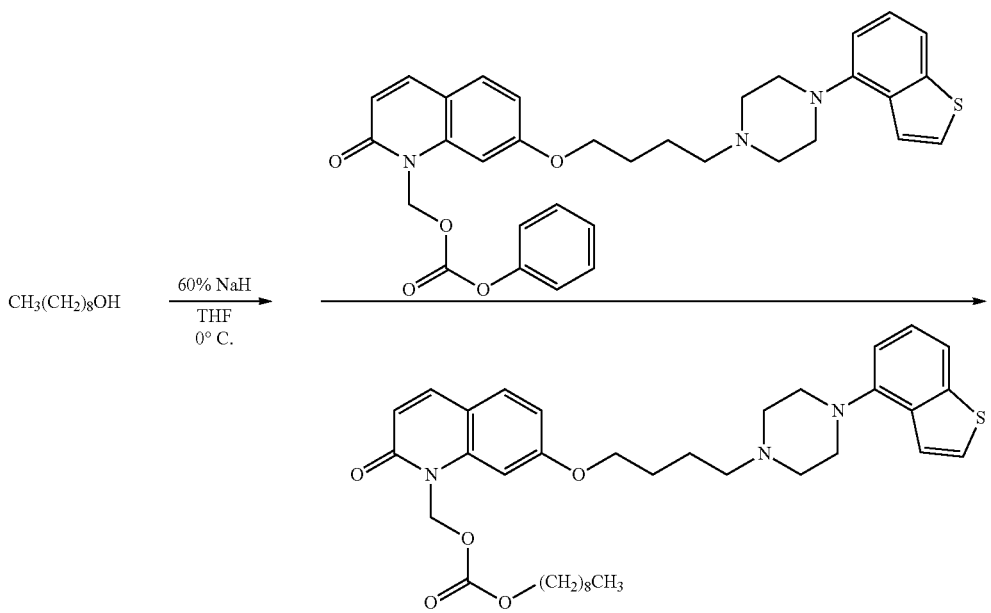

In the same manner as in Example 175, the compound was obtained (yield 40 mg, 10.8%) as a colorless oil.

30 $^1$H-NMR (CDCl$_3$) δ ppm: 0.86 (3H, t, J=6.9 Hz), 1.20-1.40 (12H, m), 1.60-1.70 (2H, m), 1.72-1.82 (2H, m), 1.85-1.95 (2H, m), 2.55 (2H, t, J=7.4 Hz), 2.68-2.78 (4H, br), 3.14-3.28 (4H, br), 4.06-4.14 (2H, m), 4.18 (2H, t, J=6.7 Hz), 6.35 (2H, s), 6.50 (1H, d, J=9.5 Hz), 6.84 (1H, dd, J=2.1, 8.6 Hz), 6.89 (1H, d, J=7.6 Hz), 6.93 (1H, d, J=2.0 Hz), 7.27 (1H, t, J=7.8 Hz), 7.36-7.46 (3H, m), 7.55 (1H, d, J=8.0 Hz), 7.61 (1H, d, J=9.5 Hz)

EXAMPLE 179

Synthesis of carbonic acid 7-[4-(4-benzo[b]thiophen-4-ylpiperazin-1-yl)butoxy]-2-oxo-2H-quinolin-1-ylmethyl ester tetradecyl ester

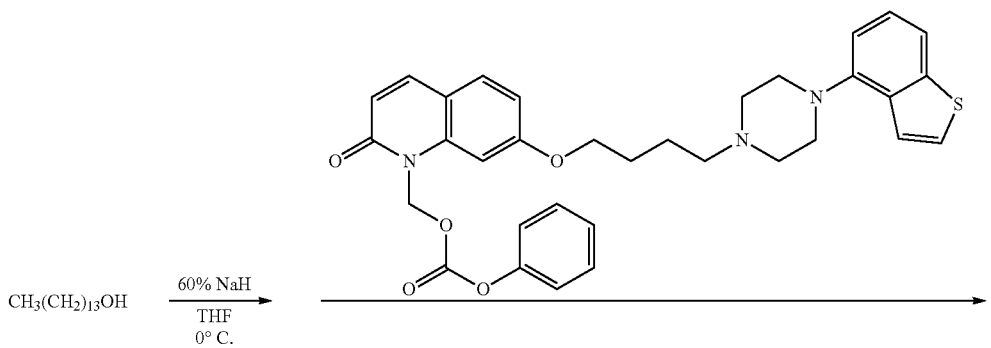

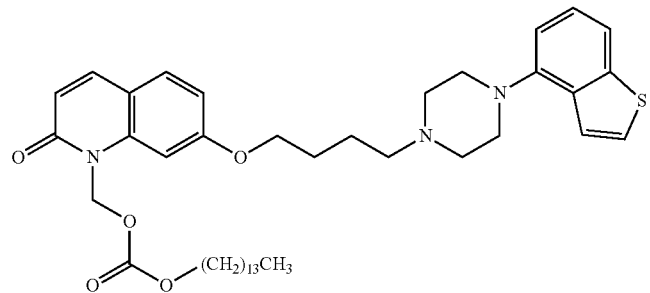
In the same manner as in Example 175, the colorless amorphous compound was obtained (yield 33 mg, 9.3%).
$^1$H-NMR (CDCl$_3$) δ ppm: 0.87 (3H, t, J=6.9 Hz), 1.20-1.40 (22H, m), 1.55-1.95 (6H, m), 2.56 (2H, t, J=7.4 Hz), 2.68-2.80 (4H, br), 3.15-3.25 (4H, br), 4.10 (2H, t, J=6.2 Hz), 4.18 (2H, t, J=6.7 Hz), 6.35 (2H, s), 6.50 (1H, d, J=9.5 Hz), 6.84 (1H, dd, J=2.2, 8.6 Hz), 6.89 (1H, d, J=7.6 Hz), 6.93 (1H, d, J=2.0 Hz), 7.27 (1H, t, J=7.8 Hz), 7.36-7.46 (3H, m), 7.55 (1H, d, J=8.0 Hz), 7.61 (1H, d, J=9.5 Hz)
EXAMPLE 180
Synthesis of carbonic acid 7-[4-(4-benzo[b]thiophen-4-ylpiperazin-1-yl)butoxy]-2-oxo-2H-quinolin-1-ylmethyl ester hexadecyl ester
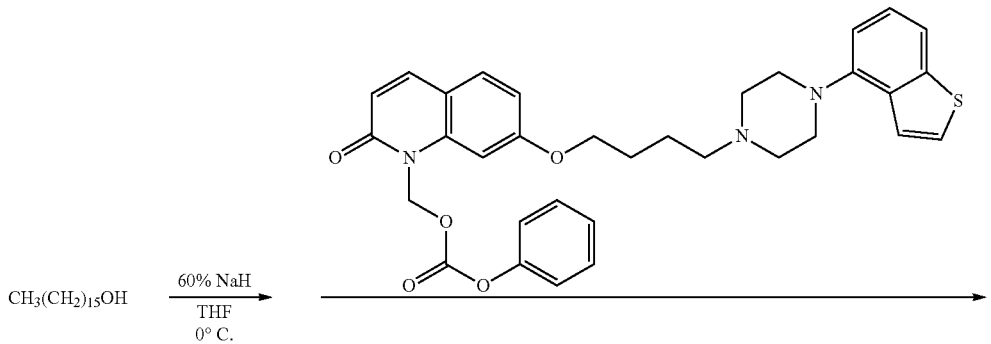
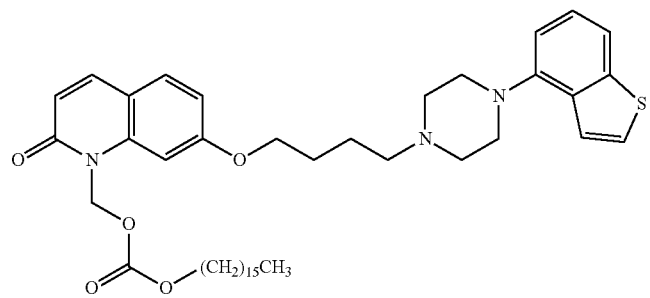

In the same manner as in Example 175, the colorless amorphous compound was obtained (yield 48 mg, 15%).

$^1$H-NMR (CDCl$_3$) δ ppm: 0.87 (3H, t, J=6.8 Hz), 1.20-1.38 (26H, m), 1.60-1.96 (6H, m), 2.55 (2H, t, J=7.4 Hz), 2.70-2.80 (4H, br), 3.16-3.24 (4H, br), 4.10 (2H, t, J=6.2 Hz), 4.18 (2H, t, J=6.7 Hz), 6.35 (2H, s), 6.50 (1H, d, J=9.5 Hz), 6.84 (1H, dd, J=2.2, 8.6 Hz), 6.89 (1H, d, J=7.6 Hz), 6.93 (1H, d, J=2.0 Hz), 7.27 (1H, t, J=7.8 Hz), 7.36-7.46 (3H, m), 7.55 (1H, d, J=8.1 Hz), 7.61 (1H, d, J=9.5 Hz)

In the same manner as in the above-mentioned Examples, the compounds described in the following Table 1 can be synthesized.

TABLE 1

| Example | Structure Formula | |
|---|---|---|
| 159 | | N-Benzyl-N-methylcarbamic acid 7-[4-(4-benzo[b]thiophen-4-ylpiperazin-1-yl)butoxy]-2-oxo-3,4-dihydro-2H-quinolin-1-ylmethyl ester |
| 160 | | N-Phenethylcarbamic acid 7-[4-(4-benzo[b]thiophen-4-ylpiperazin-1-yl)butoxy]-2-oxo-3,4-dihydro-2H-quinolin-1-ylmethyl ester |
| 161 | | (7-{4-[4-(Benzo[b]thiophen-4-yl)piperazin-1-yl]butoxy}-2-oxo-3,4-dihydro-2H-quinolin-1-yl)methyl N-methoxycarbamate |
| 162 | | N-Allylcarbamic acid 7-[4-(4-benzo[b]thiophen-4-ylpiperazin-1-yl)butoxy]-2-oxo-3,4-dihydro-2H-quinolin-1-ylmethyl ester |

TABLE 1-continued

| Example | Structure Formula | |
|---|---|---|
| 163 | | Carbonic acid 7-[4-(4-benzo[b]thiophen-4-ylpiperazin-1-yl)butoxy]-2-oxo-2H-quinolin-1-ylmethyl ester methyl ester |
| 164 | | Carbonic acid 7-[4-(4-benzo[b]thiophen-4-ylpiperazin-1-yl)butoxy]-2-oxo-3,4-dihydro-2H-quinolin-1-ylmethyl ester propyl ester |
| 165 | | Carbonic acid 7-[4-(4-benzo[b]thiophen-4-ylpiperazin-1-yl)butoxy]-2-oxo-2H-quinolin-1-ylmethyl ester propyl ester |
| 166 | | Carbonic acid 7-[4-(4-benzo[b]thiophen-4-ylpiperazin-1-yl)butoxy]-2-oxo-3,4-dihydro-2H-quinolin-1-ylmethyl ester isopropyl ester |
| 167 | | Carbonic acid 7-[4-(4-benzo[b]thiophen-4-ylpiperazin-1-yl)butoxy]-2-oxo-2H-quinolin-1-ylmethyl ester isopropyl ester |

TABLE 1-continued

| Example | Structure Formula | |
|---|---|---|
| 168 | | Carbonic acid 7-[4-(4-benzo[b]thiophen-4-ylpiperazin-1-yl)butoxy]-2-oxo-2H-quinolin-1-ylmethyl ester butyl ester |
| 169 | | Carbonic acid 7-[4-(4-benzo[b]thiophen-4-ylpiperazin-1-yl)butoxy]-2-oxo-3,4-dihydro-2H-quinolin-1-ylmethyl ester isobutyl ester |
| 170 | | Carbonic acid 7-[4-(4-benzo[b]thiophen-4-ylpiperazin-1-yl)butoxy]-2-oxo-2H-quinolin-1-ylmethyl ester isobutyl ester |
| 171 | | Carbonic acid 7-[4-(4-benzo[b]thiophen-4-ylpiperazin-1-yl)butoxy]-2-oxo-3,4-dihydro-2H-quinolin-1-ylmethyl ester pentyl ester |
| 172 | | Carbonic acid 7-[4-(4-benzo[b]thiophen-4-ylpiperazin-1-yl)butoxy]-2-oxo-2H-quinolin-1-ylmethyl ester pentyl ester |

TABLE 1-continued

| Example | Structure Formula | |
|---|---|---|
| 173 | | Carbonic acid 7-[4-(4-benzo[b]thiophen-4-ylpiperazin-1-yl)butoxy]-2-oxo-3,4-dihydro-2H-quinolin-1-ylmethyl ester 3-methylbutyl ester |
| 174 | | Carbonic acid 7-[4-(4-benzo[b]thiophen-4-ylpiperazin-1-yl)butoxy]-2-oxo-2H-quinolin-1-ylmethyl ester 3-methylbutyl ester |
| 175 | | Carbonic acid 7-[4-(4-benzo[b]thiophen-4-ylpiperazin-1-yl)butoxy]-2-oxo-2H-quinolin-1-ylmethyl ester hexyl ester |
| 176 | | Carbonic acid 7-[4-(4-benzo[b]thiophen-4-ylpiperazin-1-yl)butoxy]-2-oxo-3,4-dihydro-2H-quinolin-1-ylmethyl ester nonyl ester |
| 177 | | Carbonic acid 7-[4-(4-benzo[b]thiophen-4-ylpiperazin-1-yl)butoxy]-2-oxo-2H-quinolin-1-ylmethyl ester nonyl ester |

TABLE 1-continued

| Example | Structure Formula | |
|---|---|---|
| 178 | 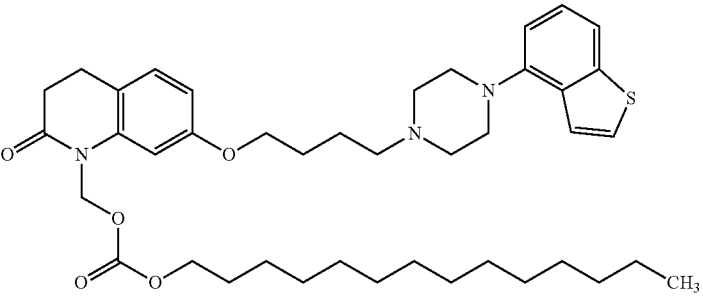 [SMILES: CCCCCCCCCCCCCCOC(=O)OCN1C(=O)CCc2ccc(OCCCCN3CCN(c4cccc5sccc45)CC3)cc21] | Carbonic acid 7-[4-(4-benzo[b]thiophen-4-ylpiperazin-1-yl)butoxy]-2-oxo-3,4-dihydro-2H-quinolin-1-ylmethyl ester tetradecyl ester |
| 179 | 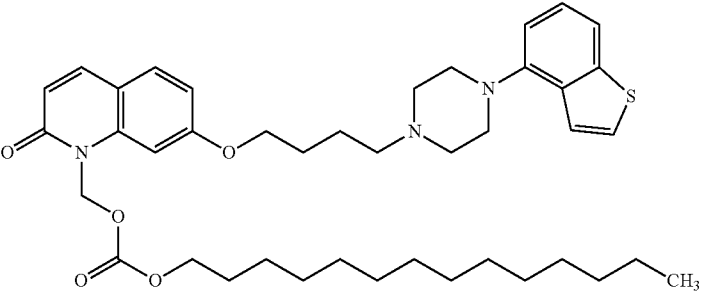 [SMILES: CCCCCCCCCCCCCCOC(=O)OCn1c(=O)ccc2ccc(OCCCCN3CCN(c4cccc5sccc45)CC3)cc21] | Carbonic acid 7-[4-(4-benzo[b]thiophen-4-ylpiperazin-1-yl)butoxy]-2-oxo-2H-quinolin-1-ylmethyl ester tetradecyl ester |
| 180 | 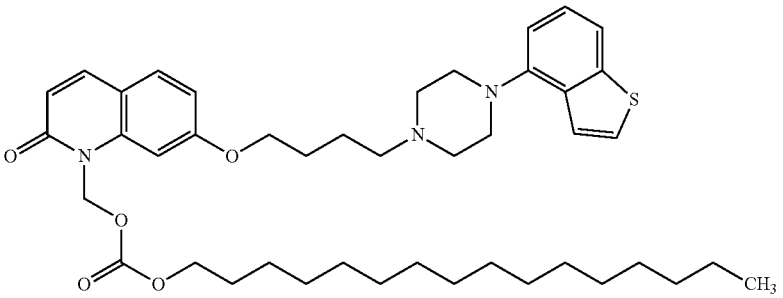 [SMILES: CCCCCCCCCCCCCCCCOC(=O)OCn1c(=O)ccc2ccc(OCCCCN3CCN(c4cccc5sccc45)CC3)cc21] | Carbonic acid 7-[4-(4-benzo[b]thiophen-4-ylpiperazin-1-yl)butoxy]-2-oxo-2H-quinolin-1-ylmethyl ester hexadecyl ester |
| 181 | 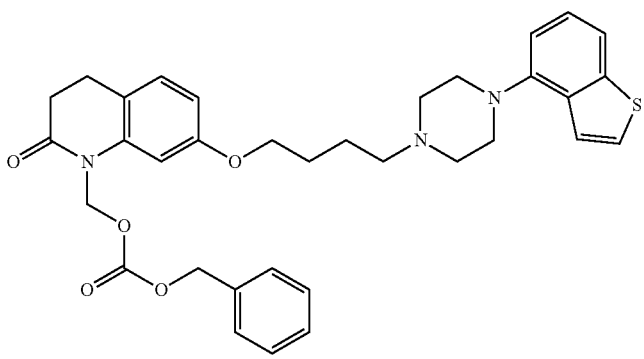 [SMILES: O=C(OCc1ccccc1)OCN1C(=O)CCc2ccc(OCCCCN3CCN(c4cccc5sccc45)CC3)cc21] | Carbonic acid 7-[4-(4-benzo[b]thiophen-4-ylpiperazin-1-yl)butoxy]-2-oxo-3,4-dihydro-2H-quinolin-1-ylmethyl ester benzyl ester |

| Example | Structure Formula | |
|---|---|---|
| 182 | *(structure)* | Carbonic acid 7-[4-(4-benzo[b]thiophen-4-ylpiperazin-1-yl)butoxy]-2-oxo-2H-quinolin-1-ylmethyl ester benzyl ester |
| 183 | *(structure)* | 7-[4-(4-Benzo[b]thiophen-4-ylpiperazin-1-yl)butoxy]-1-methoxymethyl-3,4-dihydro-1H-quinolin-2-one |
| 184 | *(structure)* | 7-[4-(4-Benzo[b]thiophen-4-ylpiperazin-1-yl)butoxy]-1-methoxymethyl-1H-quinolin-2-one |
| 185 | *(structure)* | 7-[4-(4-Benzo[b]thiophen-4-ylpiperazin-1-yl)butoxy]-2-methoxymethoxyquinoline |
| 186 | *(structure)* | 7-[4-(4-Benzo[b]thiophen-4-ylpiperazin-1-yl)butoxy]-1-ethoxymethyl-3,4-dihydro-1H-quinolin-2-one |

TABLE 1-continued

| Example | Structure Formula | |
|---|---|---|
| 187 | | 7-[4-(4-Benzo[b]thiophen-4-ylpiperazin-1-yl)butoxy]-1-ethoxymethyl-1H-quinolin-2-one |
| 188 | | 7-[4-(4-Benzo[b]thiophen-4-ylpiperazin-1-yl)butoxy]-1-isopropoxymethyl-3,4-dihydro-1H-quinolin-2-one |
| 189 | | 7-[4-(4-Benzo[b]thiophen-4-ylpiperazin-1-yl)butoxy]-1-isopropoxymethyl-1H-quinolin-2-one |
| 190 | | Aminoacetic acid 7-[4-(4-benzo[b]thiophen-4-ylpiperazin-1-yl)butoxy]-2-oxo-3,4-dihydro-2H-quinolin-1-ylmethyl ester |
| 191 | | Aminoacetic acid 7-[4-(4-benzo[b]thiophen-4-ylpiperazin-1-yl)butoxy]-2-oxo-2H-quinolin-1-ylmethyl ester |

TABLE 1-continued

| Example | Structure Formula | |
|---|---|---|
| 192 | 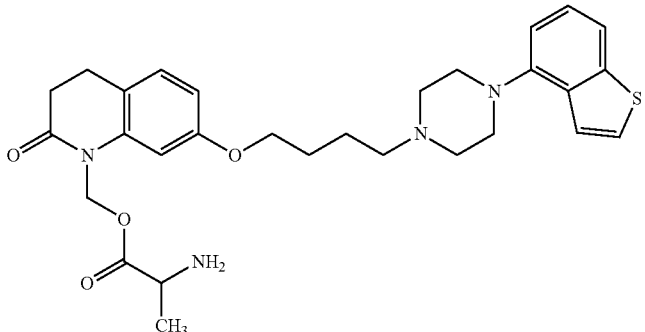 | 2-Aminopropionic acid 7-[4-(4-benzo[b]thiophen-4-ylpiperazin-1-yl)butoxy]-2-oxo-3,4-dihydro-2H-quinolin-1-ylmethyl ester |
| 193 | 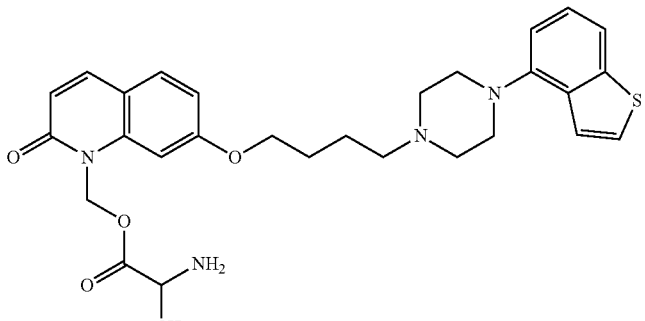 | 2-Aminopropionic acid 7-[4-(4-benzo[b]thiophen-4-ylpiperazin-1-yl)butoxy]-2-oxo-2H-quinolin-1-ylmethyl ester |
| 194 | 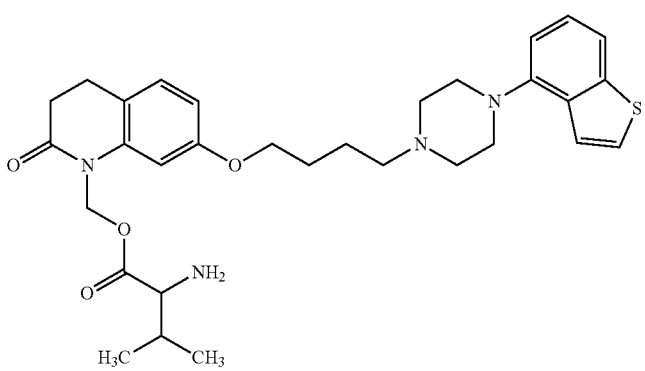 [SMILES: CC(C)C(N)C(=O)OCN1C(=O)CCc2ccc(OCCCCN3CCN(c4cccc5sccc45)CC3)cc21] | 2-Amino-3-methylbutyric acid 7-[4-(4-benzo[b]thiophen-4-ylpiperazin-1-yl)butoxy]-2-oxo-3,4-dihydro-2H-quinolin-1-ylmethyl ester |
| 195 | 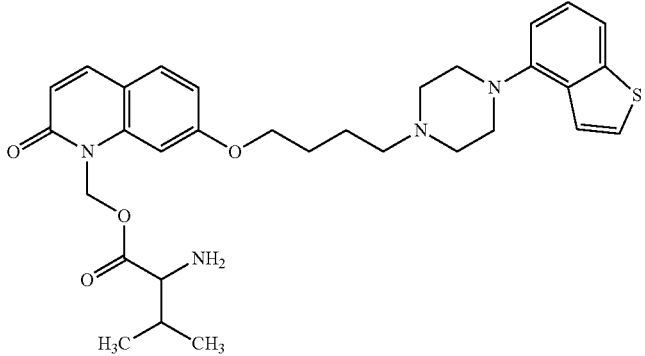 [SMILES: CC(C)C(N)C(=O)OCn1c(=O)ccc2ccc(OCCCCN3CCN(c4cccc5sccc45)CC3)cc21] | 2-Amino-3-methylbutyric acid 7-[4-(4-benzo[b]thiophen-4-ylpiperazin-1-yl)butoxy]-2-oxo-2H-quinolin-1-ylmethyl ester |

TABLE 1-continued

| Example | Structure Formula | |
|---|---|---|
| 196 | | 2-Amino-4-methylpentanoic acid 7-[4-(4-benzo[b]thiophen-4-ylpiperazin-1-yl)butoxy]-2-oxo-3,4-dihydro-2H-quinolin-1-ylmethyl ester |
| 197 | | 2-Amino-4-methylpentanoic acid 7-[4-(4-benzo[b]thiophen-4-ylpiperazin-1-yl)butoxy]-2-oxo-2H-quinolin-1-ylmethyl ester |
| 198 | | Pyrrolidine-2-carboxylic acid 7-[4-(4-benzo[b]thiophen-4-ylpiperazin-1-yl)butoxy]-2-oxo-3,4-dihydro-2H-quinolin-1-ylmethyl ester |
| 199 | | Pyrrolidine-2-carboxylic acid 7-[4-(4-benzo[b]thiophen-4-ylpiperazin-1-yl)butoxy]-2-oxo-2H-quinolin-1-ylmethyl ester |

TABLE 1-continued

| Example | Structure Formula | |
|---|---|---|
| 200 | 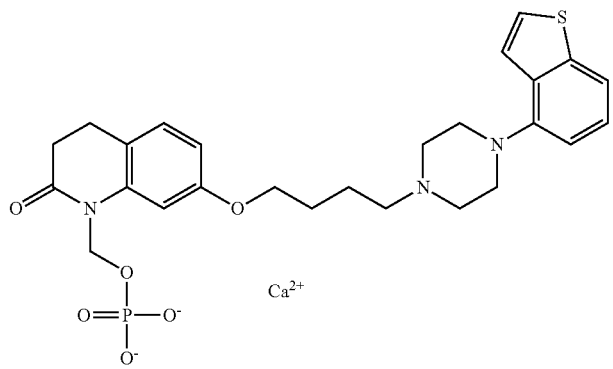 [SMILES: O=C1CCc2ccc(OCCCCN3CCN(c4cccc5sccc45)CC3)cc2N1COP(=O)([O-])[O-] ; [Ca+2]] | Calcium {7-[4-(4-(benzo[b]thiophen-4-yl)piperazin-1-yl]butoxy}-2-oxo-3,4-dihydro-2H-quinolin-1-yl)methyl phosphate |
| 201 | 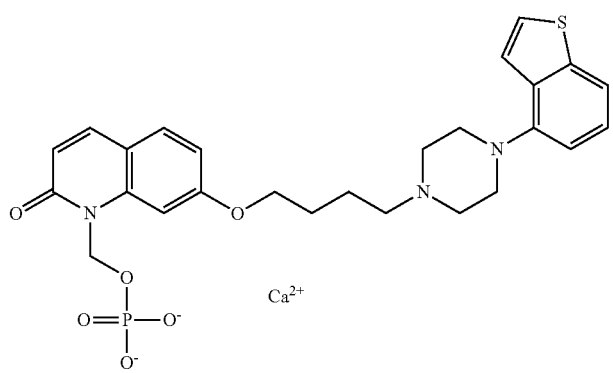 [SMILES: O=c1ccc2ccc(OCCCCN3CCN(c4cccc5sccc45)CC3)cc2n1COP(=O)([O-])[O-] ; [Ca+2]] | Calcium {7-[4-(4-(benzo[b]thiophen-4-yl)piperazin-1-yl]butoxy}-2-oxo-2H-quinolin-1-yl)methyl phosphate |
| 202 | 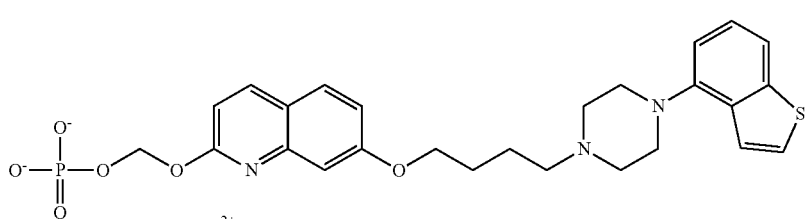 | Calcium (7-{4-[4-(benzo[b]thiophen-4-yl)piperazin-1-yl]butoxy}quinolin-2-yloxy)methyl phosphate |
| 203 | 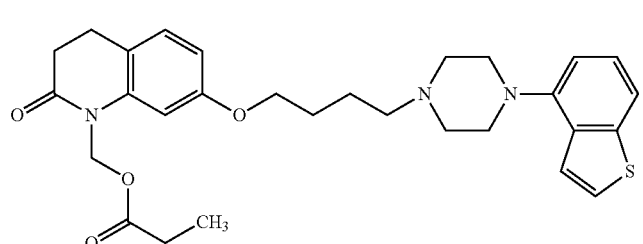 | Propionic acid 7-[4-(4-benzo[b]thiophen-4-ylpiperazin-1-yl)butoxy]-2-oxo-3,4-dihydro-2H-quinolin-1-ylmethyl ester |
| 204 | 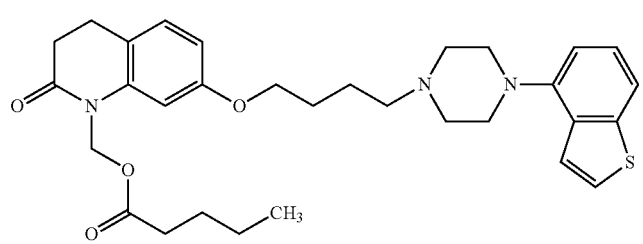 [SMILES: CCCCC(=O)OCN1C(=O)CCc2ccc(OCCCCN3CCN(c4cccc5sccc45)CC3)cc21] | Pentanoic acid 7-[4-(4-benzo[b]thiophen-4-ylpiperazin-1-yl)butoxy]-2-oxo-3,4-dihydro-2H-quinolin-1-ylmethyl ester |

TABLE 1-continued

| Example | Structure Formula | |
|---|---|---|
| 205 | 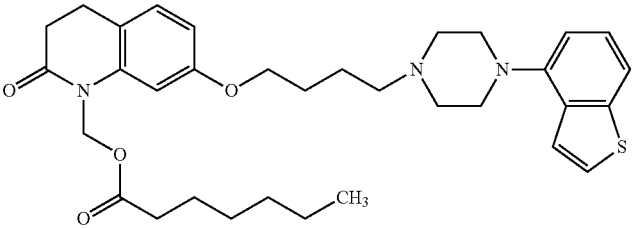 [SMILES: CCCCCCC(=O)OCN1C(=O)CCc2ccc(OCCCCN3CCN(c4cccc5sccc45)CC3)cc21] | Heptanoic acid 7-[4-(4-benzo[b]thiophen-4-ylpiperazin-1-yl)butoxy]-2-oxo-3,4-dihydro-2H-quinolin-1-ylmethyl ester |
| 206 | 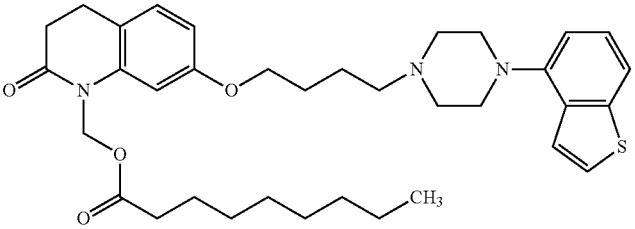 [SMILES: CCCCCCCCC(=O)OCN1C(=O)CCc2ccc(OCCCCN3CCN(c4cccc5sccc45)CC3)cc21] | Nonanoic acid 7-[4-(4-benzo[b]thiophen-4-ylpiperazin-1-yl)butoxy]-2-oxo-3,4-dihydro-2H-quinolin-1-ylmethyl ester |
| 207 | 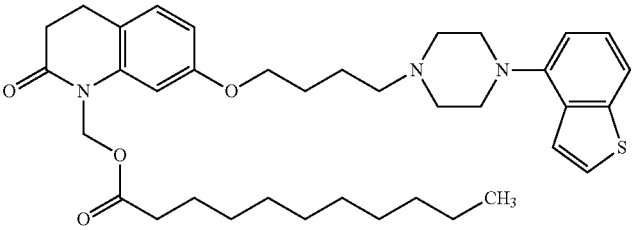 [SMILES: CCCCCCCCCCC(=O)OCN1C(=O)CCc2ccc(OCCCCN3CCN(c4cccc5sccc45)CC3)cc21] | Undecanoic acid 7-[4-(4-benzo[b]thiophen-4-ylpiperazin-1-yl)butoxy]-2-oxo-3,4-dihydro-2H-quinolin-1-ylmethyl ester |
| 208 | 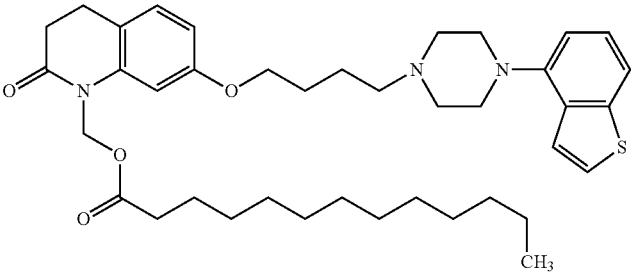 [SMILES: CCCCCCCCCCCCC(=O)OCN1C(=O)CCc2ccc(OCCCCN3CCN(c4cccc5sccc45)CC3)cc21] | Tridecanoic acid 7-[4-(4-benzo[b]thiophen-4-ylpiperazin-1-yl)butoxy]-2-oxo-3,4-dihydro-2H-quinolin-1-ylmethyl ester |
| 209 | 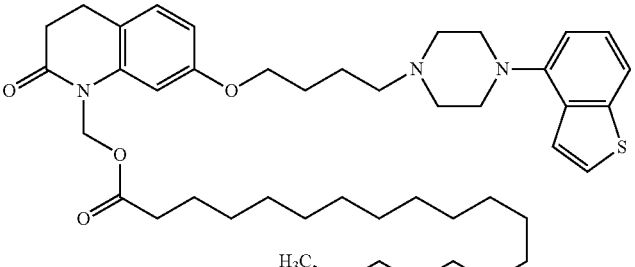 | Nonadecanoic acid 7-[4-(4-benzo[b]thiophen-4-ylpiperazin-1-yl)butoxy]-2-oxo-3,4-dihydro-2H-quinolin-1-ylmethyl ester |
| 210 | 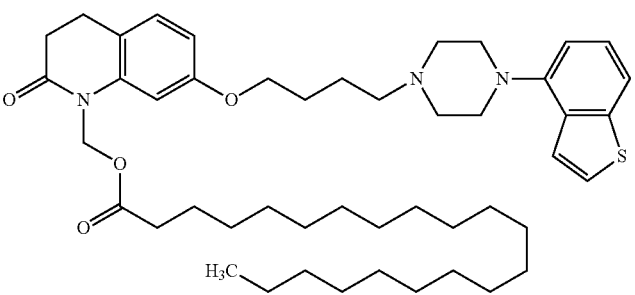 [SMILES: CCCCCCCCCCCCCCCCCCCCC(=O)OCN1C(=O)CCc2ccc(OCCCCN3CCN(c4cccc5sccc45)CC3)cc21] | Henicosanoic acid 7-[4-(4-benzo[b]thiophen-4-ylpiperazin-1-yl)butoxy]-2-oxo-3,4-dihydro-2H-quinolin-1-ylmethyl ester |

TABLE 1-continued

| Example | Structure Formula | |
|---|---|---|
| 211 | 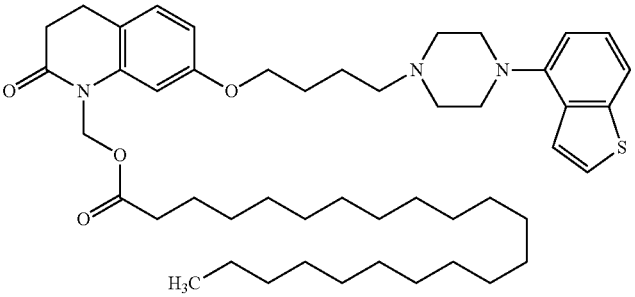 [SMILES: CCCCCCCCCCCCCCCCCCCCCC(=O)OCN1C(=O)CCc2ccc(OCCCCN3CCN(c4cccc5sccc45)CC3)cc21] | Docosanoic acid 7-[4-(4-benzo[b]thiophen-4-ylpiperazin-1-yl)butoxy]-2-oxo-3,4-dihydro-2H-quinolin-1-ylmethyl ester |
| 212 | 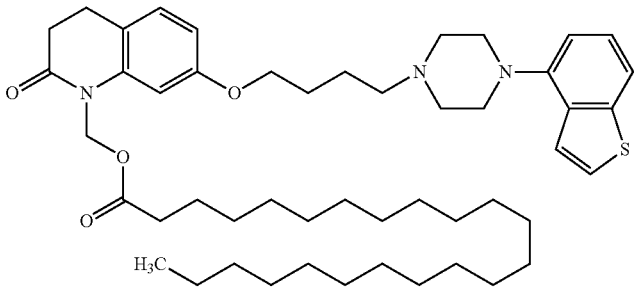 [SMILES: CCCCCCCCCCCCCCCCCCCCCCC(=O)OCN1C(=O)CCc2ccc(OCCCCN3CCN(c4cccc5sccc45)CC3)cc21] | Tricosanoic acid 7-[4-(4-benzo[b]thiophen-4-ylpiperazin-1-yl)butoxy]-2-oxo-3,4-dihydro-2H-quinolin-1-ylmethyl ester |
| 213 | 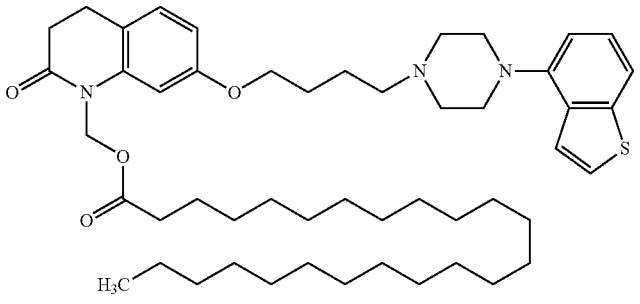 [SMILES: CCCCCCCCCCCCCCCCCCCCCCCC(=O)OCN1C(=O)CCc2ccc(OCCCCN3CCN(c4cccc5sccc45)CC3)cc21] | Tetracosanoic acid 7-[4-(4-benzo[b]thiophen-4-ylpiperazin-1-yl)butoxy]-2-oxo-3,4-dihydro-2H-quinolin-1-ylmethyl ester |
| 214 | 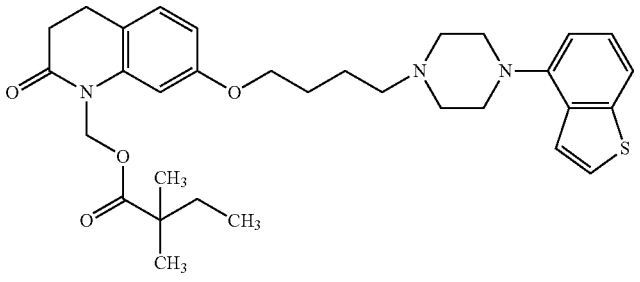 [SMILES: CCC(C)(C)C(=O)OCN1C(=O)CCc2ccc(OCCCCN3CCN(c4cccc5sccc45)CC3)cc21] | 2,2-Dimethylbutyric acid 7-[4-(4-benzo[b]thiophen-4-ylpiperazin-1-yl)butoxy]-2-oxo-3,4-dihydro-2H-quinolin-1-ylmethyl ester |
| 215 | 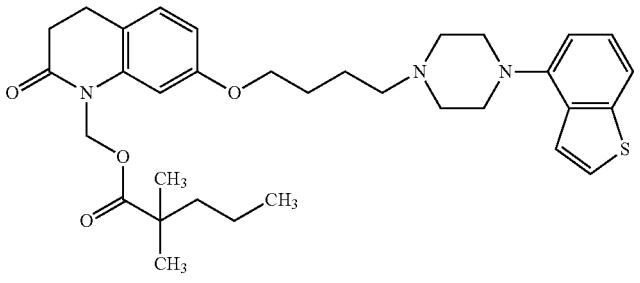 [SMILES: CCCC(C)(C)C(=O)OCN1C(=O)CCc2ccc(OCCCCN3CCN(c4cccc5sccc45)CC3)cc21] | 2,2-Dimethylpentanoic acid 7-[4-(4-benzo[b]thiophen-4-ylpiperazin-1-yl)butoxy]-2-oxo-3,4-dihydro-2H-quinolin-1-ylmethyl ester |

TABLE 1-continued

| Example | Structure Formula | |
|---|---|---|
| 216 | | 2,2-Dimethyldodecanoic acid 7-[4-(4-benzo[b]thiophen-4-ylpiperazin-1-yl)butoxy]-2-oxo-3,4-dihydro-2H-quinolin-1-ylmethyl ester |
| 217 | | Isobutyric acid 7-[4-(4-benzo[b]thiophen-4-ylpiperazin-1-yl)butoxy]-2-oxo-3,4-dihydro-2H-quinolin-1-ylmethyl ester |
| 218 | | 3-Methylbutyric acid 7-[4-(4-benzo[b]thiophen-4-ylpiperazin-1-yl)butoxy]-2-oxo-3,4-dihydro-2H-quinolin-1-ylmethyl ester |
| 219 | | Decanoic acid 1-{7-[4-(4-benzo[b]thiophen-4-ylpiperazin-1-yl)butoxy]-2-oxo-3,4-dihydro-2H-quinolin-1-yl}ethyl ester |
| 220 | | Dodecanoic acid 1-{7-[4-(4-benzo[b]thiophen-4-ylpiperazin-1-yl)butoxy]-2-oxo-3,4-dihydro-2H-quinolin-1-yl}ethyl ester |
| 221 | | Tetradecanoic acid 1-{7-[4-(4-benzo[b]thiophen-4-ylpiperazin-1-yl)butoxy]-2-oxo-3,4-dihydro-2H-quinolin-1-yl}ethyl ester |

TABLE 1-continued

| Example | Structure Formula | |
|---|---|---|
| 222 | 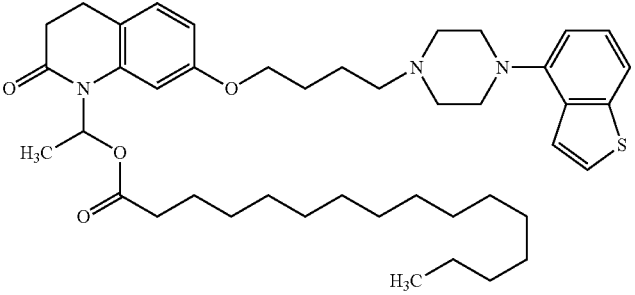 [SMILES: CCCCCCCCCCCCCCCC(=O)OC(C)N1C(=O)CCc2ccc(OCCCCN3CCN(c4cccc5sccc45)CC3)cc21] | Hexadecanoic acid 1-{7-[4-(4-benzo[b]thiophen-4-ylpiperazin-1-yl)butoxy]-2-oxo-3,4-dihydro-2H-quinolin-1-yl}ethyl ester |
| 223 | 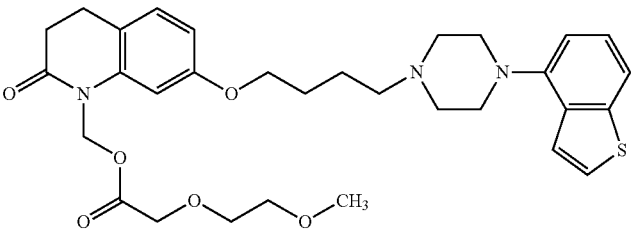 [SMILES: COCCOCC(=O)OCN1C(=O)CCc2ccc(OCCCCN3CCN(c4cccc5sccc45)CC3)cc21] | (2-Methoxyethoxy)acetic acid 7-[4-(4-benzo[b]thiophen-4-ylpiperazin-1-yl)butoxy]-2-oxo-3,4-dihydro-2H-quinolin-1-ylmethyl ester |
| 224 | 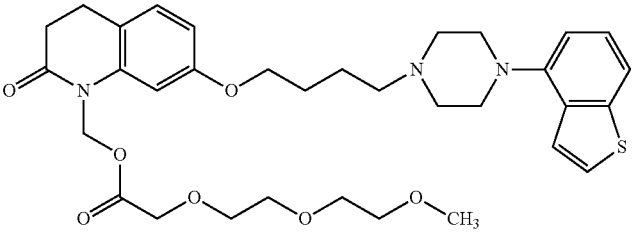 [SMILES: COCCOCCOCC(=O)OCN1C(=O)CCc2ccc(OCCCCN3CCN(c4cccc5sccc45)CC3)cc21] | [2-(2-Methoxyethoxy)ethoxy]acetic acid 7-[4-(4-benzo[b]thiophen-4-ylpiperazin-1-yl)butoxy]-2-oxo-3,4-dihydro-2H-quinolin-1-ylmethyl ester |
| 225 | 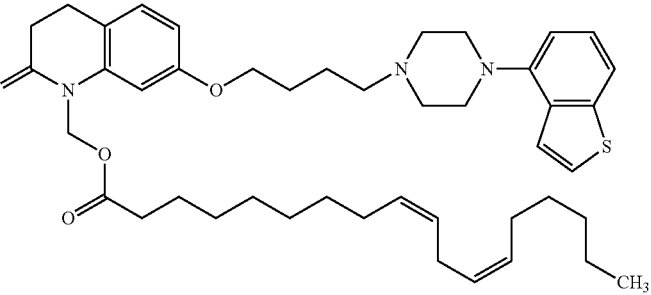 | (9Z,12Z)-Octadeca-9,12-dienoic acid 7-[4-(4-benzo[b]thiophen-4-ylpiperazin-1-yl)butoxy]-2-oxo-3,4-dihydro-2H-quinolin-1-ylmethyl ester |
| 226 | 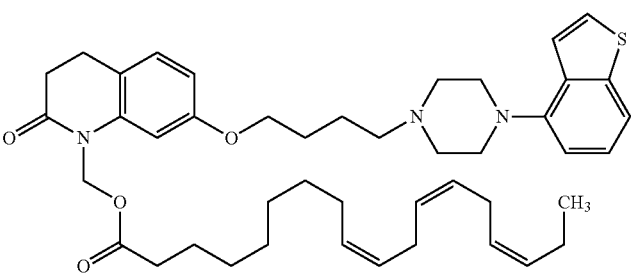 [SMILES: CC/C=C\C/C=C\C/C=C\CCCCCCCC(=O)OCN1C(=O)CCc2ccc(OCCCCN3CCN(c4cccc5sccc45)CC3)cc21] | (9Z,12Z,15Z)-Octadeca-9,12,15-trienoic acid 7-[4-(4-benzo[b]thiophen-4-ylpiperazin-1-yl)butoxy]-2-oxo-3,4-dihydro-2H-quinolin-1-ylmethyl ester |

TABLE 1-continued

| Example | Structure Formula | |
|---|---|---|
| 227 | | (4Z,7Z,10Z,13Z,16Z,19Z)-Docosa-4,7,10,13,16,19-hexaenoic acid 7-[4-(4-benzo[b]thiophen-4-ylpiperazin-1-yl)butoxy]-2-oxo-3,4-dihydro-2H-quinolin-1-ylmethyl ester |
| 228 | | (6Z,9Z,12Z,15Z)-Octadeca-6,9,12,15-tetraenoic acid 7-[4-(4-benzo[b]thiophen-4-ylpiperazin-1-yl)butoxy]-2-oxo-3,4-dihydro-2H-quinolin-1-ylmethyl ester |
| 229 | | Isonicotinic acid 7-[4-(4-benzo[b]thiophen-4-ylpiperazin-1-yl)butoxy]-2-oxo-3,4-dihydro-2H-quinolin-1-ylmethyl ester |
| 230 | | Pyrimidine-5-carboxylic acid 7-[4-(4-benzo[b]thiophen-4-ylpiperazin-1-yl)butoxy]-2-oxo-3,4-dihydro-2H-quinolin-1-ylmethyl ester |
| 231 | | Pyridazine-4-carboxylic acid 7-[4-(4-benzo[b]thiophen-4-ylpiperazin-1-yl)butoxy]-2-oxo-3,4-dihydro-2H-quinolin-1-ylmethyl ester |

TABLE 1-continued

| Example | Structure Formula | |
|---|---|---|
| 232 | | Propionic acid 7-[4-(4-benzo[b]thiophen-4-ylpiperazin-1-yl)butoxy]-2-oxo-2H-quinolin-1-ylmethyl ester |
| 233 | | Pentanoic acid 7-[4-(4-benzo[b]thiophen-4-ylpiperazin-1-yl)butoxy]-2-oxo-2H-quinolin-1-ylmethyl ester |
| 234 | | Heptanoic acid 7-[4-(4-benzo[b]thiophen-4-ylpiperazin-1-yl)butoxy]-2-oxo-2H-quinolin-1-ylmethyl ester |
| 235 | | Nonanoic acid 7-[4-(4-benzo[b]thiophen-4-ylpiperazin-1-yl)butoxy]-2-oxo-2H-quinolin-1-ylmethyl ester |
| 236 | | Undecanoic acid 7-[4-(4-benzo[b]thiophen-4-ylpiperazin-1-yl)butoxy]-2-oxo-2H-quinolin-1-ylmethyl ester |
| 237 | | Tridecanoic acid 7-[4-(4-benzo[b]thiophen-4-ylpiperazin-1-yl)butoxy]-2-oxo-2H-quinolin-1-ylmethyl ester |

TABLE 1-continued

| Example | Structure Formula | |
|---|---|---|
| 238 | 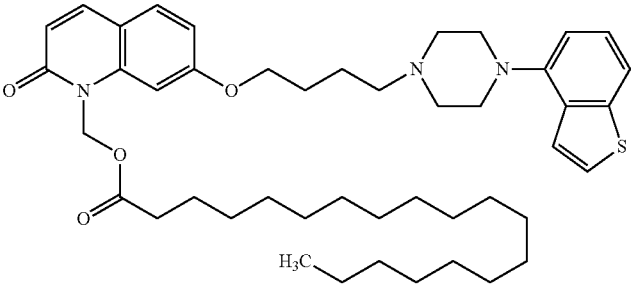 [SMILES: CCCCCCCCCCCCCCCCCCC(=O)OCn1c(=O)ccc2ccc(OCCCCN3CCN(c4cccc5sccc45)CC3)cc21] | Nonadecanoic acid 7-[4-(4-benzo[b]thiophen-4-ylpiperazin-1-yl)butoxy]-2-oxo-2H-quinolin-1-ylmethyl ester |
| 239 | 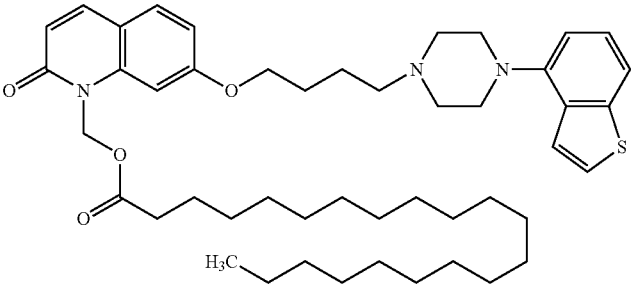 [SMILES: CCCCCCCCCCCCCCCCCCCCC(=O)OCn1c(=O)ccc2ccc(OCCCCN3CCN(c4cccc5sccc45)CC3)cc21] | Henicosanoic acid 7-[4-(4-benzo[b]thiophen-4-ylpiperazin-1-yl)butoxy]-2-oxo-2H-quinolin-1-ylmethyl ester |
| 240 | 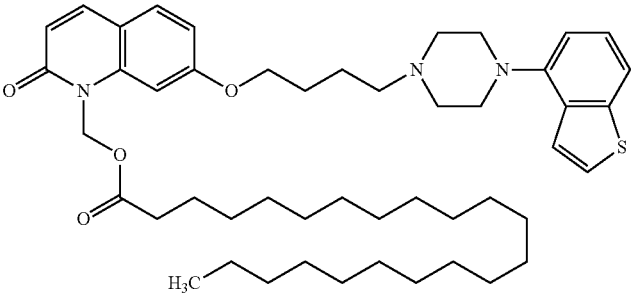 [SMILES: CCCCCCCCCCCCCCCCCCCCCC(=O)OCn1c(=O)ccc2ccc(OCCCCN3CCN(c4cccc5sccc45)CC3)cc21] | Docosanoic acid 7-[4-(4-benzo[b]thiophen-4-ylpiperazin-1-yl)butoxy]-2-oxo-2H-quinolin-1-ylmethyl ester |
| 241 | 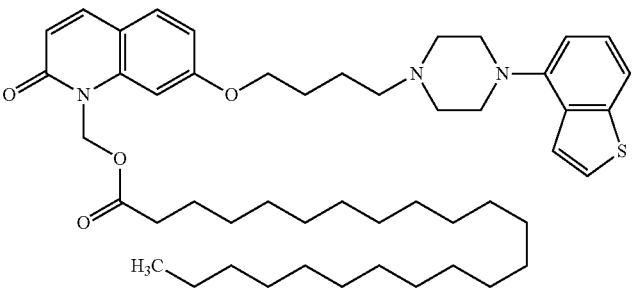 [SMILES: CCCCCCCCCCCCCCCCCCCCCCC(=O)OCn1c(=O)ccc2ccc(OCCCCN3CCN(c4cccc5sccc45)CC3)cc21] | Tricosanoic acid 7-[4-(4-benzo[b]thiophen-4-ylpiperazin-1-yl)butoxy]-2-oxo-2H-quinolin-1-ylmethyl ester |
| 242 | 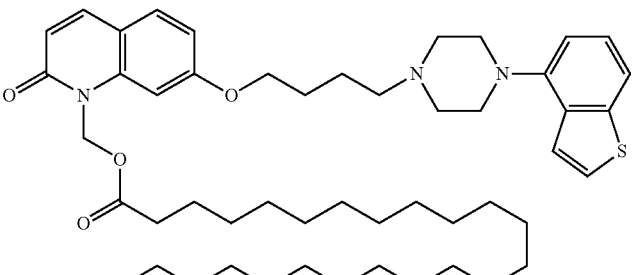 | Tetracosanoic acid 7-[4-(4-benzo[b]thiophen-4-ylpiperazin-1-yl)butoxy]-2-oxo-2H-quinolin-1-ylmethyl ester |

TABLE 1-continued

| Example | Structure Formula | |
|---|---|---|
| 243 | 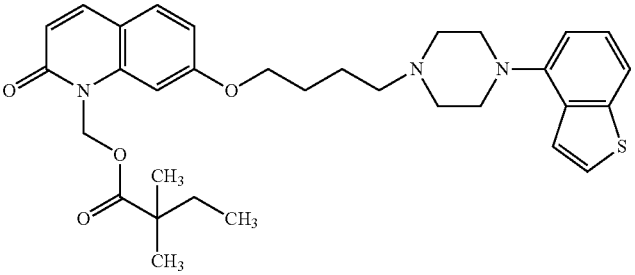 [SMILES: CCC(C)(C)C(=O)OCn1c(=O)ccc2ccc(OCCCCN3CCN(c4cccc5sccc45)CC3)cc21] | 2,2-Dimethylbutyric acid 7-[4-(4-benzo[b]thiophen-4-ylpiperazin-1-yl)butoxy]-2-oxo-2H-quinolin-1-ylmethyl ester |
| 244 | 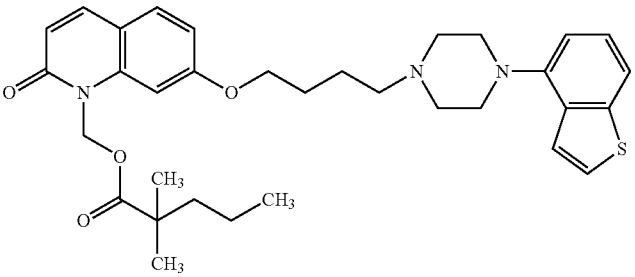 | 2,2-Dimethylpentanoic acid 7-[4-(4-benzo[b]thiophen-4-ylpiperazin-1-yl)butoxy]-2-oxo-2H-quinolin-1-ylmethyl ester |
| 245 | 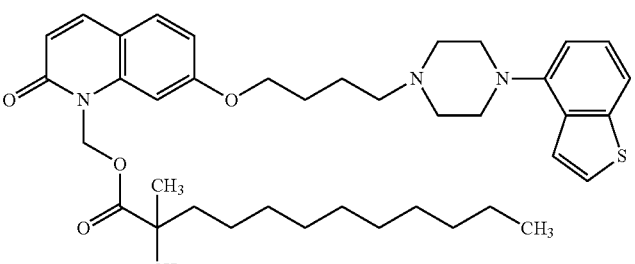 | 2,2-Dimethyldodecanoic acid 7-[4-(4-benzo[b]thiophen-4-ylpiperazin-1-yl)butoxy]-2-oxo-2H-quinolin-1-ylmethyl ester |
| 246 | 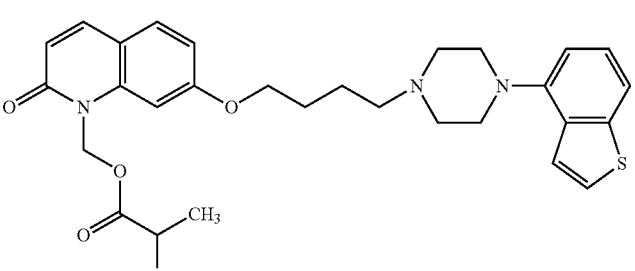 | Isobutyric acid 7-[4-(4-benzo[b]thiophen-4-ylpiperazin-1-yl)butoxy]-2-oxo-2H-quinolin-1-ylmethyl ester |
| 247 | 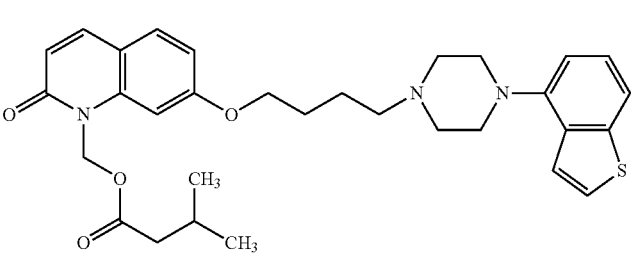 [SMILES: CC(C)CC(=O)OCn1c(=O)ccc2ccc(OCCCCN3CCN(c4cccc5sccc45)CC3)cc21] | 3-Methylbutyric acid 7-[4-(4-benzo[b]thiophen-4-ylpiperazin-1-yl)butoxy]-2-oxo-2H-quinolin-1-ylmethyl ester |

TABLE 1-continued

| Example | Structure Formula | |
|---|---|---|
| 248 | | Decanoic acid 1-{7-[4-(4-benzo[b]thiophen-4-ylpiperazin-1-yl)butoxy]-2-oxo-2H-quinolin-1-yl}ethyl ester |
| 249 | | Dodecanoic acid 1-{7-[4-(4-benzo[b]thiophen-4-ylpiperazin-1-yl)butoxy]-2-oxo-2H-quinolin-1-yl}ethyl ester |
| 250 | | Tetradecanoic acid 1-{7-[4-(4-benzo[b]thiophen-4-ylpiperazin-1-yl)butoxy]-2-oxo-2H-quinolin-1-yl}ethyl ester |
| 251 | | Hexadecanoic acid 1-{7-[4-(4-benzo[b]thiophen-4-ylpiperazin-1-yl)butoxy]-2-oxo-2H-quinolin-1-yl}ethyl ester |
| 252 | | 1-Methylpiperidine-4-carboxylic acid 7-[4-(4-benzo[b]thiophen-4-ylpiperazin-1-yl)butoxy]-2-oxo-2H-quinolin-1-ylmethyl ester |

TABLE 1-continued

| Example | Structure Formula | |
|---|---|---|
| 253 | | (2-Methoxyethoxy)acetic acid 7-[4-(4-benzo[b]thiophen-4-ylpiperazin-1-yl)butoxy]-2-oxo-2H-quinolin-1-ylmethyl ester |
| 254 | | [2-(2-Methoxyethoxy)ethoxy]acetic acid 7-[4-(4-benzo[b]thiophen-4-ylpiperazin-1-yl)butoxy]-2-oxo-2H-quinolin-1-ylmethyl ester |
| 255 | | (2-Butoxyethoxy)acetic acid 7-[4-(4-benzo[b]thiophen-4-ylpiperazin-1-yl)butoxy]-2-oxo-2H-quinolin-1-ylmethyl ester |
| 256 | | (9Z,12Z)-Octadeca-9,12-dienoic acid 7-[4-(4-benzo[b]thiophen-4-ylpiperazin-1-yl)butoxy]-2-oxo-2H-quinolin-1-ylmethyl ester |
| 257 | | (9Z,12Z,15Z)-Octadeca-9,12,15-trienoic acid 7-[4-(4-benzo[b]thiophen-4-ylpiperazin-1-yl)butoxy]-2-oxo-2H-quinolin-1-ylmethyl ester |
| 258 | | (4Z,7Z,10Z,13Z,16Z,19Z)-Docosa-4,7,10,13,16,19-hexaenoic acid 7-[4-(4-benzo[b]thiophen-4-ylpiperazin-1-yl)butoxy]-2-oxo-2H-quinolin-1-ylmethyl ester |

TABLE 1-continued

| Example | Structure Formula | |
|---|---|---|
| 259 | | (6Z,9Z,12Z,15Z)-Octadeca-6,9,12,15-tetraenoic acid 7-[4-(4-benzo[b]thiophen-4-ylpiperazin-1-yl)butoxy]-2-oxo-2H-quinolin-1-ylmethyl ester |
| 260 | | Isonicotinic acid 7-[4-(4-benzo[b]thiophen-4-ylpiperazin-1-yl)butoxy]-2-oxo-2H-quinolin-1-ylmethyl ester |
| 261 | | Nicotinic acid 7-[4-(4-benzo[b]thiophen-4-ylpiperazin-1-yl)butoxy]-2-oxo-2H-quinolin-1-ylmethyl ester |
| 262 | | Pyrimidine-5-carboxylic acid 7-[4-(4-benzo[b]thiophen-4-ylpiperazin-1-yl)butoxy]-2-oxo-2H-quinolin-1-ylmethyl ester |
| 263 | | Pyridazine-4-carboxylic acid 7-[4-(4-benzo[b]thiophen-4-ylpiperazin-1-yl)butoxy]-2-oxo-2H-quinolin-1-ylmethyl ester |

TABLE 1-continued

| Example | Structure Formula | |
|---|---|---|
| 264 | | Pyridine-2-carboxylic acid 7-[4-(4-benzo[b]thiophen-4-ylpiperazin-1-yl)butoxy]-2-oxo-3,4-dihydro-2H-quinolin-1-ylmethyl ester |
| 265 | | Pyridine-2-carboxylic acid 7-[4-(4-benzo[b]thiophen-4-ylpiperazin-1-yl)butoxy]-2-oxo-2H-quinolin-1-ylmethyl ester |
| 266 | | Furan-2-carboxylic acid 7-[4-(4-benzo[b]thiophen-4-ylpiperazin-1-yl)butoxy]-2-oxo-3,4-dihydro-2H-quinolin-1-ylmethyl ester |
| 267 | | Furan-2-carboxylic acid 7-[4-(4-benzo[b]thiophen-4-ylpiperazin-1-yl)butoxy]-2-oxo-2H-quinolin-1-ylmethyl ester |
| 268 | | Thiophene-3-carboxylic acid 7-[4-(4-benzo[b]thiophen-4-ylpiperazin-1-yl)butoxy]-2-oxo-3,4-dihydro-2H-quinolin-1-ylmethyl ester |

TABLE 1-continued

| Example | Structure Formula | |
|---|---|---|
| 269 | | Thiophene-3-carboxylic acid 7-[4-(4-benzo[b]thiophen-4-ylpiperazin-1-yl)butoxy]-2-oxo-2H-quinolin-1-ylmethyl ester |
| 270 | | Quinoline-6-carboxylic acid 7-[4-(4-benzo[b]thiophen-4-ylpiperazin-1-yl)butoxy]-2-oxo-3,4-dihydro-2H-quinolin-1-ylmethyl ester |
| 271 | | Quinoline-6-carboxylic acid 7-[4-(4-benzo[b]thiophen-4-ylpiperazin-1-yl)butoxy]-2-oxo-2H-quinolin-1-ylmethyl ester |
| 272 | | Benzoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 273 | | 2,2-Dimethylpropionic acid 7-[4-(4-benzo[b]thiophen-4-ylpiperazin-1-yl)butoxy]-4,4-dimethyl-2-oxo-3,4-dihydro-2H-quinolin-1-ylmethyl ester |

TABLE 1-continued

| Example | Structure Formula | |
|---|---|---|
| 274 | | Butyric acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 275 | | Phenylacetic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 276 | | Octanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 277 | | Cyclohexanecarboxylic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 278 | | Cyclopentanecarboxylic acid 7-[4-(4-benzo[b]thiophen-4-ylpiperazin-1-yl)butoxy]-4,4-dimethyl-2-oxo-3,4-dihydro-2H-quinolin-1-ylmethyl ester |

TABLE 1-continued

| Example | Structure Formula | |
|---|---|---|
| 279 | 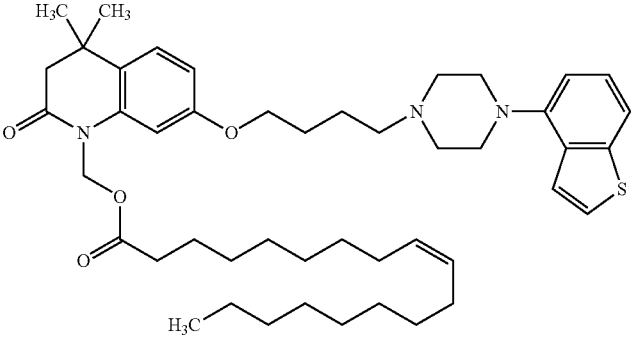 [SMILES: CCCCCCCC/C=C\CCCCCCCC(=O)OCN1C(=O)CC(C)(C)c2ccc(OCCCCN3CCN(c4cccc5sccc45)CC3)cc21] | (Z)-Octadec-9-enoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 280 | 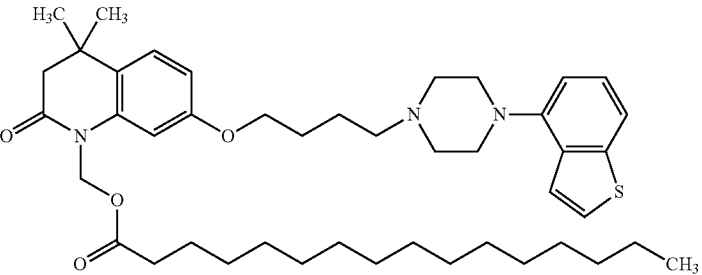 [SMILES: CCCCCCCCCCCCCCCC(=O)OCN1C(=O)CC(C)(C)c2ccc(OCCCCN3CCN(c4cccc5sccc45)CC3)cc21] | Hexadecanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 281 | 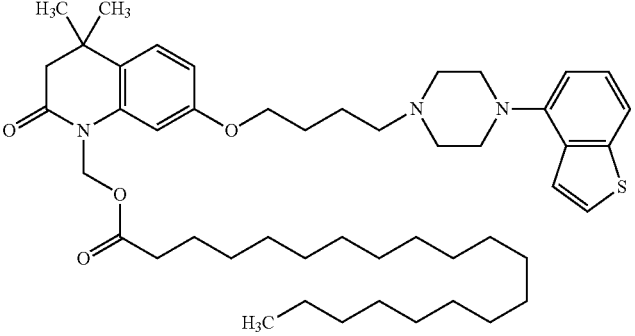 [SMILES: CCCCCCCCCCCCCCCCCCCC(=O)OCN1C(=O)CC(C)(C)c2ccc(OCCCCN3CCN(c4cccc5sccc45)CC3)cc21] | Icosanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 282 | 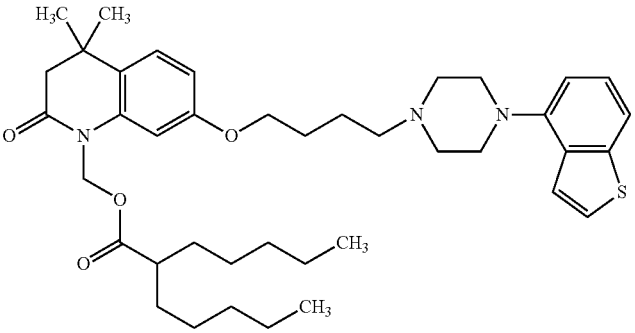 [SMILES: CCCCCC(CCCCC)C(=O)OCN1C(=O)CC(C)(C)c2ccc(OCCCCN3CCN(c4cccc5sccc45)CC3)cc21] | 2-Pentyl-heptanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 283 | 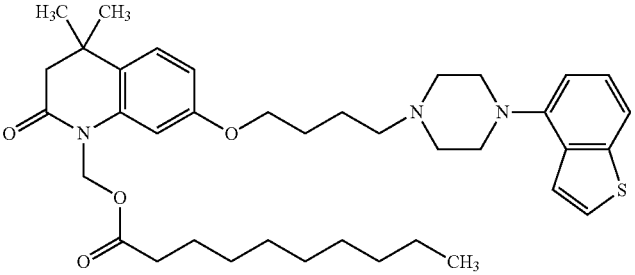 [SMILES: CCCCCCCCCC(=O)OCN1C(=O)CC(C)(C)c2ccc(OCCCCN3CCN(c4cccc5sccc45)CC3)cc21] | Decanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |

TABLE 1-continued

| Example | Structure Formula | |
|---|---|---|
| 284 | | Hexanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 285 | | Octadecanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 286 | | Acetic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 287 | | Propionic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 288 | | Pentanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |

TABLE 1-continued

| Example | Structure Formula | |
|---|---|---|
| 289 | 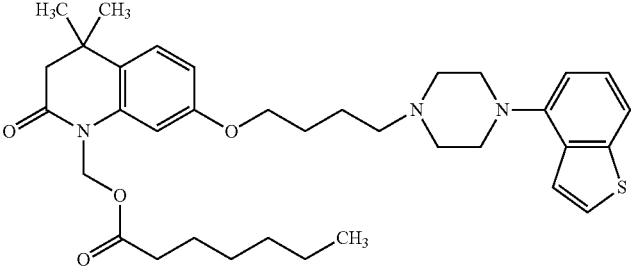 | Heptanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 290 | 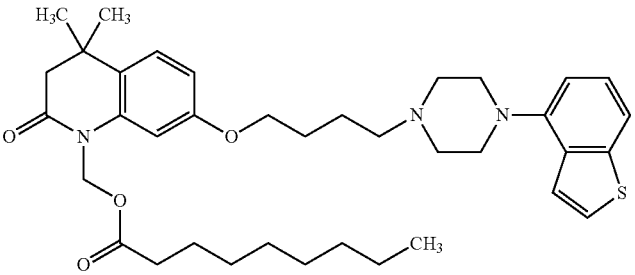 [SMILES: CCCCCCCCC(=O)OCN1C(=O)CC(C)(C)c2ccc(OCCCCN3CCN(c4cccc5sccc45)CC3)cc21] | Nonanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 291 | 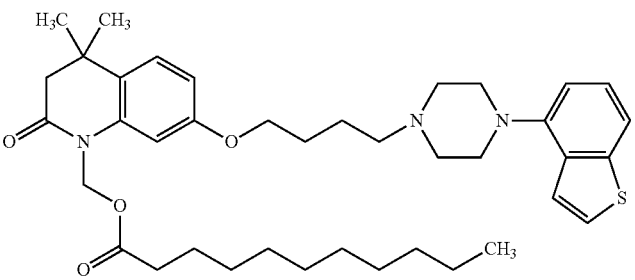 [SMILES: CCCCCCCCCCC(=O)OCN1C(=O)CC(C)(C)c2ccc(OCCCCN3CCN(c4cccc5sccc45)CC3)cc21] | Undecanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 292 | 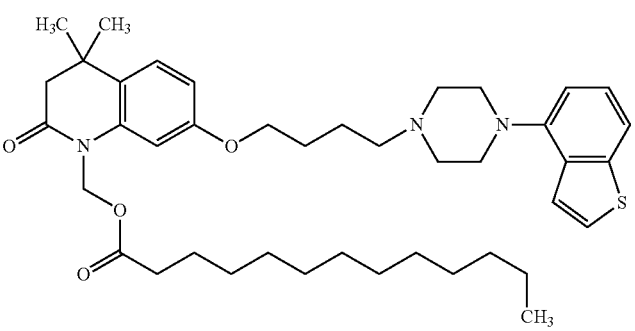 [SMILES: CCCCCCCCCCCCC(=O)OCN1C(=O)CC(C)(C)c2ccc(OCCCCN3CCN(c4cccc5sccc45)CC3)cc21] | Tridecanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 293 | 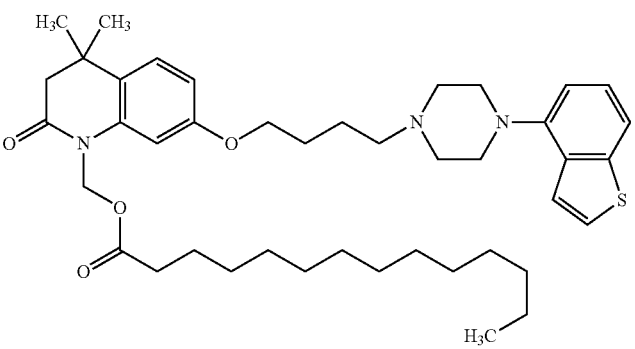 [SMILES: CCCCCCCCCCCCCC(=O)OCN1C(=O)CC(C)(C)c2ccc(OCCCCN3CCN(c4cccc5sccc45)CC3)cc21] | Tetradecanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |

TABLE 1-continued

| Example | Structure Formula | |
|---|---|---|
| 294 | 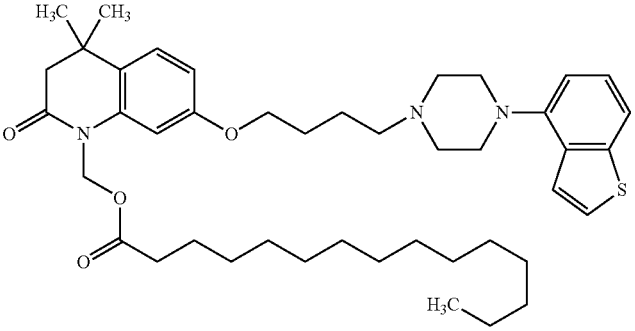 [SMILES: CCCCCCCCCCCCCCC(=O)OCN1C(=O)CC(C)(C)c2ccc(OCCCCN3CCN(c4cccc5sccc45)CC3)cc21] | Pentadecanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 295 | 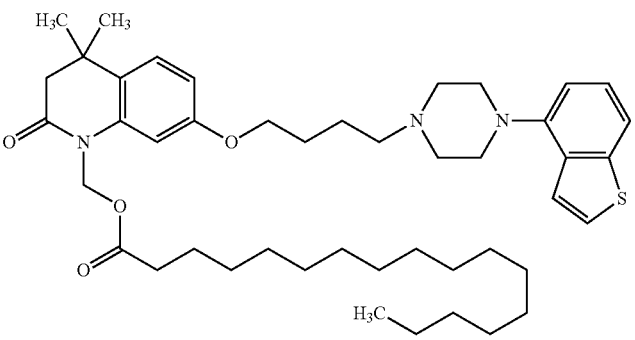 [SMILES: CCCCCCCCCCCCCCCCC(=O)OCN1C(=O)CC(C)(C)c2ccc(OCCCCN3CCN(c4cccc5sccc45)CC3)cc21] | Heptadecanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 296 | 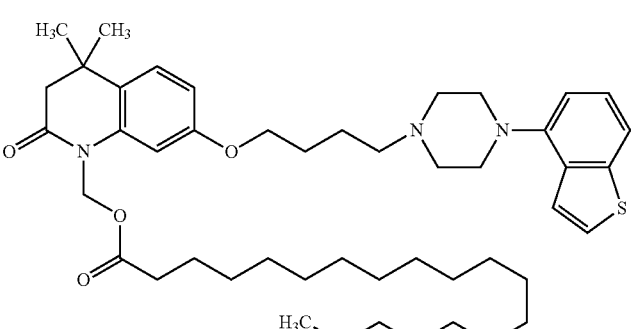 | Nonadecanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 297 | 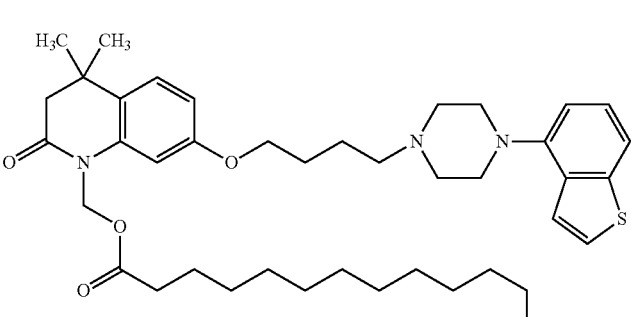 | Henicosanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |

TABLE 1-continued

| Example | Structure Formula | |
|---|---|---|
| 298 | 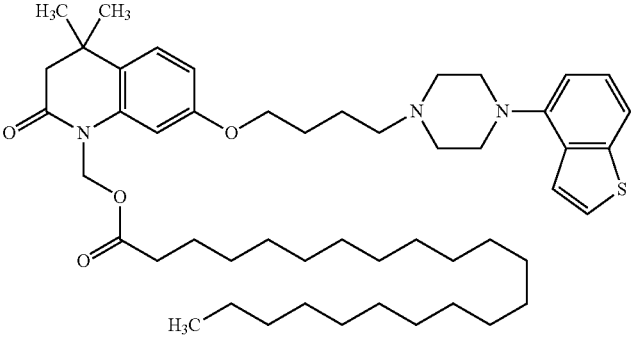 [SMILES: CCCCCCCCCCCCCCCCCCCCCC(=O)OCN1C(=O)CC(C)(C)c2ccc(OCCCCN3CCN(c4cccc5sccc45)CC3)cc21] | Docosanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 299 | 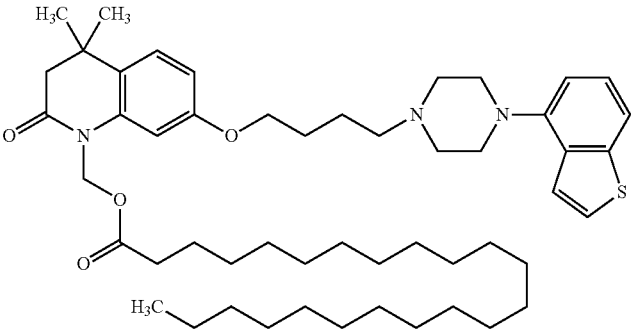 [SMILES: CCCCCCCCCCCCCCCCCCCCCCC(=O)OCN1C(=O)CC(C)(C)c2ccc(OCCCCN3CCN(c4cccc5sccc45)CC3)cc21] | Tricosanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 300 | 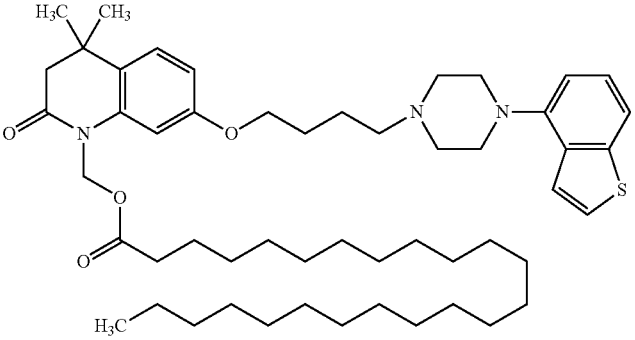 [SMILES: CCCCCCCCCCCCCCCCCCCCCCCC(=O)OCN1C(=O)CC(C)(C)c2ccc(OCCCCN3CCN(c4cccc5sccc45)CC3)cc21] | Tetracosanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 301 | 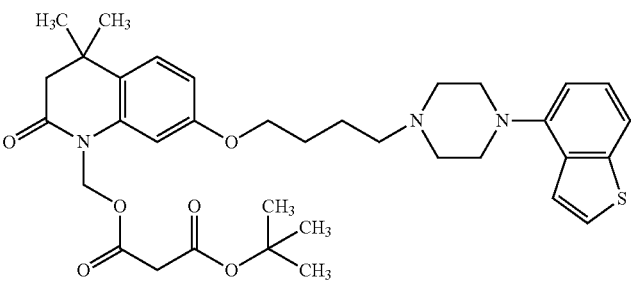 [SMILES: CC(C)(C)OC(=O)CC(=O)OCN1C(=O)CC(C)(C)c2ccc(OCCCCN3CCN(c4cccc5sccc45)CC3)cc21] | Malonic acid 7-[4-(4-benzo[b]thiophen-4-ylpiperazin-1-yl)butoxy]-4,4-dimethyl-2-oxo-3,4-dihydro-2H-quinolin-1-ylmethyl ester tert-butyl ester |

TABLE 1-continued

| Example | Structure Formula | |
|---|---|---|
| 302 | | 2-Methyl-butyric acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 303 | | 2-Methyl-pentanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 304 | | 2-Methyl-hexanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 305 | | 2,2-Dimethyl-hexanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |

TABLE 1-continued

| Example | Structure Formula | |
|---|---|---|
| 306 | | Isobutyric acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 307 | | 3-Methyl-butyric acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 308 | | 4-Methyl-pentanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 309 | | Cyclobutanecarboxylic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 310 | | Decanoic acid 1-{7-[4-(4-benzo[b]thiophen-4-ylpiperazin-1-yl)butoxy]-4,4-dimethyl-2-oxo-3,4-dihydro-2H-quinolin-1-yl}-ethyl ester |

TABLE 1-continued

| Example | Structure Formula | |
|---|---|---|
| 311 | | Dodecanoic acid 1-{7-[4-(4-benzo[b]thiophen-4-ylpiperazin-1-yl)butoxy]-4,4-dimethyl-2-oxo-3,4-dihydro-2H-quinolin-1-yl}-ethyl ester |
| 312 | | Tetradecanoic acid 1-{7-[4-(4-benzo[b]thiophen-4-ylpiperazin-1-yl)butoxy]-4,4-dimethyl-2-oxo-3,4-dihydro-2H-quinolin-1-yl}-ethyl ester |
| 313 | | Hexadecanoic acid 1-{7-[4-(4-benzo[b]thiophen-4-ylpiperazin-1-yl)butoxy]-4,4-dimethyl-2-oxo-3,4-dihydro-2H-quinolin-1-yl}-ethyl ester |
| 314 | | Tetrahydro-pyran-4-carboxylic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 315 | | (2-Methoxy-ethoxy)-acetic acid 7-[4-(4-benzo[b]thiophen-4-ylpiperazin-1-yl)butoxy]-4,4-dimethyl-2-oxo-3,4-dihydro-2H-quinolin-1-ylmethyl ester |

TABLE 1-continued

| Example | Structure Formula | |
|---|---|---|
| 316 | | [2-(2-Methoxy-ethoxy)-ethoxy]-acetic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 317 | | (2-Butoxy-ethoxy)-acetic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 318 | | Cycloheptanecarboxylic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 319 | | 4,4,4-Trifluoro-butyric acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 320 | | Piperidine-1-carboxylic acid 7-[4-(4-benzo[b]thiophen-4-ylpiperazin-1-yl)butoxy]-4,4-dimethyl-2-oxo-3,4-dihydro-2H-quinolin-1-ylmethyl ester |

TABLE 1-continued

| Example | Structure Formula | |
|---|---|---|
| 321 | | N-Butyl-N-methylcarbamic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 322 | | N,N-Dibutylcarbamic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 323 | | N-Cyclohexylmethylcarbamic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 324 | | N-Butylcarbamic acid 7-[4-(4-benzo[b]thiophen-4-ylpiperazin-1-yl)butoxy]-4,4-dimethyl-2-oxo-3,4-dihydro-2H-quinolin-1-ylmethyl ester |

TABLE 1-continued

| Example | Structure Formula | |
|---|---|---|
| 325 | | N-Methylcarbamic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 326 | | N,N-Dimethylcarbamic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 327 | | N-Ethylcarbamic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 328 | | N,N-Diethylcarbamic acid 7-[4-(4-benzo[b]thiophen-4-ylpiperazin-1-yl)butoxy]-4,4-dimethyl-2-oxo-3,4-dihydro-2H-quinolin-1-ylmethyl ester |

TABLE 1-continued

| Example | Structure Formula | |
|---|---|---|
| 329 | | N-Pentadecylcarbamic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 330 | | N-Octadecylcarbamic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 331 | | N-Methyl-N-octadecylcarbamic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 332 | | N-Cyclohexylcarbamic acid 7-[4-(4-benzo[b]thiophen-4-ylpiperazin-1-yl)butoxy]-4,4-dimethyl-2-oxo-3,4-dihydro-2H-quinolin-1-ylmethyl ester |

TABLE 1-continued

| Example | Structure Formula | |
|---|---|---|
| 333 | | N-Benzylcarbamic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 334 | | N-Benzyl-N-methylcarbamic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 335 | | N-Phenethylcarbamic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 336 | | Morpholine-4-carboxylic acid 7-[4-(4-benzo[b]thiophen-4-ylpiperazin-1-yl)butoxy]-4,4-dimethyl-2-oxo-3,4-dihydro-2H-quinolin-1-ylmethyl ester |

TABLE 1-continued

| Example | Structure Formula | |
|---|---|---|
| 337 | | N-(2-Methoxyethyl)carbamic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 338 | | {7-[4-(4-Benzo[b]thiophen-4-ylpiperazin-1-yl)butoxy]-4,4-dimethyl-2-oxo-3,4-dihydro-2H-quinolin-1-ylmethoxycarbonylamino}acetic acid methyl ester |
| 339 | | ({7-[4-(4-Benzo[b]thiophen-4-ylpiperazin-1-yl)butoxy]-4,4-dimethyl-2-oxo-3,4-dihydro-2H-quinolin-1-ylmethoxycarbonyl}-methyl-amino)acetic acid methyl ester |
| 340 | | (7-{4-[4-(Benzo[b]thiophen-4-yl)piperazin-1-yl]butoxy}-4,4-dimethyl-2-oxo-3,4-dihydro-2H-quinolin-1-yl)methyl N-methoxycarbamate |

TABLE 1-continued

| Example | Structure Formula | |
|---|---|---|
| 341 | | 7-[4-(4-benzo[b]thiophen-4-ylpiperazin-1-yl)butoxy]-4,4-dimethyl-2-oxo-3,4-dihydro-2H-quinolin-1-ylmethyl N-benzyloxy carbamate |
| 342 | | N-(3,3,3-Trifluoro-propyl)carbamic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 343 | | N-Furan-2-ylmethylcarbamic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 344 | | Carbonic acid 7-[4-(4-benzo[b]thiophen-4-ylpiperazin-1-yl)butoxy]-4,4-dimethyl-2-oxo-3,4-dihydro-2H-quinolin-1-ylmethyl ester methyl ester |
| 345 | | Carbonic acid 7-[4-(4-benzo[b]thiophen-4-ylpiperazin-1-yl)butoxy]-4,4-dimethyl-2-oxo-3,4-dihydro-2H-quinolin-1-ylmethyl ester ethyl ester |

TABLE 1-continued

| Example | Structure Formula | |
|---|---|---|
| 346 | | Carbonic acid 7-[4-(4-benzo[b]thiophen-4-ylpiperazin-1-yl)butoxy]-4,4-dimethyl-2-oxo-3,4-dihydro-2H-quinolin-1-ylmethyl ester propyl ester |
| 347 | | Carbonic acid 7-[4-(4-benzo[b]thiophen-4-ylpiperazin-1-yl)butoxy]-4,4-dimethyl-2-oxo-3,4-dihydro-2H-quinolin-1-ylmethyl ester isopropyl ester |
| 348 | | Carbonic acid 7-[4-(4-benzo[b]thiophen-4-ylpiperazin-1-yl)butoxy]-4,4-dimethyl-2-oxo-3,4-dihydro-2H-quinolin-1-ylmethyl ester butyl ester |
| 349 | | Carbonic acid 7-[4-(4-benzo[b]thiophen-4-ylpiperazin-1-yl)butoxy]-4,4-dimethyl-2-oxo-3,4-dihydro-2H-quinolin-1-ylmethyl ester isobutyl ester |
| 350 | | Carbonic acid 7-[4-(4-benzo[b]thiophen-4-ylpiperazin-1-yl)butoxy]-4,4-dimethyl-2-oxo-3,4-dihydro-2H-quinolin-1-ylmethyl ester pentyl ester |

TABLE 1-continued

| Example | Structure Formula | |
|---|---|---|
| 351 | | Carbonic acid 7-[4-(4-benzo[b]thiophen-4-ylpiperazin-1-yl)butoxy]-4,4-dimethyl-2-oxo-3,4-dihydro-2H-quinolin-1-ylmethyl ester 3-methyl-butyl ester |
| 352 | | Carbonic acid 7-[4-(4-benzo[b]thiophen-4-ylpiperazin-1-yl)butoxy]-4,4-dimethyl-2-oxo-3,4-dihydro-2H-quinolin-1-ylmethyl ester hexyl ester |
| 353 | | Carbonic acid 7-[4-(4-benzo[b]thiophen-4-ylpiperazin-1-yl)butoxy]-4,4-dimethyl-2-oxo-3,4-dihydro-2H-quinolin-1-ylmethyl ester nonyl ester |
| 354 | | Carbonic acid 7-[4-(4-benzo[b]thiophen-4-ylpiperazin-1-yl)butoxy]-4,4-dimethyl-2-oxo-3,4-dihydro-2H-quinolin-1-ylmethyl ester tetradecyl ester |
| 355 | | Carbonic acid 7-[4-(4-benzo[b]thiophen-4-ylpiperazin-1-yl)butoxy]-4,4-dimethyl-2-oxo-3,4-dihydro-2H-quinolin-1-ylmethyl ester hexadecyl ester |

TABLE 1-continued

| Example | Structure Formula | |
|---|---|---|
| 356 | | Carbonic acid 7-[4-(4-benzo[b]thiophen-4-ylpiperazin-1-yl)butoxy]-4,4-dimethyl-2-oxo-3,4-dihydro-2H-quinolin-1-ylmethyl ester benzyl ester |
| 357 | | Carbonic acid 7-[4-(4-benzo[b]thiophen-4-ylpiperazin-1-yl)butoxy]-4,4-dimethyl-2-oxo-3,4-dihydro-2H-quinolin-1-ylmethyl ester heptyl ester |
| 358 | | Carbonic acid 7-[4-(4-benzo[b]thiophen-4-ylpiperazin-1-yl)butoxy]-4,4-dimethyl-2-oxo-3,4-dihydro-2H-quinolin-1-ylmethyl ester octyl ester |
| 359 | | Carbonic acid 7-[4-(4-benzo[b]thiophen-4-ylpiperazin-1-yl)butoxy]-4,4-dimethyl-2-oxo-3,4-dihydro-2H-quinolin-1-ylmethyl ester 2,2,2-trifluoro-ethyl ester |
| 360 | | Carbonic acid 7-[4-(4-benzo[b]thiophen-4-ylpiperazin-1-yl)butoxy]-4,4-dimethyl-2-oxo-3,4-dihydro-2H-quinolin-1-ylmethyl ester cyclohexyl ester |

TABLE 1-continued

| Example | Structure Formula | |
|---|---|---|
| 361 | | 7-[4-(4-Benzo[b]thiophen-4-ylpiperazin-1-yl)butoxy]-1-methoxymethyl-4,4-dimethyl-3,4-dihydro-1H-quinolin-2-one |
| 362 | | 7-[4-(4-Benzo[b]thiophen-4-ylpiperazin-1-yl)butoxy]-1-ethoxymethyl-4,4-dimethyl-3,4-dihydro-1H-quinolin-2-one |
| 363 | | 7-[4-(4-Benzo[b]thiophen-4-ylpiperazin-1-yl)butoxy]-1-isopropoxymethyl-4,4-dimethyl-3,4-dihydro-1H-quinolin-2-one |
| 364 | | 7-[4-(4-Benzo[b]thiophen-4-ylpiperazin-1-yl)butoxy]-1-benzyloxymethyl-4,4-dimethyl-3,4-dihydro-1H-quinolin-2-one |

TABLE 1-continued

| Example | Structure Formula | |
|---|---|---|
| 365 | | 7-[4-(4-Benzo[b]thiophen-4-ylpiperazin-1-yl)butoxy]-4,4-dimethyl-1-(2,2,2-trifluoro-ethoxymethyl)-3,4-dihydro-1H-quinolin-2-one |
| 366 | | Amino-acetic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 367 | | 2-Amino-propionic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 368 | | 2-Amino-3-methyl-butyric acid 7-[4-(4-benzo[b]thiophen-4-ylpiperazin-1-yl)butoxy]-4,4-dimethyl-2-oxo-3,4-dihydro-2H-quinolin-1-ylmethyl ester |

| Example | Structure Formula | |
|---|---|---|
| 369 | (structure) | 2-Amino-4-methyl-pentanoic acid 7-[4-(4-benzo[b]thiophen-4-ylpiperazin-1-yl)butoxy]-4,4-dimethyl-2-oxo-3,4-dihydro-2H-quinolin-1-ylmethyl ester |
| 370 | (structure) | Pyrrolidine-2-carboxylic acid 7-[4-(4-benzo[b]thiophen-4-ylpiperazin-1-yl)butoxy]-4,4-dimethyl-2-oxo-3,4-dihydro-2H-quinolin-1-ylmethyl ester |

Example 371

Synthesis of 7-[4-(4-benzo[b]thiophen-4-yl-piperazin-1-yl)-butoxy]-quinolin-2-yloxymethyl dodecanoate

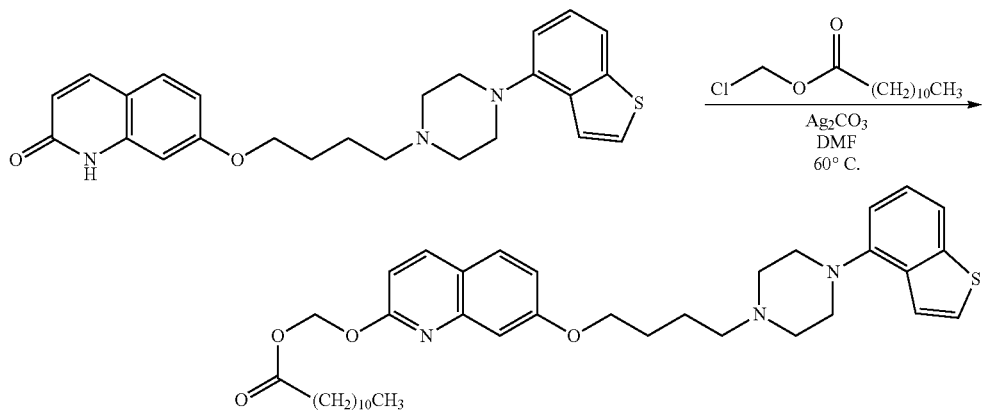

To a solution of 7-[4-(4-benzo[b]thiophen-4-yl-piperazin-1-yl)-butoxy]-1H-quinolin-2-one (800 mg) synthesized in the same manner as in WO2006/112464 (Example 1) in dimethylformamide (30 ml) was added silver carbonate (I) (0.76 g), chloromethyldodecanoate[61413-67-0] (1.15 g) was added, and the mixture was stirred at 60° C. for 6 hr. Water was added to the reaction mixture, and the mixture was extracted with ethyl acetate and dried over $Na_2SO_4$. The solvent was evaporated under reduced pressure and the residue was purified by silica gel column chromatography (ethyl acetate:n-hexane=2:1) to give 7-[4-(4-benzo[b]thiophen-4-yl-piperazin-1-yl)-butoxy]-quinolin-2-yloxymethyl dodecanoate (22 mg).

oil: colorless $^1$H-NMR (CDCl$_3$) δ ppm: 0.87 (3H, t, J=7.1 Hz), 1.16-2.10 (18H, m), 2.36 (2H, t, J=7.5 Hz), 2.58 (2H, t, J=7.5 Hz), 2.76 (4H, br), 3.21 (4H, br), 4.15 (2H, t, J=6.3 Hz), 6.25 (2H, s), 6.80 (1H, d, J=8.7 Hz), 6.90 (1H, d, J=7.4 Hz), 7.06 (1H, dd, J=2.5, 8.8 Hz), 7.22 (1H, d, J=2.3 Hz), Hz), 7.27 (1H, t, J=7.8

Hz), 7.36-7.44 (2H, m), 7.55 (1H, d, J=8.0 Hz), 7.61 (1H, d, J=8.8 Hz), 7.96 (1H, d, J=8.7 Hz)

Example 372

Synthesis of 7-[4-(4-benzo[b]thiophen-4-yl-piperazin-1-yl)-butoxy]-quinolin-2-yloxymethyl cyclohexyl carbonate

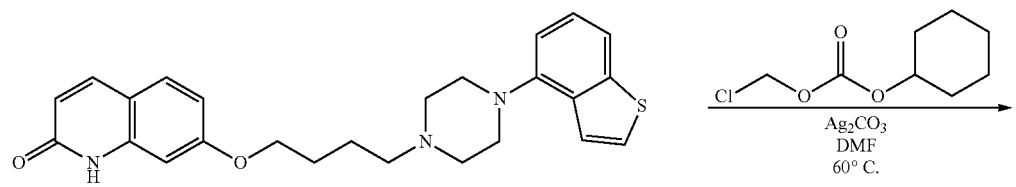

To a solution of 7-[4-(4-benzo[b]thiophen-4-yl-piperazin-1-yl)-butoxy]-1H-quinolin-2-one (700 mg) synthesized in the same manner as in WO2006/112464 (Example 1) in dimethylformamide (20 ml) was added silver carbonate (I) (0.53 g), chloromethyl cyclohexyl carbonate[40510-86-9] (0.68 g) was added, and the mixture was stirred at 60° C. for 6 hr. Water was added to the reaction mixture, and the mixture was extracted with ethyl acetate, and dried over $Na_2SO_4$. The solvent was evaporated under reduced pressure and the residue was purified by silica gel column chromatography (ethyl acetate:n-hexane=2:1) to give 7-[4-(4-benzo[b]thiophen-4-yl-piperazin-1-yl)-butoxy]-quinolin-2-yloxymethyl cyclohexyl carbonate (60 mg).

amorphous: colorless $^1$H-NMR (CDCl$_3$) δ ppm: 1.10-2.00 (14H, m), 2.56 (2H, t, J=7.5 Hz), 2.75 (4H, br), 3.21 (4H, br), 4.14 (2H, t, J=6.3 Hz), 4.64-4.74 (1H, m), 6.27 (2H, s), 6.82 (1H, d, J=8.7 Hz), 6.90 (1H, d, J=7.2 Hz), 7.06 (1H, dd, J=2.5, 8.8 Hz), 7.20-7.30 (2H, m), 7.35-7.45 (2H, m), 7.55 (1H, d, J=8.0 Hz), 7.61 (1H, d, J=8.9 Hz), 7.96 (1H, d, J=8.7 Hz)

Example 373

Synthesis of 7-[4-(4-benzo[b]thiophen-4-yl-piperazin-1-yl)-butoxy]-quinolin-2-yloxymethylhexyl carbonate

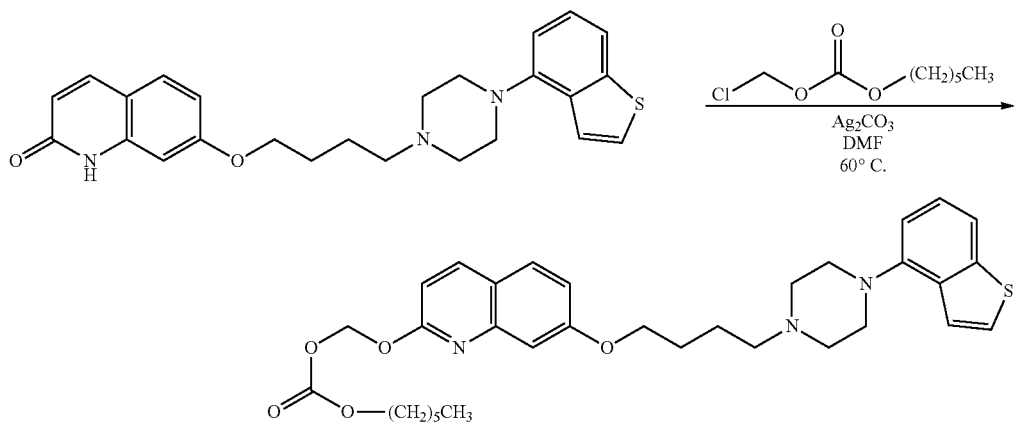

To a solution of 7-[4-(4-benzo[b]thiophen-4-yl-piperazin-1-yl)-butoxy]-1H-quinolin-2-one (730 mg) synthesized in the same manner as in WO2006/112464 (Example 1) in dimethylformamide (20 ml) was added silver carbonate (I) (0.56 g), chloromethyl hexyl carbonate[663597-51-1] (0.72 g) was added, and the mixture was stirred at 60° C. for 10 hr. Water was added to the reaction mixture, and the mixture was extracted with ethyl acetate, and dried over $Na_2SO_4$. The solvent was evaporated under reduced pressure and the residue was purified by silica gel column chromatography (ethyl acetate:n-hexane=2:1) to give 7-[4-(4-benzo[b]thiophen-4-yl-piperazin-1-yl)-butoxy]-quinolin-2-yloxymethyl hexyl carbonate (95 mg).
oil: yellow $^1$H-NMR (CDCl$_3$) δ ppm: 0.87 (3H, t, J=6.9 Hz), 1.20-1.40 (6H, m), 1.60-1.70 (2H, m), 1.74-1.84 (2H, m), 1.88-1.98 (2H, m), 2.57 (2H, t, J=7.6 Hz), 2.76 (4H, br), 3.21 (4H, br), 4.14 (2H, t, J=6.3 Hz), 4.19 (2H, t, J=6.7 Hz), 6.27 (2H, s), 6.82 (1H, d, J=8.7 Hz), 6.90 (1H, d, J=7.6 Hz), 7.06 (1H, dd, J=2.5, 8.8 Hz), 7.23 (1H, d, J=2.4 Hz), Hz), 7.27 (1H, t, J=7.9 Hz), 7.35-7.45 (2H, m), 7.55 (1H, d, J=8.0 Hz), 7.61 (1H, d, J=8.8 Hz), 7.96 (1H, d, J=8.7 Hz)

Example 374

Synthesis of 7-[4-(4-benzo[b]thiophen-4-yl-piperazin-1-yl)-butoxy]-quinolin-2-yloxymethylphenyl carbonate To a solution of 7-[4-(4-benzo[b]thiophen-4-yl-piperazin-1-yl)-butoxy]-1H-quinolin-2-one (1.5 g) synthesized in the same manner as in WO2006/112464 (Example 1) in dimethylformamide (50 ml) was added silver carbonate (I) (1.14 g), chloromethyl phenyl carbonate[35180-03-1] (1.42 g) was added, and the mixture was stirred at 60° C. for 4 hr. Water was added to the reaction mixture, and the mixture was extracted with ethyl acetate, and dried over $Na_2SO_4$. The solvent was evaporated under reduced pressure and the residue was purified by silica gel column chromatography (ethyl acetate:n-hexane=2:1) to give 7-[4-(4-benzo[b]thiophen-4-yl-piperazin-1-yl)-butoxy]-quinolin-2-yloxymethyl phenyl carbonate (20 mg).

oil: colorless $^1$H-NMR (CDCl$_3$) δ ppm: 1.70-2.10 (4H, m), 2.59 (2H, t, J=7.4 Hz), 2.78 (4H, br), 3.22 (4H, br), 4.10-4.18 (2H, m), 6.38 (2H, s), 6.80-6.95 (4H, m), 7.08 (1H, dd, J=2.4, 8.8 Hz), 7.18-7.45 (7H, m), 7.55 (1H, d, J=8.0 Hz), 7.63 (1H, d, J=8.9 Hz), 8.00 (1H, d, J=8.7 Hz)

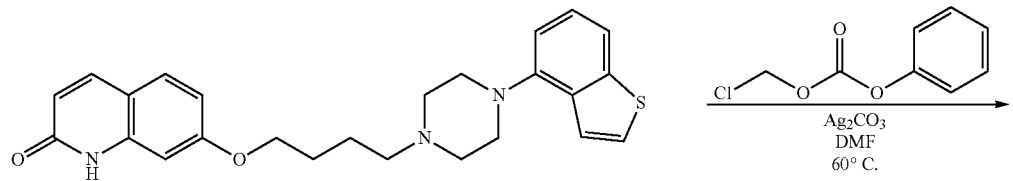

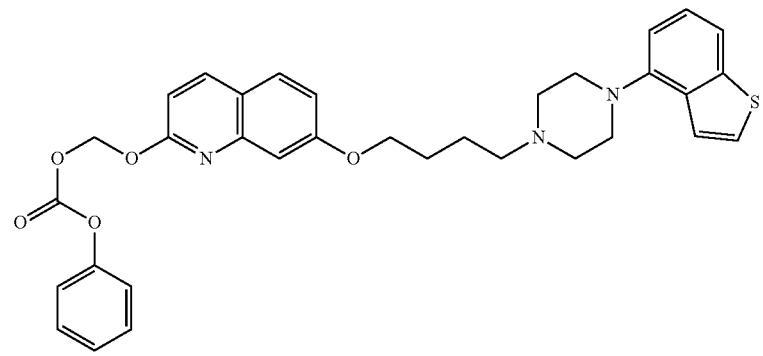

Example 375

Synthesis of 7-[4-(4-benzo[b]thiophen-4-yl-piperazin-1-yl)-butoxy]-quinolin-2-yloxymethyldecyl carbamate

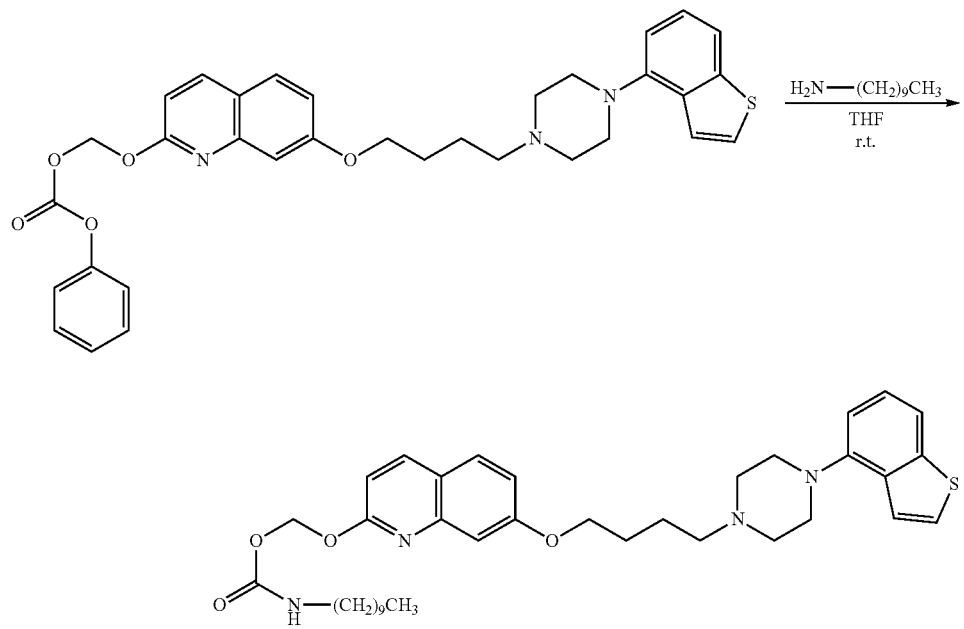

To a solution of 7-[4-(4-benzo[b]thiophen-4-yl-piperazin-1-yl)-butoxy]-quinolin-2-yloxymethyl phenyl carbonate (20 mg) synthesized in the same manner as in Example 374 in THF (10 ml) was added decylamine[2016-57-1] (0.1 ml), and the mixture was stirred at room temperature overnight. Water was added to the reaction mixture, and the mixture was extracted with ethyl acetate, and dried over $Na_2SO_4$. The solvent was evaporated under reduced pressure and the residue was purified by silica gel column chromatography (ethyl acetate:n-hexane=2:1) to give 7-[4-(4-benzo[b]thiophen-4-yl-piperazin-1-yl)-butoxy]-quinolin-2-yloxymethyl decyl carbamate (18 mg).

oil: colorless $^1$H-NMR ($CDCl_3$) δ ppm: 0.87 (3H, t, J=6.9 Hz), 1.10-2.40 (20H, m), 2.58 (2H, t, J=7.4 Hz), 2.76 (4H, br), 3.16-3.26 (6H, m), 4.15 (2H, t, J=6.3 Hz), 4.83 (1H, t, J=5.4 Hz), 6.23 (2H, s), 6.82 (1H, d, J=8.7 Hz), 6.90 (1H, d, J=7.6 Hz), 7.06 (1H, dd, J=2.5, 8.8 Hz), 7.23 (1H, d, J=2.4 Hz), Hz), 7.27 (1H, t, J=7.8 Hz), 7.36-7.44 (2H, m), 7.55 (1H, d, J=8.0 Hz), 7.61 (1H, d, J=8.8 Hz), 7.95 (1H, d, J=8.7 Hz)

Example 376

Synthesis of 7-[4-(4-benzo[b]thiophen-4-yl-piperazin-1-yl)-butoxy]-1-dodecanoyl-3,4-dihydroquinolin-2(1H)-one

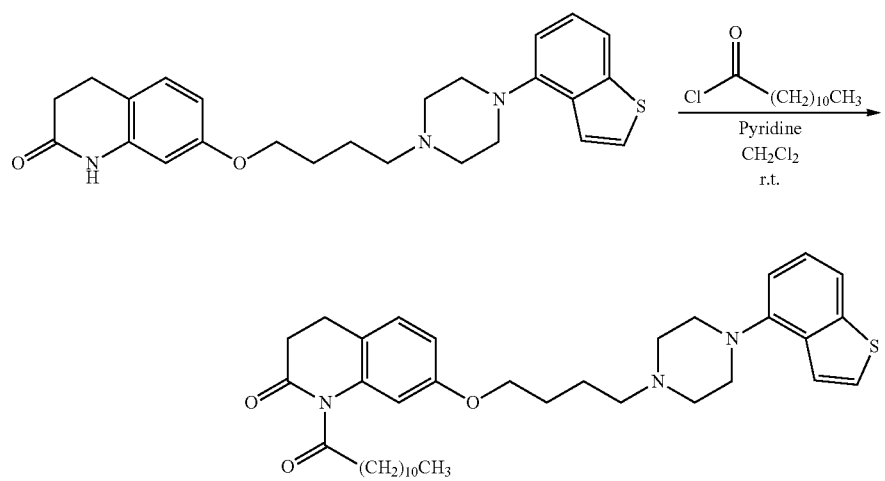

To a solution of 7-[4-(4-benzo[b]thiophen-4-ylpiperazin-1-yl)butoxy]-3,4-dihydro-1H-quinolin-2-one (0.3 g) synthesized in the same manner as in WO2006/112464 (Example 11) in methylene chloride (10 ml) was added pyridine (0.11 ml), with stirring under ice-cooling, dodecanoylchloride (0.24 ml) was added, and the mixture was stirred at room temperature overnight. Water was added to the reaction mixture and the mixture was extracted with methylene chloride, and dried over sodium sulfate. The solvent was evaporated under reduced to pressure and the residue was purified by silica gel column chromatography (ethyl acetate) to give 7-[4-(4-benzo[b]thiophen-4-ylpiperazin-1-yl)butoxy]-1-dodecanoyl-3,4-dihydro-1H-quinolin-2-one (0.4 g).
oil: colorless
$^1$H-NMR (CDCl$_3$) δ ppm: 0.88 (3H, t, J=6.8 Hz), 1.20-1.40 (16H, m), 1.68-1.90 (6H, m), 2.54 (2H, t, J=7.4 Hz), 2.65-2.80 (6H, m), 2.80-2.88 (2H, m), 2.97 (2H, t, J=7.6 Hz), 3.16-3.26 (4H, m), 3.97 (2H, t, J=6.2 Hz), 6.67 (1H, dd, J=2.4, 8.3 Hz), 6.83 (1H, dd, J=0.6, 7.7 Hz), 7.08 (1H, d, J=8.3 Hz), 7.27 (1H, t, J=7.8 Hz), 7.37-7.43 (2H, m), 7.55 (1H, d, J=8.0 Hz)

Example 377

Synthesis of 7-(4-(4-(benzo[b]thiophen-4-yl)piperazin-1-yl)butoxy)-1-(cyclohexanecarbonyl)-3,4-dihydroquinolin-2(1H)-one To a solution of 7-[4-(4-benzo[b]thiophen-4-yl-piperazin-1-yl)-butoxy]-3,4-dihydro-1H-quinolin-2-one (1 g) synthesized in the same manner as in WO2006/112464 (Example 11) in dichloromethane (30 ml) was added pyridine (0.37 ml), with stirring under ice-cooling, cyclohexanecarbonyl chloride (0.46 ml) was added and the mixture was stirred at room temperature overnight. Water was added to the reaction mixture and the mixture was extracted with ethyl acetate. The organic layer was dried over sodium sulfate, the solvent was evaporated under reduced pressure and the residue was purified by silica gel column chromatography (ethyl acetate:n-hexane=9:1) to give 7-[4-(4-benzo[b]thiophen-4-yl-piperazin-1-yl)-butoxy]-1-(cyclohexanecarbonyl)-3,4-dihydroquinolin-2(1H)-one (1.2 g).
oil: yellow
$^1$H-NMR (CDCl$_3$) δ ppm: 1.20-2.25 (14H, m), 2.53 (2H, t, J=7.5 Hz), 2.64-2.78 (6H, m), 2.84-2.90 (2H, m), 3.12-3.24 (5H, m), 3.97 (2H, t, J=6.2 Hz), 6.59 (1H, d, J=2.3 Hz), 6.63 (1H, dd, J=2.4, 8.3 Hz), 6.90 (1H, d, J=7.4 Hz), 7.08 (1H, d, J=8.3 Hz), 7.27 (1H, t, J=7.8 Hz), 7.36-7.44 (2H, m), 7.55 (1H, d, J=8.0 Hz)

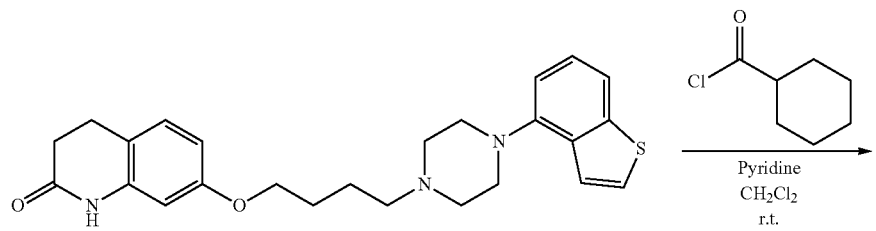

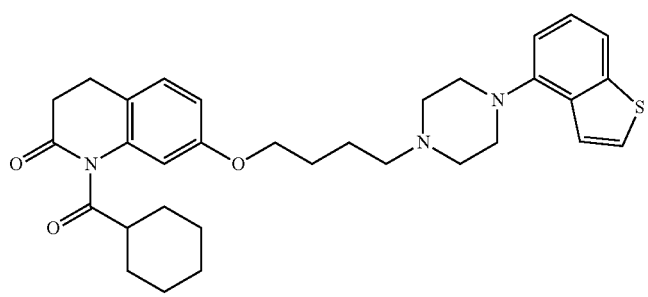

Example 378

Synthesis of 7-[4-(4-benzo[b]thiophen-4-yl-piperazin-1-yl)-butoxy]quinolin-2-yl acetate

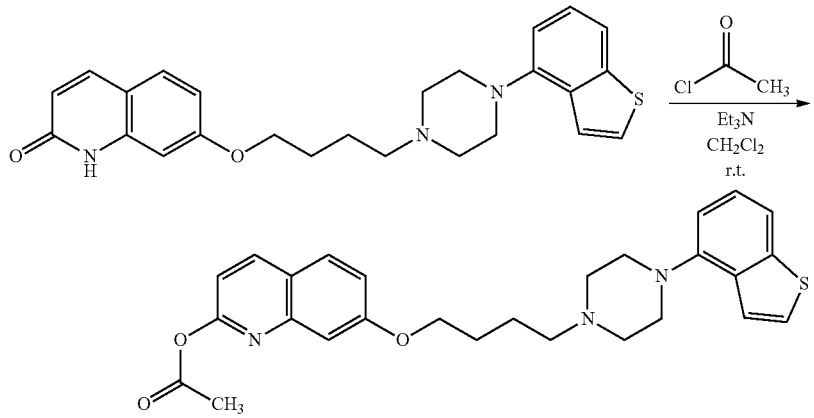

To a solution of 7-[4-(4-benzo[b]thiophen-4-ylpiperazin-1-yl)butoxy]-1H-quinolin-2-one (3.14 g) synthesized in the same manner as in WO2006/112464 (Example 1) in methylene chloride (32 mL) were added with stirring under ice-cooling triethylamine (4.0 mL) and acetyl chloride (1.5 mL), and the mixture was stirred at room temperature for 39 hr. The solvent was evaporated under reduced pressure, and the residue was purified by silica gel column chromatography (methylene chloride:ethyl acetate=7:3→1:9) to give 7-[4-(4-benzo[b]thiophen-4-ylpiperazin-1-yl)butoxy]quinolin-2-yl acetate (1.24 g).

oil: yellow $^1$H-NMR (CDCl$_3$) δ ppm: 1.62-1.81 (2H, m), 1.81-2.00 (2H, m), 2.39 (3H, s), 2.54 (2H, t, J=7.5 Hz), 2.67-2.86 (4H, m), 3.10-3.29 (4H, m), 4.15 (2H, t, J=6.3 Hz), 6.90 (1H, d, J=7.5 Hz), 7.05 (1H, d, J=8.5 Hz), 7.10-7.29 (3H, m), 7.29-7.48 (2H, m), 7.55 (1H, d, J=7.8 Hz), 7.72 (1H, d, J=9.0 Hz), 8.15 (1H, d, J=8.5 Hz)

Example 379

Synthesis of 7-[4-(4-benzo[b]thiophen-4-yl-piperazin-1-yl)-butoxy]-quinolin-2-yl dodecanoate To a solution of 7-[4-(4-benzo[b]thiophen-4-yl-piperazin-1-yl)-butoxy]-1H-quinolin-2-one (800 mg) in dichloromethane (20 ml) synthesized in the same manner as in WO2006/112464 (Example 1) was added triethylamine (0.77 ml), with stirring under ice-cooling, dodecanoylchloride (1.1 ml) was added and the mixture was stirred at room temperature for 4 hr. Water was added to the reaction mixture and the mixture was extracted with ethyl acetate. The organic layer was dried over sodium sulfate. The solvent was evaporated under reduced pressure and the residue was purified by silica gel column chromatography (ethyl acetate) to give 7-[4-(4-benzo[b]thiophen-4-yl-piperazin-1-yl)-butoxy]-quinolin-2-yl dodecanoate (1.34 g).

oil: yellow $^1$H-NMR (CDCl$_3$) δ ppm: 0.88 (3H, t, J=6.8 Hz), 1.20-1.50 (16H, m), 1.72-1.86 (4H, m), 1.86-1.98 (2H, m), 2.55 (2H, t, J=7.6 Hz), 2.66 (2H, t, J=7.6 Hz), 2.75 (4H, br), 3.20 (4H, br), 4.14 (2H, t, J=6.3 Hz), 6.90 (1H, d, J=7.5 Hz), 7.04 (1H, d, J=8.6 Hz), 7.19 (1H, dd, J=2.4, 8.9 Hz), 7.27 (1H, t, J=7.8 Hz), 7.33 (1H, d, J=2.4 Hz), 7.36-7.44 (2H, m), 7.55 (1H, d, J=8.1 Hz), 7.71 (1H, d, J=9.0 Hz), 8.14 (1H, d, J=8.6 Hz)

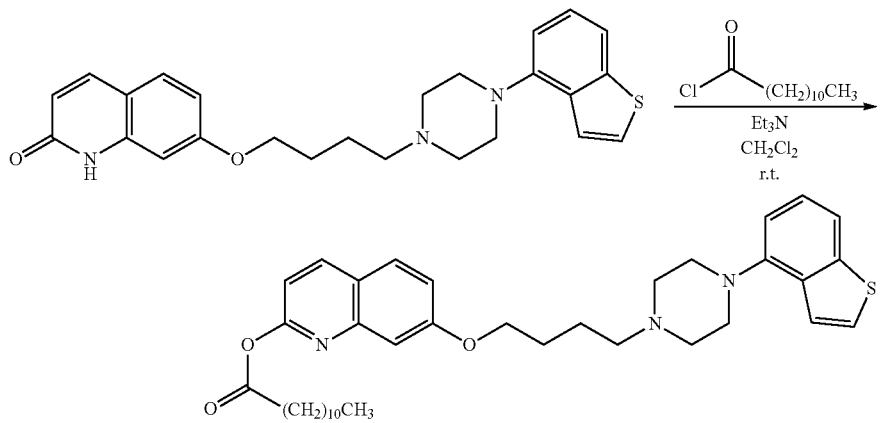

Example 380

Synthesis of 7-[4-(4-benzo[b]thiophen-4-yl-piperazin-1-yl)-butoxy]-quinolin-2-yl cyclohexanecarboxylate

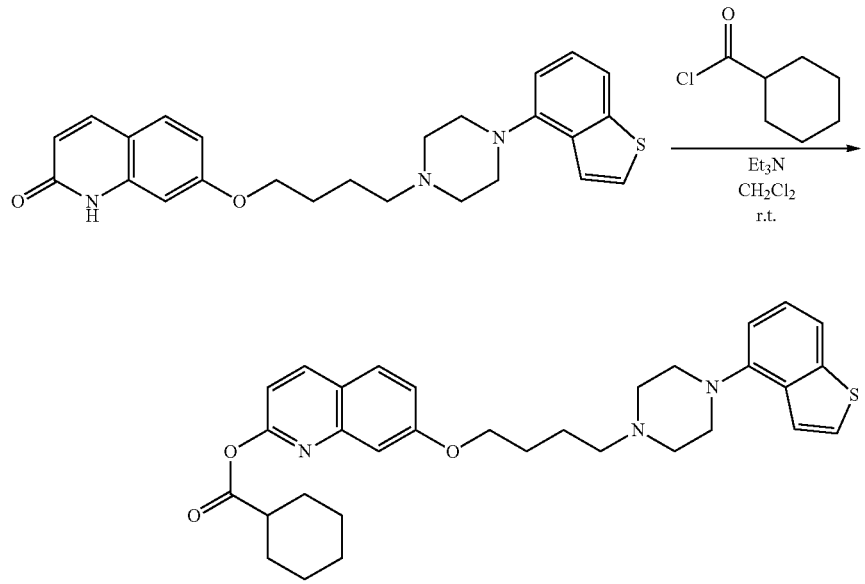

To a solution of 7-[4-(4-benzo[b]thiophen-4-yl-piperazin-1-yl)-butoxy]-1H-quinolin-2-one (800 mg) synthesized in the same manner as in WO2006/112464 (Example 1) in dichloromethane (20 ml) was added triethylamine (0.64 ml), with stirring under ice-cooling, cyclohexanecarbonyl chloride (0.49 ml) was added and the mixture was stirred at room temperature overnight. Water was added to the reaction mixture and the mixture was extracted with ethyl acetate. The organic layer was dried over sodium sulfate. The solvent was evaporated under reduced pressure and the residue was purified by silica gel column chromatography (ethyl acetate:n-hexane=4:1) to give 7-[4-(4-benzo[b]thiophen-4-yl-piperazin-1-yl)-butoxy]-quinolin-2-yl cyclohexanecarboxylate (1.08 g).

oil: yellow $^1$H-NMR (CDCl$_3$) δ ppm: 1.20-2.20 (14H, m), 2.54 (2H, t, J=7.5 Hz), 2.60-2.80 (5H, m), 3.20 (4H, br), 4.08-4.18 (2H, m), 6.89 (1H, d, J=7.6 Hz), 7.01 (1H, d, J=8.6 Hz), 7.18 (1H, dd, J=2.5, 8.9 Hz), 7.27 (1H, t, J=7.8 Hz), 7.34 (1H, d, J=2.4 Hz), 7.36-7.44 (2H, m), 7.54 (1H, d, J=8.0 Hz), 7.70 (1H, d, J=8.9 Hz), 8.12 (1H, d, J=8.6 Hz)

Example 381

Synthesis of 7-[4-(4-benzo[b]thiophen-4-yl-piperazin-1-yl)-butoxy]-quinolin-2-yl hexyl carbonate

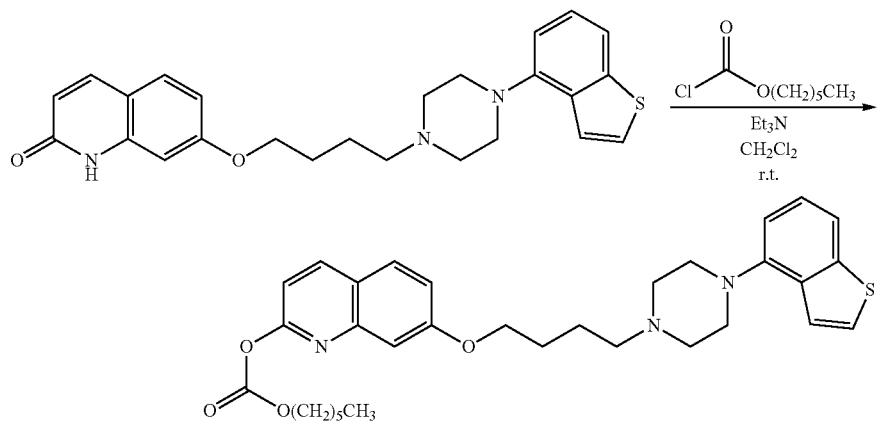

To a solution of 7-[4-(4-benzo[b]thiophen-4-yl-piperazin-1-yl)-butoxy]-1H-quinolin-2-one (800 mg) synthesized in the same manner as in WO2006/112464 (Example 1) in dichloromethane (20 ml) was added triethylamine (0.65 ml), with stirring under ice-cooling, hexylchloroformate (0.6 g) was added at room temperature overnight. Water was added to the reaction mixture and the mixture was extracted with ethyl acetate. The organic layer was dried over sodium sulfate. The solvent was evaporated under reduced pressure and the residue was purified by silica gel column chromatography (ethyl acetate:n-hexane=1:2) to give 7-[4-(4-benzo[b]thiophen-4-yl-piperazin-1-yl)-butoxy]-quinolin-2-yl hexyl carbonate (1.09 g).

oil: colorless $^1$H-NMR (CDCl$_3$) δ ppm: 0.91 (3H, t, J=7.0 Hz), 1.30-1.50 (6H, m), 1.70-1.84 (4H, m), 1.88-1.98 (2H, m), 2.54 (2H, t, J=7.5 Hz), 2.72 (4H, br), 3.20 (4H, br), 4.15 (2H, t, J=6.4 Hz), 4.30 (2H, t, J=6.7 Hz), 6.90 (1H, dd, J=0.4, 7.6 Hz), 7.08 (1H, d, J=8.6 Hz), 7.20 (1H, dd, J=2.4, 8.9 Hz), 7.27 (1H, t, J=7.8 Hz), 7.33 (1H, d, J=2.4 Hz), 7.36-7.44 (2H, m), 7.54 (1H, d, J=8.0 Hz), 7.72 (1H, d, J=9.0 Hz), 8.15 (1H, d, J=8.6 Hz)

Example 382

Synthesis of 7-[4-(4-benzo[b]thiophen-4-yl-piperazin-1-yl)-butoxy]-quinolin-2-yl diethylcarbamate perature overnight. Water, was added to the reaction mixture and the mixture was extracted with ethyl acetate. The organic layer was dried over sodium sulfate. The solvent was evaporated under reduced pressure and the residue was purified by silica gel column chromatography (ethyl acetate:n-hexane=20:1) to give 7-[4-(4-benzo[b]thiophen-4-yl-piperazin-1-yl)-butoxy]-quinolin-2-yl diethylcarbamate (120 mg).

oil: colorless $^1$H-NMR (CDCl$_3$) δ ppm: 1.23 (3H, t, J=7.1 Hz), 1.30 (3H, t, J=7.1 Hz), 1.72-1.84 (2H, m), 1.86-1.98 (2H, m), 2.54 (2H, t, J=7.5 Hz), 2.73 (4H, br), 3.20 (4H, br), 3.43 (2H, q, J=7.0 Hz), 3.52 (2H, q, J=7.1 Hz), 4.13 (2H, t, J=6.3 Hz), 6.89 (1H, d, J=7.2 Hz), 7.08 (1H, d, J=8.6 Hz), 7.16 (1H, dd, J=2.5, 8.9 Hz), 7.26 (1H, t, J=7.8 Hz), 7.34 (1H, d, J=2.4 Hz), 7.36-7.44 (2H, m), 7.54 (1H, d, J=7.9 Hz), 7.68 (1H, d, J=8.9 Hz), 8.09 (1H, d, J=8.6 Hz)

Example 383

Synthesis of 4-(benzo[b]thiophen-4-yl)-1-(dodecanoyloxymethyl)-1-(4-(2-oxo-1,2-dihydroquinolin-7-yloxy)butyl)piperazin-1-ium iodide

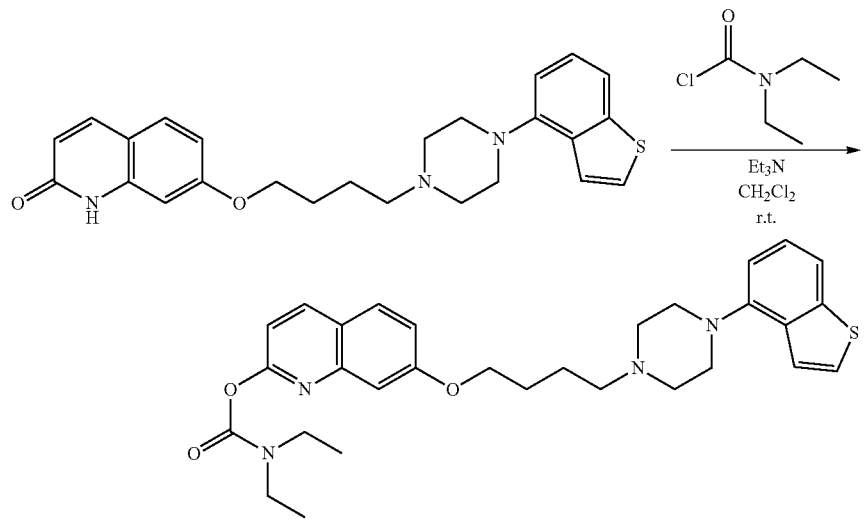

To a solution of 7-[4-(4-benzo[b]thiophen-4-yl-piperazin-1-yl)-butoxy]-1H-quinolin-2-one (800 mg) synthesized in the same manner as in WO2006/112464 (Example 1) in dichloromethane (20 ml) was added triethylamine (0.65 ml), with stirring under ice-cooling, diethylcarbamoylchloride (0.5 g) was added and the mixture was stirred at room tem-

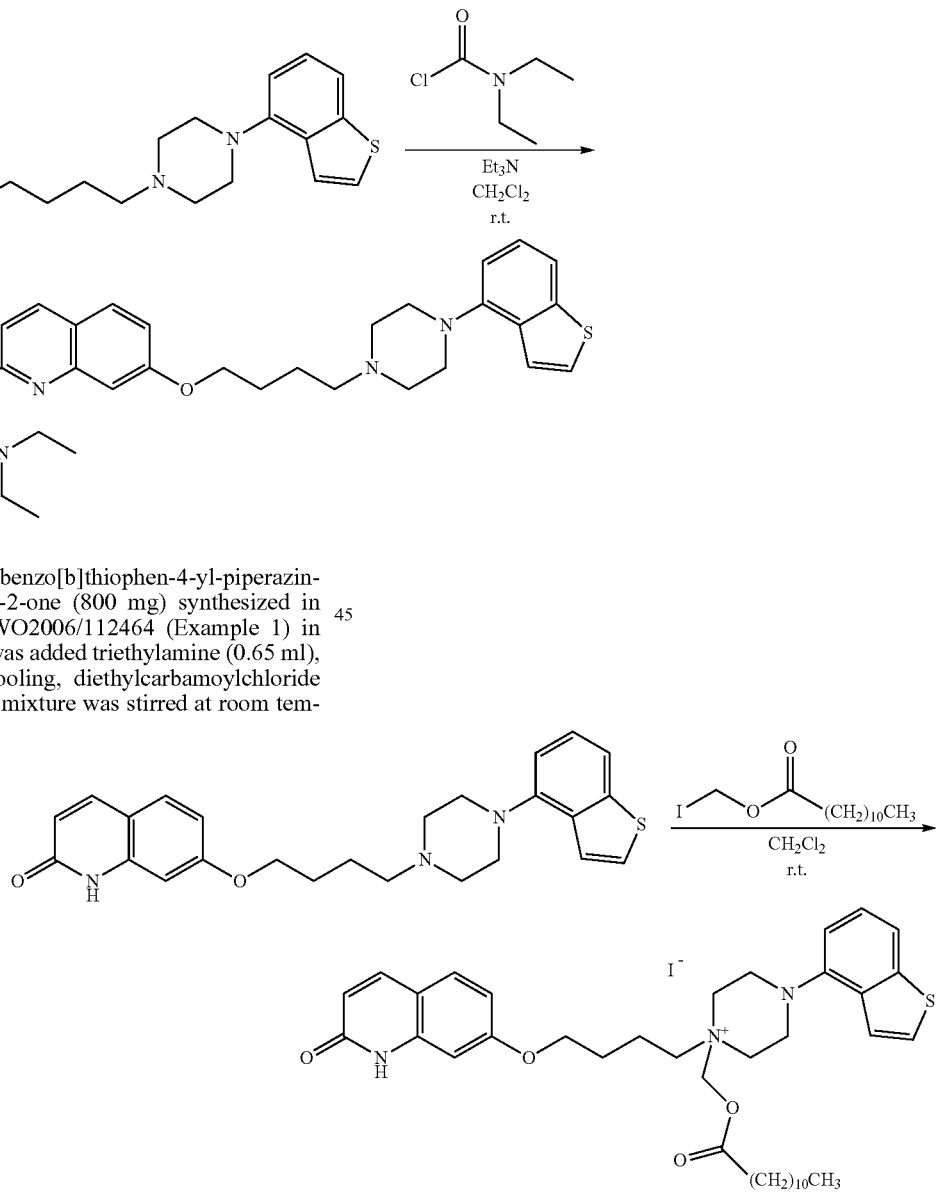

233

To a solution of 7-[4-(4-benzo[b]thiophen-4-yl-piperazin-1-yl)-butoxy]-1H-quinolin-2-one (0.85 g) synthesized in the same manner as in WO2006/112464 (Example 1) in dichloromethane (20 ml) was added iodomethyldodecanoate (1 g) synthesized in the same manner as in Reference Example 19, and the mixture was stirred at room temperature overnight. The solvent was evaporated under reduced pressure, ether was added and the mixture was left standing. The obtained crystals were collected by filtration to give 4-(benzo[b]thiophen-4-yl)-1-(dodecanoyloxymethyl)-1-(4-(2-oxo-1,2-dihydroquinolin-7-yloxy)butyl)piperazin-1-ium iodide (1.07 g).

powder: yellow $^1$H-NMR (DMSO-$d_6$) δ ppm: 0.84 (3H, t, J=6.8 Hz), 1.10-2.56 (24H, m), 3.44-3.56 (4H, m), 3.60-3.90 (6H, m), 4.09 (2H, t, J=5.5 Hz), 5.57 (2H, s), 6.31 (1H, d, J=9.4 Hz), 6.80-6.86 (2H, m), 7.05 (1H, d, J=7.6 Hz), 7.35 (1H, t, J=7.9 Hz), 7.54 (1H, d, J=5.5 Hz), 7.56-7.62 (1H, m), 7.68-7.86 (3H, m), 11.63 (1H, s)

Example 384

Synthesis of (7-(4-(4-(benzo[b]thiophen-4-yl)piperazin-1-yl)butoxy)-2-oxoquinolin-1(2H)-yl)methyl octyl carbonate

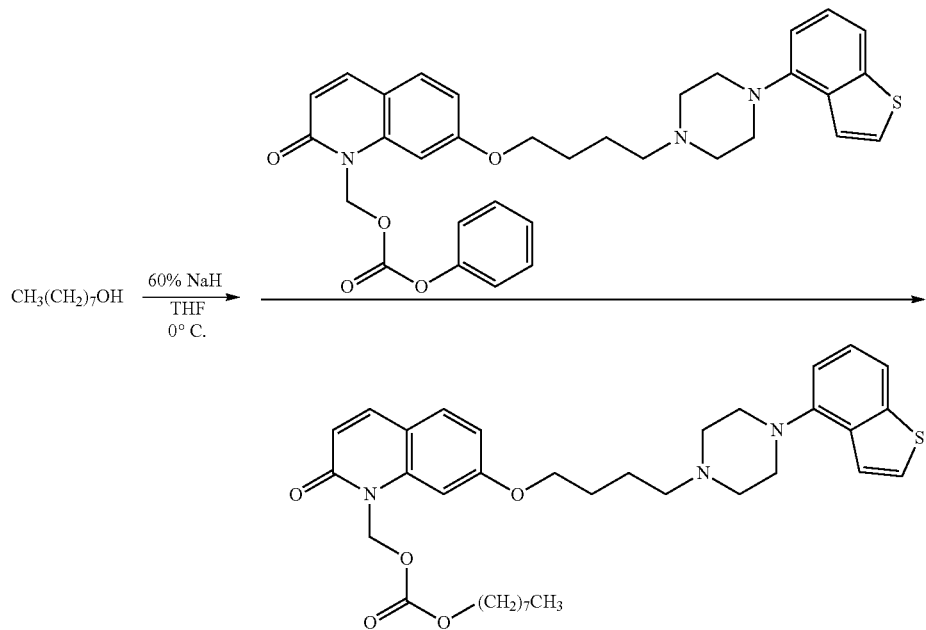

In the same manner as in Example 175, the compound was obtained (yield 25 mg, 8.7%) as a colorless oil.

$^1$H-NMR (CDCl$_3$) δ ppm: 0.86 (3H, t, J=6.9 Hz), 1.16-1.40 (10H, m), 1.58-1.72 (2H, m), 1.72-1.84 (2H, m), 1.85-1.95 (2H, m), 2.55 (2H, t, J=7.5 Hz), 2.68-2.80 (4H, br), 3.14-3.26 (4H, br), 4.10 (2H, t, J=6.2 Hz), 4.18 (2H, t, J=6.7 Hz), 6.35 (2H, s), 6.50 (1H, d, J=9.5 Hz), 6.84 (1H, dd, J=2.2, 8.6 Hz), 6.89 (1H, d, J=7.6 Hz), 6.93 (1H, d, J=2.1 Hz), 7.27 (1H, t, J=7.8 Hz), 7.36-7.46 (3H, m), 7.55 (1H, d, J=8.0 Hz), 7.61 (1H, d, J=9.5 Hz)

Example 385

Synthesis of carbonic acid 7-[4-(4-benzo[b]thiophen-4-ylpiperazin-1-yl)butoxy]-2-oxo-2H-quinolin-1-ylmethyl ester cyclohexyl ester hydrochloride

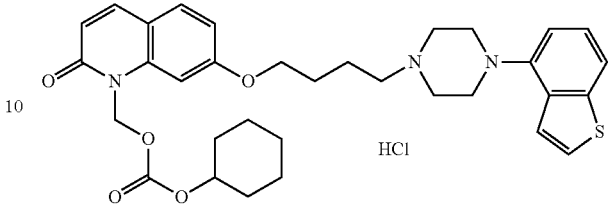

Sodium hydride (55% oil) (0.962 g, 22.04 mmol) was suspended in tetrahydrofuran (THF) (200 ml), 7-[4-(4-benzo[b]thiophen-4-yl-piperazin-1-yl)-butoxy]-1H-quinolin-2-one (8.31 g, 19.17 mmol) was added and the mixture was stirred at 50° C. for 1 hr. The mixture was cooled to 0° C., chloromethyl cyclohexyl carbonate (4.80 g, 24.92 mmol) was added dropwise and the mixture was stirred at room temperature overnight. After cooling to 0° C., excess 2N hydrochloric acid was added to quench the reaction. The precipitated solid was collected by filtration and dried. In addition, the filtrate was extracted with ethyl acetate. The organic layer was concentrated and purified by moderate-pressure silica gel column chromatography (methylene chloride:methanol=100:0 to 20:1). Likewise, the solid was purified by moderate-pressure silica gel column chromatography. Concentration under reduced pressure gave the title compound (yield, 5.04 g, 42%) as a white solid.

$^1$H-NMR (DMSO-$d_6$) δ ppm: 1.16 (m, 6H), 1.59-1.69 (m, 2H), 1.80 (m, 6H), 3.00-3.60 (m, 10H), 4.19 (t, J=5.9 Hz, 2H), 4.57-4.65 (m, 1H), 6.29 (s, 2H), 6.42 (d, J=9.5 Hz, 1H), 6.97 (dd, J=2.3, 8.5 Hz, 1H), 6.98 (dd, J=1.8, 7.7 Hz, 1H), 7.04 (d, J=2.3 Hz, 1H), 7.31 (dd, J=7.7, 7.7 Hz, 1H), 7.43 (dd, J=1.8, 5.5 Hz, 1H), 7.63-7.71 (m, 3H), 7.86 (d, J=9.5 Hz, 1H).

In the same manner as in the above-mentioned Examples, the compounds described in the following Table 2 can be synthesized.

TABLE 2

| Example | Structure Formula | |
|---|---|---|
| 386 | | (7-(4-(4-(benzo[b]thiophen-4-yl)piperazin-1-yl)butoxy)-2-oxoquinolin-1(2H)-yl)methyl dipropylcarbamate |
| 387 | | (7-(4-(4-(benzo[b]thiophen-4-yl)piperazin-1-yl)butoxy)-2-oxoquinolin-1(2H)-yl)methyl diisobutylcarbamate |
| 388 | | (7-(4-(4-(benzo[b]thiophen-4-yl)piperazin-1-yl)butoxy)-2-oxoquinolin-1(2H)-yl)methyl dihexylcarbamate |

TABLE 2-continued
| Example | Structure Formula | |
|---|---|---|
| 389 | 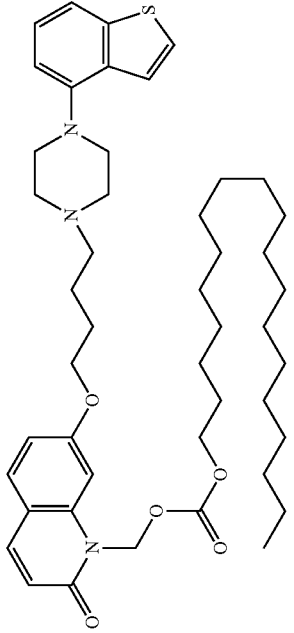 | (7-(4-(4-(benzo[b]thiophen-4-yl)piperazin-1-yl)butoxy)-2-oxoquinolin-1(2H)-yl)methyl nonadecylcarbonate |
| 390 | 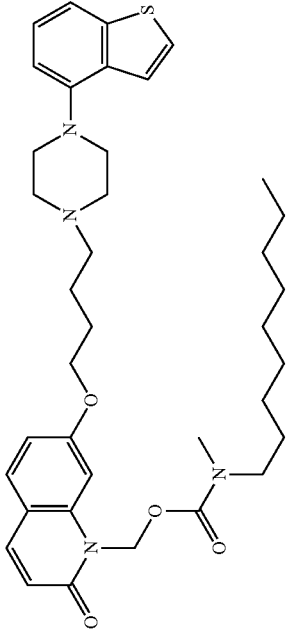 | (7-(4-(4-(benzo[b]thiophen-4-yl)piperazin-1-yl)butoxy)-2-oxoquinolin-1(2H)-yl)methyl methyl(nonyl)carbamate |
| 391 | 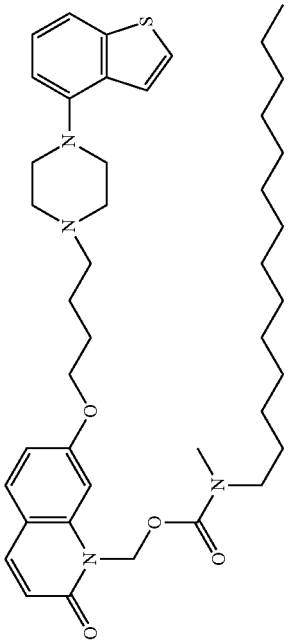 | (7-(4-(4-(benzo[b]thiophen-4-yl)piperazin-1-yl)butoxy)-2-oxoquinolin-1(2H)-yl)methyl methyl(tetradecyl)carbamate |

TABLE 2-continued

| Example | Structure Formula | |
|---|---|---|
| 392 | | (7-(4-(4-(benzo[b]thiophen-4-yl)piperazin-1-yl)butoxy)-2-oxoquinolin-1(2H)-yl)methyl ditetradecylcarbamate |
| 393 | | (7-(4-(4-(benzo[b]thiophen-4-yl)piperazin-1-yl)butoxy)-2-oxoquinolin-1(2H)-yl)methyl dinonylcarbamate |
| 394 | | (7-(4-(4-(benzo[b]thiophen-4-yl)piperazin-1-yl)butoxy)-2-oxoquinolin-1(2H)-yl)methyl 2,2-dimethyldecanoate |

TABLE 2-continued

| Example | Structure Formula | |
|---|---|---|
| 395 | | 1-(7-(4-(4-(benzo[b]thiophen-4-yl)piperazin-1-yl)butoxy)-2-oxoquinolin-1(2H)-yl)-2-ethoxy-2-oxoethyl decanoate |
| 396 | | (7-(4-(4-(benzo[b]thiophen-4-yl)piperazin-1-yl)butoxy)-2-oxoquinolin-1(2H)-yl)methyl 2,2-dimethyloctanoate |
| 397 | | 1-(7-(4-(4-(benzo[b]thiophen-4-yl)piperazin-1-yl)butoxy)-2-oxoquinolin-1(2H)-yl)ethyl butyrate |
| 398 | | 1-(7-(4-(4-(benzo[b]thiophen-4-yl)piperazin-1-yl)butoxy)-2-oxoquinolin-1(2H)-yl)ethyl 3-methylbutanoate |

TABLE 2-continued
| Example | Structure Formula | |
|---|---|---|
| 399 |  | 1-(7-(4-(4-(benzo[b]thiophen-4-yl)piperazin-1-yl)butoxy)-2-oxoquinolin-1(2H)-yl)ethyl hexanoate |
| 400 |  | (7-(4-(4-(benzo[b]thiophen-4-yl)piperazin-1-yl)butoxy)-2-oxoquinolin-1(2H)-yl)methyl 2-hydroxyethylcarbamate |
| 401 | 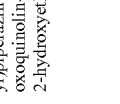 | (7-(4-(4-(benzo[b]thiophen-4-yl)piperazin-1-yl)butoxy)-2-oxoquinolin-1(2H)-yl)methyl bis(2-hydroxyethyl)carbamate |

TABLE 2-continued

| Example | Structure Formula | |
|---|---|---|
| 402 | | (7-(4-(4-(benzo[b]thiophen-4-yl)piperazin-1-yl)butoxy)-2-oxoquinolin-1(2H)-yl)methyl 4-methylpiperazine-1-carboxylate |
| 403 | | (7-(4-(4-(benzo[b]thiophen-4-yl)piperazin-1-yl)butoxy)-2-oxoquinolin-1(2H)-yl)methyl 1,4'-bipiperidine-1'-carboxylate |
| 404 | | calcium 1-(7-(4-(4-(benzo[b]thiophen-4-yl)piperazin-1-yl)butoxy)-2-oxoquinolin-1(2H)-yl)-2-methylpropyl phosphate |

TABLE 2-continued
| Example | Structure Formula | |
|---|---|---|
| 405 |  | 1-(7-(4-(4-(benzo[b]thiophen-4-yl)piperazin-1-yl)butoxy)-2-oxoquinolin-1(2H)-yl)ethyl dimethylcarbamate |
| 406 |  | 1-(7-(4-(4-(benzo[b]thiophen-4-yl)piperazin-1-yl)butoxy)-2-oxoquinolin-1(2H)-yl)ethyl methyl(tetradecyl)carbamate |
| 407 |  | (7-(4-(4-(benzo[b]thiophen-4-yl)piperazin-1-yl)butoxy)-2-oxoquinolin-1(2H)-yl)methyl 4-acetamidobutanoate |

TABLE 2-continued

| Example | Structure Formula | |
|---|---|---|
| 408 | | (7-(4-(4-(benzo[b]thiophen-4-yl)piperazin-1-yl)butoxy)-2-oxoquinolin-1(2H)-yl)methyl 4-heptanamidobutanoate |
| 409 | | 1-(7-(4-(4-(benzo[b]thiophen-4-yl)piperazin-1-yl)butoxy)-2-oxoquinolin-1(2H)-yl)ethyl dinonylcarbamate |
| 410 | | 1-(7-(4-(4-(benzo[b]thiophen-4-yl)piperazin-1-yl)butoxy)-2-oxoquinolin-1(2H)-yl)ethyl ditetradecylcarbamate |

TABLE 2-continued

| Example | Structure Formula | |
|---|---|---|
| 411 | | (7-(4-(4-(benzo[b]thiophen-4-yl)piperazin-1-yl)butoxy)-2-oxoquinolin-1(2H)-yl)methyl 4-heptanamidobutanoate |
| 412 | | (5Z,8Z,11Z,14Z,17Z)-(7-(4-(4-(benzo[b]thiophen-4-yl)piperazin-1-yl)butoxy)-2-oxoquinolin-1(2H)-yl)methyl henicosa-5,8,11,14,17-pentaenoate |
| 413 | | (7Z,10Z,13Z,16Z,19Z)-(7-(4-(4-(benzo[b]thiophen-4-yl)piperazin-1-yl)butoxy)-2-oxoquinolin-1(2H)-yl)methyl pentacosa-7,10,13,16,19-pentaenoate |

TABLE 2-continued

| Example | Structure Formula | |
|---|---|---|
| 414 | | (7-(4-(4-(benzo[b]thiophen-4-yl)piperazin-1-yl)butoxy)quinolin-2-yloxy)methyl acetate |
| 415 | | (7-(4-(4-(benzo[b]thiophen-4-yl)piperazin-1-yl)butoxy)quinolin-2-yloxy)methyl propionate |
| 416 | | (7-(4-(4-(benzo[b]thiophen-4-yl)piperazin-1-yl)butoxy)quinolin-2-yloxy)methyl butyrate |
| 417 | | (7-(4-(4-(benzo[b]thiophen-4-yl)piperazin-1-yl)butoxy)quinolin-2-yloxy)methyl pentanoate |
| 418 | | (7-(4-(4-(benzo[b]thiophen-4-yl)piperazin-1-yl)butoxy)quinolin-2-yloxy)methyl hexanoate |

TABLE 2-continued

| Example | Structure Formula | |
|---|---|---|
| 419 | [structure] | (7-(4-(4-(benzo[b]thiophen-4-yl)piperazin-1-yl)butoxy)quinolin-2-yloxy)methyl heptanoate |
| 420 | [structure] | (7-(4-(4-(benzo[b]thiophen-4-yl)piperazin-1-yl)butoxy)quinolin-2-yloxy)methyl octanoate |
| 421 | [structure] | (7-(4-(4-(benzo[b]thiophen-4-yl)piperazin-1-yl)butoxy)quinolin-2-yloxy)methyl nonanoate |
| 422 | [structure] | (7-(4-(4-(benzo[b]thiophen-4-yl)piperazin-1-yl)butoxy)quinolin-2-yloxy)methyl decanoate |
| 423 | [structure] | (7-(4-(4-(benzo[b]thiophen-4-yl)piperazin-1-yl)butoxy)quinolin-2-yloxy)methyl undecanoate |

TABLE 2-continued

| Example | Structure Formula | |
|---|---|---|
| 424 | [structure] | (7-(4-(4-(benzo[b]thiophen-4-yl)piperazin-1-yl)butoxy)quinolin-2-yl)oxy)methyl tridecanoate |
| 425 | [structure] | (7-(4-(4-(benzo[b]thiophen-4-yl)piperazin-1-yl)butoxy)quinolin-2-yl)oxy)methyl tetradecanoate |
| 426 | [structure] | (7-(4-(4-(benzo[b]thiophen-4-yl)piperazin-1-yl)butoxy)quinolin-2-yl)oxy)methyl pentadecanoate |
| 427 | [structure] | (7-(4-(4-(benzo[b]thiophen-4-yl)piperazin-1-yl)butoxy)quinolin-2-yl)oxy)methyl palmitate |
| 428 | [structure] | (7-(4-(4-(benzo[b]thiophen-4-yl)piperazin-1-yl)butoxy)quinolin-2-yl)oxy)methyl heptadecanoate |

TABLE 2-continued

| Example | Structure Formula | |
|---|---|---|
| 429 | | (7-(4-(4-(benzo[b]thiophen-4-yl)piperazin-1-yl)butoxy)quinolin-2-yloxy)methyl stearate |
| 430 | | (7-(4-(4-(benzo[b]thiophen-4-yl)piperazin-1-yl)butoxy)quinolin-2-yloxy)methyl icosanoate |
| 431 | | (7-(4-(4-(benzo[b]thiophen-4-yl)piperazin-1-yl)butoxy)quinolin-2-yloxy)methyl 2,2-dimethyltetradecanoate |
| 432 | | (7-(4-(4-(benzo[b]thiophen-4-yl)piperazin-1-yl)butoxy)quinolin-2-yloxy)methyl pivalate |
| 433 | | (7-(4-(4-(benzo[b]thiophen-4-yl)piperazin-1-yl)butoxy)quinolin-2-yloxy)methyl 2,2-dimethylbutanoate |

TABLE 2-continued

| Example | Structure Formula | |
|---|---|---|
| 434 | | (7-(4-(4-(benzo[b]thiophen-4-yl)piperazin-1-yl)butoxy)quinolin-2-yloxy)methyl isobutyrate |
| 435 | | (7-(4-(4-(benzo[b]thiophen-4-yl)piperazin-1-yl)butoxy)quinolin-2-yloxy)methyl 2-hydroxyacetate |
| 436 | | (7-(4-(4-(benzo[b]thiophen-4-yl)piperazin-1-yl)butoxy)quinolin-2-yloxy)methyl cyclopropanecarboxylate |
| 437 | | (7-(4-(4-(benzo[b]thiophen-4-yl)piperazin-1-yl)butoxy)quinolin-2-yloxy)methyl cyclobutanecarboxylate |
| 438 | | (7-(4-(4-(benzo[b]thiophen-4-yl)piperazin-1-yl)butoxy)quinolin-2-yloxy)methyl cyclopentanecarboxylate |

TABLE 2-continued

| Example | Structure Formula | |
|---|---|---|
| 439 | | (7-(4-(4-(benzo[b]thiophen-4-yl)piperazin-1-yl)butoxy)quinolin-2-yl)oxy)methyl cyclohexanecarboxylate |
| 440 | | (7-(4-(4-(benzo[b]thiophen-4-yl)piperazin-1-yl)butoxy)quinolin-2-yl)oxy)methyl benzoate |
| 441 | | (7-(4-(4-(benzo[b]thiophen-4-yl)piperazin-1-yl)butoxy)quinolin-2-yl)oxy)methyl 2-phenylacetate |
| 442 | | (9Z,12Z,15Z)-(7-(4-(4-(benzo[b]thiophen-4-yl)piperazin-1-yl)butoxy)quinolin-2-yl)oxy)methyl octadeca-9,12,15-trienoate |

TABLE 2-continued

| Example | Structure Formula | |
|---|---|---|
| 443 | 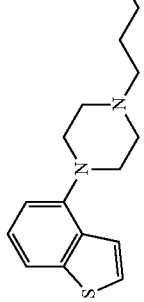 | (5Z,8Z,11Z,14Z,17Z)-(7-(4-(4-(benzo[b]thiophen-4-yl)piperazin-1-yl)butoxy)methyl henicosa-5,8,11,14,17-pentaenoate |
| 444 | 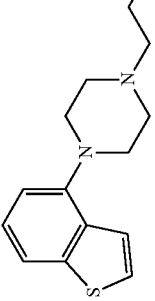 | (4Z,7Z,10Z,13Z,16Z,19Z)-(7-(4-(4-(benzo[b]thiophen-4-yl)piperazin-1-yl)butoxy)quinolin-2-yloxy)methyl docosa-4,7,10,13,16,19-hexaenoate |
| 445 | 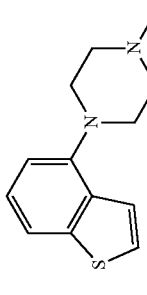 | (6Z,9Z,12Z,15Z)-(7-(4-(4-(benzo[b]thiophen-4-yl)piperazin-1-yl)butoxy)quinolin-2-yloxy)methyl octadeca-6,9,12,15-tetraenoate |
| 446 | 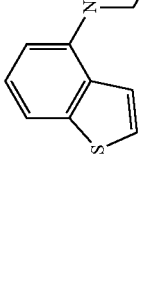 | (7-(4-(4-(benzo[b]thiophen-4-yl)piperazin-1-yl)butoxy)quinolin-2-yloxy)methyl methyl carbonate |

TABLE 2-continued

| Example | Structure Formula | |
|---|---|---|
| 447 | [structure] | (7-(4-(4-(benzo[b]thiophen-4-yl)piperazin-1-yl)butoxy)quinolin-2-yloxy)methyl ethyl carbonate |
| 448 | [structure] | (7-(4-(4-(benzo[b]thiophen-4-yl)piperazin-1-yl)butoxy)quinolin-2-yloxy)methyl butyl carbonate |
| 449 | [structure] | (7-(4-(4-(benzo[b]thiophen-4-yl)piperazin-1-yl)butoxy)quinolin-2-yloxy)methyl pentyl carbonate |
| 450 | [structure] | (7-(4-(4-(benzo[b]thiophen-4-yl)piperazin-1-yl)butoxy)quinolin-2-yloxy)methyl 2-methoxyethyl carbonate |
| 451 | [structure] | calcium (7-(4-(4-(benzo[b]thiophen-4-yl)piperazin-1-yl)butoxy)quinolin-2-yloxy)methyl phosphate |

TABLE 2-continued

| Example | Structure Formula | |
|---|---|---|
| 452 | | (7-(4-(4-(benzo[b]thiophen-4-yl)piperazin-1-yl)butoxy)quinolin-2-yloxy)methyl methylcarbamate |
| 453 | | (7-(4-(4-(benzo[b]thiophen-4-yl)piperazin-1-yl)butoxy)quinolin-2-yloxy)methyl ethylcarbamate |
| 454 | | (7-(4-(4-(benzo[b]thiophen-4-yl)piperazin-1-yl)butoxy)quinolin-2-yloxy)methyl propylcarbamate |
| 455 | | (7-(4-(4-(benzo[b]thiophen-4-yl)piperazin-1-yl)butoxy)quinolin-2-yloxy)methyl butylcarbamate |
| 456 | | (7-(4-(4-(benzo[b]thiophen-4-yl)piperazin-1-yl)butoxy)quinolin-2-yloxy)methyl pentylcarbamate |

TABLE 2-continued

| Example | Structure Formula | |
|---|---|---|
| 457 | | (7-(4-(4-(benzo[b]thiophen-4-yl)piperazin-1-yl)butoxy)quinolin-2-yl)oxy)methyl hexylcarbamate |
| 458 | | (7-(4-(4-(benzo[b]thiophen-4-yl)piperazin-1-yl)butoxy)quinolin-2-yl)oxy)methyl octylcarbamate |
| 459 | | (7-(4-(4-(benzo[b]thiophen-4-yl)piperazin-1-yl)butoxy)quinolin-2-yl)oxy)methyl dodecylcarbamate |
| 460 | | (7-(4-(4-(benzo[b]thiophen-4-yl)piperazin-1-yl)butoxy)quinolin-2-yl)oxy)methyl tetradecylcarbamate |
| 461 | | (7-(4-(4-(benzo[b]thiophen-4-yl)piperazin-1-yl)butoxy)quinolin-2-yl)oxy)methyl hexadecylcarbamate |

TABLE 2-continued

| Example | Structure Formula | |
|---|---|---|
| 462 | | (7-(4-(4-(benzo[b]thiophen-4-yl)piperazin-1-yl)butoxy)quinolin-2-yl)methyl dimethylcarbamate |
| 463 | | (7-(4-(4-(benzo[b]thiophen-4-yl)piperazin-1-yl)butoxy)quinolin-2-yl)methyl diethylcarbamate |
| 464 | | (7-(4-(4-(benzo[b]thiophen-4-yl)piperazin-1-yl)butoxy)quinolin-2-yl)methyl dipropylcarbamate |
| 465 | | (7-(4-(4-(benzo[b]thiophen-4-yl)piperazin-1-yl)butoxy)quinolin-2-yl)methyl diisobutylcarbamate |

TABLE 2-continued

| Example | Structure Formula | |
|---|---|---|
| 466 |  | (7-(4-(4-(benzo[b]thiophen-4-yl)piperazin-1-yl)butoxy)quinolin-2-yl)oxy)methyl dibutylcarbamate |
| 467 |  | (7-(4-(4-(benzo[b]thiophen-4-yl)piperazin-1-yl)butoxy)quinolin-2-yl)oxy)methyl dihexylcarbamate |
| 468 |  | (7-(4-(4-(benzo[b]thiophen-4-yl)piperazin-1-yl)butoxy)quinolin-2-yl)oxy)methyl dioctylcarbamate |
| 469 |  | (7-(4-(4-(benzo[b]thiophen-4-yl)piperazin-1-yl)butoxy)quinolin-2-yl)oxy)methyl didecylcarbamate |

TABLE 2-continued

| Example | Structure Formula | |
|---|---|---|
| 470 | [structure] | (7-(4-(4-(benzo[b]thiophen-4-yl)piperazin-1-yl)butoxy)quinolin-2-yloxy)methyl didodecylcarbamate |
| 471 | [structure] | (7-(4-(4-(benzo[b]thiophen-4-yl)piperazin-1-yl)butoxy)quinolin-2-yloxy)methyl ditetradecylcarbamate |
| 472 | [structure] | (7-(4-(4-(benzo[b]thiophen-4-yl)piperazin-1-yl)butoxy)quinolin-2-yloxy)methyl dihexadecylcarbamate |
| 473 | [structure] | (7-(4-(4-(benzo[b]thiophen-4-yl)piperazin-1-yl)butoxy)quinolin-2-yloxy)methyl bis(2-hydroxyethyl)carbamate |

TABLE 2-continued

| Example | Structure Formula | |
|---|---|---|
| 474 | | (7-(4-(4-(benzo[b]thiophen-4-yl)piperazin-1-yl)butoxy)quinolin-2-yloxy)methyl piperidine-1-carboxylate |
| 475 | | (7-(4-(4-(benzo[b]thiophen-4-yl)piperazin-1-yl)butoxy)quinolin-2-yloxy)methyl 4-methylpiperazine-1-carboxylate |
| 476 | | (7-(4-(4-(benzo[b]thiophen-4-yl)piperazin-1-yl)butoxy)quinolin-2-yloxy)methyl 1,4'-bipiperidine-1'-carboxylate |
| 477 | | 1-acetyl-7-(4-(4-(benzo[b]thiophen-4-yl)piperazin-1-yl)butoxy)quinolin-2(1H)-one |

TABLE 2-continued

| Example | Structure Formula | |
|---|---|---|
| 478 | | 7-(4-(4-(benzo[b]thiophen-4-yl)piperazin-1-yl)butoxy)-1-propionylquinolin-2(1H)-one |
| 479 | | 7-(4-(4-(benzo[b]thiophen-4-yl)piperazin-1-yl)butoxy)-1-butyrylquinolin-2(1H)-one |
| 480 | | 7-(4-(4-(benzo[b]thiophen-4-yl)piperazin-1-yl)butoxy)-1-pentanoylquinolin-2(1H)-one |
| 481 | | 7-(4-(4-(benzo[b]thiophen-4-yl)piperazin-1-yl)butoxy)-1-(3-methylbutanoyl)quinolin-2(1H)-one |
| 482 | | 7-(4-(4-(benzo[b]thiophen-4-yl)piperazin-1-yl)butoxy)-1-hexanoylquinolin-2(1H)-one |

TABLE 2-continued

| Example | Structure Formula | |
|---|---|---|
| 483 | | 7-(4-(4-(benzo[b]thiophen-4-yl)piperazin-1-yl)butoxy)-1-hexanoyl-3,4-dihydroquinolin-2(1H)-one |
| 484 | | 7-(4-(4-(benzo[b]thiophen-4-yl)piperazin-1-yl)butoxy)-1-heptanoylquinolin-2(1H)-one |
| 485 | | 7-(4-(4-(benzo[b]thiophen-4-yl)piperazin-1-yl)butoxy)-1-octanoylquinolin-2(1H)-one |
| 486 | | 7-(4-(4-(benzo[b]thiophen-4-yl)piperazin-1-yl)butoxy)-1-octanoyl-3,4-dihydroquinolin-2(1H)-one |
| 487 | | 7-(4-(4-(benzo[b]thiophen-4-yl)piperazin-1-yl)butoxy)-1-nonanoylquinolin-2(1H)-one |

TABLE 2-continued

| Example | Structure Formula | |
|---|---|---|
| 488 | | 7-(4-(4-(benzo[b]thiophen-4-yl)piperazin-1-yl)butoxy)-1-decanoylquinolin-2(1H)-one |
| 489 | | 7-(4-(4-(benzo[b]thiophen-4-yl)piperazin-1-yl)butoxy)-1-undecanoylquinolin-2(1H)-one |
| 490 | | 7-(4-(4-(benzo[b]thiophen-4-yl)piperazin-1-yl)butoxy)-1-dodecanoylquinolin-2(1H)-one |
| 491 | | 7-(4-(4-(benzo[b]thiophen-4-yl)piperazin-1-yl)butoxy)-1-tridecanoylquinolin-2(1H)-one |
| 492 | | 7-(4-(4-(benzo[b]thiophen-4-yl)piperazin-1-yl)butoxy)-1-tetradecanoylquinolin-2(1H)-one |

TABLE 2-continued

| Example | Structure Formula | |
|---|---|---|
| 493 | | 7-(4-(4-(benzo[b]thiophen-4-yl)piperazin-1-yl)butoxy)-1-pentadecanoylquinolin-2(1H)-one |
| 494 | | 7-(4-(4-(benzo[b]thiophen-4-yl)piperazin-1-yl)butoxy)-1-palmitoylquinolin-2(1H)-one |
| 495 | | 7-(4-(4-(benzo[b]thiophen-4-yl)piperazin-1-yl)butoxy)-1-heptadecanoylquinolin-2(1H)-one |
| 496 | | 7-(4-(4-(benzo[b]thiophen-4-yl)piperazin-1-yl)butoxy)-1-stearoylquinolin-2(1H)-one |

TABLE 2-continued

| Example | Structure Formula | |
|---|---|---|
| 497 | | 7-(4-(4-(benzo[b]thiophen-4-yl)piperazin-1-yl)butoxy)-1-nonadecanoylquinolin-2(1H)-one |
| 498 | | 7-(4-(4-(benzo[b]thiophen-4-yl)piperazin-1-yl)butoxy)-1-icosanoylquinolin-2(1H)-one |
| 499 | | 7-(4-(4-(benzo[b]thiophen-4-yl)piperazin-1-yl)butoxy)-1-henicosanoylquinolin-2(1H)-one |
| 500 | | 7-(4-(4-(benzo[b]thiophen-4-yl)piperazin-1-yl)butoxy)-1-docosanoylquinolin-2(1H)-one |

TABLE 2-continued

| Example | Structure Formula | |
|---|---|---|
| 501 | | 7-(4-(4-(benzo[b]thiophen-4-yl)piperazin-1-yl)butoxy)-1-tricosanoylquinolin-2(1H)-one |
| 502 | | 7-(4-(4-(benzo[b]thiophen-4-yl)piperazin-1-yl)butoxy)-1-tetracosanoylquinolin-2(1H)-one |
| 503 | | 7-(4-(4-(benzo[b]thiophen-4-yl)piperazin-1-yl)butoxy)-1-(2-methylbutanoyl)quinolin-2(1H)-one |
| 504 | | 7-(4-(4-(benzo[b]thiophen-4-yl)piperazin-1-yl)butoxy)-1-isobutyrylquinolin-2(1H)-one |

TABLE 2-continued

| Example | Structure Formula | |
|---|---|---|
| 505 | | 7-(4-(4-(benzo[b]thiophen-4-yl)piperazin-1-yl)butoxy)-1-isobutyryl-3,4-dihydroquinolin-2(1H)-one |
| 506 | | 7-(4-(4-(benzo[b]thiophen-4-yl)piperazin-1-yl)butoxy)-1-(2-methylpentanoyl)quinolin-2(1H)-one |
| 507 | | 7-(4-(4-(benzo[b]thiophen-4-yl)piperazin-1-yl)butoxy)-1-(2-methylhexanoyl)quinolin-2(1H)-one |
| 508 | | 7-(4-(4-(benzo[b]thiophen-4-yl)piperazin-1-yl)butoxy)-1-(2,2-dimethylhexanoyl)quinolin-2(1H)-one |
| 509 | | 7-(4-(4-(benzo[b]thiophen-4-yl)piperazin-1-yl)butoxy)-1-(2,2-dimethyloctanoyl)quinolin-2(1H)-one |

TABLE 2-continued

| Example | Structure Formula | |
|---|---|---|
| 510 | | 7-(4-(4-(benzo[b]thiophen-4-yl)piperazin-1-yl)butoxy)-1-(2,2-dimethyloctanoyl)-3,4-dihydroquinolin-2(1H)-one |
| 511 | | 7-(4-(4-(benzo[b]thiophen-4-yl)piperazin-1-yl)butoxy)-1-(2,2-dimethyldecanoyl)quinolin-2(1H)-one |
| 512 | | 7-(4-(4-(benzo[b]thiophen-4-yl)piperazin-1-yl)butoxy)-1-(2-phenylacetyl)quinolin-2(1H)-one |
| 513 | | 7-(4-(4-(benzo[b]thiophen-4-yl)piperazin-1-yl)butoxy)-1-benzoylquinolin-2(1H)-one |

TABLE 2-continued

| Example | Structure Formula | |
|---|---|---|
| 514 | (structure) | 7-(4-(4-(benzo[b]thiophen-4-yl)piperazin-1-yl)butoxy)-1-benzoyl-3,4-dihydroquinolin-2(1H)-one |
| 515 | (structure) | 7-(4-(4-(benzo[b]thiophen-4-yl)piperazin-1-yl)butoxy)-1-(cyclobutanecarbonyl)quinolin-2(1H)-one |
| 516 | (structure) | 7-(4-(4-(benzo[b]thiophen-4-yl)piperazin-1-yl)butoxy)-1-(cyclopentanecarbonyl)quinolin-2(1H)-one |
| 517 | (structure) | 7-(4-(4-(benzo[b]thiophen-4-yl)piperazin-1-yl)butoxy)-1-(cyclohexanecarbonyl)quinolin-2(1H)-one |

TABLE 2-continued

| Example | Structure Formula | |
|---|---|---|
| 518 | [structure] | 7-(4-(4-(benzo[b]thiophen-4-yl)piperazin-1-yl)butoxy)-1-(cycloheptanecarbonyl)quinolin-2(1H)-one |
| 519 | [structure] | 7-(4-(4-(benzo[b]thiophen-4-yl)piperazin-1-yl)butoxy)-1-pivaloylquinolin-2(1H)-one |
| 520 | [structure] | 7-(4-(4-(benzo[b]thiophen-4-yl)piperazin-1-yl)butoxy)-1-(2-hydroxyacetyl)quinolin-2(1H)-one |
| 521 | [structure] | 7-(4-(4-(benzo[b]thiophen-4-yl)piperazin-1-yl)butoxy)-1-(2-hydroxyacetyl)-3,4-dihydroquinolin-2(1H)-one |

TABLE 2-continued

| Example | Structure Formula | |
|---|---|---|
| 522 | | 7-(4-(4-(benzo[b]thiophen-4-yl)piperazin-1-yl)butoxy)-1-(4Z,7Z,10Z,13Z,16Z,19Z)-docosa-4,7,10,13,16,19-hexaenoyl)quinolin-2(1H)-one |
| 523 | | 7-(4-(4-(benzo[b]thiophen-4-yl)piperazin-1-yl)butoxy)-1-(9Z,12Z,15Z)-octadeca-9,12,15-trienoyl)quinolin-2(1H)-one |
| 524 | | 7-(4-(4-(benzo[b]thiophen-4-yl)piperazin-1-yl)butoxy)-1-(5Z,8Z,11Z,14Z,17Z)-henicosa-5,8,11,14,17-pentaenoyl)quinolin-2(1H)-one |

TABLE 2-continued

| Example | Structure Formula | |
|---|---|---|
| 525 | | 7-(4-(4-(benzo[b]thiophen-4-yl)piperazin-1-yl)butoxy)-1-(6Z,9Z,12Z,15Z)-octadeca-6,9,12,15-tetraenoylquinolin-2(1H)-one |
| 526 | | 7-(4-(4-(benzo[b]thiophen-4-yl)piperazin-1-yl)butoxy)-1-(7Z,10Z,13Z,16Z,19Z)-docosa-7,10,13,16,19-pentaenoylquinolin-2(1H)-one |
| 527 | | 7-(4-(4-(benzo[b]thiophen-4-yl)piperazin-1-yl)butoxy)-1-(4Z,7Z,10Z,13Z,16Z)-docosa-4,7,10,13,16-pentaenoylquinolin-2(1H)-one |

TABLE 2-continued

| Example | Structure Formula | |
|---|---|---|
| 528 | | 7-(4-(4-(benzo[b]thiophen-4-yl)piperazin-1-yl)butoxy)-1-(4Z,7Z,10Z,13Z,16Z,19Z)-docosa-4,7,10,13,16,19-hexaenoyl]quinolin-2(1H)-one |
| 529 | | 2-amino-N-(2-(7-(4-(4-(benzo[b]thiophen-4-yl)piperazin-1-yl)butoxy)-2-oxoquinolin-1(2H)-yl)-2-oxoethyl)acetamide |
| 530 | | 2-amino-N-(2-(7-(4-(4-(benzo[b]thiophen-4-yl)piperazin-1-yl)butoxy)-2-oxoquinolin-1(2H)-yl)-2-oxoethyl)propanamide |

TABLE 2-continued

| Example | Structure Formula | |
|---|---|---|
| 531 | (structure) | 2-amino-N-(2-(7-(4-(4-(benzo[b]thiophen-4-yl)piperazin-1-yl)butoxy)-2-oxoquinolin-1(2H)-yl)-2-oxoethyl)-3-methylbutanamide |
| 532 | (structure) | 2-amino-N-(2-(7-(4-(4-(benzo[b]thiophen-4-yl)piperazin-1-yl)butoxy)-2-oxoquinolin-1(2H)-yl)-2-oxoethyl)-4-methylpentanamide |
| 533 | (structure) | N-(4-(7-(4-(4-(benzo[b]thiophen-4-yl)piperazin-1-yl)butoxy)-2-oxoquinolin-1(2H)-yl)-4-oxobutyl)acetamide |

TABLE 2-continued

| Example | Structure Formula | |
|---|---|---|
| 534 | [structure] | N-(4-(7-(4-(4-(benzo[b]thiophen-4-yl)piperazin-1-yl)butoxy)-2-oxo-3,4-dihydroquinolin-1(2H)-yl)-4-oxobutyl)acetamide |
| 535 | [structure] | N-(4-(7-(4-(4-(benzo[b]thiophen-4-yl)piperazin-1-yl)butoxy)-2-oxoquinolin-1(2H)-yl)-4-oxobutyl)heptanamide |
| 536 | [structure] | 1-(2-aminoacetyl)-7-(4-(4-(benzo[b]thiophen-4-yl)piperazin-1-yl)butoxy)quinolin-2(1H)-one |
| 537 | [structure] | 1-(2-aminopropanoyl)-7-(4-(4-(benzo[b]thiophen-4-yl)piperazin-1-yl)butoxy)quinolin-2(1H)-one |

TABLE 2-continued

| Example | Structure Formula | |
|---|---|---|
| 538 | | 1-(2-amino-4-methylpentanoyl)-7-(4-(4-(benzo[b]thiophen-4-yl)piperazin-1-yl)butoxy)quinolin-2(1H)-one |
| 539 | | 2-amino-N-(2-(7-(4-(4-(benzo[b]thiophen-4-yl)piperazin-1-yl)butoxy)-2-oxoquinolin-1(2H)-yl)-2-oxoethyl)acetamide |
| 540 | | 2-amino-N-(1-(7-(4-(4-(benzo[b]thiophen-4-yl)piperazin-1-yl)butoxy)-2-oxoquinolin-1(2H)-yl)-3-methyl-1-oxobutan-2-yl)acetamide |
| 541 | | 7-(4-(4-(benzo[b]thiophen-4-yl)piperazin-1-yl)butoxy)-1-(pyrrolidine-2-carbonyl)quinolin-2(1H)-one |

TABLE 2-continued

| Example | Structure Formula | |
|---|---|---|
| 542 | | 1-(1-(2-aminoacetyl)pyrrolidine-2-carbonyl)-7-(4-(4-(benzo[b]thiophen-4-yl)piperazin-1-yl)butoxy)quinolin-2(1H)-one |
| 543 | | 7-(4-(4-(benzo[b]thiophen-4-yl)piperazin-1-yl)butoxy)-1-(2-methoxyethoxy)acetyl)quinolin-2(1H)-one |
| 544 | | 7-(4-(4-(benzo[b]thiophen-4-yl)piperazin-1-yl)butoxy)-1-(2-methoxyethoxy)acetyl)-3,4-dihydroquinolin-2(1H)-one |
| 545 | | 7-(4-(4-(benzo[b]thiophen-4-yl)piperazin-1-yl)butoxy)-1-(2-(2-methoxyethoxy)acetyl)quinolin-2(1H)-one |
| 546 | | methyl 7-(4-(4-(benzo[b]thiophen-4-yl)piperazin-1-yl)butoxy)-2-oxoquinoline-1(2H)-carboxylate |

TABLE 2-continued

| Example | Structure Formula | |
|---|---|---|
| 547 | | methyl 7-(4-(4-(benzo[b]thiophen-4-yl)piperazin-1-yl)butoxy)-2-oxo-3,4-dihydroquinoline-1(2H)-carboxylate |
| 548 | | ethyl 7-(4-(4-(benzo[b]thiophen-4-yl)piperazin-1-yl)butoxy)-2-oxoquinoline-1(2H)-carboxylate |
| 549 | | propyl 7-(4-(4-(benzo[b]thiophen-4-yl)piperazin-1-yl)butoxy)-2-oxoquinoline-1(2H)-carboxylate |
| 550 | | propyl 7-(4-(4-(benzo[b]thiophen-4-yl)piperazin-1-yl)butoxy)-2-oxo-3,4-dihydroquinoline-1(2H)-carboxylate |
| 551 | | isobutyl 7-(4-(4-(benzo[b]thiophen-4-yl)piperazin-1-yl)butoxy)-2-oxoquinoline-1(2H)-carboxylate |

TABLE 2-continued

| Example | Structure Formula | |
|---|---|---|
| 552 | | butyl 7-(4-(4-(benzo[b]thiophen-4-yl)piperazin-1-yl)butoxy)-2-oxoquinoline-1(2H)-carboxylate |
| 553 | | pentyl 7-(4-(4-(benzo[b]thiophen-4-yl)piperazin-1-yl)butoxy)-2-oxoquinoline-1(2H)-carboxylate |
| 554 | | pentyl 7-(4-(4-(benzo[b]thiophen-4-yl)piperazin-1-yl)butoxy)-2-oxo-3,4-dihydroquinoline-1(2H)-carboxylate |
| 555 | | hexyl 7-(4-(4-(benzo[b]thiophen-4-yl)piperazin-1-yl)butoxy)-2-oxoquinoline-1(2H)-carboxylate |
| 556 | | isopentyl 7-(4-(4-(benzo[b]thiophen-4-yl)piperazin-1-yl)butoxy)-2-oxoquinoline-1(2H)-carboxylate |

TABLE 2-continued

| Example | Structure Formula | |
|---|---|---|
| 557 | [structure] | isopropyl 7-(4-(4-(benzo[b]thiophen-4-yl)piperazin-1-yl)butoxy)-2-oxoquinoline-1(2H)-carboxylate |
| 558 | [structure] | isopropyl 7-(4-(4-(benzo[b]thiophen-4-yl)piperazin-1-yl)butoxy)-2-oxo-3,4-dihydroquinoline-1(2H)-carboxylate |
| 559 | [structure] | cyclohexyl 7-(4-(4-(benzo[b]thiophen-4-yl)piperazin-1-yl)butoxy)-2-oxoquinoline-1(2H)-carboxylate |
| 560 | [structure] | cyclohexyl 7-(4-(4-(benzo[b]thiophen-4-yl)piperazin-1-yl)butoxy)-2-oxo-3,4-dihydroquinoline-1(2H)-carboxylate |

TABLE 2-continued

| Example | Structure Formula | |
|---|---|---|
| 561 | | heptyl 7-(4-(4-(benzo[b]thiophen-4-yl)piperazin-1-yl)butoxy)-2-oxoquinoline-1(2H)-carboxylate |
| 562 | | heptyl 7-(4-(4-(benzo[b]thiophen-4-yl)piperazin-1-yl)butoxy)-2-oxo-3,4-dihydroquinoline-1(2H)-carboxylate |
| 563 | | octyl 7-(4-(4-(benzo[b]thiophen-4-yl)piperazin-1-yl)butoxy)-2-oxoquinoline-1(2H)-carboxylate |
| 564 | | nonyl 7-(4-(4-(benzo[b]thiophen-4-yl)piperazin-1-yl)butoxy)-2-oxoquinoline-1(2H)-carboxylate |
| 565 | | decyl 7-(4-(4-(benzo[b]thiophen-4-yl)piperazin-1-yl)butoxy)-2-oxoquinoline-1(2H)-carboxylate |

TABLE 2-continued

| Example | Structure Formula | |
|---|---|---|
| 566 | | undecyl 7-(4-(4-(benzo[b]thiophen-4-yl)piperazin-1-yl)butoxy)-2-oxoquinoline-1(2H)-carboxylate |
| 567 | | undecyl 7-(4-(4-(benzo[b]thiophen-4-yl)piperazin-1-yl)butoxy)-2-oxo-3,4-dihydroquinoline-1(2H)-carboxylate |
| 568 | | dodecyl 7-(4-(4-(benzo[b]thiophen-4-yl)piperazin-1-yl)butoxy)-2-oxoquinoline-1(2H)-carboxylate |
| 569 | | tridecyl 7-(4-(4-(benzo[b]thiophen-4-yl)piperazin-1-yl)butoxy)-2-oxoquinoline-1(2H)-carboxylate |

TABLE 2-continued

| Example | Structure Formula | |
|---|---|---|
| 570 | | tetradecyl 7-(4-(4-(benzo[b]thiophen-4-yl)piperazin-1-yl)butoxy)-2-oxoquinoline-1(2H)-carboxylate |
| 571 | | pentadecyl 7-(4-(4-(benzo[b]thiophen-4-yl)piperazin-1-yl)butoxy)-2-oxoquinoline-1(2H)-carboxylate |
| 572 | | hexadecyl 7-(4-(4-(benzo[b]thiophen-4-yl)piperazin-1-yl)butoxy)-2-oxoquinoline-1(2H)-carboxylate |
| 573 | | heptadecyl 7-(4-(4-(benzo[b]thiophen-4-yl)piperazin-1-yl)butoxy)-2-oxoquinoline-1(2H)-carboxylate |

TABLE 2-continued

| Example | Structure Formula | |
|---|---|---|
| 574 | | octadecyl 7-(4-(4-(benzo[b]thiophen-4-yl)piperazin-1-yl)butoxy)-2-oxoquinoline-1(2H)-carboxylate |
| 575 | | nonadecyl 7-(4-(4-(benzo[b]thiophen-4-yl)piperazin-1-yl)butoxy)-2-oxoquinoline-1(2H)-carboxylate |
| 576 | | icosyl 7-(4-(4-(benzo[b]thiophen-4-yl)piperazin-1-yl)butoxy)-2-oxoquinoline-1(2H)-carboxylate |
| 577 | | henicosyl 7-(4-(4-(benzo[b]thiophen-4-yl)piperazin-1-yl)butoxy)-2-oxoquinoline-1(2H)-carboxylate |

TABLE 2-continued

| Example | Structure Formula | |
|---|---|---|
| 578 | | docosyl 7-(4-(4-(benzo[b]thiophen-4-yl)piperazin-1-yl)butoxy)-2-oxoquinoline-1(2H)-carboxylate |
| 579 | | benzyl 7-(4-(4-(benzo[b]thiophen-4-yl)piperazin-1-yl)butoxy)-2-oxoquinoline-1(2H)-carboxylate |
| 580 | | 7-(4-(4-(benzo[b]thiophen-4-yl)piperazin-1-yl)butoxy)-N-benzyl-2-oxoquinoline-1(2H)-carboxamide |
| 581 | | calcium 7-(4-(4-(benzo[b]thiophen-4-yl)piperazin-1-yl)butoxy)-2-oxoquinolin-1(2H)-yl phosphate |

TABLE 2-continued

| Example | Structure Formula | |
|---|---|---|
| 582 | 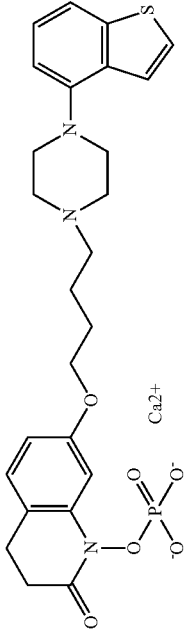 | calcium 7-(4-(4-(benzo[b]thiophen-4-yl)piperazin-1-yl)butoxy)-2-oxo-3,4-dihydroquinolin-1(2H)-yl phosphate |
| 583 | 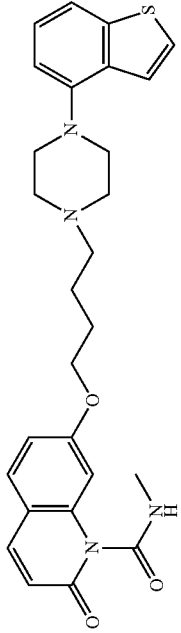 | 7-(4-(4-(benzo[b]thiophen-4-yl)piperazin-1-yl)butoxy)-N-methyl-2-oxo-3,4-dihydroquinoline-1(2H)-carboxamide |
| 584 | 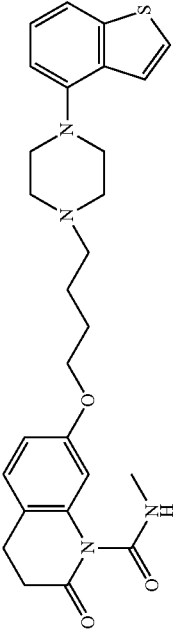 | 7-(4-(4-(benzo[b]thiophen-4-yl)piperazin-1-yl)butoxy)-N-methyl-2-oxo-3,4-dihydroquinoline-1(2H)-carboxamide |
| 585 | 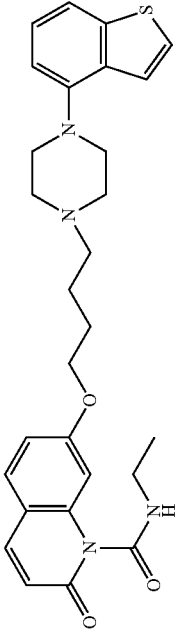 | 7-(4-(4-(benzo[b]thiophen-4-yl)piperazin-1-yl)butoxy)-N-ethyl-2-oxoquinoline-1(2H)-carboxamide |
| 586 | 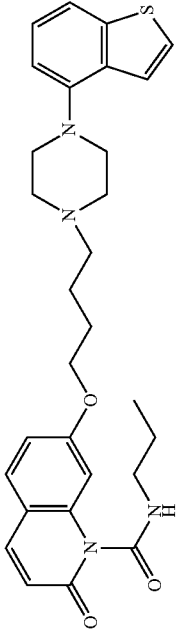 | 7-(4-(4-(benzo[b]thiophen-4-yl)piperazin-1-yl)butoxy)-2-oxo-N-propylquinoline-1(2H)-carboxamide |

TABLE 2-continued

| Example | Structure Formula | |
|---|---|---|
| 587 | | 7-(4-(4-(benzo[b]thiophen-4-yl)piperazin-1-yl)butoxy)-N-butyl-2-oxoquinoline-1(2H)-carboxamide |
| 588 | | 7-(4-(4-(benzo[b]thiophen-4-yl)piperazin-1-yl)butoxy)-2-oxo-N-pentylquinoline-1(2H)-carboxamide |
| 589 | | 7-(4-(4-(benzo[b]thiophen-4-yl)piperazin-1-yl)butoxy)-N-hexyl-2-oxoquinoline-1(2H)-carboxamide |
| 590 | | 7-(4-(4-(benzo[b]thiophen-4-yl)piperazin-1-yl)butoxy)-N-heptyl-2-oxoquinoline-1(2H)-carboxamide |
| 591 | | 7-(4-(4-(benzo[b]thiophen-4-yl)piperazin-1-yl)butoxy)-N-heptyl-2-oxo-3,4-dihydroquinoline-1(2H)-carboxamide |

TABLE 2-continued

| Example | Structure Formula | |
|---|---|---|
| 592 | | 7-(4-(4-(benzo[b]thiophen-4-yl)piperazin-1-yl)butoxy)-N-octyl-2-oxoquinoline-1(2H)-carboxamide |
| 593 | | 7-(4-(4-(benzo[b]thiophen-4-yl)piperazin-1-yl)butoxy)-N-nonyl-2-oxoquinoline-1(2H)-carboxamide |
| 594 | | 7-(4-(4-(benzo[b]thiophen-4-yl)piperazin-1-yl)butoxy)-N-decyl-2-oxoquinoline-1(2H)-carboxamide |
| 595 | | 7-(4-(4-(benzo[b]thiophen-4-yl)piperazin-1-yl)butoxy)-N-(2-hydroxyethyl)-2-oxoquinoline-1(2H)-carboxamide |
| 596 | | 7-(4-(4-(benzo[b]thiophen-4-yl)piperazin-1-yl)butoxy)-N,N-dimethyl-2-oxoquinoline-1(2H)-carboxamide |

TABLE 2-continued

| Example | Structure Formula | |
|---|---|---|
| 597 | | 7-(4-(4-(benzo[b]thiophen-4-yl)piperazin-1-yl)butoxy)-N,N-dimethyl-2-oxo-3,4-dihydroquinoline-1(2H)-carboxamide |
| 598 | | 7-(4-(4-(benzo[b]thiophen-4-yl)piperazin-1-yl)butoxy)-N,N-diethyl-2-oxoquinoline-1(2H)-carboxamide |
| 599 | | 7-(4-(4-(benzo[b]thiophen-4-yl)piperazin-1-yl)butoxy)-2-oxo-N,N-dipropylquinoline-1(2H)-carboxamide |
| 600 | | 7-(4-(4-(benzo[b]thiophen-4-yl)piperazin-1-yl)butoxy)-N,N-dibutyl-2-oxoquinoline-1(2H)-carboxamide |

TABLE 2-continued

| Example | Structure Formula | |
|---|---|---|
| 601 | | 7-(4-(4-(benzo[b]thiophen-4-yl)piperazin-1-yl)butoxy)-2-oxo-N,N-dipentylquinoline-1(2H)-carboxamide |
| 602 | | 7-(4-(4-(benzo[b]thiophen-4-yl)piperazin-1-yl)butoxy)-N,N-dihexyl-2-oxoquinoline-1(2H)-carboxamide |
| 603 | | 7-(4-(4-(benzo[b]thiophen-4-yl)piperazin-1-yl)butoxy)-N,N-diheptyl-2-oxoquinoline-1(2H)-carboxamide |
| 604 | | 7-(4-(4-(benzo[b]thiophen-4-yl)piperazin-1-yl)butoxy)-N,N-diheptyl-2-oxo-3,4-dihydroquinoline-1(2H)-carboxamide |

TABLE 2-continued

| Example | Structure Formula | |
|---|---|---|
| 605 | | 7-(4-(4-(benzo[b]thiophen-4-yl)piperazin-1-yl)butoxy)-N,N-dinonyl-2-oxoquinoline-1(2H)-carboxamide |
| 606 | | 7-(4-(4-(benzo[b]thiophen-4-yl)piperazin-1-yl)butoxy)-2-oxo-N,N-ditetradecylquinoline-1(2H)-carboxamide |
| 607 | | 7-(4-(4-(benzo[b]thiophen-4-yl)piperazin-1-yl)butoxy)-N-methyl-2-oxo-N-tetradecylquinoline-1(2H)-carboxamide |
| 608 | | 7-(4-(4-(benzo[b]thiophen-4-yl)piperazin-1-yl)butoxy)-N-methyl-N-nonyl-2-oxoquinoline-1(2H)-carboxamide |

TABLE 2-continued

| Example | Structure Formula | |
|---|---|---|
| 609 | (structure) | 7-(4-(4-(benzo[b]thiophen-4-yl)piperazin-1-yl)butoxy)-1-(morpholine-4-carbonyl)quinolin-2(1H)-one |
| 610 | (structure) | 7-(4-(4-(benzo[b]thiophen-4-yl)piperazin-1-yl)butoxy)-1-(morpholine-4-carbonyl)-3,4-dihydroquinolin-2(1H)-one |
| 611 | (structure) | 7-(4-(4-(benzo[b]thiophen-4-yl)piperazin-1-yl)butoxy)-N,N-bis(2-hydroxyethyl)-2-oxoquinoline-1(2H)-carboxamide |
| 612 | (structure) | 7-(4-(4-(benzo[b]thiophen-4-yl)piperazin-1-yl)butoxy)-N,N-dibenzyl-2-oxoquinoline-1(2H)-carboxamide |

TABLE 2-continued

| Example | Structure Formula | |
|---|---|---|
| 613 | | 7-(4-(4-(benzo[b]thiophen-4-yl)piperazin-1-yl)butoxy)-1-(4-methylpiperazine-1-carbonyl)quinolin-2(1H)-one |
| 614 | | 1-(1,4'-bipiperidine-1'-carbonyl)-7-(4-(4-(benzo[b]thiophen-4-yl)piperazin-1-yl)butoxy)quinolin-2(1H)-one |
| 615 | | 7-(4-(4-(benzo[b]thiophen-4-yl)piperazin-1-yl)butoxy)-1-(cyclopropanecarbonyl)quinolin-2(1H)-one |
| 616 | | 7-(4-(4-(benzo[b]thiophen-4-yl)piperazin-1-yl)butoxy)quinolin-2-yl propionate |

TABLE 2-continued

| Example | Structure Formula | |
|---|---|---|
| 617 | [structure] | 7-(4-(4-(benzo[b]thiophen-4-yl)piperazin-1-yl)butoxy)quinolin-2-yl butyrate |
| 618 | [structure] | 7-(4-(4-(benzo[b]thiophen-4-yl)piperazin-1-yl)butoxy)quinolin-2-yl pentanoate |
| 619 | [structure] | 7-(4-(4-(benzo[b]thiophen-4-yl)piperazin-1-yl)butoxy)quinolin-2-yl hexanoate |
| 620 | [structure] | 7-(4-(4-(benzo[b]thiophen-4-yl)piperazin-1-yl)butoxy)quinolin-2-yl heptanoate |
| 621 | [structure] | 7-(4-(4-(benzo[b]thiophen-4-yl)piperazin-1-yl)butoxy)quinolin-2-yl octanoate |

TABLE 2-continued

| Example | Structure Formula | |
|---|---|---|
| 622 | [structure] | 7-(4-(4-(benzo[b]thiophen-4-yl)piperazin-1-yl)butoxy)quinolin-2-yl nonanoate |
| 623 | [structure] | 7-(4-(4-(benzo[b]thiophen-4-yl)piperazin-1-yl)butoxy)quinolin-2-yl decanoate |
| 624 | [structure] | 7-(4-(4-(benzo[b]thiophen-4-yl)piperazin-1-yl)butoxy)quinolin-2-yl undecanoate |
| 625 | [structure] | 7-(4-(4-(benzo[b]thiophen-4-yl)piperazin-1-yl)butoxy)quinolin-2-yl tridecanoate |
| 626 | [structure] | 7-(4-(4-(benzo[b]thiophen-4-yl)piperazin-1-yl)butoxy)quinolin-2-yl tetradecanoate |

TABLE 2-continued

| Example | Structure Formula | |
|---|---|---|
| 627 | 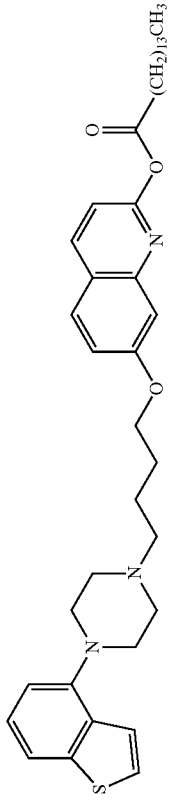 | 7-(4-(4-(benzo[b]thiophen-4-yl)piperazin-1-yl)butoxy)quinolin-2-yl pentadecanoate |
| 628 | 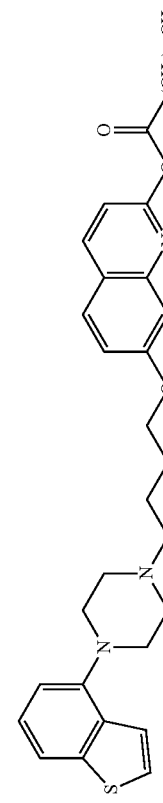 | 7-(4-(4-(benzo[b]thiophen-4-yl)piperazin-1-yl)butoxy)quinolin-2-yl palmitate |
| 629 | 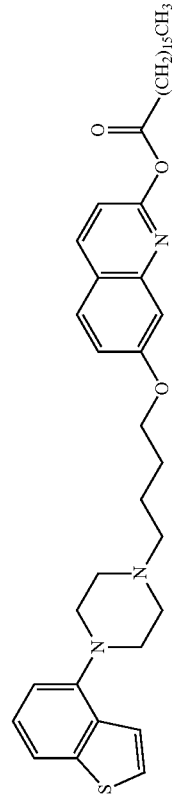 | 7-(4-(4-(benzo[b]thiophen-4-yl)piperazin-1-yl)butoxy)quinolin-2-yl heptadecanoate |
| 630 | 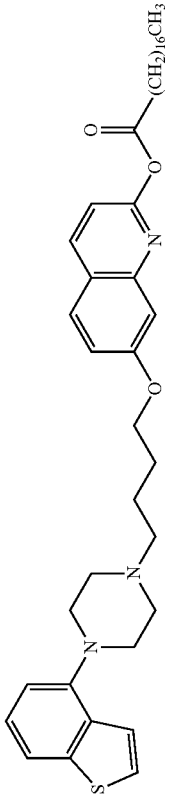 | 7-(4-(4-(benzo[b]thiophen-4-yl)piperazin-1-yl)butoxy)quinolin-2-yl stearate |
| 631 | 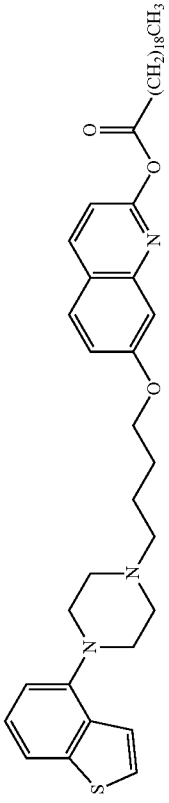 | 7-(4-(4-(benzo[b]thiophen-4-yl)piperazin-1-yl)butoxy)quinolin-2-yl icosanoate |

TABLE 2-continued

| Example | Structure Formula | |
|---|---|---|
| 632 | | 7-(4-(4-(benzo[b]thiophen-4-yl)piperazin-1-yl)butoxy)quinolin-2-yl 2,2-dimethyltetradecanoate |
| 633 | | 7-(4-(4-(benzo[b]thiophen-4-yl)piperazin-1-yl)butoxy)quinolin-2-yl pivalate |
| 634 | | 7-(4-(4-(benzo[b]thiophen-4-yl)piperazin-1-yl)butoxy)quinolin-2-yl 2,2-dimethylbutanoate |
| 635 | | 7-(4-(4-(benzo[b]thiophen-4-yl)piperazin-1-yl)butoxy)quinolin-2-yl isobutyrate |
| 636 | | 7-(4-(4-(benzo[b]thiophen-4-yl)piperazin-1-yl)butoxy)quinolin-2-yl 2-hydroxyacetate |

TABLE 2-continued

| Example | Structure Formula | |
|---|---|---|
| 637 | | 7-(4-(4-(benzo[b]thiophen-4-yl)piperazin-1-yl)butoxy)quinolin-2-yl cyclopropanecarboxylate |
| 638 | | 7-(4-(4-(benzo[b]thiophen-4-yl)piperazin-1-yl)butoxy)quinolin-2-yl cyclobutanecarboxylate |
| 639 | | 7-(4-(4-(benzo[b]thiophen-4-yl)piperazin-1-yl)butoxy)quinolin-2-yl cyclopentanecarboxylate |
| 640 | | 7-(4-(4-(benzo[b]thiophen-4-yl)piperazin-1-yl)butoxy)quinolin-2-yl benzoate |

TABLE 2-continued

| Example | Structure Formula | |
|---|---|---|
| 641 | | 7-(4-(4-(benzo[b]thiophen-4-yl)piperazin-1-yl)butoxy)quinolin-2-yl 2-phenylacetate |
| 642 | | (9Z,12Z,15Z)-7-(4-(4-(benzo[b]thiophen-4-yl)piperazin-1-yl)butoxy)quinolin-2-yl octadeca-9,12,15-trienoate |
| 643 | | (5Z,8Z,11Z,14Z,17Z)-7-(4-(4-(benzo[b]thiophen-4-yl)piperazin-1-yl)butoxy)quinolin-2-yl henicosa-5,8,11,14,17-pentaenoate |
| 644 | | (4Z,7Z,10Z,13Z,16Z,19Z)-7-(4-(4-(benzo[b]thiophen-4-yl)piperazin-1-yl)butoxy)quinolin-2-yl docosa-4,7,10,13,16,19-hexaenoate |

TABLE 2-continued

| Example | Structure Formula | |
|---|---|---|
| 645 | | (6Z,9Z,12Z,15Z)-7-(4-(4-(benzo[b]thiophen-4-yl)piperazin-1-yl)butoxy)quinolin-2-yl octadeca-6,9,12,15-tetraenoate |
| 646 | | 7-(4-(4-(benzo[b]thiophen-4-yl)piperazin-1-yl)butoxy)quinolin-2-yl methyl carbonate |
| 647 | | 7-(4-(4-(benzo[b]thiophen-4-yl)piperazin-1-yl)butoxy)quinolin-2-yl ethyl carbonate |
| 648 | | 7-(4-(4-(benzo[b]thiophen-4-yl)piperazin-1-yl)butoxy)quinolin-2-yl butyl carbonate |
| 649 | | 7-(4-(4-(benzo[b]thiophen-4-yl)piperazin-1-yl)butoxy)quinolin-2-yl pentyl carbonate |

TABLE 2-continued

| Example | Structure Formula | |
|---|---|---|
| 650 | | 7-(4-(4-(benzo[b]thiophen-4-yl)piperazin-1-yl)butoxy)quinolin-2-yl cyclohexyl carbonate |
| 651 | | 7-(4-(4-(benzo[b]thiophen-4-yl)piperazin-1-yl)butoxy)quinolin-2-yl 2-methoxyethyl carbonate |
| 652 | | 7-(4-(4-(benzo[b]thiophen-4-yl)piperazin-1-yl)butoxy)quinolin-2-yl diethyl phosphate |
| 653 | | 7-(4-(4-(benzo[b]thiophen-4-yl)piperazin-1-yl)butoxy)quinolin-2-yl methylcarbamate |
| 654 | | 7-(4-(4-(benzo[b]thiophen-4-yl)piperazin-1-yl)butoxy)quinolin-2-yl ethylcarbamate |

TABLE 2-continued

| Example | Structure Formula | |
|---|---|---|
| 655 | [structure] | 7-(4-(4-(benzo[b]thiophen-4-yl)piperazin-1-yl)butoxy)quinolin-2-yl propylcarbamate |
| 656 | [structure] | 7-(4-(4-(benzo[b]thiophen-4-yl)piperazin-1-yl)butoxy)quinolin-2-yl butylcarbamate |
| 657 | [structure] | 7-(4-(4-(benzo[b]thiophen-4-yl)piperazin-1-yl)butoxy)quinolin-2-yl pentylcarbamate |
| 658 | [structure] | 7-(4-(4-(benzo[b]thiophen-4-yl)piperazin-1-yl)butoxy)quinolin-2-yl hexylcarbamate |
| 659 | [structure] | 7-(4-(4-(benzo[b]thiophen-4-yl)piperazin-1-yl)butoxy)quinolin-2-yl octylcarbamate |

TABLE 2-continued

| Example | Structure Formula | |
|---|---|---|
| 660 | | 7-(4-(4-(benzo[b]thiophen-4-yl)piperazin-1-yl)butoxy)quinolin-2-yl decylcarbamate |
| 661 | | 7-(4-(4-(benzo[b]thiophen-4-yl)piperazin-1-yl)butoxy)quinolin-2-yl dodecylcarbamate |
| 662 | | 7-(4-(4-(benzo[b]thiophen-4-yl)piperazin-1-yl)butoxy)quinolin-2-yl tetradecylcarbamate |
| 663 | | 7-(4-(4-(benzo[b]thiophen-4-yl)piperazin-1-yl)butoxy)quinolin-2-yl hexadecylcarbamate |
| 664 | | 7-(4-(4-(benzo[b]thiophen-4-yl)piperazin-1-yl)butoxy)quinolin-2-yl dimethylcarbamate |

TABLE 2-continued

| Example | Structure Formula | |
|---|---|---|
| 665 | [structure] | 7-(4-(4-(benzo[b]thiophen-4-yl)piperazin-1-yl)butoxy)quinolin-2-yl dipropylcarbamate |
| 666 | [structure] | 7-(4-(4-(benzo[b]thiophen-4-yl)piperazin-1-yl)butoxy)quinolin-2-yl diisobutylcarbamate |
| 667 | [structure] | 7-(4-(4-(benzo[b]thiophen-4-yl)piperazin-1-yl)butoxy)quinolin-2-yl dibutylcarbamate |
| 668 | [structure] | 7-(4-(4-(benzo[b]thiophen-4-yl)piperazin-1-yl)butoxy)quinolin-2-yl dihexylcarbamate |

TABLE 2-continued

| Example | Structure Formula | |
|---|---|---|
| 669 | (structure) | 7-(4-(4-(benzo[b]thiophen-4-yl)piperazin-1-yl)butoxy)quinolin-2-yl dioctylcarbamate |
| 670 | (structure) | 7-(4-(4-(benzo[b]thiophen-4-yl)piperazin-1-yl)butoxy)quinolin-2-yl didecylcarbamate |
| 671 | (structure) | 7-(4-(4-(benzo[b]thiophen-4-yl)piperazin-1-yl)butoxy)quinolin-2-yl didodecylcarbamate |
| 672 | (structure) | 7-(4-(4-(benzo[b]thiophen-4-yl)piperazin-1-yl)butoxy)quinolin-2-yl ditetradecylcarbamate |

TABLE 2-continued

| Example | Structure Formula | |
|---|---|---|
| 673 | | 7-(4-(4-(benzo[b]thiophen-4-yl)piperazin-1-yl)butoxy)quinolin-2-yl dihexadecylcarbamate |
| 674 | | 7-(4-(4-(benzo[b]thiophen-4-yl)piperazin-1-yl)butoxy)quinolin-2-yl bis(2-hydroxyethyl)carbamate |
| 675 | | 7-(4-(4-(benzo[b]thiophen-4-yl)piperazin-1-yl)butoxy)quinolin-2-yl piperidine-1-carboxylate |
| 676 | | 7-(4-(4-(benzo[b]thiophen-4-yl)piperazin-1-yl)butoxy)quinolin-2-yl 4-methylpiperazine-1-carboxylate |

TABLE 2-continued

| Example | Structure Formula | |
|---|---|---|
| 677 | | 7-(4-(4-(benzo[b]thiophen-4-yl)piperazin-1-yl)butoxy)quinolin-2-yl 1,4'-bipiperidine-1'-carboxylate |
| 678 | | 4-(benzo[b]thiophen-4-yl)-1-(4-(2-oxo-1,2-dihydroquinolin-7-yloxy)butyl)-1-(propionyloxymethyl)piperazin-1-ium chloride |
| 679 | | 4-(benzo[b]thiophen-4-yl)-1-(butyryloxymethyl)-1-(4-(2-oxo-1,2-dihydroquinolin-7-yloxy)butyl)piperazin-1-ium chloride |

TABLE 2-continued

| Example | Structure Formula | |
|---|---|---|
| 680 | (structure) | 4-(benzo[b]thiophen-4-yl)-1-(4-(2-oxo-1,2-dihydroquinolin-7-yloxy)butyl)-1-(pentanoyloxymethyl)piperazin-1-ium chloride |
| 681 | (structure) | 4-(benzo[b]thiophen-4-yl)-1-(hexanoyloxymethyl)-1-(4-(2-oxo-1,2-dihydroquinolin-7-yloxy)butyl)piperazin-1-ium chloride |
| 682 | (structure) | 4-(benzo[b]thiophen-4-yl)-1-(heptanoyloxymethyl)-1-(4-(2-oxo-1,2-dihydroquinolin-7-yloxy)butyl)piperazin-1-ium chloride |

TABLE 2-continued

| Example | Structure Formula | |
|---|---|---|
| 683 | | 4-(benzo[b]thiophen-4-yl)-1-(octanoyloxymethyl)-1-(4-(2-oxo-1,2-dihydroquinolin-7-yloxy)butyl)piperazin-1-ium chloride |
| 684 | | 4-(benzo[b]thiophen-4-yl)-1-(nonanoyloxymethyl)-1-(4-(2-oxo-1,2-dihydroquinolin-7-yloxy)butyl)piperazin-1-ium chloride |
| 685 | | 4-(benzo[b]thiophen-4-yl)-1-(decanoyloxymethyl)-1-(4-(2-oxo-1,2-dihydroquinolin-7-yloxy)butyl)piperazin-1-ium chloride |

TABLE 2-continued

| Example | Structure Formula | |
|---|---|---|
| 686 | | 4-(benzo[b]thiophen-4-yl)-1-(4-(2-oxo-1,2-dihydroquinolin-7-yloxy)butyl)-1-(undecanoyloxymethyl)piperazin-1-ium iodide |
| 687 | | 4-(benzo[b]thiophen-4-yl)-1-(4-(2-oxo-1,2-dihydroquinolin-7-yloxy)butyl)-1-(tetradecanoyloxymethyl)piperazin-1-ium iodide |
| 688 | | 4-(benzo[b]thiophen-4-yl)-1-(4-(2-oxo-1,2-dihydroquinolin-7-yloxy)butyl)-1-(palmitoyloxymethyl)piperazin-1-ium iodide |

TABLE 2-continued

| Example | Structure Formula | |
|---|---|---|
| 689 | | 4-(benzo[b]thiophen-4-yl)-1-(4-(2-oxo-1,2-dihydroquinolin-7-yloxy)butyl)-1-(stearoyloxymethyl)piperazin-1-ium iodide |
| 690 | | 4-(benzo[b]thiophen-4-yl)-1-(icosanoyloxymethyl)-1-(4-(2-oxo-1,2-dihydroquinolin-7-yloxy)butyl)piperazin-1-ium iodide |
| 691 | | 4-(benzo[b]thiophen-4-yl)-1-(docosanoyloxymethyl)-1-(4-(2-oxo-1,2-dihydroquinolin-7-yloxy)butyl)piperazin-1-ium iodide |

TABLE 2-continued

| Example | Structure Formula | |
|---|---|---|
| 692 | [structure] | 4-(benzo[b]thiophen-4-yl)-1-(cyclopentanecarbonyloxymethyl)-1-(4-(2-oxo-1,2-dihydroquinolin-7-yloxy)butyl)piperazin-1-ium iodide |
| 693 | [structure] | 4-(benzo[b]thiophen-4-yl)-1-(cyclohexanecarbonyloxymethyl)-1-(4-(2-oxo-1,2-dihydroquinolin-7-yloxy)butyl)piperazin-1-ium iodide |
| 694 | [structure] | 4-(benzo[b]thiophen-4-yl)-1-(isobutyryloxymethyl)-1-(4-(2-oxo-1,2-dihydroquinolin-7-yloxy)butyl)piperazin-1-ium chloride |

TABLE 2-continued

| Example | Structure Formula | |
|---|---|---|
| 695 | [structure] | 4-(benzo[b]thiophen-4-yl)-1-(4-(2-oxo-1,2-dihydroquinolin-7-yloxy)butyl)-1-((2-propylpentanoyloxy)methyl)piperazin-1-ium iodide |
| 696 | [structure] | 4-(benzo[b]thiophen-4-yl)-1-(4-(2-oxo-1,2-dihydroquinolin-7-yloxy)butyl)-1-((2-pentylheptanoyloxy)methyl)piperazin-1-ium iodide |
| 697 | [structure] | 4-(benzo[b]thiophen-4-yl)-1-(4-(2-oxo-1,2-dihydroquinolin-7-yloxy)butyl)-1-(pivaloyloxymethyl)piperazin-1-ium chloride |

TABLE 2-continued

| Example | Structure Formula | |
|---|---|---|
| 698 | [structure] I⁻ | 4-(benzo[b]thiophen-4-yl)-1-(((2,2-dimethylbutanoyloxy)methyl)-1-(4-(2-oxo-1,2-dihydroquinolin-7-yloxy)butyl)piperazin-1-ium iodide |
| 699 | [structure] I⁻ | 4-(benzo[b]thiophen-4-yl)-1-(((2,2-dimethylpentanoyloxy)methyl)-1-(4-(2-oxo-1,2-dihydroquinolin-7-yloxy)butyl)piperazin-1-ium iodide |
| 700 | [structure] I⁻ | 4-(benzo[b]thiophen-4-yl)-1-(((2,2-dimethylhexanoyloxy)methyl)-1-(4-(2-oxo-1,2-dihydroquinolin-7-yloxy)butyl)piperazin-1-ium iodide |

TABLE 2-continued

| Example | Structure Formula | |
|---|---|---|
| 701 | (structure) | 4-(benzo[b]thiophen-4-yl)-1-((2,2-dimethyltetradecanoyloxy)methyl)-1-(4-(2-oxo-1,2-dihydroquinolin-7-yloxy)butyl)piperazin-1-ium iodide |
| 702 | (structure) | 4-(benzo[b]thiophen-4-yl)-1-(((1-methylcyclohexanecarbonyloxy)methyl)-1-(4-(2-oxo-1,2-dihydroquinolin-7-yloxy)butyl)piperazin-1-ium iodide |
| 703 | (structure) | 4-(benzo[b]thiophen-4-yl)-1-((hexylcarbamoyloxy)methyl)-1-(4-(2-oxo-1,2-dihydroquinolin-7-yloxy)butyl)piperazin-1-ium iodide |

TABLE 2-continued

| Example | Structure Formula | |
|---|---|---|
| 704 | | 4-(benzo[b]thiophen-4-yl)-1-(((diethylcarbamoyl)oxy)methyl)-1-(4-(2-oxo-1,2-dihydroquinolin-7-yloxy)butyl)piperazin-1-ium iodide |
| 705 | | 4-(benzo[b]thiophen-4-yl)-1-(((dibenzylcarbamoyl)oxy)methyl)-1-(4-(2-oxo-1,2-dihydroquinolin-7-yloxy)butyl)piperazin-1-ium iodide |
| 706 | | 4-(benzo[b]thiophen-4-yl)-1-(4-(2-oxo-1,2-dihydroquinolin-7-yloxy)butyl)-1-((piperidine-1-carbonyloxy)methyl)piperazin-1-ium iodide |

TABLE 2-continued

| Example | Structure Formula | |
|---|---|---|
| 707 | 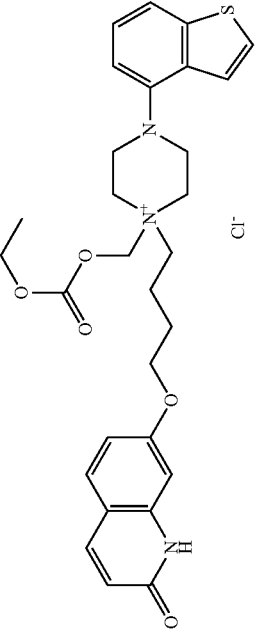 | 4-(benzo[b]thiophen-4-yl)-1-((ethoxycarbonyloxy)methyl)-1-(4-(2-oxo-1,2-dihydroquinolin-7-yloxy)butyl)piperazin-1-ium chloride |
| 708 | 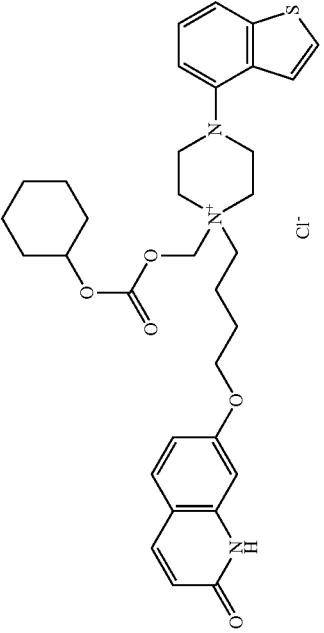 | 4-(benzo[b]thiophen-4-yl)-1-((cyclohexyloxycarbonyloxy)methyl)-1-(4-(2-oxo-1,2-dihydroquinolin-7-yloxy)butyl)piperazin-1-ium chloride |
| 709 | 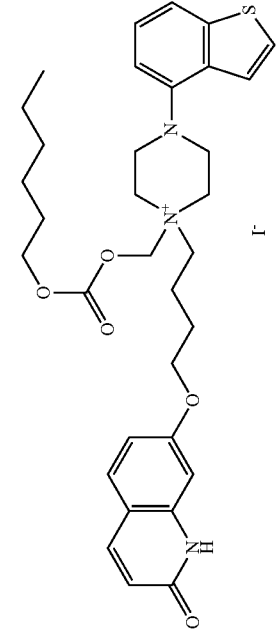 | 4-(benzo[b]thiophen-4-yl)-1-((hexyloxycarbonyloxy)methyl)-1-(4-(2-oxo-1,2-dihydroquinolin-7-yloxy)butyl)piperazin-1-ium iodide |

TABLE 2-continued

| Example | Structure Formula | |
|---|---|---|
| 710 | | 4-(benzo[b]thiophen-4-yl)-1-(4-(2-oxo-1,2-dihydroquinolin-7-yloxy)butyl)-1-(((pentan-3-yloxy)carbonyloxy)methyl)piperazin-1-ium iodide |
| 711 | | 4-(benzo[b]thiophen-4-yl)-1-(benzoyloxymethyl)-1-(4-(2-oxo-1,2-dihydroquinolin-7-yloxy)butyl)piperazin-1-ium chloride |
| 712 | | 4-(benzo[b]thiophen-4-yl)-1-(4-(2-oxo-1,2-dihydroquinolin-7-yloxy)butyl)-1-((2-phenylacetoxy)methyl)piperazin-1-ium chloride |

TABLE 2-continued
| Example | Structure Formula | |
|---|---|---|
| 713 | 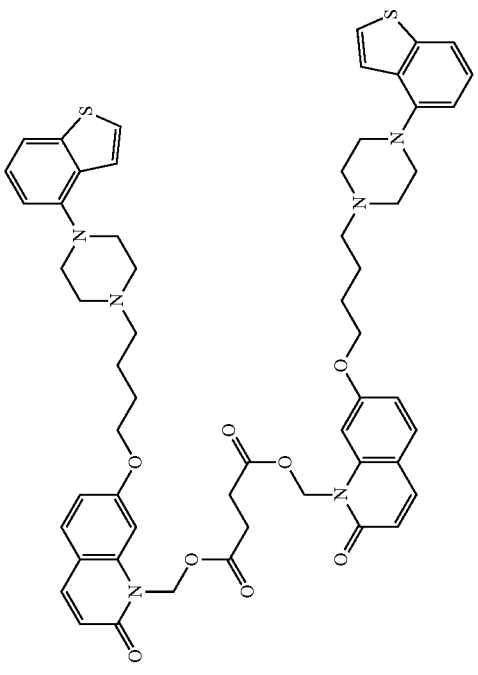 | bis((7-(4-(4-(benzo[b]thiophen-4-yl)piperazin-1-yl)butoxy)-2-oxoquinolin-1(2H)-yl)methyl) succinate |
| 714 | 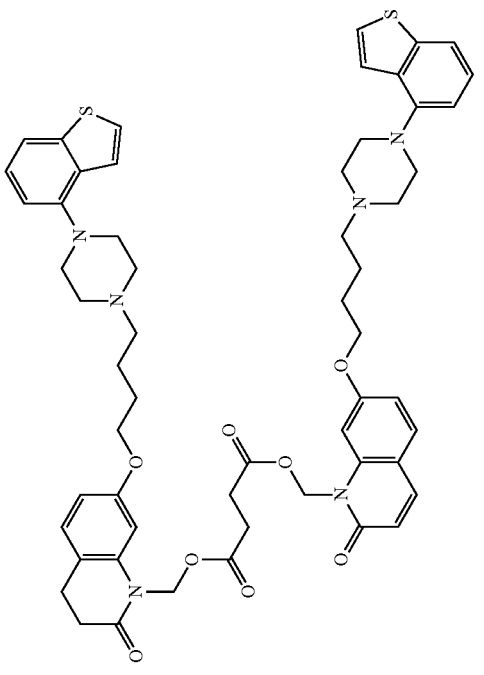 | bis((7-(4-(4-(benzo[b]thiophen-4-yl)piperazin-1-yl)butoxy)-2-oxo-3,4-dihydroquinolin-1(2H)-yl)methyl) succinate |

TABLE 2-continued

| Example | Structure Formula | |
|---|---|---|
| 715 | | bis((7-(4-(4-(benzo[b]thiophen-4-yl)piperazin-1-yl)butoxy)-2-oxoquinolin-1(2H)-yl)methyl) glutarate |
| 716 | | bis((7-(4-(4-(benzo[b]thiophen-4-yl)piperazin-1-yl)butoxy)-2-oxo-3,4-dihydroquinolin-1(2H)-yl)methyl) glutarate |

TABLE 2-continued

| Example | Structure Formula | |
|---|---|---|
| 717 | [structure] | bis((7-(4-(4-(benzo[b]thiophen-4-yl)piperazin-1-yl)butoxy)-2-oxoquinolin-1(2H)-yl)methyl) adipate |
| 718 | [structure] | bis((7-(4-(4-(benzo[b]thiophen-4-yl)piperazin-1-yl)butoxy)-2-oxo-3,4-dihydroquinolin-1(2H)-yl)methyl) adipate |

TABLE 2-continued

| Example | Structure Formula | |
|---|---|---|
| 719 | | bis((7-(4-(4-(benzo[b]thiophen-4-yl)piperazin-1-yl)butoxy)-2-oxoquinolin-1(2H)-yl)methyl) heptanedioate |
| 720 | | bis((7-(4-(4-(benzo[b]thiophen-4-yl)piperazin-1-yl)butoxy)-2-oxo-3,4-dihydroquinolin-1(2H)-yl)methyl) heptanedioate |

TABLE 2-continued
| Example | Structure Formula | |
|---|---|---|
| 721 |  | bis((7-(4-(4-(benzo[b]thiophen-4-yl)piperazin-1-yl)butoxy)-2-oxoquinolin-1(2H)-yl)methyl) octanedioate |
| 722 |  | bis((7-(4-(4-(benzo[b]thiophen-4-yl)piperazin-1-yl)butoxy)-2-oxo-3,4-dihydroquinolin-1(2H)-yl)methyl) octanedioate |

TABLE 2-continued
| Example | Structure Formula | |
|---|---|---|
| 723 |  | bis((7-(4-(4-(benzo[b]thiophen-4-yl)piperazin-1-yl)butoxy)-2-oxoquinolin-1(2H)-yl)methyl) decanedioate |
| 724 |  | bis((7-(4-(4-(benzo[b]thiophen-4-yl)piperazin-1-yl)butoxy)-2-oxo-3,4-dihydroquinolin-1(2H)-yl)methyl) decanedioate |

TABLE 2-continued

| Example | Structure Formula | |
|---|---|---|
| 725 | | bis((7-(4-(4-(benzo[b]thiophen-4-yl)piperazin-1-yl)butoxy)-2-oxoquinolin-1(2H)-yl)methyl) dodecanedioate |
| 726 | | bis((7-(4-(4-(benzo[b]thiophen-4-yl)piperazin-1-yl)butoxy)-2-oxo-3,4-dihydroquinolin-1(2H)-yl)methyl) dodecanedioate |

TABLE 2-continued

| Example | Structure Formula | |
|---|---|---|
| 727 | | bis((7-(4-(4-(benzo[b]thiophen-4-yl)piperazin-1-yl)butoxy)-2-oxoquinolin-1(2H)-yl)methyl) tetradecanedioate |
| 728 | | bis((7-(4-(4-(benzo[b]thiophen-4-yl)piperazin-1-yl)butoxy)-2-oxo-3,4-dihydroquinolin-1(2H)-yl)methyl) tetradecanedioate |

TABLE 2-continued

| Example | Structure Formula | |
|---|---|---|
| 729 | | bis((7-(4-(4-(benzo[b]thiophen-4-yl)piperazin-1-yl)butoxy)-2-oxoquinolin-1(2H)-yl)methyl) hexadecanedioate |
| 730 | | bis((7-(4-(4-(benzo[b]thiophen-4-yl)piperazin-1-yl)butoxy)-2-oxo-3,4-dihydroquinolin-1(2H)-yl)methyl) hexadecanedioate |

TABLE 2-continued

| Example | Structure Formula | |
|---|---|---|
| 731 | | bis((7-(4-(4-(benzo[b]thiophen-4-yl)piperazin-1-yl)butoxy)-2-oxoquinolin-1(2H)-yl)methyl) octadecanedioate |
| 732 | | bis((7-(4-(4-(benzo[b]thiophen-4-yl)piperazin-1-yl)butoxy)-2-oxo-3,4-dihydroquinolin-1(2H)-yl)methyl) octadecanedioate |

TABLE 2-continued
| Example | Structure Formula | |
|---|---|---|
| 733 |  | bis((7-(4-(4-(benzo[b]thiophen-4-yl)piperazin-1-yl)butoxy)-2-oxoquinolin-1(2H)-yl)methyl) icosanedioate |
| 734 | 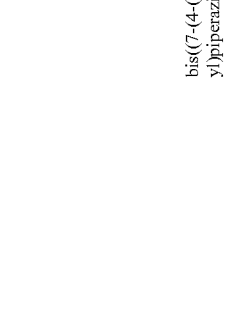 | bis((7-(4-(4-(benzo[b]thiophen-4-yl)piperazin-1-yl)butoxy)-2-oxo-3,4-dihydroquinolin-1(2H)-yl)methyl) icosanedioate |

TABLE 2-continued

| Example | Structure Formula | |
|---|---|---|
| 735 | | bis((7-(4-(4-(benzo[b]thiophen-4-yl)piperazin-1-yl)butoxy)-2-oxoquinolin-1(2H)-yl)methyl) docosanedioate |
| 736 | | bis((7-(4-(4-(benzo[b]thiophen-4-yl)piperazin-1-yl)butoxy)-2-oxo-3,4-dihydroquinolin-1(2H)-yl)methyl) docosanedioate |

TABLE 2-continued

| Example | Structure Formula | |
|---|---|---|
| 737 | | bis((7-(4-(4-(benzo[b]thiophen-4-yl)piperazin-1-yl)butoxy)quinolin-2-yloxy)methyl) succinate |
| 738 | | bis((7-(4-(4-(benzo[b]thiophen-4-yl)piperazin-1-yl)butoxy)quinolin-2-yloxy)methyl) glutarate |
| 739 | | bis((7-(4-(4-(benzo[b]thiophen-4-yl)piperazin-1-yl)butoxy)quinolin-2-yloxy)methyl) adipate |

TABLE 2-continued

| Example | Structure Formula | |
|---|---|---|
| 740 | | bis((7-(4-(4-(benzo[b]thiophen-4-yl)piperazin-1-yl)butoxy)quinolin-2-yloxy)methyl) heptanedioate |
| 741 | | bis((7-(4-(4-(benzo[b]thiophen-4-yl)piperazin-1-yl)butoxy)quinolin-2-yloxy)methyl) octanedioate |
| 742 | | bis((7-(4-(4-(benzo[b]thiophen-4-yl)piperazin-1-yl)butoxy)quinolin-2-yloxy)methyl) decanedioate |

TABLE 2-continued

| Example | Structure Formula | |
|---|---|---|
| 743 | | bis((7-(4-(4-(benzo[b]thiophen-4-yl)piperazin-1-yl)butoxy)quinolin-2-yloxy)methyl) dodecanedioate |
| 744 | | bis((7-(4-(4-(benzo[b]thiophen-4-yl)piperazin-1-yl)butoxy)quinolin-2-yloxy)methyl) tetradecanedioate |
| 745 | | bis((7-(4-(4-(benzo[b]thiophen-4-yl)piperazin-1-yl)butoxy)quinolin-2-yloxy)methyl) hexadecanedioate |

TABLE 2-continued
| Example | Structure Formula | |
|---|---|---|
| 746 | 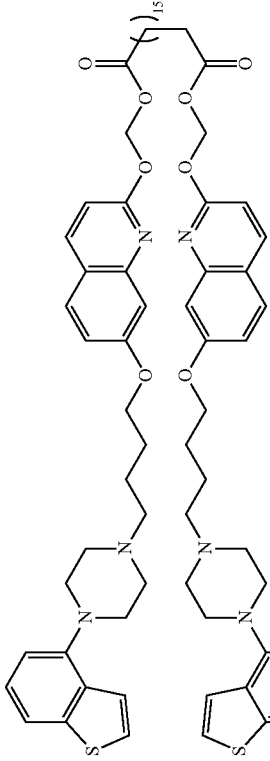 | bis((7-(4-(4-(benzo[b]thiophen-4-yl)piperazin-1-yl)butoxy)quinolin-2-yl)oxy)methyl) octadecanedioate |
| 747 | 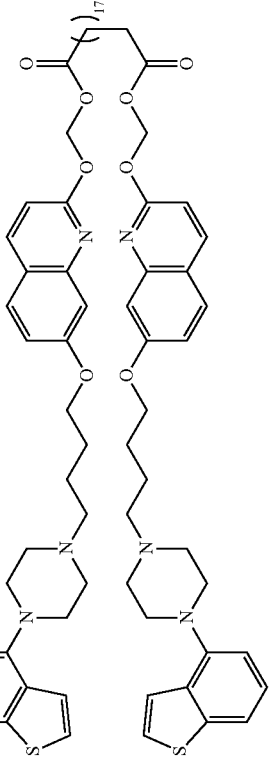 | bis((7-(4-(4-(benzo[b]thiophen-4-yl)piperazin-1-yl)butoxy)quinolin-2-yl)oxy)methyl) icosanedioate |
| 748 | 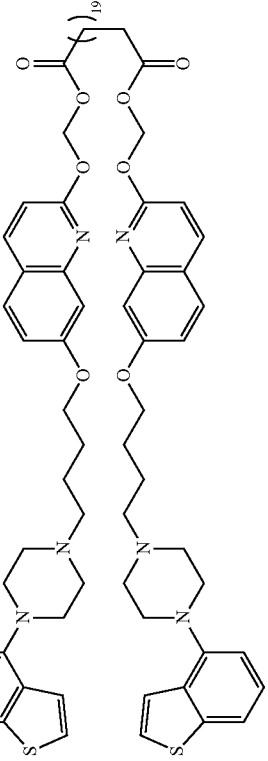 | bis((7-(4-(4-(benzo[b]thiophen-4-yl)piperazin-1-yl)butoxy)quinolin-2-yl)oxy)methyl) docosanedioate |

TABLE 2-continued

| Example | Structure Formula | |
|---|---|---|
| 749 | | bis(7-(4-(4-(benzo[b]thiophen-4-yl)piperazin-1-yl)butoxy)quinolin-2-yl) succinate |
| 750 | | bis(7-(4-(4-(benzo[b]thiophen-4-yl)piperazin-1-yl)butoxy)quinolin-2-yl) glutarate |
| 751 | | bis(7-(4-(4-(benzo[b]thiophen-4-yl)piperazin-1-yl)butoxy)quinolin-2-yl) adipate |

TABLE 2-continued

| Example | Structure Formula | |
|---|---|---|
| 752 | | bis(7-(4-(4-(benzo[b]thiophen-4-yl)piperazin-1-yl)butoxy)quinolin-2-yl) heptanedioate |
| 753 | | bis(7-(4-(4-(benzo[b]thiophen-4-yl)piperazin-1-yl)butoxy)quinolin-2-yl) octanedioate |
| 754 | | bis(7-(4-(4-(benzo[b]thiophen-4-yl)piperazin-1-yl)butoxy)quinolin-2-yl) decanedioate |

TABLE 2-continued
| Example | Structure Formula | |
|---|---|---|
| 755 |  | bis(7-(4-(4-(benzo[b]thiophen-4-yl)piperazin-1-yl)butoxy)quinolin-2-yl) dodecanedioate |
| 756 |  | bis(7-(4-(4-(benzo[b]thiophen-4-yl)piperazin-1-yl)butoxy)quinolin-2-yl) tetradecanedioate |
| 757 |  | bis(7-(4-(4-(benzo[b]thiophen-4-yl)piperazin-1-yl)butoxy)quinolin-2-yl) hexadecanedioate |

TABLE 2-continued

| Example | Structure Formula | |
|---|---|---|
| 758 | | bis(7-(4-(4-(benzo[b]thiophen-4-yl)piperazin-1-yl)butoxy) quinolin-2-yl) octadecanedioate |
| 759 | | bis(7-(4-(4-(benzo[b]thiophen-4-yl)piperazin-1-yl)butoxy)quinolin-2-yl) icosanedioate |
| 760 | | bis(7-(4-(4-(benzo[b]thiophen-4-yl)piperazin-1-yl)butoxy)quinolin-2-yl) docosanedioate |

Example A

Synthesis of deuteride of 7-[4-(4-benzo[b]thiophen-4-yl-piperazin-1-yl)-butoxy]-1H-quinolin-2-one

A-1: Synthesis of 7-[4-(4-benzo[b]thiophen-4-yl-piperazin-1-yl)-butoxy-1,1,2,2,3,3,4,4-$d_8$]-1H-quinolin-2-one

Synthesis Method 1

Step 1: Synthesis of 2-benzyloxy-7-(4-bromobutoxy-1,1,2,2,3,3,4,4-$d_8$)quinoline

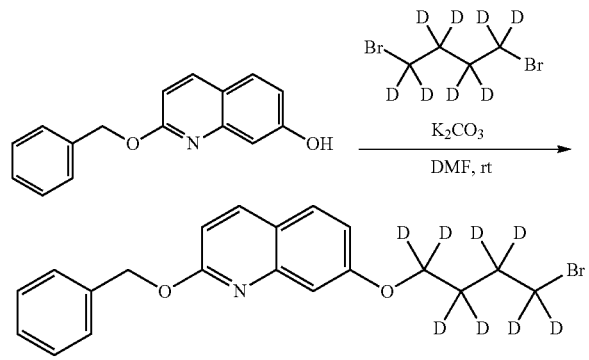

To a mixture of 2-benzyloxy-7-hydroxy quinoline (2.52 g) and potassium carbonate (1.67 g) in dimethylformamide (25 ml) was added 1,4-dibromobutane-$d_8$ (99.6 atom % D: 2.4 ml), and the mixture was stirred at room temperature overnight. To the reaction mixture was added water, ethyl acetate, the insoluble material was filtered off, and the filtrate was partitioned, washed with water, and dried over sodium sulfate. The solvent was evaporated under reduced pressure. The residue was purified by silica gel column chromatography (n-hexane:ethyl acetate=10:0→9:1) to give 2-benzyloxy-7-(4-bromobutoxy-1,1,2,2,3,3,4,4-$d_8$)quinoline (3.14 g).

2-benzyloxy-7-(4-bromobutoxy-1,1,2,2,3,3,4,4-$d_8$)quinoline: white powder, $^1$H-NMR (CDCl$_3$) δ: 5.52 (2H, s), 6.81 (1H, d, J=8.7 Hz), 7.02 (1H, dd, J=8.8, 2.5 Hz), 7.21 (1H, d, J=2.5 Hz), 7.29-7.47 (3H, m), 7.49-7.56 (2H, m), 7.60 (1H, d, J=8.8 Hz), 7.91 (1H, d, J=8.7 Hz)

Step 2: Synthesis of 2-benzyloxy-7-[4-(4-benzo[b]thiophen-4-yl-piperazin-1-yl)-butoxy-1,1,2,2,3,3,4,4-$d_8$]quinoline

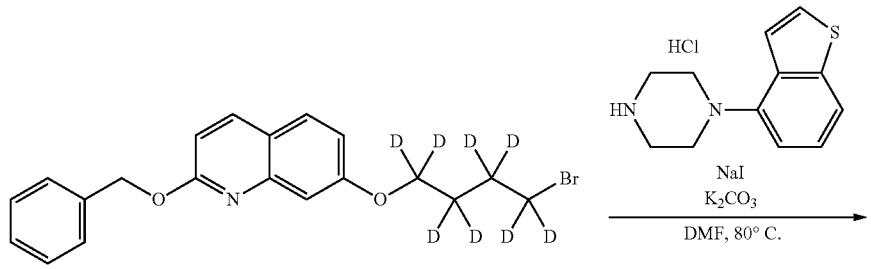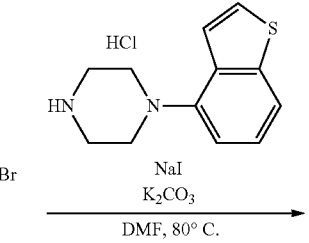

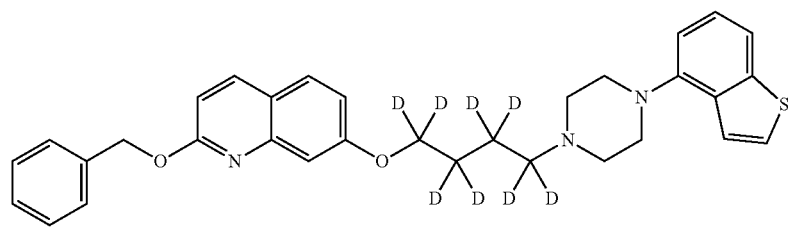

A mixture of 2-benzyloxy-7-(4-bromobutoxy-1,1,2,2,3,3,4,4-d₈)quinoline (3.14 g), 1-benzothiophene-4-piperazine hydrochloride (2.43 g), sodium iodide (1.31 g) and potassium carbonate (2.64 g) in dimethylformamide (60 ml) was stirred at 80° C. for 5 hr. Water was added to the reaction mixture, and the mixture was extracted with ethyl acetate, washed with water, and dried over sodium sulfate. The solvent was evaporated under reduced pressure and the residue was purified by silica gel column chromatography (n-hexane:ethyl acetate=7:3→5:5) to give 2-benzyloxy-7-[4-(4-benzo[b]thiophen-4-yl-piperazin-1-yl)-butoxy-1,1,2,2,3,3,4,4-d₈]quinoline (3.73 g).

2-benzyloxy-7-[4-(4-benzo[b]thiophen-4-yl-piperazin-1-yl)-butoxy-1,1,2,2,3,3,4,4-d₈]quinoline: pale-yellow amorphous solid, ¹H-NMR (CDCl₃) δ: 2.64-2.83 (4H, m), 3.14-3.25 (4H, m), 5.53 (2H, s), 6.81 (1H, d, J=8.8 Hz), 6.89 (1H, d, J=7.6 Hz), 7.03-7.08 (1H, m), 7.25-7.49 (7H, m), 7.50-7.63 (4H, m), 7.91 (1H, d, J=8.8 Hz)

Step 3: Synthesis of 7-[4-(4-benzo[b]thiophen-4-yl-piperazin-1-yl)-butoxy-1,1,2,2,3,3,4,4-d₈]-1H-quinolin-2-one

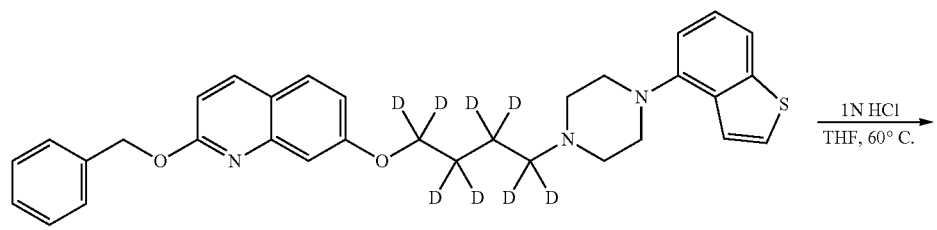

A mixture of 2-benzyloxy-7-[4-(4-benzo[b]thiophen-4-yl-piperazin-1-yl)-butoxy-1,1,2,2,3,3,4,4-d₈]quinoline (3.73 g) and 1N hydrochloric acid (35.1 ml) in tetrahydrofuran (60 ml) was stirred at 60° C. for 4 hr, and ice-cooled. Ice water was added, and the mixture was stirred. The precipitated solid was collected by filtration, washed with water and dried under reduced pressure. To a mixture of the obtained powder in ethanol (70 ml) was added under ice-cooling 1N sodium hydroxide to basify the mixture. The solvent was evaporated under reduced pressure and the residue was washed with water, and recrystallized from a mixture of ethanol and water to give 7-[4-(4-benzo[b]thiophen-4-yl-piperazin-1-yl)-butoxy-1,1,2,2,3,3,4,4-d₈]-1H-quinolin-2-one (2.29 g).

7-[4-(4-benzo[b]thiophen-4-yl-piperazin-1-yl)-butoxy-1,1,2,2,3,3,4,4-d₈]-1H-quinolin-2-one: white powder, ¹H-NMR (DMSO-d₆) δ: 2.54-2.67 (4H, m), 2.91-3.15 (4H, m), 6.29 (1H, d, J=9.5 Hz), 6.75-6.83 (2H, m), 6.88 (1H, d, J=7.6 Hz), 7.21-7.30 (1H, m), 7.39 (1H, d, J=5.5 Hz), 7.50-7.66 (2H, m), 7.69 (1H, d, J=5.5 Hz), 7.80 (1H, d, J=9.5 Hz), 11.58 (1H, s)

Synthesis Method 2

Step 1: Synthesis of 7-(4-bromobutoxy-1,1,2,2,3,3,4,4-d₈)-1H-quinolin-2-one

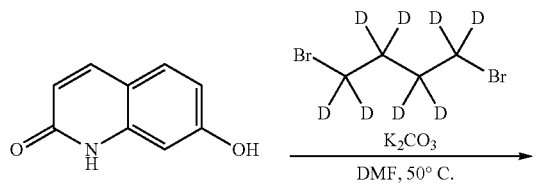

-continued

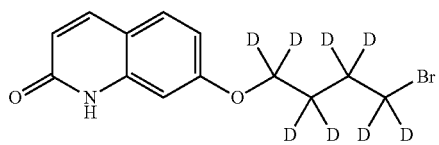

To a mixture of 7-hydroxy-1H-quinolin-2-one [70500-72-0] (0.72 g) and potassium carbonate (0.68 g) in dimethylformamide (20 ml) was added 1,4-dibromobutane-d₈ (99.6 atom % D: 3 g), and the mixture was stirred at 50° C. for 5 hr. Water was added to the reaction mixture, and the mixture was extracted with ethyl acetate, washed with water, and dried over sodium sulfate. The solvent was evaporated under reduced pressure and the residue was purified by silica gel column chromatography (dichloromethane:methanol=100:1) to give 7-(4 bromobutoxy-1,1,2,2,3,3,4,4-d₈)-1H-quinolin-2-one (1.1 g).

7-(4-bromobutoxy-1,1,2,2,3,3,4,4-d₈)-1H-quinolin-2-one: white powder like, ¹H-NMR (CDCl₃) δ: 6.56 (1H, d, J=9.4 Hz), 6.78-6.84 (2H, m), 7.45 (1H, d, J=8.6 Hz), 7.74 (1H, d, J=9.4 Hz), 12.33 (1H, brs).

Step 2: Synthesis of 7-[4-(4-benzo[b]thiophen-4-yl-piperazin-1-yl)-butoxy-1,1,2,2,3,3,4,4-d₈]-1H-quinolin-2-one

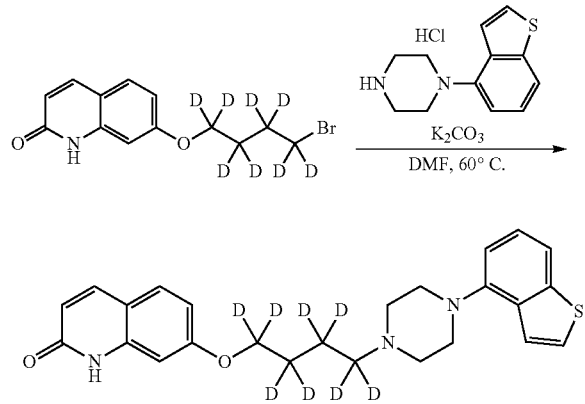

A mixture of 7-(4-bromobutoxy-1,1,2,2,3,3,4,4-d₈)-1H-quinolin-2-one (0.4 g), 1-benzothiophene-4-piperazine hydrochloride (0.37 g), potassium carbonate (0.45 g) and dimethylformamide (20 ml) was stirred at 60° C. for 6 hr. Water was added to the reaction mixture, and the mixture was extracted with ethyl acetate, washed with water, and dried over sodium sulfate. The solvent was evaporated under reduced pressure and the residue was purified by silica gel column chromatography (dichloromethane:methanol=30:1) to give 7-[4-(4-benzo[b]thiophen-4-yl-piperazin-1-yl)-butoxy-1,1,2,2,3,3,4,4-d₈]-1H-quinolin-2-one (0.3 g).

7-[4-(4-Benzo[b]thiophen-4-yl-piperazin-1-yl)-butoxy-1,1,2,2,3,3,4,4-d₈]-1H-quinolin-2-one same as that synthesized in synthesis method 1 was obtained.

white powder m.p. 177-179° C. (recrystallized from EtOH)

A-2: Synthesis of 7-[4-(4-benzo[b]thiophen-4-yl-piperazin-1-yl-2,2,3,3,5,5,6,6-d₈)-butoxy-1,1,2,2,3,3,4,4-d₈]-1H-quinolin-2-one Step 1: Synthesis of tert-butyl 4-(benzo[b]thiophen-4-yl)piperazine-2,2,3,3,5,5,6,6-d₈-1-carboxylate

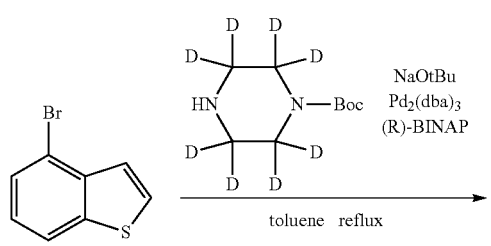

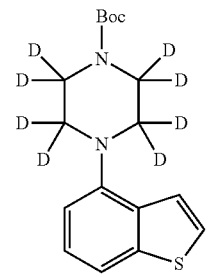

A mixture of 4-bromo-benzo[b]thiophene [5118-13-8] (0.55 g), tert-butyl 1-piperazine-2,2,3,3,5,5,6,6-d₈-carboxylate (98.3 atom % D: 0.5 g), sodium t-butoxide (0.25 g), (R)-(+)-BINAP (30 mg), tris(dibenzylideneacetone)dipalladium(0) (30 mg) and toluene (20 ml) was heated under reflux under an argon atmosphere for 3 hr. Water was poured into the reaction mixture, and the mixture was extracted with ethyl acetate, washed with water, and dried over magnesium sulfate. The solvent was evaporated under reduced pressure and the residue was purified by silica gel column chromatography (ethyl acetate:n-hexane=1:100) to give tert-butyl 4-(benzo[b]thiophen-4-yl)piperazine-2,2,3,3,5,5,6,6-d₈-1-carboxylate (0.41 g).

tert-butyl 4-(benzo[b]thiophen-4-yl)piperazine-2,2,3,3,5,5,6,6-d₈-1-carboxylate:
yellow powder
¹H-NMR (CDCl₃) δ: 1.50 (9H, s), 3.03-3.09 (0.06H, br), 3.59-3.65 (0.06H, br), 6.87 (1H, dd, J=0.8, 7.7 Hz), 7.28 (1H, t, J=7.8 Hz), 7.41 (2H, s), 7.57 (1H, d, J=8.0 Hz).
Confirmed by ¹H-NMR (CDCl₃): at least 98 atom % D.

Step 2: Synthesis of 1-benzo[b]thiophen-4-yl-piperazine-2,2,3,3,5,5,6,6-d₈

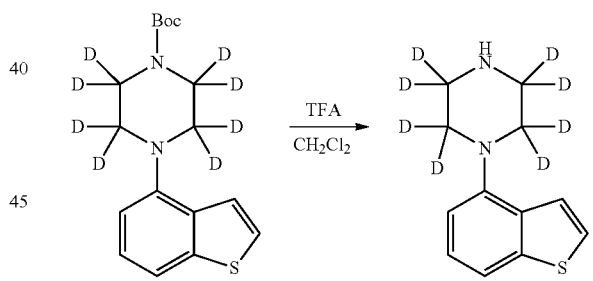

To a solution of tert-butyl 4-(benzo[b]thiophen-4-yl)piperazine-2,2,3,3,5,5,6,6-d₈-1-carboxylate (0.57 g) in dichloromethane (5 ml) was added trifluoroacetic acid (1 ml) and the mixture was stirred at room temperature for 3 hr. Water was poured into the reaction mixture, alkalified with aqueous sodium hydroxide solution, and the mixture was extracted with dichloromethane, washed with water, and dried over magnesium sulfate. The solvent was evaporated under reduced pressure and the residue was purified by silica gel column chromatography (basic silica gel, ethyl acetate:methanol=20:1) to give 1-benzo[b]thiophen-4-yl-piperazine-2,2,3,3,5,5,6,6-d₈ (0.31 g).

1-benzo[b]thiophen-4-yl-piperazine-2,2,3,3,5,5,6,6-d₈:
oil brown
¹H-NMR (CDCl₃) δ: 3.06-3.10 (0.13H, br), 6.88 (1H, dd, J=0.8, 7.6 Hz), 7.27 (1H, t, J=7.8 Hz), 7.38 (1H, d, J=5.4 Hz), 7.42 (1H, dd, J=0.7, 5.5 Hz), 7.54 (1H, d, J=8.1 Hz).
Confirmed by ¹H-NMR (CDCl₃): at least 98 atom % D.

Step 3: Synthesis of 7-[4-(4-benzo[b]thiophen-4-yl-piperazin-1-yl-2,2,3,3,5,5,6,6-d$_8$)-butoxy-1,1,2,2,3,3,4,4-d$_8$]-1H-quinolin-2-one

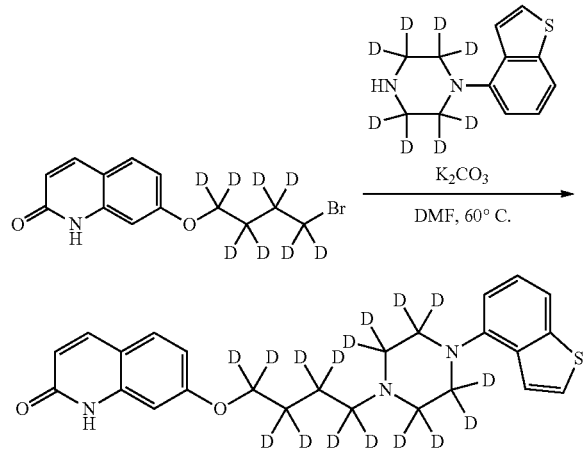

A mixture of 7-(4-bromobutoxy-1,1,2,2,3,3,4,4-d$_8$)-1H-quinolin-2-one (633 mg) obtained in Example A-1, synthesis method 2, step 1,1-benzo[b]thiophen-4-yl-piperazine-2,2,3,3,5,5,6,6-d$_8$ (471 mg) obtained in this Example, step 2, potassium carbonate (374 mg) and dimethylformamide (20 ml) was stirred at 60° C. for 6 hr. Water was added to the reaction mixture, and the mixture was extracted with ethyl acetate, washed with water, and dried over sodium sulfate. The solvent was evaporated under reduced pressure and the residue was purified by silica gel column chromatography (dichloromethane:methanol=30:1) to give 7-[4-(4-benzo[b]thiophen-4-yl-piperazin-1-yl-2,2,3,3,5,5,6,6-d$_8$)-butoxy-1,1,2,2,3,3,4,4-d$_8$]-1H-quinolin-2-one (0.45 g).

7-[4-(4-benzo[b]thiophen-4-yl-piperazin-1-yl-2,2,3,3,5,5,6,6-d$_8$)-butoxy-1,1,2,2,3,3,4,4-d$_8$]-1H-quinolin-2-one: yellow powder m.p. 176-178° C. (recrystallized from EtOH)

$^1$H-NMR (CDCl$_3$) δ: 2.64-2.72 (0.06H, m), 3.02-3.20 (0.06H, m), 6.55 (1H, d, J=9.4 Hz), 6.79-6.86 (2H, m), 6.89 (1H, dd, J=0.7, 7.6 Hz), 7.26 (1H, t, J=7.8 Hz), 7.36-7.46 (3H, m), 7.54 (1H, d, J=8.0 Hz), 7.72 (1H, d, J=9.4 Hz), 12.34 (1H, brs).

A-3: Synthesis of 7-[4-(4-benzo[b]thiophen-4-yl-piperazin-1-yl-2,2,3,3,5,5,6,6-d$_8$)-butoxy]-1H-quinolin-2-one

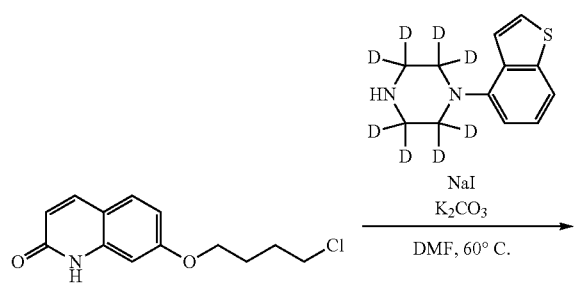

A mixture of 7-(4-chlorobutoxy)-1H-quinolin-2-one (340 mg), 1-benzo[b]thiophen-4-yl-piperazine-2,2,3,3,5,5,6,6-d$_8$ (310 mg) obtained in Example A-2, step 2, sodium iodide (220 mg), potassium carbonate (240 mg) and dimethylformamide (10 ml) was stirred at 60° C. for 6 hr. Water was added to the reaction mixture, and the mixture was extracted with ethyl acetate, washed with water, and dried over sodium sulfate. The solvent was evaporated under reduced pressure and the residue was purified by silica gel column chromatography (dichloromethane:methanol=30:1) to give 7-[4-(4-benzo[b]thiophen-4-yl-piperazin-1-yl-2,2,3,3,5,5,6,6-d$_8$)-butoxy]-1H-quinolin-2-one (0.31 g).

7-[4-(4-benzo[b]thiophen-4-yl-piperazin-1-yl-2,2,3,3,5,5,6,6-d$_8$)-butoxy]-1H-quinolin-2-one: yellow powder m.p. 175.5-177° C. (recrystallized from EtOH)

$^1$H-NMR (CDCl$_3$) δ: 1.70-1.84 (2H, m), 1.84-1.96 (2H, m), 2.54 (2H, t, J=7.5 Hz), 2.66-2.72 (0.06H, m), 3.14-3.18 (0.06H, m), 4.12 (2H, t, J=6.2 Hz), 6.54 (1H, d, J=9.4 Hz), 6.79-6.86 (2H, m), 6.89 (1H, dd, J=0.6, 7.6 Hz), 7.26 (1H, t, J=7.9 Hz), 7.36-7.48 (3H, m), 7.54 (1H, d, J=8.0 Hz), 7.72 (1H, d, J=9.4 Hz), 12.27 (1H, brs).

A-4: Synthesis of 7-[4-(4-benzo[b]thiophen-4-yl-piperazin-1-yl-2,2,3,3,5,5,6,6-d$_8$)-butoxy]-1H-quinolin-2-one-3,4,5,6,8-d$_8$ Step 1: Synthesis of 7-(4-bromobutoxy)-1H-quinolin-2-one-3,4,5,6,8-d$_8$

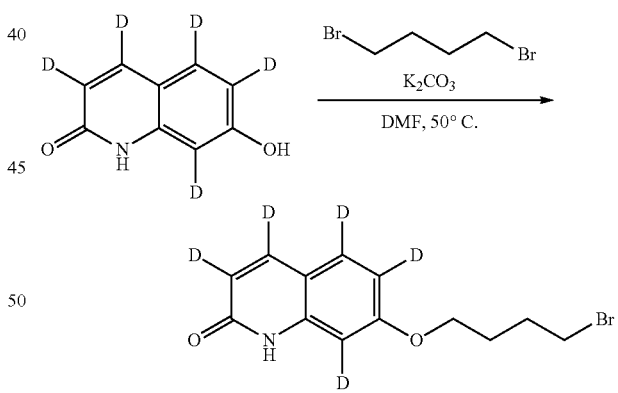

To a mixture of 7-hydroxy-1H-quinolin-2-one-3,4,5,6,8-d$_5$ (99 atom % D: 3 g) obtained by a deuteration reaction (Org. Lett. 2004, 6, 1485.; Bull. Chem. Soc. Jpn. 2008, 81, 278.) of 7-hydroxy-1H-quinolin-2-one [70500-72-0] and potassium carbonate (3 g) in dimethylformamide (120 ml) was added 1,4-dibromobutane (6.5 ml), and the mixture was stirred at 50° C. for 4 hr. Water was added to the reaction mixture, and the mixture was extracted with ethyl acetate, washed with water, and dried over sodium sulfate. The solvent was evaporated under reduced pressure and the residue was purified by silica gel column chromatography (dichloromethane:methanol=100:1) to give 7-(4-bromobutoxy)-1H-quinolin-2-one-3,4,5,6,8-d$_5$ (3.45 g).

7-(4-bromobutoxy)-1H-quinolin-2-one-3,4,5,6,8-$d_5$: white powder like $^1$H-NMR (CDCl$_3$) δ ppm: 1.94-2.05 (2H, m), 2.05-2.15 (2H, m), 3.51 (2H, t, J=6.5 Hz), 4.10 (2H, t, J=6.0 Hz), 6.55 (0.01H, s), 6.79-6.81 (2H, m), 7.52 (0.008H, s), 7.73 (0.008H, s), 11.89 (1H, brs).

Step 2: Synthesis of 7-[4-(4-benzo[b]thiophen-4-yl-piperazin-1-yl-2,2,3,3,5,5,6,6-$d_8$)-butoxy]-1H-quinolin-2-one-3,4,5,6,8-$d_5$

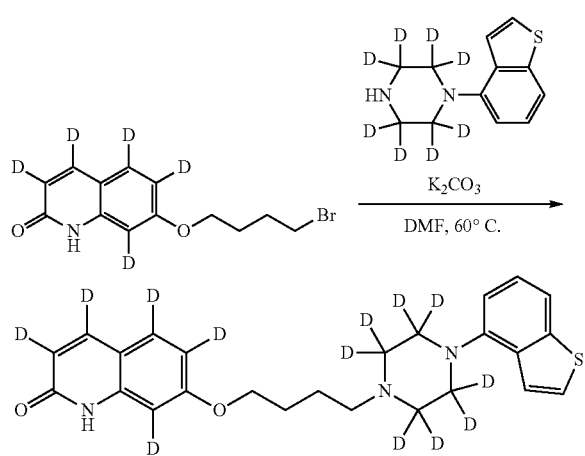

A mixture of 7-(4-bromobutoxy)-1H-quinolin-2-one-3,4,5,6,8-$d_5$ (0.6 g), 1-benzo[b]thiophen-4-yl-piperazine-2,2,3,3,5,5,6,6-$d_8$ (0.5 g), potassium carbonate (360 mg) and dimethylformamide (20 ml) was stirred at 60° C. for 5 hr. Water was added to the reaction mixture, and the mixture was extracted with ethyl acetate, washed with water, and dried over sodium sulfate. The solvent was evaporated under reduced pressure and the residue was purified by silica gel column chromatography (dichloromethane:methanol=30:1) to give 7-[4-(4-benzo[b]thiophen-4-yl-piperazin-1-yl-2,2,3,3,5,5,6,6-$d_8$)-butoxy]-1H-quinolin-2-one-3,4,5,6,8-$d_5$ (0.45 g).

7-[4-(4-benzo[b]thiophen-4-yl-piperazin-1-yl-2,2,3,3,5,5,6,6-$d_8$)-butoxy]-1H-quinolin-2-one-3,4,5,6,8-$d_5$: white powder m.p. 175.5-177.5° C. (recrystallized from EtOH)

$^1$H-NMR (CDCl$_3$) δ ppm: 1.70-1.84 (2H, m), 1.80-1.96 (2H, m), 2.54 (2H, t, J=7.4 Hz), 2.66-2.72 (<0.07H, br), 3.14-3.20 (<0.06H, br), 4.12 (2H, t, J=6.2 Hz), 6.54 (<0.008H, s), 6.82 (<0.025H, d, J=5.7 Hz), 6.89 (1H, dd, J=0.6, 7.7 Hz), 7.26 (1H, t, J=7.9 Hz), 7.38 (1H, d, J=5.5 Hz), 7.42 (1H, d, J=5.9 Hz), 7.54 (1H, d, J=8.0 Hz), 7.72 (<0.01H, s), 12.10 (1H, brs).

A-5: Synthesis of 7-[4-(4-benzo[b]thiophen-4-yl-piperazin-1-yl)-butoxy]-1H-quinolin-2-one-3,4,5,6,8-$d_5$

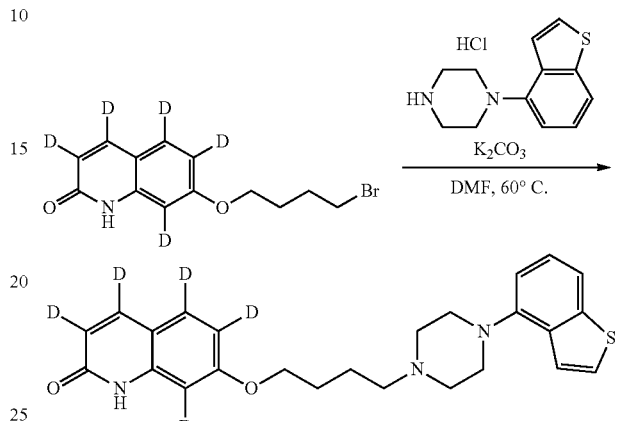

A mixture of 7-(4-bromobutoxy)-1H-quinolin-2-one-3,4,5,6,8-$d_5$ (0.6 g) obtained in Example A-4, step 1,1-benzothiophene-4-piperazine hydrochloride (0.56 g), potassium carbonate (690 mg) and dimethylformamide (20 ml) was stirred at 60° C. for 6 hr. Water was added to the reaction mixture, and the mixture was extracted with ethyl acetate, washed with water, and dried over sodium sulfate. The solvent was evaporated under reduced pressure and the residue was purified by silica gel column chromatography (dichloromethane:methanol=30:1) to give 7-[4-(4-benzo[b]thiophen-4-yl-piperazin-1-yl)-butoxy]-1H-quinolin-2-one-3,4,5,6,8-$d_5$ (0.5 g).

7-[4-(4-benzo[b]thiophen-4-yl-piperazin-1-yl)-butoxy]-1H-quinolin-2-one-3,4,5,6,8-$d_5$: white powder m.p. 177-179° C. (recrystallized from EtOH)

$^1$H-NMR (CDCl$_3$) δ ppm: 1.70-1.85 (2H, m), 1.85-1.95 (2H, m), 2.54 (2H, t, J=7.4 Hz), 2.66-2.82 (4H, br), 3.14-3.28 (4H, br), 4.08-4.12 (2H, m), 6.54 (<0.01H, s), 6.83 (<0.02H, d, J=10.3 Hz), 6.89 (1H, d, J=7.7 Hz), 7.26 (1H, t, J=7.8 Hz), 7.36 (1H, d, J=5.5 Hz), 7.42 (1H, dd, J=0.6, 5.5 Hz), 7.54 (1H, d, J=8.0 Hz), 7.72 (<0.01H, s), 12.24 (1H, brs).

A-6: Synthesis of 7-[4-(4-benzo[b]thiophen-4-yl-5,7-$d_2$-piperazin-1-yl)-butoxy]-1H-quinolin-2-one-3,4,5,6,8-$d_5$

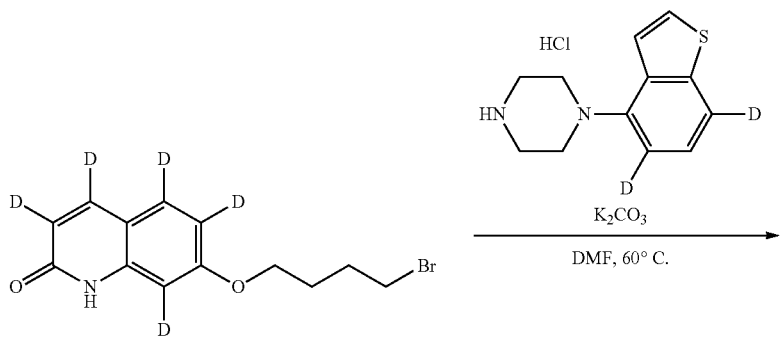

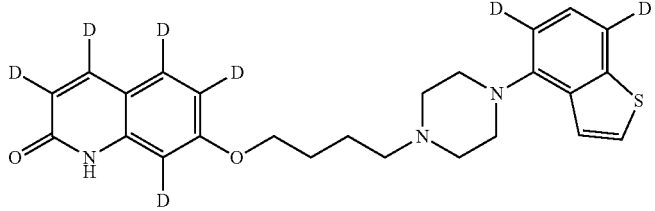

A mixture of 7-(4-bromobutoxy)-1H-quinolin-2-one-3,4,5,6,8-$d_5$ (0.6 g) obtained in Example A-4, step 1, 1-benzo[b]thiophen-4-yl-5,7-$d_2$-piperazine hydrochloride (0.56 g) obtained by a deuteration reaction (Org. Lett. 2004, 6, 1485.; Bull. Chem. Soc. Jpn. 2008, 81, 278.) of 1-benzothiophene-4-piperazine hydrochloride, potassium carbonate (690 mg) and dimethylformamide (20 ml) was stirred at 60° C. for 5 hr. Water was added to the reaction mixture, and the mixture was extracted with ethyl acetate, washed with water, and dried over sodium sulfate. The solvent was evaporated under reduced pressure and the residue was purified by silica gel column chromatography (dichloromethane:methanol=30:1) to give 7-[4-(4-benzo[b]thiophen-4-yl-5,7-$d_2$-piperazin-1-yl)-butoxy]-1H-quinolin-2-one-3,4,5,6,8-$d_5$ (0.42 g).

7-[4-(4-benzo[b]thiophen-4-yl-5,7-$d_2$-piperazin-1-yl)-butoxy]-1H-quinolin-2-one-3,4,5,6,8-$d_5$: white powder m.p. 176.5-178.5° C. (recrystallized from EtOH)

$^1$H-NMR (CDCl$_3$) δ ppm: 1.70-1.98 (4H, m), 2.54 (2H, t, J=7.4 Hz), 2.66-2.80 (4H, br), 3.14-3.26 (4H, br), 4.12 (2H, t, J=6.1 Hz), 6.54 (<0.01H, s), 6.83 (<0.02H, d, J=10.0 Hz), 6.89 (<0.01H, d, J=7.7 Hz), 7.08 (<0.02H, m), 7.25-7.28 (1H, m), 7.38 (0.89H, d, J=5.5 Hz), 7.42 (1H, d, J=5.5 Hz), 7.54 (0.06H, d, J=8.1 Hz), 7.72 (<0.01H, s), 12.23 (1H, brs).

A-7: Synthesis of 7-[4-(4-benzo[b]thiophen-4-yl-piperazin-1-yl)-butoxy-1,1,2,2,3,3,4,4-$d_8$]-1H-quinolin-2-one-3,4,5,6,8-$d_5$ step 1: Synthesis of 7-(4-bromobutoxy-1,1,2,2,3,3,4,4-$d_8$)-1H-quinolin-2-one-3,4,5,6,8-$d_5$

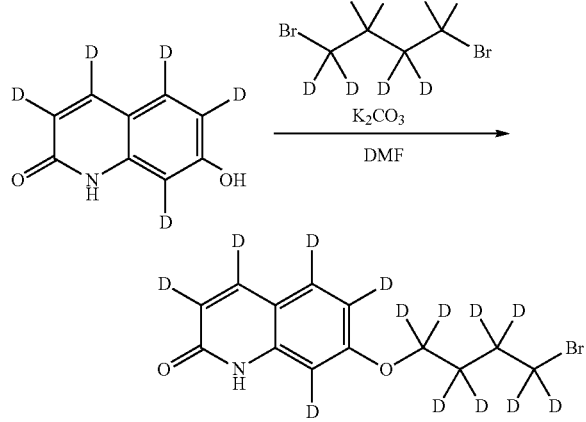

To a mixture of 7-hydroxy-1H-quinolin-2-one-3,4,5,6,8-$d_5$ (99 atom % D: 1.65 g) obtained by a deuteration reaction (Org. Lett. 2004, 6, 1485.; Bull. Chem. Soc. Jpn. 2008, 81, 278.) of 7-hydroxy-1H-quinolin-2-one [70500-72-0] and potassium carbonate (1.51 g) in dimethylformamide (40 ml) was added 1,4-dibromobutane-$d_8$ (99.6 atom % D: 5.55 g), and the mixture was stirred at 50° C. for 4 hr. Water was added to the reaction mixture, and the mixture was extracted with ethyl acetate, washed with water, and dried over sodium sulfate. The solvent was evaporated under reduced pressure and the residue was purified by silica gel column chromatography (dichloromethane:methanol=100:1) to give 7-(4-bromobutoxy-1,1,2,2,3,3,4,4-$d_8$)-1H-quinolin-2-one-3,4,5,6,8-$d_5$ (1.1 g).

7-(4-bromobutoxy-1,1,2,2,3,3,4,4-$d_8$)-1H-quinolin-2-one-3,4,5,6,8-$d_5$: white powder like, $^1$H-NMR (CDCl$_3$) δ ppm: 6.55 (0.008H, s), 6.81 (0.021H, d, J=9.6 Hz), 7.45 (0.008H, s), 7.74 (0.008H, s), 12.28 (1H, brs).

Step 2: Synthesis of 7-[4-(4-benzo[b]thiophen-4-yl-piperazin-1-yl)-butoxy-1,1,2,2,3,3,4,4-$d_8$]-1H-quinolin-2-one-3,4,5,6,8-$d_5$

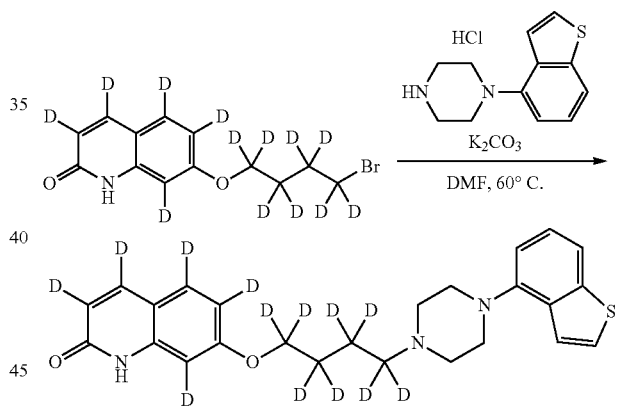

A mixture of 7-(4-bromobutoxy-1,1,2,2,3,3,4,4-$d_8$)-1H-quinolin-2-one-3,4,5,6,8-$d_5$ (0.5 g) obtained in this Example, step 1,1-benzothiophene-4-piperazine hydrochloride (0.45 g), potassium carbonate (0.56 g) and dimethylformamide (20 ml) was stirred at 60° C. for 6 hr. Water was added to the reaction mixture, and the mixture was extracted with ethyl acetate, washed with water, and dried over sodium sulfate. The solvent to was evaporated under reduced pressure and the residue was purified by silica gel column chromatography (dichloromethane:methanol=30:1) to give 7-[4-(4-benzo[b]thiophen-4-yl-piperazin-1-yl)-butoxy-1,1,2,2,3,3,4,4-$d_8$]-1H-quinolin-2-one-3,4,5,6,8-$d_5$ (0.24 g).

7-[4-(4-benzo[b]thiophen-4-yl-piperazin-1-yl)-butoxy-1,1,2,2,3,3,4,4-$d_8$]-1H-quinolin-2-one-3,4,5,6,8-$d_5$: white powder m.p. 176-177.5° C. (recrystallized from EtOH)

$^1$H-NMR (CDCl$_3$) δ ppm: 2.60-2.84 (4H, br), 3.10-3.28 (4H, br), 6.54 (<0.007H, s), 6.82 (<0.02H, d, J=6.0 Hz), 6.89 (1H, dd, J=0.5, 7.6 Hz), 7.27 (1H, t, J=7.8 Hz), 7.38 (1H, d, J=5.6 Hz), 7.42 (1H, dd, J=0.5, 5.6 Hz), 7.54 (1H, d, J=8.0 Hz), 7.72 (<0.009H, s), 12.13 (1H, brs).

A-8: Synthesis of 7-[4-(4-benzo[b]thiophen-4-yl-5,7-d$_2$-piperazin-1-yl)-butoxy]-1H-quinolin-2-one

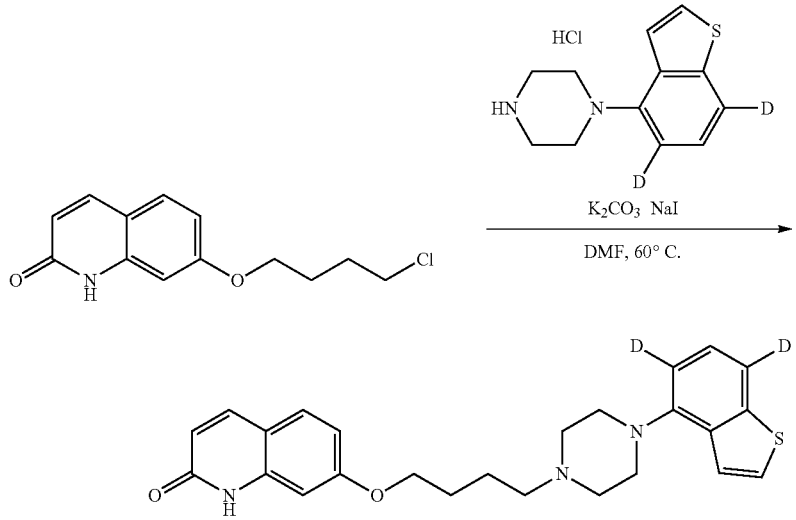

A mixture of 7-(4-chlorobutoxy)-1H-quinolin-2-one (0.5 g), 1-benzo[b]thiophen-4-yl-5,7-d$_2$-piperazine hydrochloride (0.56 g) obtained by a deuteration reaction (Org. Lett. 2004, 6, 1485.; Bull. Chem. Soc. Jpn. 2008, 81, 278.) of 1-benzothiophene-4-piperazine hydrochloride, sodium iodide (0.33 g), potassium carbonate (690 mg) and dimethylformamide (20 ml) was stirred at 60° C. for 6 hr. Water was added to the reaction mixture, and the mixture was extracted with ethyl acetate, washed with water, and dried over sodium sulfate. The solvent was evaporated under reduced pressure and the residue was purified by silica gel column chromatography (dichloromethane:methanol=30:1) to give 7-[4-(4-benzo[b]thiophen-4-yl-5,7-d$_2$-piperazin-1-yl)-butoxy]-1H-quinolin-2-one (0.31 g).

7-[4-(4-benzo[b]thiophen-4-yl-5,7-d$_2$-piperazin-1-yl)-butoxy]-1H-quinolin-2-one: white powder m.p. 179.5-181.5° C. (recrystallized from EtOH)

$^1$H-NMR (CDCl$_3$) δ ppm: 1.68-1.84 (2H, m), 1.84-1.96 (2H, m), 2.54 (2H, t, J=7.4 Hz), 2.66-2.80 (4H, br), 3.16-3.26 (4H, br), 4.12 (2H, t, J=6.2 Hz), 6.54 (1H, d, J=9.4 Hz), 6.78-6.86 (2H, m), 6.90 (<0.02H, d, J=7.7 Hz), 7.25-7.28 (1H, m), 7.38 (0.82H, d, J=5.6 Hz), 7.40-7.48 (2H, m), 7.54 (0.05H, d, J=8.6 Hz), 7.72 (1H, d, J=9.4 Hz), 12.09 (1H, brs).

A-9: Synthesis of 7-[4-(4-benzo[b]thiophen-4-yl-5,7-d$_2$-piperazin-1-yl)-butoxy-1,1,2,2,3,3,4,4-d$_8$]-1H-quinolin-2-one

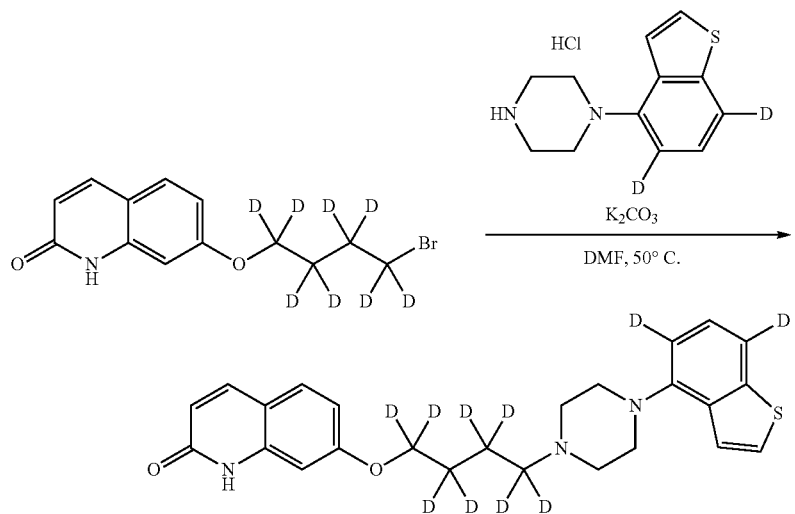

A mixture of 7-(4-bromobutoxy-1,1,2,2,3,3,4,4-d$_8$)-1H-quinolin-2-one (0.5 g) obtained in Example A-1, synthesis method 2, step 1,1-benzo[b]thiophen-4-yl-5,7-d$_2$-piperazine hydrochloride (0.46 g) obtained by a deuteration reaction (Org. Lett. 2004, 6, 1485.; Bull. Chem. Soc. Jpn. 2008, 81, 278.) of 1-benzothiophene-4-piperazine hydrochloride, potassium carbonate (0.57 g) and dimethylformamide (20 ml) was stirred at 50° C. for 6 hr. Water was added to the reaction mixture, and the mixture was extracted with ethyl acetate, washed with water, and dried over sodium sulfate. The solvent was evaporated under reduced pressure and the residue was purified by silica gel column chromatography (dichloromethane:methanol=30:1) to give 7-[4-(4-benzo[b]thiophen-4-yl-5,7-d$_2$-piperazin-1-yl)-butoxy-1,1,2,2,3,3,4,4-d$_8$]-1H-quinolin-2-one (0.35 g).

7-[4-(4-benzo[b]thiophen-4-yl-5,7-d$_2$-piperazin-1-yl)-butoxy-1,1,2,2,3,3,4,4-d$_8$]-1H-quinolin-2-one: white powder m.p. 176.5-178.5° C. (recrystallized from EtOH)

$^1$H-NMR (CDCl$_3$) δ ppm: 2.66-2.80 (4H, br), 3.10-3.28 (4H, br), 6.55 (1H, d, J=9.4 Hz), 6.81 (1H, dd, J=2.4, 8.6 Hz), 6.85 (1H, d, J=2.3 Hz), 6.89 (<0.04H, d, J=7.7 Hz), 7.24-7.28 (1H, m), 7.38 (0.85H, d, J=5.6 Hz), 7.40-7.46 (2H, m), 7.54 (0.06H, dd, J=0.5, 8.0 Hz), 7.72 (1H, d, J=9.4 Hz), 12.47 (1H, brs).

A-10: Synthesis of 7-[4-(4-benzo[b]thiophen-4-yl-piperazin-1-yl-2,2,3,3,5,5,6,6-d$_8$)-butoxy-1,1,2,2,3,3,4,4-d$_8$]-1H-quinolin-2-one-3,4,5,6,8-d$_5$

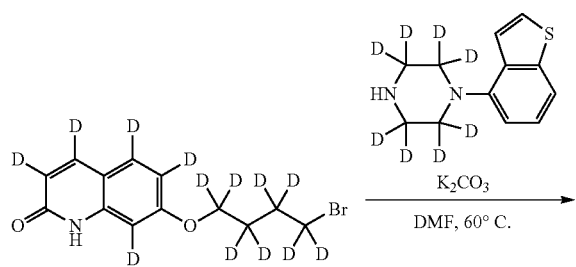

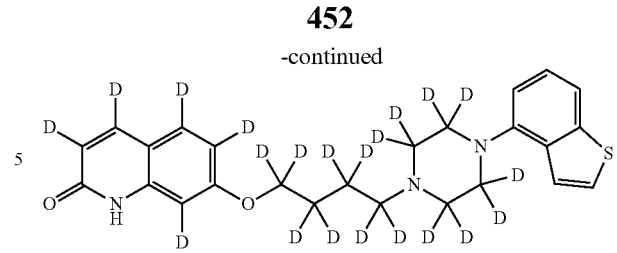

A mixture of 7-(4-bromobutoxy-1,1,2,2,3,3,4,4-d$_8$)-1H-quinolin-2-one-3,4,5,6,8-d$_5$ (0.6 g) obtained in Example A-7, step 1,1-benzo[b]thiophen-4-yl-piperazine-2,2,3,3,5,5,6,6-d$_8$ (0.57 g) obtained in Example A-2, step 2, potassium carbonate (380 mg) and dimethylformamide (20 ml) was stirred at 60° C. for 5 hr. Water was added to the reaction mixture, and the mixture was extracted with ethyl acetate, washed with water, and dried over sodium sulfate. The solvent was evaporated under reduced pressure and the residue was purified by silica gel column chromatography (dichloromethane:methanol=30:1) to give 7-[4-(4-Benzo[b]thiophen-4-yl-piperazin-1-yl-2,2,3,3,5,5,6,6-d$_8$)-butoxy-1,1,2,2,3,3,4,4-d$_8$]-1H-quinolin-2-one-3,4,5,6,8-d$_5$ (0.45 g).

7-[4-(4-benzo[b]thiophen-4-yl-piperazin-1-yl-2,2,3,3,5,5,6,6-d$_8$)-butoxy-1,1,2,2,3,3,4,4-d$_8$]-1H-quinolin-2-one-3,4,5,6,8-d$_5$: white powder m.p. 175.5-177.5° C. (recrystallized from EtOH)

$^1$H-NMR (CDCl$_3$) δ ppm: 2.64-2.72 (<0.06H, br), 3.14-3.20 (<0.06H, br), 6.54 (<0.01H, s), 6.80-6.86 (<0.04H, m), 6.89 (1H, dd, J=0.8, 7.6 Hz), 7.26 (1H, t, J=7.9 Hz), 7.38 (1H, d, J=5.5 Hz), 7.41 (1H, dd, J=0.7, 5.6 Hz), 7.54 (1H, d, J=8.0 Hz), 7.72 (<0.01H, s), 12.35 (1H, brs).

A-11: Synthesis of 7-[4-(4-benzo[b]thiophen-4-yl-5,7-d$_2$-piperazin-1-yl)-butoxy-1,1,2,2,3,3,4,4-d$_8$]-1H-quinolin-2-one-3,4,5,6,8-d$_5$

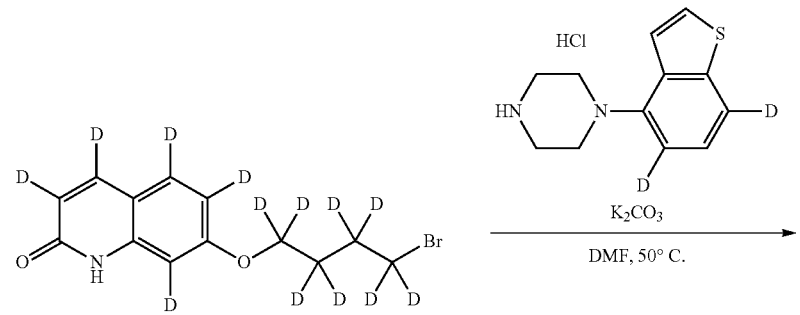

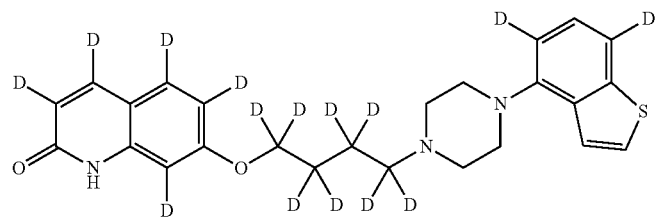

A mixture of 7-(4-bromobutoxy-1,1,2,2,3,3,4,4-$d_8$)-1H-quinolin-2-one-3,4,5,6,8-$d_5$ (0.5 g) obtained in Example A-7, step 1,1-benzo[b]thiophen-4-yl-5,7-$d_2$-piperazine hydrochloride (0.46 g) obtained by a deuteration reaction (Org. Lett. 2004, 6, 1485.; Bull. Chem. Soc. Jpn. 2008, 81, 278.) of 1-benzothiophene-4-piperazine hydrochloride, potassium carbonate (0.56 g) and dimethylformamide (20 ml) was stirred at 50° C. for 6 hr. Water was added to the reaction mixture, and the mixture was extracted with ethyl acetate, washed with water, and dried over sodium sulfate. The solvent was evaporated under reduced pressure and the residue was purified by silica gel column chromatography (dichloromethane:methanol=30:1) to give 7-[4-(4-benzo[b]thiophen-4-yl-5,7-$d_2$-piperazin-1-yl)-butoxy-1,1,2,2,3,3,4,4-$d_8$]-1H-quinoline-2-one-3,4,5,6,8-$d_5$ (0.34 g).

7-[4-(4-benzo[b]thiophen-4-yl-5,7-$d_2$-piperazin-1-yl)-butoxy-1,1,2,2,3,3,4,4-$d_8$]-1H-quinolin-2-one-3,4,5,6,8-$d_5$: white powder m.p. 175.5-177.5° C. (recrystallized from EtOH)

$^1$H-NMR (CDCl$_3$) δ ppm: 2.66-2.80 (4H, br), 3.14-3.26 (4H, br), 6.54 (<0.01H, s), 6.83 (<0.02H, d, J=11.2 Hz), 6.89 (<0.01H, d, J=7.6 Hz), 7.06-7.10 (<0.02H, m), 7.25-7.28 (1H, m), 7.38 (0.86H, d, J=5.6 Hz), 7.42 (1H, d, J=5.6 Hz), 7.54 (<0.05H, dd, J=0.6, 8.0 Hz), 7.72 (<0.01H, s), 12.28 (1H, brs).

Example B

Synthesis of salt of 7-[4-(4-benzo[b]thiophen-4-yl-piperazin-1-yl)-butoxy]-1H-quinolin-2-one

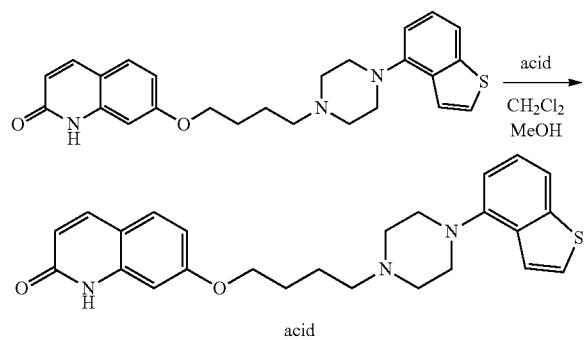

Phosphate:

A suspension of 7-[4-(4-benzo[b]thiophen-4-yl-piperazin-1-yl)-butoxy]-1H-quinolin-2-one (15 g) in dichloromethane (100 ml) and methanol (100 ml) was warmed to 60° C., dissolved, and phosphoric acid (4.39 g) was added at room temperature. The precipitated crystals were collected by filtration, and dried to give 7-[4-(4-Benzo[b]thiophen-4-yl-piperazin-1-yl)-butoxy]-1H-quinolin-2-one phosphate (17.9 g).

7-[4-(4-Benzo[b]thiophen-4-yl-piperazin-1-yl)-butoxy]-1H-quinolin-2-one phosphate (17.5 g) was recrystallized from ethanol (550 ml) and water (550 ml) to give 7-[4-(4-benzo[b]thiophen-4-yl-piperazin-1-yl)-butoxy]-1H-quinolin-2-one phosphate (14.4 g).

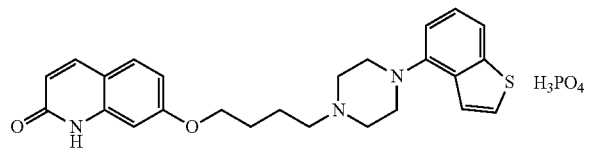

7-[4-(4-benzo[b]thiophen-4-yl-piperazin-1-yl)-butoxy]-1H-quinolin-2-one phosphate: colorless crystals: m.p. 226-228° C. (recrystallized from EtOH—H$_2$O)

$^1$H-NMR (DMSO-d$_6$) δ ppm: 1.66-1.76 (2H, m), 1.76-1.86 (2H, m), 2.63 (2H, t, J=7.0 Hz), 2.76-2.86 (4H, br), 3.08-3.18 (4H, br), 4.07 (2H, t, J=6.2 Hz), 6.30 (1H, d, J=9.4 Hz), 6.78-6.84 (2H, m), 6.90 (1H, d, J=7.4 Hz), 7.28 (1H, t, J=7.8 Hz), 7.42 (1H, d, J=5.5 Hz), 7.56 (1H, d, J=9.4 Hz), 7.63 (1H, d, J=8.0 Hz), 7.71 (1H, d, J=5.5 Hz), 7.81 (1H, d, J=9.5 Hz), 11.2-12.2 (1H, br).

DL-Malate:

A suspension of 7-[4-(4-benzo[b]thiophen-4-yl-piperazin-1-yl)-butoxy]-1H-quinolin-2-one (15 g) in dichloromethane (100 ml) and methanol (100 ml) was warmed to 60° C., dissolved, and DL-malic acid (5.11 g) dissolved in water (10 ml) was added at room temperature. The precipitated crystals were collected by filtration, and dried to give 7-[4-(4-benzo[b]thiophen-4-yl-piperazin-1-yl)-butoxy]-1H-quinolin-2-one DL-malate (20 g).

7-[4-(4-Benzo[b]thiophen-4-yl-piperazin-1-yl)-butoxy]-1H-quinolin-2-one DL-malate (20 g) was recrystallized from ethanol (350 ml) and water (50 ml) to give 7-[4-(4-benzo[b]thiophen-4-yl-piperazin-1-yl)-butoxy]-1H-quinolin-2-one DL-malate (14.5 g).

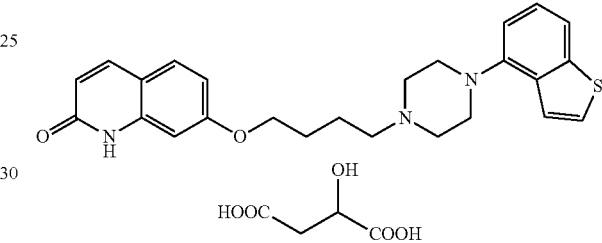

7-[4-(4-benzo[b]thiophen-4-yl-piperazin-1-yl)-butoxy]-1H-quinolin-2-one DL-malate: colorless crystal: m.p. 136-139° C. (recrystallized from EtOH—H$_2$O)

$^1$H-NMR (DMSO-d$_6$) δ ppm: 1.64-1.76 (2H, m), 1.76-1.86 (2H, m), 2.62 (2H, t, J=7.1 Hz), 2.74-2.86 (4H, br), 3.06-3.18 (4H, br), 4.06 (2H, t, J=6.0 Hz), 4.21 (2H, s), 6.30 (1H, d, J=9.4 Hz), 6.78-6.84 (2H, m), 6.90 (1H, d, J=7.4 Hz), 7.28 (1H, t, J=7.8 Hz), 7.42 (1H, d, J=5.5 Hz), 7.56 (1H, d, J=9.3 Hz), 7.63 (1H, d, J=8.0 Hz), 7.71 (1H, d, J=5.5 Hz), 7.81 (1H, d, J=9.5 Hz), 11.59 (1H, brs).

L(+)-Tartrate:

A suspension of 7-[4-(4-benzo[b]thiophen-4-yl-piperazin-1-yl)-butoxy]-1H-quinolin-2-one (15 g) in dichloromethane (100 ml) and methanol (100 ml) was heated to 60° C., dissolved, and L(+)-tartaric acid (5.72 g) dissolved in water (10 ml) was added at room temperature. The precipitated crystals were collected by filtration, and dried to give 7-[4-(4 benzo[b]thiophen-4-yl-piperazin-1-yl)-butoxy]-1H-quinolin-2-one L(+)-tartrate (19.3 g).

7-[4-(4-Benzo[b]thiophen-4-yl-piperazin-1-yl)-butoxy]-1H-quinolin-2-one L(+)-tartrate (19.3 g) was recrystallized from ethanol (700 ml) and water (250 ml) to give 7-[4-(4-benzo[b]thiophen-4-yl-piperazin-1-yl)-butoxy]-1H-quinolin-2-one L(+)-tartrate (16.5 g).

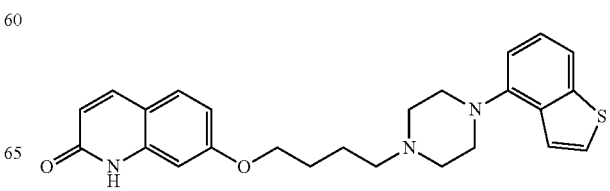

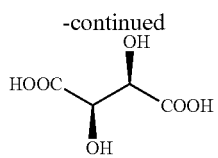

7-[4-(4-benzo[b]thiophen-4-yl-piperazin-1-yl)-butoxy]-1H-quinolin-2-one L(+)-tartrate: colorless crystal: m.p. 198-203° C. (recrystallized from EtOH—H₂O)

$^1$H-NMR (DMSO-d$_6$) δ ppm: 1.64-1.76 (2H, m), 1.76-1.86 (2H, m), 2.41 (1H, dd, J=6.7, 15.6 Hz), 2.59 (1H, dd, J=6.4, 15.6 Hz), 2.66 (2H, t, J=7.2 Hz), 2.78-2.88 (4H, br), 3.06-3.18 (4H, br), 4.07 (2H, t, J=6.2 Hz), 4.16 (1H, t, J=6.5 Hz), 6.30 (1H, d, J=9.4 Hz), 6.78-6.84 (2H, m), 6.90 (1H, d, J=7.2 Hz), 7.29 (1H, t, J=7.8 Hz), 7.43 (1H, dd, J=0.6, 5.5 Hz), 7.56 (1H, d, J=9.3 Hz), 7.63 (1H, d, J=8.0 Hz), 7.71 (1H, d, J=5.5 Hz), 7.81 (1H, d, J=9.5 Hz), 11.59 (1H, brs).

Oxalate:

A suspension of 7-[4-(4-benzo[b]thiophen-4-yl-piperazin-1-yl)-butoxy]-1H-quinolin-2-one (3 g) in dichloromethane (20 ml) and methanol (20 ml) was warmed to 60° C., dissolved, and oxalic acid (0.69 g) dissolved in methanol (5 ml) was added at room temperature. The precipitated crystals were collected by filtration, and dried to give 7-[4-(4-benzo[b]thiophen-4-yl-piperazin-1-yl)-butoxy]-1H-quinolin-2-one oxalate (3.3 g).

7-[4-(4-Benzo[b]thiophen-4-yl-piperazin-1-yl)-butoxy]-1H-quinolin-2-one oxalate (1 g) was recrystallized from ethanol (20 ml) and water (20 ml) to give 7-[4-(4-benzo[b]thiophen-4-yl-piperazin-1-yl)-butoxy]-1H-quinolin-2-one oxalate (0.8 g).

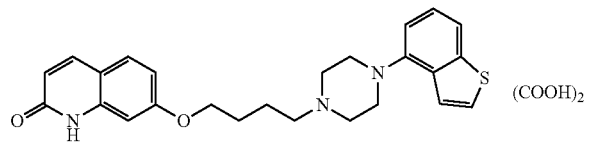

7-[4-(4-benzo[b]thiophen-4-yl-piperazin-1-yl)-butoxy]-1H-quinolin-2-one oxalate: colorless crystal: m.p. 126.5-128° C. (recrystallized from EtOH—H₂O)

$^1$H-NMR (DMSO-d$_6$) δ ppm: 1.78-1.90 (4H, br), 3.06-3.14 (2H, br), 3.24-3.36 (4H, br), 3.62-4.24 (6H, br), 6.31 (1H, d, J=9.4 Hz), 6.78-6.86 (2H, m), 6.95 (1H, d, J=7.4 Hz), 7.31 (1H, t, J=7.9 Hz), 7.48 (1H, dd, J=0.4, 5.6 Hz), 7.57 (1H, d, J=9.4 Hz), 7.69 (1H, d, J=8.1 Hz), 7.75 (1H, d, J=5.5 Hz), 7.81 (1H, d, J=9.5 Hz), 11.62 (1H, brs).

Succinate:

A suspension of 7-[4-(4-benzo[b]thiophen-4-yl-piperazin-1-yl)-butoxy]-1H-quinolin-2-one (2 g) in dichloromethane (20 ml) and methanol (20 ml) was warmed to 60° C., dissolved, and succinic acid (0.6 g) dissolved in methanol-water was added at room temperature. The precipitated crystals were collected by filtration, and dried to give 7-[4-(4-benzo[b]thiophen-4-yl-piperazin-1-yl)-butoxy]-1H-quinolin-2-one succinate (2.4 g).

7-[4-(4-Benzo[b]thiophen-4-yl-piperazin-1-yl)-butoxy]-1H-quinolin-2-one succinate (1 g) was recrystallized from ethanol (20 ml) and water (8 ml) to give 7-[4-(4-benzo[b]thiophen-4-yl-piperazin-1-yl)-butoxy]-1H-quinolin-2-one succinate (0.74 g).

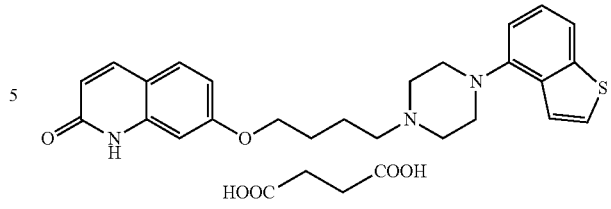

7-[4-(4-benzo[b]thiophen-4-yl-piperazin-1-yl)-butoxy]-1H-quinolin-2-one succinate: colorless crystal: m.p. 158.5-160° C. (recrystallized from EtOH—H₂O)

$^1$H-NMR (DMSO-d$_6$) δ ppm: 1.60-1.70 (2H, m), 1.76-1.86 (2H, m), δ 2.41 (4H, s), 2.44-2.50 (2H, m), 2.60-2.70 (4H, br), 3.04-3.10 (4H, br), 4.06 (2H, t, J=6.4 Hz), 6.29 (1H, d, J=9.4 Hz), 6.78-6.84 (2H, m), 6.89 (1H, d, J=7.3 Hz), 7.27 (1H, t, J=7.8 Hz), 7.40 (1H, dd, J=0.4, 5.6 Hz), 7.56 (1H, d, J=9.3 Hz), 7.61 (1H, d, J=8.0 Hz), 7.69 (1H, d, J=5.5 Hz), 7.81 (1H, d, J=9.5 Hz), 11.58 (1H, brs).

1/2 Succinate:

A suspension of 7-[4-(4-benzo[b]thiophen-4-yl-piperazin-1-yl)-butoxy]-1H-quinolin-2-one (2 g) in dichloromethane (20 ml) and methanol (20 ml) was warmed to 60° C., dissolved, and succinic acid (0.3 g) dissolved in methanol-water was added at room temperature. The precipitated crystals were collected by filtration, and dried to give 7-[4-(4-benzo[b]thiophen-4-yl-piperazin-1-yl)-butoxy]-1H-quinolin-2-one 1/2 succinate (1.84 g).

7-[4-(4-Benzo[b]thiophen-4-yl-piperazin-1-yl)-butoxy]-1H-quinolin-2-one 1/2 succinate (1 g) was recrystallized from ethanol (20 ml) and water (5 ml) to give 7-[4-(4-benzo[b]thiophen-4-yl-piperazin-1-yl)-butoxy]-1H-quinolin-2-one 1/2 succinate (0.69 g).

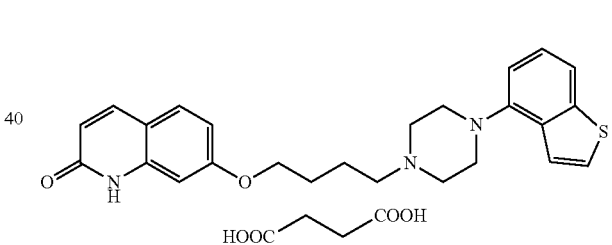

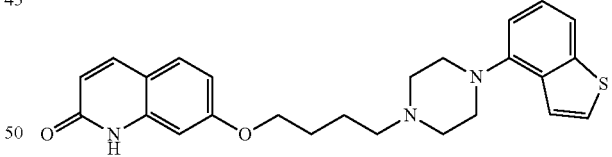

7-[4-(4-benzo[b]thiophen-4-yl-piperazin-1-yl)-butoxy]-1H-quinolin-2-one 1/2 succinate: colorless crystal: m.p. 158-160° C. (recrystallized from EtOH—H₂O)

$^1$H-NMR (DMSO-d$_6$) δ ppm: 1.60-1.70 (2H, m), 1.76-1.86 (2H, m), 2.41 (2H, s), 2.47 (2H, t, J=7.2 Hz), 2.60-2.70 (4H, br), 3.02-3.10 (4H, br), 4.06 (2H, t, J=6.4 Hz), 6.30 (1H, d, J=9.4 Hz), 6.78-6.84 (2H, m), 6.88 (1H, d, J=7.3 Hz), 7.28 (1H, t, J=7.8 Hz), 7.40 (1H, dd, J=0.4, 5.5 Hz), 7.56 (1H, d, J=9.4 Hz), 7.61 (1H, d, J=7.6 Hz), 7.69 (1H, d, J=5.5 Hz), 7.80 (1H, d, J=9.5 Hz), 11.59 (1H, brs).

Hydrobromide:

A suspension of 7-[4-(4-benzo[b]thiophen-4-yl-piperazin-1-yl)-butoxy]-1H-quinolin-2-one (2 g) in dichloromethane (20 ml) and methanol (20 ml) was warmed to 60° C., dissolved, and a solution of 47% hydrobromic acid (0.86 g) in methanol was added at room temperature. The precipitated crystals were collected by filtration, and dried to give 7-[4-(4-Benzo[b]thiophen-4-yl-piperazin-1-yl)-butoxy]-1H-quinolin-2-one hydrobromide (2.2 g).

7-[4-(4-Benzo[b]thiophen-4-yl-piperazin-1-yl)-butoxy]-1H-quinolin-2-one hydrobromide (1 g) was recrystallized from ethanol (20 ml) and water (5 ml) to give 7-[4-(4-benzo[b]thiophen-4-yl-piperazin-1-yl)-butoxy]-1H-quinolin-2-one hydrobromide (0.81 g).

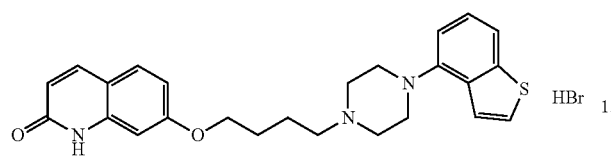

7-[4-(4-benzo[b]thiophen-4-yl-piperazin-1-yl)-butoxy]-1H-quinolin-2-one hydrobromide: colorless crystal: m.p. 223-228° C. (recrystallized from EtOH—H$_2$O)

$^1$H-NMR (DMSO-d$_6$) δ ppm: 1.80-2.00 (4H, br), 3.06-3.20 (2H, m), 3.26-3.40 (4H, br), 3.50-3.74 (4H, m), 4.09 (2H, t, J=5.4 Hz), 6.31 (1H, d, J=9.4 Hz), 6.80-6.86 (2H, m), 6.99 (1H, d, J=7.6 Hz), 7.33 (1H, t, J=7.9 Hz), 7.51 (1H, d, J=5.5 Hz), 7.59 (1H, d, J=9.2 Hz), 7.72 (1H, d, J=8.0 Hz), 7.78 (1H, d, J=5.5 Hz), 7.82 (1H, d, J=9.5 Hz), 9.65 (1H, brs), 11.62 (1H, s).

Malonate:

A suspension of 7-[4-(4-benzo[b]thiophen-4-yl-piperazin-1-yl)-butoxy]-1H-quinolin-2-one (2 g) in dichloromethane (20 ml) and methanol (20 ml) was warmed to 60° C., dissolved, and malonic acid (0.53 g) dissolved in methanol was added at room temperature. The precipitated crystals were collected by filtration, and dried to give 7-[4-(4-benzo[b]thiophen-4-yl-piperazin-1-yl)-butoxy]-1H-quinolin-2-one malonate (2.4 g).

7-[4-(4-Benzo[b]thiophen-4-yl-piperazin-1-yl)-butoxy]-1H-quinolin-2-one malonate (1 g) was recrystallized from ethanol (4 ml) and water (10 ml) to give 7-[4-(4-benzo[b]thiophen-4-yl-piperazin-1-yl)-butoxy]-1H-quinolin-2-one malonate (0.72 g).

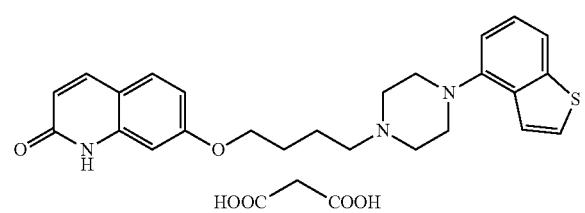

7-[4-(4-benzo[b]thiophen-4-yl-piperazin-1-yl)-butoxy]-1H-quinolin-2-one malonate: colorless crystal: m.p. 134-136° C. (recrystallized from EtOH—H$_2$O)

$^1$H-NMR (DMSO-d$_6$) δ ppm: 1.68-1.88 (4H, m), 2.82 (2H, brs), 2.92-3.08 (6H, m), 3.12-3.22 (4H, br), 4.07 (2H, t, J=5.8 Hz), 6.30 (1H, d, J=9.4 Hz), 6.78-6.84 (2H, m), 6.93 (1H, d, J=7.6 Hz), 7.30 (1H, t, J=7.8 Hz), 7.45 (1H, d, J=5.5 Hz), 7.57 (1H, d, J=9.4 Hz), 7.66 (1H, d, J=8.1 Hz), 7.73 (1H, d, J=5.5 Hz), 7.81 (1H, d, J=9.5 Hz), 11.60 (1H, brs).

1/2 Pamoate:

A suspension of 7-[4-(4-benzo[b]thiophen-4-yl-piperazin-1-yl)-butoxy]-1H-quinolin-2-one (1 g) in dimethylformamide (10 ml) and acetonitrile (10 ml) was warmed to give a solution, and pamoic acid (0.49 g) was added. The mixture was warmed to 60° C., dissolved, and the mixture was stood at room temperature. Water was added, the suspended substances were collected by filtration, and dried to give 7-[4-(4-benzo[b]thiophen-4-yl-piperazin-1-yl)-butoxy]-1H-quinolin-2-one 1/2 pamoate (1.5 g).

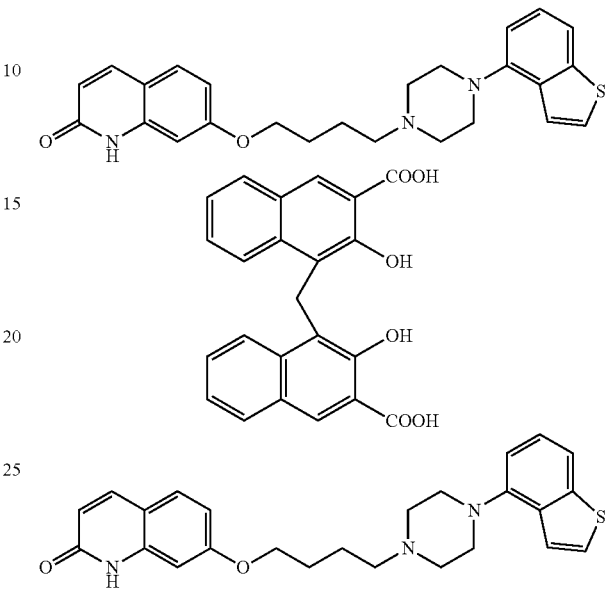

7-[4-(4-benzo[b]thiophen-4-yl-piperazin-1-yl)-butoxy]-1H-quinolin-2-one 1/2 pamoate: yellow amorphous $^1$H-NMR (DMSO-d$_6$) δ ppm: 1.78-1.92 (4H, m), 3.4-3.8 (10H, br), 4.05-4.12 (2H, m), 4.71 (1H, s), 6.31 (1H, d, J=9.5 Hz), 6.78-6.84 (2H, m), 6.96 (1H, d, J=7.6 Hz), 7.04 (1H, t, J=7.4 Hz), 7.13-7.19 (1H, m), 7.31 (1H, t, J=7.8 Hz), 7.49 (1H, d, J=5.5 Hz), 7.56 (1H, d, J=8.7 Hz), 7.69 (2H, d, J=8.0 Hz), 7.76 (1H, d, J=5.5 Hz), 7.81 (1H, d, J=9.5 Hz), 8.18 (1H, d, J=8.6 Hz), 8.25 (1H, s), 11.63 (1H, brs).

Experimental Example 1

Each of the Example compounds was examined for the solubility in oil (sesame oil, benzyl benzoate).

For the specific gravity of an oil, the following values were applied.

sesame oil (specific gravity: 0.914-0.921)
benzyl benzoate (specific gravity: 1.123)

(Method)

Example compound is measured in a microtube and an oil (sesame oil, or, benzyl benzoate) in an amount to make the concentration 10 mg/0.1 ml is added. After stirring, the solubility is evaluated by visual observation. When the compound is not dissolved, the mixture is heated, and the solubility is evaluated after cooling.

The results are shown in Table 3 and Table 4. In the Tables, ◯ means soluble.

TABLE 3

| Example No. | Sesame oil |
|---|---|
| Example 17 | ◯ |
| Example 21 | ◯ |
| Example 28 | ◯ |
| Example 44 | ◯ |
| Example 45 | ◯ |

TABLE 3-continued

| Example No. | Sesame oil |
|---|---|
| Example 52 | ○ |
| Example 57 | ○ |
| Example 60 | ○ |
| Example 75 | ○ |
| Example 76 | ○ |
| Example 79 | ○ |
| Example 134 | ○ |
| Example 135 | ○ |
| Example 142 | ○ |
| Example 144 | ○ |
| Example 149 | ○ |
| Example 150 | ○ |
| Example 154 | ○ |
| Example 156 | ○ |
| Example 158 | ○ |
| Example 177 | ○ |
| Example 179 | ○ |
| Example 180 | ○ |
| Example 373 | ○ |
| Example 379 | ○ |
| Example 380 | ○ |
| Example 381 | ○ |
| Example 384 | ○ |

TABLE 4

| Example No. | benzyl benzoate |
|---|---|
| Example 9 | ○ |
| Example 10 | ○ |
| Example 11 | ○ |
| Example 12 | ○ |
| Example 13 | ○ |
| Example 14 | ○ |
| Example 15 | ○ |
| Example 16 | ○ |
| Example 17 | ○ |
| Example 18 | ○ |
| Example 19 | ○ |
| Example 20 | ○ |
| Example 21 | ○ |
| Example 22 | ○ |
| Example 23 | ○ |
| Example 24 | ○ |
| Example 25 | ○ |
| Example 26 | ○ |
| Example 27 | ○ |
| Example 28 | ○ |
| Example 29 | ○ |
| Example 30 | ○ |
| Example 31 | ○ |
| Example 32 | ○ |
| Example 33 | ○ |
| Example 34 | ○ |
| Example 35 | ○ |
| Example 36 | ○ |
| Example 37 | ○ |
| Example 38 | ○ |
| Example 39 | ○ |
| Example 40 | ○ |
| Example 41 | ○ |
| Example 42 | ○ |
| Example 43 | ○ |
| Example 44 | ○ |
| Example 45 | ○ |
| Example 46 | ○ |
| Example 47 | ○ |
| Example 48 | ○ |
| Example 49 | ○ |
| Example 50 | ○ |
| Example 51 | ○ |
| Example 52 | ○ |
| Example 53 | ○ |
| Example 54 | ○ |
| Example 55 | ○ |

TABLE 4-continued

| Example No. | benzyl benzoate |
|---|---|
| Example 56 | ○ |
| Example 57 | ○ |
| Example 58 | ○ |
| Example 59 | ○ |
| Example 60 | ○ |
| Example 61 | ○ |
| Example 62 | ○ |
| Example 63 | ○ |
| Example 64 | ○ |
| Example 65 | ○ |
| Example 67 | ○ |
| Example 68 | ○ |
| Example 69 | ○ |
| Example 70 | ○ |
| Example 71 | ○ |
| Example 72 | ○ |
| Example 73 | ○ |
| Example 74 | ○ |
| Example 75 | ○ |
| Example 76 | ○ |
| Example 77 | ○ |
| Example 78 | ○ |
| Example 79 | ○ |
| Example 80 | ○ |
| Example 81 | ○ |
| Example 82 | ○ |
| Example 83 | ○ |
| Example 84 | ○ |
| Example 85 | ○ |
| Example 86 | ○ |
| Example 87 | ○ |
| Example 88 | ○ |
| Example 89 | ○ |
| Example 90 | ○ |
| Example 91 | ○ |
| Example 92 | ○ |
| Example 93 | ○ |
| Example 94 | ○ |
| Example 95 | ○ |
| Example 96 | ○ |
| Example 97 | ○ |
| Example 98 | ○ |
| Example 99 | ○ |
| Example 100 | ○ |
| Example 101 | ○ |
| Example 102 | ○ |
| Example 103 | ○ |
| Example 104 | ○ |
| Example 105 | ○ |
| Example 106 | ○ |
| Example 107 | ○ |
| Example 108 | ○ |
| Example 109 | ○ |
| Example 110 | ○ |
| Example 111 | ○ |
| Example 112 | ○ |
| Example 113 | ○ |
| Example 114 | ○ |
| Example 115 | ○ |
| Example 116 | ○ |
| Example 117 | ○ |
| Example 118 | ○ |
| Example 119 | ○ |
| Example 120 | ○ |
| Example 121 | ○ |
| Example 122 | ○ |
| Example 123 | ○ |
| Example 124 | ○ |
| Example 125 | ○ |
| Example 126 | ○ |
| Example 127 | ○ |
| Example 128 | ○ |
| Example 129 | ○ |
| Example 130 | ○ |
| Example 131 | ○ |
| Example 132 | ○ |
| Example 134 | ○ |
| Example 135 | ○ |

TABLE 4-continued

| Example No. | benzyl benzoate |
|---|---|
| Example 136 | ○ |
| Example 137 | ○ |
| Example 139 | ○ |
| Example 140 | ○ |
| Example 141 | ○ |
| Example 142 | ○ |
| Example 143 | ○ |
| Example 144 | ○ |
| Example 145 | ○ |
| Example 146 | ○ |
| Example 147 | ○ |
| Example 148 | ○ |
| Example 149 | ○ |
| Example 150 | ○ |
| Example 151 | ○ |
| Example 152 | ○ |
| Example 153 | ○ |
| Example 154 | ○ |
| Example 156 | ○ |
| Example 158 | ○ |
| Example 163 | ○ |
| Example 165 | ○ |
| Example 168 | ○ |
| Example 170 | ○ |
| Example 175 | ○ |
| Example 177 | ○ |
| Example 179 | ○ |
| Example 180 | ○ |
| Example 371 | ○ |
| Example 372 | ○ |
| Example 373 | ○ |
| Example 379 | ○ |
| Example 380 | ○ |
| Example 381 | ○ |
| Example 382 | ○ |
| Example 384 | ○ |

Experimental Example 2

Pharmacokinetics of Intramuscular Preparations

A suspended fine particle preparation used as a sustainable injection requires re-suspending before administration, and the particle surface area markedly affects the drug release profile. Thus, the particle size after re-suspending needs to be strictly controlled, so that coagulation and the like will not occur.

On the other hand, since an oil-soluble preparation contains a drug completely dissolved therein, re-suspending before administration is not necessary and, since the drug is released depending on the oil-water distribution coefficient, control of the particle size is not necessary. Furthermore, since sterilization by filtration, which has been unattainable for suspended fine particle preparations, has become possible, a preparation can be prepared more conveniently.

Since the compound disclosed in patent document 1 shows low solubility in an oil base material such as benzyl benzoate and the like, an oil-soluble preparation cannot be produced. When a soluble preparation is produced, an aqueous base material using a solubilizing agent such as Captisol (Sulfobutylether-β-cyclodextrin) and the like needs to be used. In contrast, since the compound of the present invention shows high solubility in an oil base material, an oil-soluble preparation can be produced.

Thus, an oil-soluble preparation of the compound of the present invention and an water soluble preparation of the compound disclosed in patent document 1 were prepared, intramuscularly administered to rats and pharmacokinetics of these preparations were evaluated.

Animal 7-week-old male rats were purchased from CHARLES RIVER LABORATORIES JAPAN, INC, preliminarily bred and rats weighing 265.2 g-288.6 g were used for the experiment. The experiment was performed under the conditions of no fasting, free access to water and feed, and the following breeding environment. Rats per cage: 4, temperature: 23±2° C., humidity: 60±10%, light-on time: 7:00-19:00

Production Method of Preparation

As the compound disclosed in patent document 1, used was 7-[4-(4-benzo[b]thiophen-4-yl-piperazin-1-yl)butoxy]-1H-quinolin-2-one (control compound) disclosed in Example 1 that expresses desired efficacy. A water-soluble preparation was obtained by dissolving the control compound in aqueous 15% Captisol and 0.78% tartaric acid solution to a concentration of 0.5%, and the pH was adjusted to 4.3 with 5N aqueous sodium hydroxide solution.

An oil-soluble preparation was obtained by dissolving the compound of the present invention disclosed in Example 146 in benzyl benzoate to a concentration of 15%, and adjusted.

Methods of Administration and Blood Sampling

Under isoflurane anesthesia, non-fasting male rats were intramuscularly administered at left leg region (about 4 mm depth) using a syringe with 24G needle. The dose is as described below.

Test preparation 1: low dose of oil-soluble preparation of the compound of the present invention: 25 mg/kg (based on control compound)

Test preparation 2: high dose of oil-soluble preparation of the compound of the present invention: 50 mg/kg (based on control compound)

Test preparation 3: water-soluble preparation of control compound: 0.1 mg/kg

The test preparation was administered to the rats. For test preparation 3, about 0.3 mL each of blood samples were collected from the jugular vein 5 min, 15 min, 30 min, 1 hr, 2 hr, 4 hr and 20 hr later. For test preparations 1 and 2, about 0.3 mL each of blood samples were collected from the jugular vein 6 hr, 1 day, 3 days, 7 days, 14 days, 21 days and 28 days later. For collection of blood samples, a 1 mL syringe treated with EDTA-lithium fluoride-heparin was used. The collected blood was preserved under ice-cooling, the plasma was rapidly separated by centrifugation, and the concentration of the control compound was quantified by LCMS. The pharmacokinetics parameters such as Cmax, Tmax, AUClast, AUCinf, t½ and the like were determined by WinNonlin Professional Version 6.1 (model-independent method, Pharsight corporation).

Results

The results are shown in FIG. 1 (blood concentration profile of control compound after administration of test preparations 1, 2 and 3) and Table 5 (pharmacokinetics parameters of test preparations 1, 2 and 3).

TABLE 5

|  | Cmax (μg/mL) | Tmax (day) | AUClast (μg · day/mL) | AUCinf (μg · day/mL) | t½ (day) |
|---|---|---|---|---|---|
| Test preparation 1 | 0.0258 | 5.00 | 0.270 | 0.473 | 27.99 |
| Test preparation 2 | 0.0423 | 5.31 | 0.480 | 0.621 | 16.99 |
| Test preparation 3 | 0.0629 | 0.01 | 0.003 | 0.003 | 0.05 |

Each parameter shows mean value (n = 4)

Discussion

In test preparation 3, the control compound disappeared immediately after intramuscular administration. On the other hand, in test preparations 1 and 2, the control compound showed a sustained blood concentration profile. Therefrom it was shown that the improved solubility of the compound of the present invention in an oily substrate has enabled the production of a dissolution preparation that shows blood concentration sustainability of the compound of patent document 1.

The invention claimed is:
1. A heterocyclic compound represented by the formula

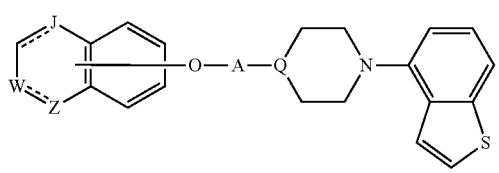 (I)

wherein
A is a lower alkylene group;

in the monocyclic heterocycle containing Q is

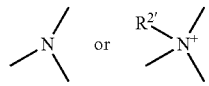

wherein
$R^{2'}$ is the following group

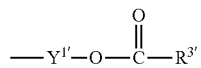

wherein
$Y^{1'}$ is a lower alkylene group,
$R^{3'}$ is
(1) an alkyl group,
(2) a cycloalkyl group optionally substituted by a lower alkyl group,
(3) a phenyl group,
(4) a phenyl lower alkyl group
(5) a lower alkoxy group,
(6) a cycloaikyloxy group,
(7) an amino group optionally having 1 or 2 substituents selected from the group consisting of an alkyl group and a phenyl lower alkyl group, or
(8) a piperidyl group optionally haying a piperidyl group;

at the 3-position and the 4-position of the bicyclic heterocycle skeleton containing Z and W is —CH=CH— or

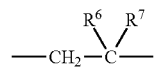

wherein $R^6$ and $R^7$ are the same or different and each is a hydrogen or a lower alkyl group;

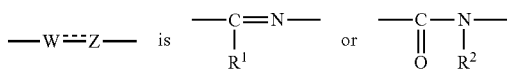

wherein
$R^2$ is a hydrogen or
the following group

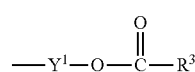 (1)

 (2)

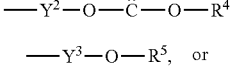 (3)

(4)

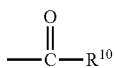

wherein
$Y^1$ is a lower alkylene group optionally substituted by
(1) a lower alkoxycarbonyl group or
(2) a lower alkyl group,
$Y^2$ is a lower alkylene group,
$Y^3$ is a single bond or a lower alkylene group optionally substituted by a lower alkyl group,
R3 is
(1) an alkyl group,
(2) a halogen-substituted lower alkyl group,
(3) an alkenyl group,
(4) an amino lower alkyl group,
(5) a cycloalkyl group,
(6) a phenyl group,
(7) a phenyl lower alkyl group,
(8) a piperidyl group optionally having 1or 2substituents selected from the group consisting of a lower alkyl group and a piperidyl group,
(9) a halogen-substituted piperidyl group,
(10) a morpholinyl group,
(11) a pyrrolidinyl group,
(12) a tetrahydropyranyl group,
(13) a furyl group,
(14) a thienyl group,
(15) a pyridyl group,
(16) a pyrimidinyl group,
(17) a pyridazinyl group,
(18) a benzofuryl group,
(19) a quinolyl group,
(20) a lower alkoxycarbonyl lower alkyl group,
(21) a lower alkoxy lower alkoxy lower alkyl group,
(22) a lower alkoxy lower alkoxy lower alkoxy lower alkyl group,
(23) an amino group optionally having 1 or 2 substituents selected from the group consisting of an alkyl group, a cycloalkyl group, a cycloalkyl lower alkyl group, a lower alkenyl group, a halogen-substituted lower alkyl group, a lower alkoxy group, a lower alkoxy lower alkyl group, a lower alkoxycarbonyl lower alkyl group, a phenyl lower alkyl group, a phenyl lower alkoxy group, a furyl lower alkyl group, a pyridyl lower alkyl group, a hydroxy-substituted lower alkyl group,

(24) an amino lower alkyl group optionally having a lower alkylcarbonyl group,
(25) a piperazinyl group optionally having a lower alkyl group, or
(26) the following group

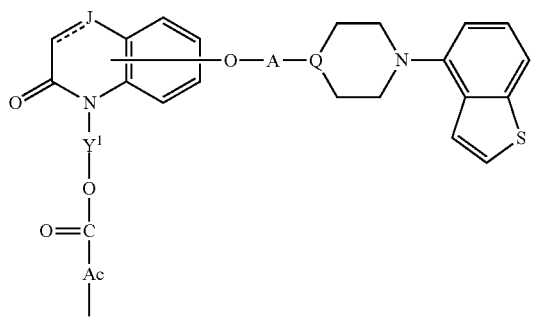

wherein Ac is an alkylene group, and other symbols are defined above, $R^4$ is
(1) an alkyl group,
(2) a phenyl group,
(3) a phenyl lower alkyl group,
(4) a halogen-substituted lower alkyl group, or
(5) a cycloalkyl group, $R^5$ is
(1) a hydrogen,
(2) a lower alkyl group,
(3) a halogen-substituted lower alkyl group,
(4) a phenyl lower alkyl group,
(5) a phenyl lower alkoxy lower alkyl group,
(6) a tri-lower alkylsilyl group,
(7) a tetrahydropyranyl group, or
(8) a phosphono group, $R^{10}$ is
(1) an alkenyl group,
(2) a phenyl lower alkyl group,
(3) a hydroxy-substituted lower alkyl group,
(4) a cycloalkyl group,
(5) an amino lower alkyl group optionally having 1 or 2 substituents selected from the group consisting of an amino lower alkylcarbonyl group and a lower alkylcarbonyl group,
(6) a pyrrolidinyl group optionally having an amino lower alkylcarbonyl group,
(7) an alkoxy group,
(8) a lower alkoxy lower alkoxy lower alkyl group,
(9) a lower alkoxy lower alkoxy lower alkoxy lower alkyl group,
(10) a phenyl lower alkoxy group,
(11) an amino group optionally having 1 or 2 substituents selected from the group consisting of an alkyl group, a hydroxy-substituted lower alkyl group and a phenyl lower alkyl group,
(12) a morpholino group,
(13) a piperazinyl group optionally having a lower alkyl group,
(14) a piperidyl group optionally having a piperidyl group, or
(15) a cycloalkyloxy group;
provided when

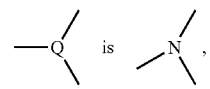

then
$R^2$ is not a hydrogen, or a salt thereof.

2. The heterocyclic compound according to claim 1, which is represented by the formula (II)

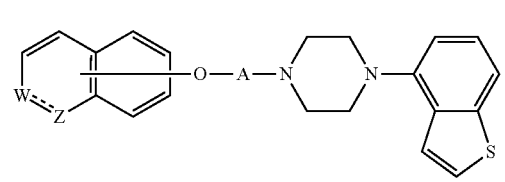

wherein each symbol is as defined in claim 1, or a salt thereof.

3. The heterocyclic compound according to claim 1, which is represented by the formula (III)

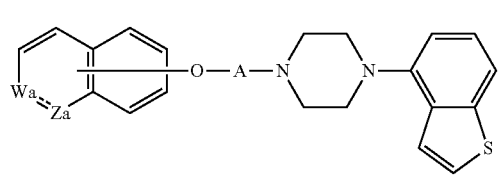

wherein —Wa═Za— is

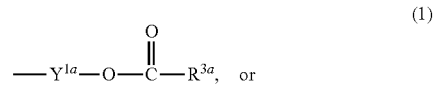 (placeholder)

wherein
$R^{2a}$ is
the following group

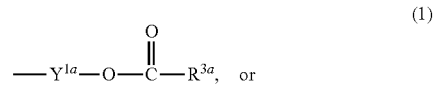

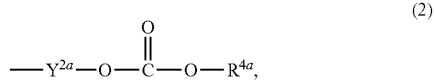

wherein
$Y^{1a}$ is a lower alkylene group,
$Y^{2a}$ is a lower alkylene group,
$R^{3a}$ is
(1) an alkyl group,
(2) a cycloalkyl group,
(3) a piperidyl group optionally having 1 or 2 substituents selected from the group consisting of a lower alkyl group,
(4) a tetrahydropyranyl group,
(5) a lower alkoxycarbonyl lower alkyl group,
(6) a lower alkoxy lower aikoxy lower alkyl group (7) an amino lower alkyl group optionally having a lower alkylcarbonyl group, or
(8) the following group

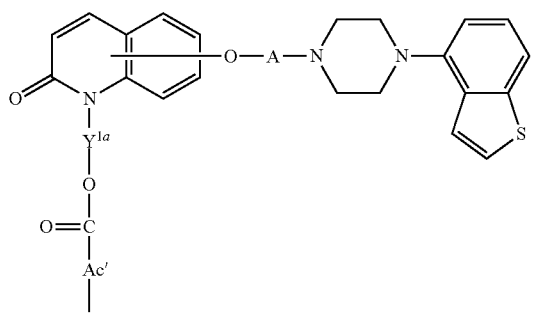

wherein Ac' is an alkylene group, $Y^{1a}$ is a lower alkylene group and other symbols are as defined in claim 1,
$R^{4a}$ is
(1) an alkyl group, or
(2) a cycloalkyl group; and
A is a lower alkylene group,
or a salt thereof.

4. The heterocyclic compound according to claim 2, wherein
$R^2$ is
the following group

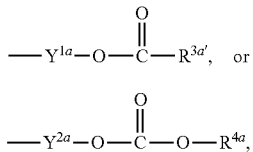

wherein
$Y^{1a}$ is a lower alkylene group,
$Y^{2a}$ is a lower alkylene group,
$R^{3a'}$ is
(1) an alkyl group,
(2) a cycloalkyl group
(3) a piperidyl group optionally having 1 or 2 substituents selected from the group consisting of a lower alkyl group,
(4) a tetrahydropyranyl group,
(5) a lower alkoxycarbonyl lower alkyl group,
(6) a lower alkoxy lower alkoxy lower alkyl group
(7) an amino lower alkyl group optionally having a lower alkylcarbonyl group,
$R^{4a}$ is
(1) an alkyl group, or
(2) a cycloalkyl group;
or a salt thereof.

5. A method of producing a heterocyclic compound represented by the formula (I)

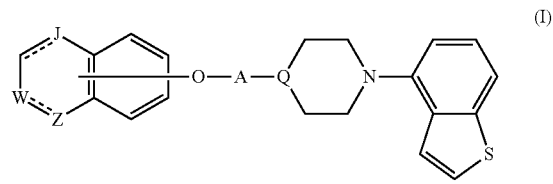

wherein each symbol is as defined in claim 1,
or a salt thereof, comprising reacting a compound represented by the formula

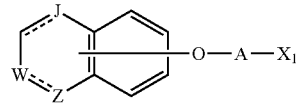

wherein $X_1$ is a halogen atom or a group that causes a substitution reaction similar to that by a halogen atom, and other symbols are as defined in claim 1, or a salt thereof, with a compound represented by

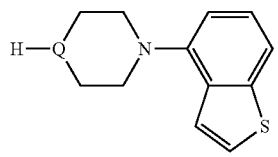

wherein Q is as defined in claim 1, or a salt thereof.

* * * * *